(12) United States Patent
Wall et al.

(10) Patent No.: US 8,901,314 B2
(45) Date of Patent: Dec. 2, 2014

(54) SUBSTITUTED PYRAZOLES AS N-TYPE CALCIUM CHANNEL BLOCKERS

(71) Applicant: Janssen Pharmaceutica NV, Beerse (BE)

(72) Inventors: Mark Wall, Lansdale, PA (US); Nalin Subasinghe, Exton, PA (US); Zhihua Sui, Piscataway, NJ (US); Christopher Flores, Lansdale, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/968,473

(22) Filed: Aug. 16, 2013

(65) Prior Publication Data

US 2014/0163031 A1    Jun. 12, 2014

Related U.S. Application Data

(60) Provisional application No. 61/683,777, filed on Aug. 16, 2012.

(51) Int. Cl.
| | | |
|---|---|---|
| C07D 231/00 | (2006.01) | |
| C07D 277/22 | (2006.01) | |
| C07D 239/02 | (2006.01) | |
| C07D 401/14 | (2006.01) | |
| A61K 31/505 | (2006.01) | |
| A61K 31/425 | (2006.01) | |
| A61K 31/415 | (2006.01) | |
| A61K 31/44 | (2006.01) | |
| C07D 405/14 | (2006.01) | |
| C07D 409/04 | (2006.01) | |
| C07D 405/04 | (2006.01) | |
| C07D 417/14 | (2006.01) | |
| C07D 409/14 | (2006.01) | |

(52) U.S. Cl.
CPC ............ *C07D 417/14* (2013.01); *C07D 405/14* (2013.01); *C07D 409/04* (2013.01); *C07D 405/04* (2013.01); *C07D 409/14* (2013.01)
USPC .................... 548/365.7; 548/203; 546/274.1; 544/318

(58) Field of Classification Search
None
See application file for complete search history.

(56) References Cited

FOREIGN PATENT DOCUMENTS

WO    WO 2004033432 A1 *    4/2004
WO    WO 2010/014257 A2    2/2010

OTHER PUBLICATIONS

International Search Report mailed Oct. 10, 2013 for Application No. PCT/US2013/055271.
Berge, St., et al., "Pharmaceutical Salts", Journal of Pharmaceutical Sciences, vol. 66, No. 1, pp. 1-19 (Jan. 1977).
Gould, Philip L., "Salt Selection for Basic Drugs", International Journal of Pharmaceutics, vol. 33, pp. 201-217 (1986).
Lim, D., et al., "Direct Carbon-Carbon Bond Formation via Soft Enolization: A Facile and Efficient Synthesis of 1,3-Diketones", Organic Letters, vol. 9, No. 21, pp. 4139-4142 (2007).
Subasinghe, N., et al, "A Novel Series of Pyrazolylpiperidine N-Type Calcium Channel Blockers", Bioorganic & Medicinal Chemistry Letters, vol. 22, p. 4080-4083 (2012).

* cited by examiner

*Primary Examiner* — Nyeemah A Grazier
(74) *Attorney, Agent, or Firm* — Peter L. Herridge

(57) ABSTRACT

The present invention relates to compounds of Formula (I),

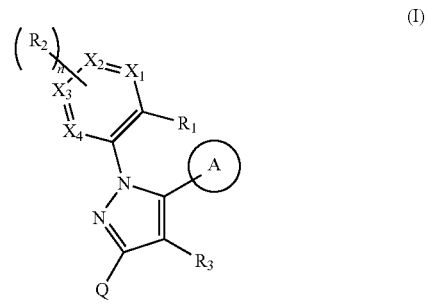

wherein $X_1$, $X_2$, $X_3$, $X_4$, $R_1$, $R_2$, $R_3$, and Q are as defined herein, useful as N-type calcium channel blockers.

21 Claims, 1 Drawing Sheet

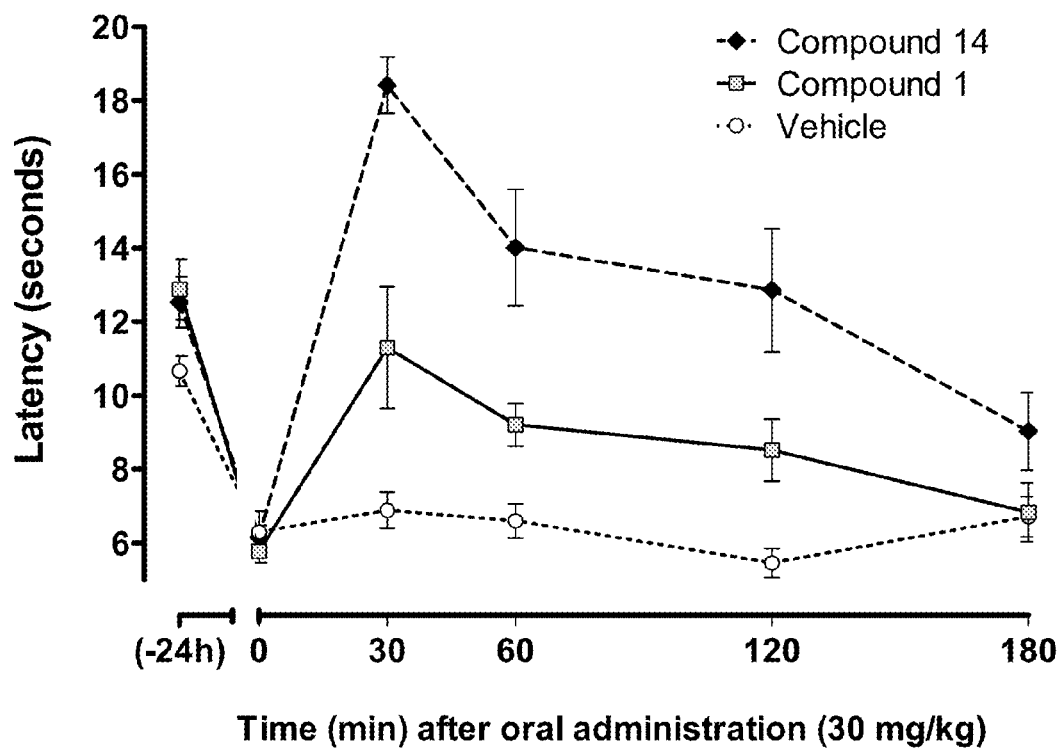

SUBSTITUTED PYRAZOLES AS N-TYPE CALCIUM CHANNEL BLOCKERS

CROSS REFERENCE TO RELATED APPLICATIONS

This application claims priority of the benefits of the filing of U.S. Provisional Application Ser. No. 61/683,777, filed Aug. 16, 2012. The complete disclosures of the aforementioned related U.S. patent application is/are hereby incorporated herein by reference for all purposes.

FIELD OF THE INVENTION

The present invention relates to substituted pyrazoles compounds useful as N-type calcium channel blockers. More particularly, the present invention relates to substituted pyrazole compounds useful as N-type calcium channel blockers and methods of preparation and use thereof.

BACKGROUND OF THE INVENTION

Calcium ions play a fundamental role in the physiology and biochemistry of organisms and of cells. The entry of calcium into cells through ion channels mediates a variety of cellular and physiological responses, including gene expression, signal transduction, neurotransmitter release, muscle contraction and hormone secretion. Ion channels are classified by gating, or what opens and closes the channel to the flux of ions. Voltage-gated ion channels open or close depending on the voltage gradient across the plasma membrane, whereas ligand-gated ion channels open or close depending on the binding of ligands to the channel. The classification of voltage-gated calcium channels divides them into three groups: (i) high voltage-activated channels, which include L-, N-, P- and Q-type channels; (ii) intermediate voltage-activated R-type channels; and (iii) low voltage activated T-type channels.

The N-type calcium channel is distributed mainly in central and peripheral neurons, being localized primarily to presynaptic nerve terminals. This channel regulates the calcium flux required for depolarization-evoked release of neurotransmitters from synaptic endings. The transmission of pain signals from the periphery to the central nervous system (CNS) is mediated, inter alia, by N-type calcium channels located in the spinal cord. Inhibition of the N-type calcium channel in the superficial dorsal horn leads to a decrease in membrane excitability and neurotransmitter release, resulting in pain relief. In addition, knock-out mice lacking the N-type calcium channel exhibit reduced nociceptive behaviors in animal models of pain.

N-type calcium channels have been shown to mediate the development and maintenance of the neuronal sensitization processes associated with neuropathic pain and therefore provide attractive targets for the development of analgesic drugs. Three N-type calcium channel modulators are currently approved for the treatment of pain: ω-conotoxin MVIIA (ziconotide), marketed as Prialt®, potently and selectively blocks the N-type calcium channel and is indicated for the management of severe chronic pain; gabapentin, marketed as Neurontin®, and pregabalin, marketed as Lyrica®, bind with high affinity to the $\alpha_2\delta$ subunit of the N-type calcium channel and are indicated for the treatment of fibromyalgia, diabetic nerve pain and/or post-herpetic neuralgia pain.

SUMMARY OF THE INVENTION

In its many embodiments, the present invention provides novel compounds useful as, for example, N-type calcium channel inhibitors, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with N-type calcium channels using such compounds or pharmaceutical compositions.

One aspect of the present invention features a compound of Formula (I)

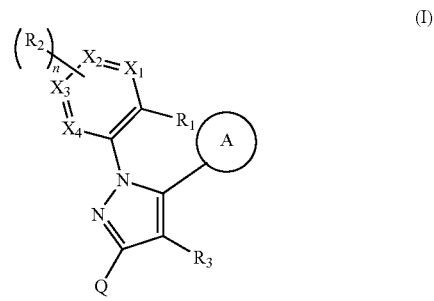

wherein
$X_1$, $X_2$, $X_3$ and $X_4$ are independently CH or N;
n is 0, 1 or 2;
$R_1$ is selected from the group consisting of $C_{1-4}$alkyl, $C_{1-4}$alkoxy, di($C_{1-4}$alkyl)amino, $C_{1-4}$alkyl-amino, amino, pyrrolidin-1-yl, nitro, halo, trifluoromethoxy, trifluoromethyl, and cyano;
$R_2$ is $C_{1-4}$alkoxy, halo, or trifluoromethyl;
wherein $R_1$ and $R_2$ alternatively can form a 6-membered heteroaryl ring with n being 1 and $R_2$ bound to $X_1$; $R_3$ is hydrogen or bromo;
ring A is selected from the group consisting of pyridine-N-oxide, benzo[1,3]dioxol-5-yl, 4,4-dimethylcyclohex-1-en-1-yl, indolyl, 1-methyl-indolyl, 2,3-dihydrobenzo[b][1,4]-dioxin-6-yl, cyclopent-1-en-1-yl, benzofuranyl, phenyl, and heteroaryl, wherein said heteroaryl is a 5 to 6 membered ring optionally containing 1 additional heteroatom selected from the group consisting of N, O and S;
wherein said phenyl and said heteroaryl is optionally substituted with $R_4$;
$R_4$ is selected from the group consisting of hydroxyl, halo, cyano, amino, carboxy, $C_{1-4}$alkyl, $C_{1-4}$alkoxy, $C_{1-4}$alkylthio, di($C_{1-4}$alkyl)amino, $C_{1-4}$alkylcarbonyl, $C_{1-4}$alkoxycarbonyl, $C_{1-4}$alkylcarbonylamino, di($C_{1-4}$alkyl)amino-carbonyl, hydroxyl-$C_{1-4}$alkyl, morpholin-4-yl-$C_{1-4}$alkoxy, imidazol-1-yl-$C_{1-4}$alkoxy, di($C_{1-4}$alkyl)amino-$C_{1-4}$alkoxy, $C_{1-4}$alkylsulfonyl, morpholin-4-yl-carbonyl, di($C_{1-4}$alkyl)amino-$C_{1-4}$alkyl-aminocarbonyl, aminocarbonyl, 1-methyl-piperidin-4-yl-carbonyl, hydroxyl-$C_{1-4}$alkyl-aminocarbonyl and $C_{1-4}$alkyl-sulfinyl; and
Q is selected from the group consisting of

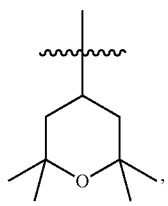

-continued
Q2 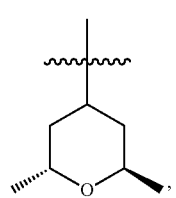
Q3 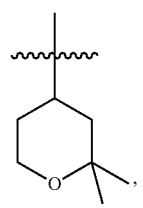
Q4 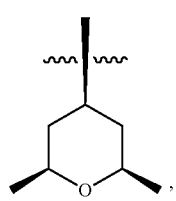
Q5 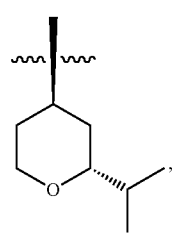
Q6 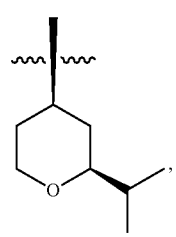
Q7 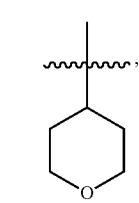
Q8 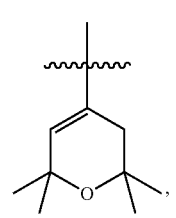
Q9 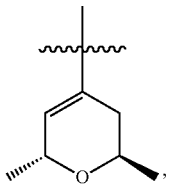
Q10 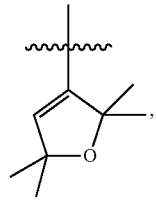
Q11 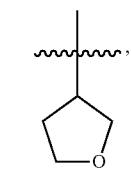
Q12 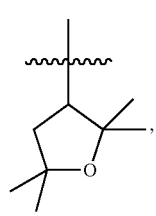
Q13 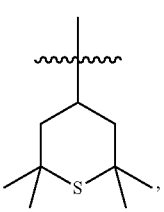
Q14 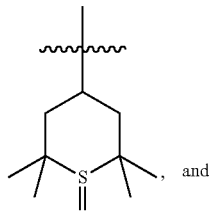, and
Q15 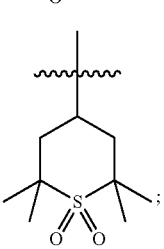
or an enantiomer, diastereomer, solvate or pharmaceutically acceptable salt thereof.
Another aspect of the present invention features a pharmaceutical composition comprising at least one compound of Formula (I) and at least one pharmaceutically acceptable carrier.

The present invention also features a method of treating a subject suffering from or diagnosed with a disease, disorder, or condition mediated by N-type calcium channel activity, comprising administering to the subject a therapeutically effective amount of at least one compound of Formula (I). Such disease, disorder, or condition can include, but is not limited to pain and the diseases that lead to such pain.

The present invention further features a process for making a pharmaceutical composition comprising mixing any of the compounds according to Formula (I) and a pharmaceutically acceptable carrier.

The invention further provides methods for using a compound or composition of the invention. For example, one embodiment of the invention is a method for treating a condition associated with N-type calcium channel activity in a subject in need thereof comprising administering to the subject an effective amount of any of the disclosed compounds or the disclosed pharmaceutical compositions. It is also an aspect of the invention to provide a method of treating, ameliorating or preventing pain by the administration of a compound of Formula (I).

Additional embodiments and advantages of the invention will become apparent from the detailed discussion, schemes, examples, and claims below.

BRIEF DESCRIPTION OF THE DRAWINGS

FIG. 1 shows the antihyperalgesic effect of vehicle and compounds 1 and 14 in a rat CFA radiant heat model of inflammatory pain.

DETAILED DESCRIPTION OF THE INVENTION

This invention relates to novel N-type calcium channel blockers and compositions thereof for the treatment, amelioration, prevention or inhibition of numerous conditions, including but not limited to pain and the diseases that lead to such pain, and associated symptoms or complications thereof.

One aspect of the present invention features a compound of Formula (I)

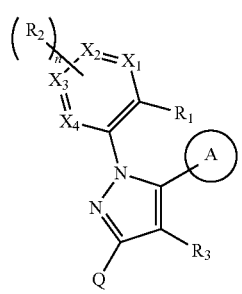

wherein
$X_1$, $X_2$, $X_3$ and $X_4$ are independently CH or N;
n is 0, 1 or 2;
$R_1$ is selected from the group consisting of $C_{1-4}$alkyl, $C_{1-4}$alkoxy, di($C_{1-4}$alkyl)amino, $C_{1-4}$alkyl-amino, amino, pyrrolidin-1-yl, nitro, halo, trifluoromethoxy, trifluoromethyl, and cyano;
$R_2$ is $C_{1-4}$alkoxy, halo, or trifluoromethyl;
wherein $R_1$ and $R_2$ alternatively can form a 6-membered heteroaryl ring with n being 1 and $R_2$ bound to $X_1$; $R_3$ is hydrogen or bromo;

ring A is selected from the group consisting of pyridine-N-oxide, benzo[1,3]dioxol-5-yl, 4,4-dimethylcyclohex-1-en-1-yl, indolyl, 1-methyl-indolyl, 2,3-dihydrobenzo[b][1,4]-dioxin-6-yl, cyclopent-1-en-1-yl, benzofuranyl, phenyl, and heteroaryl, wherein said heteroaryl is a 5 to 6 membered ring optionally containing 1 additional heteroatom selected from the group consisting of N, O and S;

wherein said phenyl and said heteroaryl is optionally substituted with $R_4$;

$R_4$ is selected from the group consisting of hydroxyl, halo, cyano, amino, carboxy, $C_{1-4}$alkyl, $C_{1-4}$alkoxy, $C_{1-4}$alkylthio, di($C_{1-4}$alkyl)amino, $C_{1-4}$alkylcarbonyl, $C_{1-4}$alkoxycarbonyl, $C_{1-4}$alkylcarbonylamino, di($C_{1-4}$alkyl)amino-carbonyl, hydroxyl-$C_{1-4}$alkyl, morpholin-4-yl-$C_{1-4}$alkoxy, imidazol-1-yl-$C_{1-4}$alkoxy, di($C_{1-4}$alkyl)amino-$C_{1-4}$alkoxy, $C_{1-4}$alkylsulfonyl, morpholin-4-yl-carbonyl, di($C_{1-4}$alkyl)amino-$C_{1-4}$alkyl-aminocarbonyl, aminocarbonyl, 1-methyl-piperidin-4-yl-carbonyl, hydroxyl-$C_{1-4}$alkyl-aminocarbonyl and $C_{1-4}$alkyl-sulfinyl; and Q is selected from the group consisting of

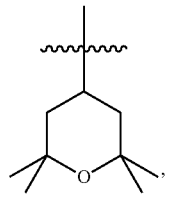
Q1

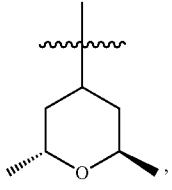
Q2

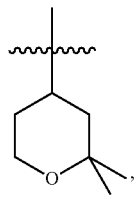
Q3

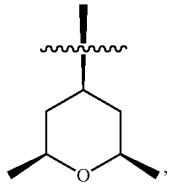
Q4

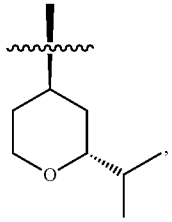
Q5

-continued

Q6 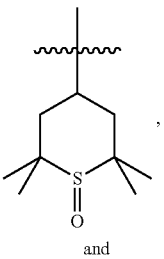

Q7 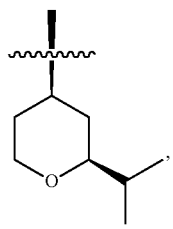

Q8 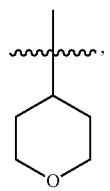

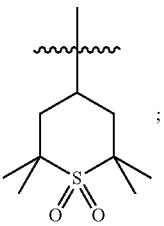

and

Q15 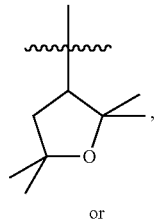

Q9 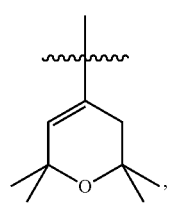

or an enantiomer, diastereomer, solvate or pharmaceutically acceptable salt thereof.

Particularly, $R_1$ is methoxy. And particularly, n is 0.

In another embodiment of the present invention $R_1$ is $C_{1-4}$alkoxy. Yet, in another embodiment the ring A is phenyl, thiophen-2-yl or pyridine, wherein $R_4$ is halo, cyano or $C_{1-4}$alkoxy.

Another embodiment of the invention comprises a compound of Formula (I), wherein Q is Q10 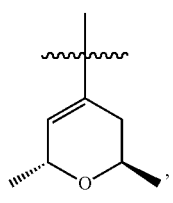

Q12 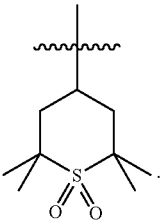

or

Q11 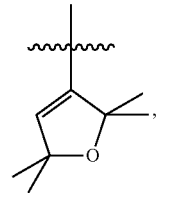

Q15 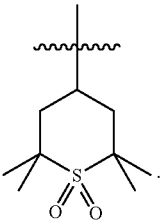

Q12 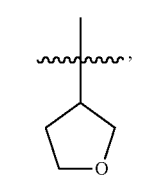

Yet, in another embodiment the ring A is phenyl, wherein $R_1$ is $C_{1-4}$alkoxy and $R_4$ is halo.

It is an embodiment of the present invention to provide a compound selected from:

5-(4-Chloro-phenyl)-1-(2-methoxy-phenyl)-3-(2,2,6,6-tetramethyl-tetrahydro-pyran-4-yl)-1H-pyrazole, Q13 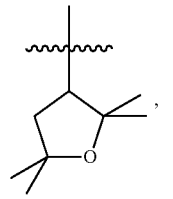

4-[1-(2-Methoxyphenyl)-3-(2,2,6,6-tetramethyltetrahydro-2H-pyran-4-yl)-1H-pyrazol-5-yl]-benzonitrile, 5-(4-Chloro-2-fluorophenyl)-1-(2-methoxyphenyl)-3-(2,2,6,6-tetramethyltetrahydro-2H-pyran-4-yl)-1H-pyrazole, 5-(1,3-Benzodioxol-5-yl)-1-(2-methoxyphenyl)-3-(2,2,6,6-tetramethyltetrahydro-2H-pyran-4-yl)-1H-pyrazole, 1-(2-Methoxyphenyl)-5-(4-methoxyphenyl)-3-(2,2,6,6-tetramethyltetrahydro-2H-pyran-4-yl)-1H-pyrazole,

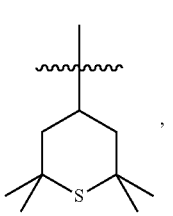

1-(2-Methoxyphenyl)-5-[4-(methylsulfanyl)phenyl]-3-(2,2,6,6-tetramethyltetrahydro-2H-pyran-4-yl)-1H-pyrazole, 5-(4-Chlorophenyl)-1-[2-(1-methylethoxy)phenyl]-3-(2,2,6,6-tetramethyltetrahydro-2H-pyran-4-yl)-1H-pyrazole, 5-(4,4-Dimethylcyclohex-1-en-1-yl)-1-(2-methoxyphenyl)-3-(2,2,6,6-tetramethyltetrahydro-2H-pyran-4-yl)-1H-pyrazole, 5-(4-Ethoxyphenyl)-1-(2-methoxyphenyl)-3-(2,2,6,6-tetramethyltetrahydro-2H-pyran-4-yl)-1H-pyrazole, 1-(2-Methoxyphenyl)-5-(4-methylphenyl)-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-N,N-dimethylaniline, 1-{4-[1-(2-Methoxyphenyl)-3-(2,2,6,6-tetramethyltetrahydro-2H-pyran-4-yl)-1H-pyrazol-5-yl]phenyl}ethanone, 2-Methoxy-5-[1-(2-methoxyphenyl)-3-(2,2,6,6-tetramethyltetrahydro-2H-pyran-4-yl)-1H-pyrazol-5-yl]pyridine, 5-(5-Chlorothiophen-2-yl)-1-(2-methoxyphenyl)-3-(2,2,6,6-tetramethyltetrahydro-2H-pyran-4-yl)-1H-pyrazole, 5-(4-tert-Butylphenyl)-1-(2-methoxyphenyl)-3-(2,2,6,6-tetramethyltetrahydro-2H-pyran-4-yl)-1H-pyrazole, 1-(2-Methoxyphenyl)-5-phenyl-3-(2,2,6,6-tetramethyltetrahydro-2H-pyran-4-yl)-1H-pyrazole, Ethyl 4-[1-(2-methoxyphenyl)-3-(2,2,6,6-tetramethyltetrahydro-2H-pyran-4-yl)-1H-pyrazol-5-yl]benzoate, 1-(2-Methoxyphenyl)-5-(4-methylthiophen-2-yl)-3-(2,2,6,6-tetramethyltetrahydro-2H-pyran-4-yl)-1H-pyrazole, 2-Ethoxy-5-[1-(2-methoxyphenyl)-3-(2,2,6,6-tetramethyltetrahydro-2H-pyran-4-yl)-1H-pyrazol-5-yl]-pyridine, 1-(2-Methoxyphenyl)-5-(3-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1-methyl-1H-indole, 2-[1-(2-Methoxyphenyl)-3-(2,2,6,6-tetramethyltetrahydro-2H-pyran-4-yl)-1H-pyrazol-5-yl]-aniline, 5-[1-(2-Methoxyphenyl)-3-(2,2,6,6-tetramethyltetrahydro-2H-pyran-4-yl)-1H-pyrazol-5-yl]-2-methylpyridine, 1-(2-Methoxyphenyl)-5-[4-(1-methylethoxy)phenyl]-3-(2,2,6,6-tetramethyltetrahydro-2H-pyran-4-yl)-1H-pyrazole, 2-Chloro-4-[1-(2-methoxyphenyl)-3-(2,2,6,6-tetramethyltetrahydro-2H-pyran-4-yl)-1H-pyrazol-5-yl]pyridine, 1-(2-Methoxyphenyl)-3-(2,2,6,6-tetramethyltetrahydro-2H-pyran-4-yl)-5-thiophen-2-yl-1H-pyrazole, 5-(2,3-Dihydro-1,4-benzodioxin-6-yl)-1-(2-methoxyphenyl)-3-(2,2,6,6-tetramethyltetrahydro-2H-pyran-4-yl)-1H-pyrazole, 1-(2-Methoxyphenyl)-5-(5-methylfuran-2-yl)-3-(2,2,6,6-tetramethyltetrahydro-2H-pyran-4-yl)-1H-pyrazole, 5-(3,4-Dimethoxyphenyl)-1-(2-methoxyphenyl)-3-(2,2,6,6-tetramethyltetrahydro-2H-pyran-4-yl)-1H-pyrazole, N-{5-[1-(2-Methoxyphenyl)-3-(2,2,6,6-tetramethyltetrahydro-2H-pyran-4-yl)-1H-pyrazol-5-yl]pyridin-2-yl}acetamide, 5-[1-(2-Methoxyphenyl)-3-(2,2,6,6-tetramethyltetrahydro-2H-pyran-4-yl)-1H-pyrazol-5-yl]-N,N-dimethylpyridin-2-amine, 4-[1-(2-Methoxyphenyl)-3-(2,2,6,6-tetramethyltetrahydro-2H-pyran-4-yl)-1H-pyrazol-5-yl]pyridine, 4-[1-(2-Methoxyphenyl)-3-(2,2,6,6-tetramethyltetrahydro-2H-pyran-4-yl)-1H-pyrazol-5-yl]-2-methylpyridine, 3-Methoxy-5-[1-(2-methoxyphenyl)-3-(2,2,6,6-tetramethyltetrahydro-2H-pyran-4-yl)-1H-pyrazol-5-yl]-pyridine, 2-Methoxy-3-[1-(2-methoxyphenyl)-3-(2,2,6,6-tetramethyltetrahydro-2H-pyran-4-yl)-1H-pyrazol-5-yl]-pyridine, N-{2-[1-(2-Methoxyphenyl)-3-(2,2,6,6-tetramethyltetrahydro-2H-pyran-4-yl)-1H-pyrazol-5-yl]-phenyl}-acetamide, 5-Cyclopent-1-en-1-yl-1-(2-methoxyphenyl)-3-(2,2,6,6-tetramethyltetrahydro-2H-pyran-4-yl)-1H-pyrazole, 2-[1-(2-Methoxyphenyl)-3-(2,2,6,6-tetramethyltetrahydro-2H-pyran-4-yl)-1H-pyrazol-5-yl]-5-methyl-1,3-thiazole, 2-Methoxy-5-[1-(2-methoxyphenyl)-3-(2,2,6,6-tetramethyltetrahydro-2H-pyran-4-yl)-1H-pyrazol-5-yl]pyrimidine, N,N-Diethyl-4-[1-(2-methoxyphenyl)-3-(2,2,6,6-tetramethyltetrahydro-2H-pyran-4-yl)-1H-pyrazol-5-yl]-benzamide, 5-(1-Benzofuran-2-yl)-1-(2-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1H-indole, 5-(3,5-Dimethoxyphenyl)-1-(2-methoxyphenyl)-3-(2,2,6,6-tetramethyltetrahydro-2H-pyran-4-yl)-1H-pyrazole, 1-{4-[1-(2-Methoxyphenyl)-3-(2,2,6,6-tetramethyltetrahydro-2H-pyran-4-yl)-1H-pyrazol-5-yl]-phenyl}ethanol, 3-[1-(2-Methoxyphenyl)-3-(2,2,6,6-tetramethyltetrahydro-2H-pyran-4-yl)-1H-pyrazol-5-yl]-pyridine, 4-[1-(2-Methoxyphenyl)-3-(2,2,6,6-tetramethyltetrahydro-2H-pyran-4-yl)-1H-pyrazol-5-yl]-benzoic acid, 5-(4-Methanesulfinyl-phenyl)-1-(2-methoxy-phenyl)-3-(2,2,6,6-tetramethyl-tetrahydro-pyran-4-yl)-1H-pyrazole, 1-(2-tert-Butoxyphenyl)-5-(4-chlorophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N,N-dimethylaniline, 2-[5-(4-Chloro-phenyl)-3-(2,2,6,6-tetramethyl-tetrahydro-pyran-4-yl)-pyrazol-1-yl]-pyridine, 4-[5-(4-Chlorophenyl)-3-(2,2,6,6-tetramethyltetrahydro-2H-pyran-4-yl)-1H-pyrazol-1-yl]-pyridine, 3-[5-(4-Chlorophenyl)-3-(2,2,6,6-tetramethyltetrahydro-2H-pyran-4-yl)-1H-pyrazol-1-yl]-pyridine, 4-[1-Pyrazin-2-yl-3-(2,2,6,6-tetramethyltetrahydro-2H-pyran-4-yl)-1H-pyrazol-5-yl]-benzonitrile, 4-[1-Pyridin-3-yl-3-(2,2,6,6-tetramethyltetrahydro-2H-pyran-4-yl)-1H-pyrazol-5-yl]-benzonitrile, 4-[1-Pyridin-2-yl-3-(2,2,6,6-tetramethyltetrahydro-2H-pyran-4-yl)-1H-pyrazol-5-yl]-benzonitrile, 4-[1-Pyridin-4-yl-3-(2,2,6,6-tetramethyltetrahydro-2H-pyran-4-yl)-1H-pyrazol-5-yl]-benzonitrile, 4-[1-Quinolin-8-yl-3-(2,2,6,6-tetramethyltetrahydro-2H-pyran-4-yl)-1H-pyrazol-5-yl]-benzonitrile, 5-(4-Chloro-phenyl)-1-(2-methoxy-phenyl)-3-(2,2,6,6-tetramethyl-tetrahydro-thiopyran-4-yl)-1H-pyrazole, 5-(4-Chlorophenyl)-1-(2-methoxyphenyl)-3-(2,2,6,6-tetramethyl-1,1-dioxidotetrahydro-2H-thiopyran-4-yl)-1H-pyrazole, 2-[5-(4-Chlorophenyl)-3-(2,2,6,6-tetramethyltetrahydro-2H-pyran-4-yl)-1H-pyrazol-1-yl]-N-methylaniline, 5-(4-Chlorophenyl)-3-[(trans)-2,6-dimethyltetrahydro-2H-pyran-4-yl]-1-(2-methoxyphenyl)-1H-pyrazole, 5-(4-Chlorophenyl)-3-(2,2-dimethyltetrahydro-2H-pyran-4-yl)-1-(2-methoxyphenyl)-1H-pyrazole, 5-(4-Chlorophenyl)-3-[(2R,4r,6S)-2,6-dimethyltetrahydro-2H-pyran-4-yl]-1-(2-methoxyphenyl)-1H-pyrazole, 5-(4-Chlorophenyl)-1-(2-methoxyphenyl)-3-[(2R,4S)-2-(1-methylethyl)tetrahydro-2H-pyran-4-yl]-1H-pyrazole, 5-(4-Chlorophenyl)-1-(2-nitrophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N-ethylaniline, 3-[(trans)-2,6-Dimethyltetrahydro-2H-pyran-4-yl]-1-(2-methoxyphenyl)-5-phenyl-1H-pyrazole, 2-[5-(4-Chlorophenyl)-3-(2,2,6,6-tetramethyltetrahydro-2H-pyran-4-yl)-1H-pyrazol-1-yl]-aniline, 5-(4-Chlorophenyl)-1-(2-methoxyphenyl)-3-[(trans)-2-(1-methylethyl)tetrahydro-2H-pyran-4-yl]-1H-pyrazole, 4-Bromo-5-(4-chlorophenyl)-1-(2-methoxyphenyl)-3-(2,2,6,6-tetramethyltetrahydro-2H-pyran-4-yl)-1H-pyrazole, 5-(4-Chlorophenyl)-1-(2-methoxyphenyl)-3-(tetrahydro-2H-pyran-4-yl)-1H-pyrazole, 4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine, 2-[5-(4-Chlorophenyl)-3-(2,2,6,6-tetramethyltetrahydro-2H-pyran-4-yl)-1H-pyrazol-1-yl]-N,N-diethylaniline, 1-(2-Chlorophenyl)-5-(4-chlorophenyl)-3-(tetrahydro-2H-pyran-4-yl)-1H-pyrazole, 5-(4-Chlorophenyl)-3-(2,2-dimethyltetrahydro-2H-pyran-4-yl)-1-(4-methoxy-2-methylphenyl)-1H-pyrazole, 5-(4-Chlorophenyl)-1-(2-pyrrolidin-1-ylphenyl)-3-(2,2,6,6-tetramethyltetrahydro-2H-pyran-4-yl)-1H-pyrazole, 5-(4-Chlorophenyl)-1-(2-ethylphenyl)-3-(tetrahydro-2H-pyran-4-yl)-1H-pyrazole, 5-(4-Chlorophenyl)-1-(2,4-dichlorophenyl)-3-(tetrahydro-2H-pyran-4-yl)-1H-pyrazole, 5-(4-Chlorophenyl)-3-(tetrahydro-2H-pyran-4-yl)-1-[2-(trifluoromethoxy)phenyl]-1H-pyrazole, 5-(4-Chlorophenyl)-1-(2,6-dichlorophenyl)-3-(tetrahydro-2H-pyran-4-yl)-1H-pyrazole, 5-{4-[2-(1H-Imidazol-1-yl)ethoxy]phenyl}-1-(2-methoxyphenyl)-3-(2,2,6,6-tetramethyltetrahydro-2H-pyran-4-yl)-1H-pyrazole, 2-{4-[1-(2-Methoxyphenyl)-3-(2,2,6,6-tetramethyltetrahydro-2H-pyran-4-yl)-1H-pyrazol-5-yl]phenoxy}-N,N-dimethylethanamine, 1-(2-Methoxyphenyl)-5-[4-(methylsulfonyl)phenyl]-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-phenol, 5-[1-(2-Methoxyphenyl)-3-(2,2,6,6-tetramethyltetrahydro-2H-pyran-4-yl)-1H-pyrazol-5-yl]-pyridin-2-amine, 4-({4-[1-(2-Methoxyphenyl)-3-(2,2,6,6-tetramethyltetrahydro-2H-pyran-4-yl)-1H-pyrazol-5-yl]phenyl}carbonyl)morpholine, N-[2-(Dimethylamino)ethyl]-4-[1-(2-methoxyphenyl)-3-(2,2,6,6-tetramethyltetrahydro-2H-pyran-4-yl)-1H-pyrazol-5-yl]benzamide, 4-[1-(2-Methoxyphenyl)-3-(2,2,6,6-tetramethyltetrahydro-2H-pyran-4-yl)-1H-pyrazol-5-yl]benzamide, 1-({4-[1-(2-Methoxyphenyl)-3-(2,2,6,6-tetramethyltetrahydro-2H-pyran-4-yl)-1H-pyrazol-5-yl]phenyl}carbonyl)-4-methyl piperazine, N-(2-Hydroxyethyl)-4-[1-(2-methoxyphenyl)-3-(2,2,6,6-tetramethyltetrahydro-2H-pyran-4-yl)-1H-pyrazol-5-yl]-benzamide, 3-[1-(2-Methoxyphenyl)-3-(2,2,6,6-tetramethyltetrahydro-2H-pyran-4-yl)-1H-pyrazol-5-yl]-pyridine-1-oxide, 5-(4-Chlorophenyl)-1-[2,4-dichloro-6-(trifluoromethyl)phenyl]-3-(tetrahydro-2H-pyran-4-yl)-1H-pyrazole, 5-(4-Chlorophenyl)-1-[2,6-dichloro-4-(trifluoromethyl)phenyl]-3-(tetrahydro-2H-pyran-4-yl)-1H-pyrazole, 2-[5-(4-Chlorophenyl)-3-(tetrahydro-2H-pyran-4-yl)-1H-pyrazol-1-yl]-benzonitrile, 5-(4-Chlorophenyl)-1-(2-methoxyphenyl)-3-(2,2,6,6-tetramethyl-3,6-dihydro-2H-pyran-4-yl)-1H-pyrazole, 5-(4-Chlorophenyl)-3-[(trans)-2,6-dimethyl-3,6-dihydro-2H-pyran-4-yl]-1-(2-methoxyphenyl)-1H-pyrazole, 5-(4-Chlorophenyl)-1-(2-methoxyphenyl)-3-(2,2,5,5-tetramethyl-2,5-di hydrofuran-3-yl)-1H-pyrazole, 5-(4-Chlorophenyl)-1-(2-methoxyphenyl)-3-(2,2,5,5-tetramethyl-2,5-dihydrofuran-3-yl)-1H-pyrazole, and 5-(4-Chlorophenyl)-1-(2-methoxyphenyl)-3-(2,2,5,5-tetramethyl-tetrahydrofuran-3-yl)-1H-pyrazole.

Particularly, an embodiment of the present invention comprises a compound selected from:

5-(4-Chloro-phenyl)-1-(2-methoxy-phenyl)-3-(2,2,6,6-tetramethyl-tetrahydro-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-benzonitrile, 5-(4-Chloro-2-fluorophenyl)-1-(2-methoxyphenyl)-3-(2,2,6,6-tetramethyltetrahydro-2H-pyran-4-yl)-1H-pyrazole, 5-(1,3-Benzodioxol-5-yl)-1-(2-methoxyphenyl)-3-(2,2,6,6-tetramethyltetrahydro-2H-pyran-4-yl)-1H-pyrazole, 1-(2-Methoxyphenyl)-5-(4-methoxyphenyl)-3-(2,2,6,6-tetramethyltetrahydro-2H-pyran-4-yl)-1H-pyrazole, 1-(2-Methoxyphenyl)-5-[4-(methylsulfanyl)phenyl]-3-(2,2,6,6-tetramethyltetrahydro-2H-pyran-4-yl)-1H-pyrazole, 5-(4-Chlorophenyl)-1-[2-(1-methylethoxy)phenyl]-3-(2,2,6,6-tetramethyltetrahydro-2H-pyran-4-yl)-1H-pyrazole, 5-(4,4-Dimethylcyclohex-1-en-1-yl)-1-(2-methoxyphenyl)-3-(2,2,6,6-tetramethyltetrahydro-2H-pyran-4-yl)-1H-pyrazole, 5-(4-Ethoxyphenyl)-1-(2-methoxyphenyl)-3-(2,2,6,6-tetramethyltetrahydro-2H-pyran-4-yl)-1H-pyrazole, 1-(2-Methoxyphenyl)-5-(4-methylphenyl)-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-N,N-dimethylaniline, 1-{4-[1-(2-Methoxyphenyl)-3-(2,2,6,6-tetramethyltetrahydro-2H-pyran-4-yl)-1H-pyrazol-5-yl]phenyl}ethanone, 2-Methoxy-5-[1-(2-methoxyphenyl)-3-(2,2,6,6-tetramethyltetrahydro-2H-pyran-4-yl)-1H-pyrazol-5-yl]pyridine, 5-(5-Chlorothiophen-2-yl)-1-(2-methoxyphenyl)-3-(2,2,6,6-tetramethyltetrahydro-2H-pyran-4-yl)-1H-pyrazole, 5-(4-tert-Butylphenyl)-1-(2-methoxyphenyl)-3-(2,2,6,6-tetramethyltetrahydro-2H-pyran-4-yl)-1H-pyrazole, 1-(2-Methoxyphenyl)-5-phenyl-3-(2,2,6,6-tetramethyltetrahydro-2H-pyran-4-yl)-1H-pyrazole, Ethyl 4-[1-(2-methoxyphenyl)-3-(2,2,6,6-tetramethyltetrahydro-2H-pyran-4-yl)-1H-pyrazol-5-yl]benzoate, 1-(2-Methoxyphenyl)-5-(4-methylthiophen-2-yl)-3-(2,2,6,6-tetramethyltetrahydro-2H-pyran-4-yl)-1H-pyrazole, 2-Ethoxy-5-[1-(2-methoxyphenyl)-3-(2,2,6,6-tetramethyltetrahydro-2H-pyran-4-yl)-1H-pyrazol-5-yl]-pyridine, 1-(2-Methoxyphenyl)-5-(3-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1-methyl-1H-indole, 2-[1-(2-Methoxyphenyl)-3-(2,2,6,6-tetramethyltetrahydro-2H-pyran-4-yl)-1H-pyrazol-5-yl]-aniline, 5-[1-(2-Methoxyphenyl)-3-(2,2,6,6-tetramethyltetrahydro-2H-pyran-4-yl)-1H-pyrazol-5-yl]-2-methylpyridine, 1-(2-Methoxyphenyl)-5-[4-(1-methylethoxy)phenyl]-3-(2,2,6,6-tetramethyltetrahydro-2H-pyran-4-yl)-1H-pyrazole, 2-Chloro-4-[1-(2-methoxyphenyl)-3-(2,2,6,6-tetramethyltetrahydro-2H-pyran-4-yl)-1H-pyrazol-5-yl]pyridine, 1-(2-Methoxyphenyl)-3-(2,2,6,6-tetramethyltetrahydro-2H-pyran-4-yl)-5-thiophen-2-yl-1H-pyrazole, 5-(2,3-Dihydro-1,4-benzodioxin-6-yl)-1-(2-methoxyphenyl)-3-(2,2,6,6-tetramethyltetrahydro-2H-pyran-4-yl)-1H-pyrazole, 1-(2-Methoxyphenyl)-5-(5-methylfuran-2-yl)-3-(2,2,6,6-tetramethyltetrahydro-2H-pyran-4-yl)-1H-pyrazole, 5-(3,4-Dimethoxyphenyl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-N,N-dimethylpyridin-2-amine,
4-[1-(2-Methoxyphenyl)-3-(2,2,6,6-tetramethyltetrahydro-2H-pyran-4-yl)-1H-pyrazol-5-yl]pyridine,
4-[1-(2-Methoxyphenyl)-3-(2,2,6,6-tetramethyltetrahydro-2H-pyran-4-yl)-1H-pyrazol-5-yl]-2-methylpyridine,
3-Methoxy-5-[1-(2-methoxyphenyl)-3-(2,2,6,6-tetramethyltetrahydro-2H-pyran-4-yl)-1H-pyrazol-5-yl]-pyridine,
N-{2-[1-(2-Methoxyphenyl)-3-(2,2,6,6-tetramethyltetrahydro-2H-pyran-4-yl)-1H-pyrazol-5-yl]-phenyl}-acetamide,
5-Cyclopent-1-en-1-yl-1-(2-methoxyphenyl)-3-(2,2,6,6-tetramethyltetrahydro-2H-pyran-4-yl)-1H-pyrazole,
2-[1-(2-Methoxyphenyl)-3-(2,2,6,6-tetramethyltetrahydro-2H-pyran-4-yl)-1H-pyrazol-5-yl]-5-methyl-1,3-thiazole,
2-Methoxy-5-[1-(2-methoxyphenyl)-3-(2,2,6,6-tetramethyltetrahydro-2H-pyran-4-yl)-1H-pyrazol-5-yl]pyrimidine,
5-(1-Benzofuran-2-yl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1H-indole,
5-(3,5-Dimethoxyphenyl)-1-(2-methoxyphenyl)-3-(2,2,6,6-tetramethyltetrahydro-2H-pyran-4-yl)-1H-pyrazole,
1-{4-[1-(2-Methoxyphenyl)-3-(2,2,6,6-tetramethyltetrahydro-2H-pyran-4-yl)-1H-pyrazol-5-yl]-phenyl}-ethanol,
3-[1-(2-Methoxyphenyl)-3-(2,2,6,6-tetramethyltetrahydro-2H-pyran-4-yl)-1H-pyrazol-5-yl]-pyridine,
1-(2-tert-Butoxyphenyl)-5-(4-chlorophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N,N-dimethylaniline,
2-[5-(4-Chlorophenyl)-3-(2,2,6,6-tetramethyltetrahydro-2H-pyran-4-yl)-1H-pyrazol-1-yl]-N-methylaniline,
5-(4-Chlorophenyl)-3-[(trans)-2,6-dimethyltetrahydro-2H-pyran-4-yl]-1-(2-methoxyphenyl)-1H-pyrazole,
5-(4-Chlorophenyl)-3-(2,2-dimethyltetrahydro-2H-pyran-4-yl)-1-(2-methoxyphenyl)-1H-pyrazole,
5-(4-Chlorophenyl)-3-[(2R,4r,6S)-2,6-dimethyltetrahydro-2H-pyran-4-yl]-1-(2-methoxyphenyl)-1H-pyrazole,
5-(4-Chlorophenyl)-1-(2-methoxyphenyl)-3-[(2R,4S)-2-(1-methylethyl)tetrahydro-2H-pyran-4-yl]-1H-pyrazole,
5-(4-Chlorophenyl)-1-(2-nitrophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N-ethylaniline,
3-[(trans)-2,6-Dimethyltetrahydro-2H-pyran-4-yl]-1-(2-methoxyphenyl)-5-phenyl-1H-pyrazole,
2-[5-(4-Chlorophenyl)-3-(2,2,6,6-tetramethyltetrahydro-2H-pyran-4-yl)-1H-pyrazol-1-yl]-aniline,
5-(4-Chlorophenyl)-1-(2-methoxyphenyl)-3-[(trans)-2-(1-methylethyl)tetrahydro-2H-pyran-4-yl]-1H-pyrazole,
4-Bromo-5-(4-chlorophenyl)-1-(2-methoxyphenyl)-3-(2,2,6,6-tetramethyltetrahydro-2H-pyran-4-yl)-1H-pyrazole,
5-(4-Chlorophenyl)-1-(2-methoxyphenyl)-3-(tetrahydro-2H-pyran-4-yl)-1H-pyrazole,
4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine,
2-[5-(4-Chlorophenyl)-3-(2,2,6,6-tetramethyltetrahydro-2H-pyran-4-yl)-1H-pyrazol-1-yl]-N,N-diethylaniline,
1-(2-Chlorophenyl)-5-(4-chlorophenyl)-3-(tetrahydro-2H-pyran-4-yl)-1H-pyrazole,
5-(4-Chlorophenyl)-3-(2,2-dimethyltetrahydro-2H-pyran-4-yl)-1-(4-methoxy-2-methylphenyl)-1H-pyrazole,
5-(4-Chlorophenyl)-1-(2-pyrrolidin-1-ylphenyl)-3-(2,2,6,6-tetramethyltetrahydro-2H-pyran-4-yl)-1H-pyrazole,
5-(4-Chlorophenyl)-1-(2-ethylphenyl)-3-(tetrahydro-2H-pyran-4-yl)-1H-pyrazole,
2-Methoxy-3-[1-(2-methoxyphenyl)-3-(2,2,6,6-tetramethyltetrahydro-2H-pyran-4-yl)-1H-pyrazol-5-yl]pyridine,
5-(4-Chlorophenyl)-1-(2,4-dichlorophenyl)-3-(tetrahydro-2H-pyran-4-yl)-1H-pyrazole,
5-(4-Chlorophenyl)-1-(2-methoxyphenyl)-3-(2,2,6,6-tetramethyl-3,6-dihydro-2H-pyran-4-yl)-1H-pyrazole,
5-(4-Chlorophenyl)-3-[(trans)-2,6-dimethyl-3,6-di hydro-2H-pyran-4-yl]-1-(2-methoxyphenyl)-1H-pyrazole,
5-(4-Chlorophenyl)-1-(2-methoxyphenyl)-3-(2,2,5,5-tetramethyl-2,5-di hydrofuran-3-yl)-1H-pyrazole,
5-(4-Chlorophenyl)-1-(2-methoxyphenyl)-3-(2,2,5,5-tetramethyl-2,5-dihydrofuran-3-yl)-1H-pyrazole, and
5-(4-Chlorophenyl)-1-(2-methoxyphenyl)-3-(2,2,5,5-tetramethyl-tetrahydrofuran-3-yl)-1H-pyrazole.

More particularly, an embodiment of the present invention comprises a compound selected from:
5-(4-Chloro-phenyl)-1-(2-methoxy-phenyl)-3-(2,2,6,6-tetramethyl-tetrahydro-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-benzonitrile,
5-(4-Chloro-2-fluorophenyl)-1-(2-methoxyphenyl)-3-(2,2,6,6-tetramethyltetrahydro-2H-pyran-4-yl)-1H-pyrazole,
5-(1,3-Benzodioxol-5-yl)-1-(2-methoxyphenyl)-3-(2,2,6,6-tetramethyltetrahydro-2H-pyran-4-yl)-1H-pyrazole,
1-(2-Methoxyphenyl)-5-(4-methoxyphenyl)-3-(2,2,6,6-tetramethyltetrahydro-2H-pyran-4-yl)-1H-pyrazole,
1-(2-Methoxyphenyl)-5-[4-(methylsulfanyl)phenyl]-3-(2,2,6,6-tetramethyltetrahydro-2H-pyran-4-yl)-1H-pyrazole,
5-(4-Chlorophenyl)-1-[2-(1-methylethoxy)phenyl]-3-(2,2,6,6-tetramethyltetrahydro-2H-pyran-4-yl)-1H-pyrazole,
5-(4,4-Dimethylcyclohex-1-en-1-yl)-1-(2-methoxyphenyl)-3-(2,2,6,6-tetramethyltetrahydro-2H-pyran-4-yl)-1H-pyrazole,
5-(4-Ethoxyphenyl)-1-(2-methoxyphenyl)-3-(2,2,6,6-tetramethyltetrahydro-2H-pyran-4-yl)-1H-pyrazole,
1-(2-Methoxyphenyl)-5-(4-methylphenyl)-3-(2,2,6,6-tetramethyltetrahydro-2H-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-N,N-dimethylaniline,
1-{4-[1-(2-Methoxyphenyl)-3-(2,2,6,6-tetramethyltetrahydro-2H-pyran-4-yl)-1H-pyrazol-5-yl]phenyl}ethanone,
2-Methoxy-5-[1-(2-methoxyphenyl)-3-(2,2,6,6-tetramethyltetrahydro-2H-pyran-4-yl)-1H-pyrazol-5-yl]pyridine,
5-(5-Chlorothiophen-2-yl)-1-(2-methoxyphenyl)-3-(2,2,6,6-tetramethyltetrahydro-2H-pyran-4-yl)-1H-pyrazole,
5-(4-tert-Butylphenyl)-1-(2-methoxyphenyl)-3-(2,2,6,6-tetramethyltetrahydro-2H-pyran-4-yl)-1H-pyrazole,
1-(2-Methoxyphenyl)-5-phenyl-3-(2,2,6,6-tetramethyltetrahydro-2H-pyran-4-yl)-1H-pyrazole,
Ethyl 4-[1-(2-methoxyphenyl)-3-(2,2,6,6-tetramethyltetrahydro-2H-pyran-4-yl)-1H-pyrazol-5-yl]benzoate,
1-(2-Methoxyphenyl)-5-(4-methylthiophen-2-yl)-3-(2,2,6,6-tetramethyltetrahydro-2H-pyran-4-yl)-1H-pyrazole,
2-Ethoxy-5-[1-(2-methoxyphenyl)-3-(2,2,6,6-tetramethyltetrahydro-2H-pyran-4-yl)-1H-pyrazol-5-yl]-pyridine,
1-(2-Methoxyphenyl)-5-(3-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1-methyl-1H-indole,
2-[1-(2-Methoxyphenyl)-3-(2,2,6,6-tetramethyltetrahydro-2H-pyran-4-yl)-1H-pyrazol-5-yl]-aniline, 5-[1-(2-Methoxyphenyl)-3-(2,2,6,6-tetramethyltetrahydro-2H-pyran-4-yl)-1H-pyrazol-5-yl]-2-methylpyridine,
1-(2-Methoxyphenyl)-5-[4-(1-methylethoxy)phenyl]-3-(2,2,6,6-tetramethyltetrahydro-2H-pyran-4-yl)-1H-pyrazole,
2-Chloro-4-[1-(2-methoxyphenyl)-3-(2,2,6,6-tetramethyltetrahydro-2H-pyran-4-yl)-1H-pyrazol-5-yl]pyridine,
1-(2-Methoxyphenyl)-3-(2,2,6,6-tetramethyltetrahydro-2H-pyran-4-yl)-5-thiophen-2-yl-1H-pyrazole,
5-(2,3-Dihydro-1,4-benzodioxin-6-yl)-1-(2-methoxyphenyl)-3-(2,2,6,6-tetramethyltetrahydro-2H-pyran-4-yl)-1H-pyrazole,
1-(2-Methoxyphenyl)-5-(5-methylfuran-2-yl)-3-(2,2,6,6-tetramethyltetrahydro-2H-pyran-4-yl)-1H-pyrazole,
5-(3,4-Dimethoxyphenyl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-N,N-dimethylpyridin-2-amine,
4-[1-(2-Methoxyphenyl)-3-(2,2,6,6-tetramethyltetrahydro-2H-pyran-4-yl)-1H-pyrazol-5-yl]-2-methylpyridine,
5-Cyclopent-1-en-1-yl-1-(2-methoxyphenyl)-3-(2,2,6,6-tetramethyltetrahydro-2H-pyran-4-yl)-1H-pyrazole,
2-Methoxy-5-[1-(2-methoxyphenyl)-3-(2,2,6,6-tetramethyltetrahydro-2H-pyran-4-yl)-1H-pyrazol-5-yl]pyrimidine,
5-(1-Benzofuran-2-yl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1H-indole,
5-(3,5-Dimethoxyphenyl)-1-(2-methoxyphenyl)-3-(2,2,6,6-tetramethyltetrahydro-2H-pyran-4-yl)-1H-pyrazole,
1-{4-[1-(2-Methoxyphenyl)-3-(2,2,6,6-tetramethyltetrahydro-2H-pyran-4-yl)-1H-pyrazol-5-yl]-phenyl}ethanol,
3-[1-(2-Methoxyphenyl)-3-(2,2,6,6-tetramethyltetrahydro-2H-pyran-4-yl)-1H-pyrazol-5-yl]-pyridine,
2-[5-(4-Chlorophenyl)-3-(2,2,6,6-tetramethyltetrahydro-2H-pyran-4-yl)-1H-pyrazol-1-yl]-N,N-dimethylaniline,
2-[5-(4-Chlorophenyl)-3-(2,2,6,6-tetramethyltetrahydro-2H-pyran-4-yl)-1H-pyrazol-1-yl]-N-methylaniline,
5-(4-Chlorophenyl)-3-[(trans)-2,6-dimethyltetrahydro-2H-pyran-4-yl]-1-(2-methoxyphenyl)-1H-pyrazole,
5-(4-Chlorophenyl)-3-(2,2-dimethyltetrahydro-2H-pyran-4-yl)-1-(2-methoxyphenyl)-1H-pyrazole,
5-(4-Chlorophenyl)-3-[(2R,4r,6S)-2,6-dimethyltetrahydro-2H-pyran-4-yl]-1-(2-methoxyphenyl)-1H-pyrazole,
5-(4-Chlorophenyl)-1-(2-methoxyphenyl)-3-[(2R,4S)-2-(1-methylethyl)tetrahydro-2H-pyran-4-yl]-1H-pyrazole,
5-(4-Chlorophenyl)-1-(2-nitrophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N-ethylaniline,
3-[(trans)-2,6-Dimethyltetrahydro-2H-pyran-4-yl]-1-(2-methoxyphenyl)-5-phenyl-1H-pyrazole,
2-[5-(4-Chlorophenyl)-3-(2,2,6,6-tetramethyltetrahydro-2H-pyran-4-yl)-1H-pyrazol-1-yl]-aniline,
5-(4-Chlorophenyl)-1-(2-methoxyphenyl)-3-[(trans)-2-(1-methylethyl)tetrahydro-2H-pyran-4-yl]-1H-pyrazole,
4-Bromo-5-(4-chlorophenyl)-1-(2-methoxyphenyl)-3-(2,2,6,6-tetramethyltetrahydro-2H-pyran-4-yl)-1H-pyrazole,
5-(4-Chlorophenyl)-1-(2-methoxyphenyl)-3-(tetrahydro-2H-pyran-4-yl)-1H-pyrazole,
4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine,
2-[5-(4-Chlorophenyl)-3-(2,2,6,6-tetramethyltetrahydro-2H-pyran-4-yl)-1H-pyrazol-1-yl]-N,N-diethylaniline,
1-(2-Chlorophenyl)-5-(4-chlorophenyl)-3-(tetrahydro-2H-pyran-4-yl)-1H-pyrazole,
5-(4-Chlorophenyl)-3-(2,2-dimethyltetrahydro-2H-pyran-4-yl)-1-(4-methoxy-2-methylphenyl)-1H-pyrazole,
5-(4-Chlorophenyl)-1-(2-methoxyphenyl)-3-(2,2,6,6-tetramethyl-3,6-dihydro-2H-pyran-4-yl)-1H-pyrazole,
5-(4-Chlorophenyl)-3-[(trans)-2,6-dimethyl-3,6-dihydro-2H-pyran-4-yl]-1-(2-methoxyphenyl)-1H-pyrazole,
5-(4-Chlorophenyl)-1-(2-methoxyphenyl)-3-(2,2,5,5-tetramethyl-2,5-di hydrofuran-3-yl)-1H-pyrazole,
5-(4-Chlorophenyl)-1-(2-methoxyphenyl)-3-(2,2,5,5-tetramethyl-2,5-dihydrofuran-3-yl)-1H-pyrazole, and
5-(4-Chlorophenyl)-1-(2-methoxyphenyl)-3-(2,2,5,5-tetramethyl-tetrahydrofuran-3-yl)-1H-pyrazole.

Most particularly, an embodiment of the present invention comprises a compound selected from:
5-(4-Chloro-phenyl)-1-(2-methoxy-phenyl)-3-(2,2,6,6-tetramethyl-tetrahydro-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-benzonitrile,
1-(2-Methoxyphenyl)-5-(4-methoxyphenyl)-3-(2,2,6,6-tetramethyltetrahydro-2H-pyran-4-yl)-1H-pyrazole,
5-(4-Ethoxyphenyl)-1-(2-methoxyphenyl)-3-(2,2,6,6-tetramethyltetrahydro-2H-pyran-4-yl)-1H-pyrazole,
2-Methoxy-5-[1-(2-methoxyphenyl)-3-(2,2,6,6-tetramethyltetrahydro-2H-pyran-4-yl)-1H-pyrazol-5-yl]pyridine,
5-(5-Chlorothiophen-2-yl)-1-(2-methoxyphenyl)-3-(2,2,6,6-tetramethyltetrahydro-2H-pyran-4-yl)-1H-pyrazole,
2-Ethoxy-5-[1-(2-methoxyphenyl)-3-(2,2,6,6-tetramethyltetrahydro-2H-pyran-4-yl)-1H-pyrazol-5-yl]-pyridine,
5-(4-Chlorophenyl)-1-(2-methoxyphenyl)-3-(2,2,6,6-tetramethyl-1,1-dioxidotetrahydro-2H-thiopyran-4-yl)-1H-pyrazole, and
5-(4-Chlorophenyl)-1-(2-methoxyphenyl)-3-(2,2,5,5-tetramethyl-tetrahydrofuran-3-yl)-1H-pyrazole.

A pharmaceutical composition of the present invention comprises at least a compound selected from:
5-(4-Chloro-phenyl)-1-(2-methoxy-phenyl)-3-(2,2,6,6-tetramethyl-tetrahydro-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-benzonitrile,
5-(4-Chloro-2-fluorophenyl)-1-(2-methoxyphenyl)-3-(2,2,6,6-tetramethyltetrahydro-2H-pyran-4-yl)-1H-pyrazole,
5-(1,3-Benzodioxol-5-yl)-1-(2-methoxyphenyl)-3-(2,2,6,6-tetramethyltetrahydro-2H-pyran-4-yl)-1H-pyrazole,
1-(2-Methoxyphenyl)-5-(4-methoxyphenyl)-3-(2,2,6,6-tetramethyltetrahydro-2H-pyran-4-yl)-1H-pyrazole,
1-(2-Methoxyphenyl)-5-[4-(methylsulfanyl)phenyl]-3-(2,2,6,6-tetramethyltetrahydro-2H-pyran-4-yl)-1H-pyrazole,
5-(4-Chlorophenyl)-1-[2-(1-methylethoxy)phenyl]-3-(2,2,6,6-tetramethyltetrahydro-2H-pyran-4-yl)-1H-pyrazole,
5-(4,4-Dimethylcyclohex-1-en-1-yl)-1-(2-methoxyphenyl)-3-(2,2,6,6-tetramethyltetrahydro-2H-pyran-4-yl)-1H-pyrazole,
5-(4-Ethoxyphenyl)-1-(2-methoxyphenyl)-3-(2,2,6,6-tetramethyltetrahydro-2H-pyran-4-yl)-1H-pyrazole,
1-(2-Methoxyphenyl)-5-(4-methylphenyl)-3-(2,2,6,6-tetramethyltetrahydro-2H-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-N,N-dimethylaniline,
1-{4-[1-(2-Methoxyphenyl)-3-(2,2,6,6-tetramethyltetrahydro-2H-pyran-4-yl)-1H-pyrazol-5-yl]phenyl}ethanone,
2-Methoxy-5-[1-(2-methoxyphenyl)-3-(2,2,6,6-tetramethyltetrahydro-2H-pyran-4-yl)-1H-pyrazol-5-yl]pyridine,
5-(5-Chlorothiophen-2-yl)-1-(2-methoxyphenyl)-3-(2,2,6,6-tetramethyltetrahydro-2H-pyran-4-yl)-1H-pyrazole, 5-(4-tert-Butylphenyl)-1-(2-methoxyphenyl)-3-(2,2,6,6-tetramethyltetrahydro-2H-pyran-4-yl)-1H-pyrazole, 1-(2-Methoxyphenyl)-5-phenyl-3-(2,2,6,6-tetramethyltetrahydro-2H-pyran-4-yl)-1H-pyrazole, Ethyl 4-[1-(2-methoxyphenyl)-3-(2,2,6,6-tetramethyltetrahydro-2H-pyran-4-yl)-1H-pyrazol-5-yl]benzoate, 1-(2-Methoxyphenyl)-5-(4-methylthiophen-2-yl)-3-(2,2,6,6-tetramethyltetrahydro-2H-pyran-4-yl)-1H-pyrazole, 2-Ethoxy-5-[1-(2-methoxyphenyl)-3-(2,2,6,6-tetramethyltetrahydro-2H-pyran-4-yl)-1H-pyrazol-5-yl]-pyridine, 1-(2-Methoxyphenyl)-5-(3-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1-methyl-1H-indole, 2-[1-(2-Methoxyphenyl)-3-(2,2,6,6-tetramethyltetrahydro-2H-pyran-4-yl)-1H-pyrazol-5-yl]-aniline, 5-[1-(2-Methoxyphenyl)-3-(2,2,6,6-tetramethyltetrahydro-2H-pyran-4-yl)-1H-pyrazol-5-yl]-2-methylpyridine, 1-(2-Methoxyphenyl)-5-[4-(1-methylethoxy)phenyl]-3-(2,2,6,6-tetramethyltetrahydro-2H-pyran-4-yl)-1H-pyrazole, 2-Chloro-4-[1-(2-methoxyphenyl)-3-(2,2,6,6-tetramethyltetrahydro-2H-pyran-4-yl)-1H-pyrazol-5-yl]pyridine, 1-(2-Methoxyphenyl)-3-(2,2,6,6-tetramethyltetrahydro-2H-pyran-4-yl)-5-thiophen-2-yl-1H-pyrazole, 5-(2,3-Dihydro-1,4-benzodioxin-6-yl)-1-(2-methoxyphenyl)-3-(2,2,6,6-tetramethyltetrahydro-2H-pyran-4-yl)-1H-pyrazole, 1-(2-Methoxyphenyl)-5-(5-methylfuran-2-yl)-3-(2,2,6,6-tetramethyltetrahydro-2H-pyran-4-yl)-1H-pyrazole, 5-(3,4-Dimethoxyphenyl)-1-(2-methoxyphenyl)-3-(2,2,6,6-tetramethyltetrahydro-2H-pyran-4-yl)-1H-pyrazole, N-{5-[1-(2-Methoxyphenyl)-3-(2,2,6,6-tetramethyltetrahydro-2H-pyran-4-yl)-1H-pyrazol-5-yl]pyridin-2-yl}acetamide, 5-[1-(2-Methoxyphenyl)-3-(2,2,6,6-tetramethyltetrahydro-2H-pyran-4-yl)-1H-pyrazol-5-yl]-N,N-dimethylpyridin-2-amine, 4-[1-(2-Methoxyphenyl)-3-(2,2,6,6-tetramethyltetrahydro-2H-pyran-4-yl)-1H-pyrazol-5-yl]pyridine, 4-[1-(2-Methoxyphenyl)-3-(2,2,6,6-tetramethyltetrahydro-2H-pyran-4-yl)-1H-pyrazol-5-yl]-2-methylpyridine, 3-Methoxy-5-[1-(2-methoxyphenyl)-3-(2,2,6,6-tetramethyltetrahydro-2H-pyran-4-yl)-1H-pyrazol-5-yl]-pyridine, 2-Methoxy-3-[1-(2-methoxyphenyl)-3-(2,2,6,6-tetramethyltetrahydro-2H-pyran-4-yl)-1H-pyrazol-5-yl]-pyridine, N-{2-[1-(2-Methoxyphenyl)-3-(2,2,6,6-tetramethyltetrahydro-2H-pyran-4-yl)-1H-pyrazol-5-yl]-phenyl}-acetamide, 5-Cyclopent-1-en-1-yl-1-(2-methoxyphenyl)-3-(2,2,6,6-tetramethyltetrahydro-2H-pyran-4-yl)-1H-pyrazole, 2-[1-(2-Methoxyphenyl)-3-(2,2,6,6-tetramethyltetrahydro-2H-pyran-4-yl)-1H-pyrazol-5-yl]-5-methyl-1,3-thiazole, 2-Methoxy-5-[1-(2-methoxyphenyl)-3-(2,2,6,6-tetramethyltetrahydro-2H-pyran-4-yl)-1H-pyrazol-5-yl]pyrimidine, N,N-Diethyl-4-[1-(2-methoxyphenyl)-3-(2,2,6,6-tetramethyltetrahydro-2H-pyran-4-yl)-1H-pyrazol-5-yl]-benzamide, 5-(1-Benzofuran-2-yl)-1-(2-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1H-indole, 5-(3,5-Dimethoxyphenyl)-1-(2-methoxyphenyl)-3-(2,2,6,6-tetramethyltetrahydro-2H-pyran-4-yl)-1H-pyrazole, 1-{4-[1-(2-Methoxyphenyl)-3-(2,2,6,6-tetramethyltetrahydro-2H-pyran-4-yl)-1H-pyrazol-5-yl]-phenyl}ethanol, 3-[1-(2-Methoxyphenyl)-3-(2,2,6,6-tetramethyltetrahydro-2H-pyran-4-yl)-1H-pyrazol-5-yl]-pyridine, 4-[1-(2-Methoxyphenyl)-3-(2,2,6,6-tetramethyltetrahydro-2H-pyran-4-yl)-1H-pyrazol-5-yl]-benzoic acid, 5-(4-Methanesulfinyl-phenyl)-1-(2-methoxy-phenyl)-3-(2,2,6,6-tetramethyl-tetrahydro-pyran-4-yl)-1H-pyrazole, 1-(2-tert-Butoxyphenyl)-5-(4-chlorophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N,N-dimethylaniline, 2-[5-(4-Chloro-phenyl)-3-(2,2,6,6-tetramethyl-tetrahydro-pyran-4-yl)-pyrazol-1-yl]-pyridine, 4-[5-(4-Chlorophenyl)-3-(2,2,6,6-tetramethyltetrahydro-2H-pyran-4-yl)-1H-pyrazol-1-yl]-pyridine, 3-[5-(4-Chlorophenyl)-3-(2,2,6,6-tetramethyltetrahydro-2H-pyran-4-yl)-1H-pyrazol-1-yl]-pyridine, 4-[1-Pyrazin-2-yl-3-(2,2,6,6-tetramethyltetrahydro-2H-pyran-4-yl)-1H-pyrazol-5-yl]-benzonitrile, 4-[1-Pyridin-3-yl-3-(2,2,6,6-tetramethyltetrahydro-2H-pyran-4-yl)-1H-pyrazol-5-yl]-benzonitrile, 4-[1-Pyridin-2-yl-3-(2,2,6,6-tetramethyltetrahydro-2H-pyran-4-yl)-1H-pyrazol-5-yl]-benzonitrile, 4-[1-Pyridin-4-yl-3-(2,2,6,6-tetramethyltetrahydro-2H-pyran-4-yl)-1H-pyrazol-5-yl]-benzonitrile, 4-[1-Quinolin-8-yl-3-(2,2,6,6-tetramethyltetrahydro-2H-pyran-4-yl)-1H-pyrazol-5-yl]-benzonitrile, 5-(4-Chloro-phenyl)-1-(2-methoxy-phenyl)-3-(2,2,6,6-tetramethyl-tetrahydro-thiopyran-4-yl)-1H-pyrazole, 5-(4-Chlorophenyl)-1-(2-methoxyphenyl)-3-(2,2,6,6-tetramethyl-1,1-dioxidotetrahydro-2H-thiopyran-4-yl)-1H-pyrazole, 2-[5-(4-Chlorophenyl)-3-(2,2,6,6-tetramethyltetrahydro-2H-pyran-4-yl)-1H-pyrazol-1-yl]-N-methylaniline, 5-(4-Chlorophenyl)-3-[(trans)-2,6-dimethyltetrahydro-2H-pyran-4-yl]-1-(2-methoxyphenyl)-1H-pyrazole, 5-(4-Chlorophenyl)-3-(2,2-dimethyltetrahydro-2H-pyran-4-yl)-1-(2-methoxyphenyl)-1H-pyrazole, 5-(4-Chlorophenyl)-3-[(2R,4r,6S)-2,6-di methyltetrahydro-2H-pyran-4-yl]-1-(2-methoxyphenyl)-1H-pyrazole, 5-(4-Chlorophenyl)-1-(2-methoxyphenyl)-3-[(2R,4S)-2-(1-methylethyl)tetrahydro-2H-pyran-4-yl]-1H-pyrazole, 5-(4-Chlorophenyl)-1-(2-nitrophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N-ethylaniline, 3-[(trans)-2,6-Dimethyltetrahydro-2H-pyran-4-yl]-1-(2-methoxyphenyl)-5-phenyl-1H-pyrazole, 2-[5-(4-Chlorophenyl)-3-(2,2,6,6-tetramethyltetrahydro-2H-pyran-4-yl)-1H-pyrazol-1-yl]-aniline, 5-(4-Chlorophenyl)-1-(2-methoxyphenyl)-3-[(trans)-2-(1-methylethyl)tetrahydro-2H-pyran-4-yl]-1H-pyrazole, 4-Bromo-5-(4-chlorophenyl)-1-(2-methoxyphenyl)-3-(2,2,6,6-tetramethyltetrahydro-2H-pyran-4-yl)-1H-pyrazole, 5-(4-Chlorophenyl)-1-(2-methoxyphenyl)-3-(tetrahydro-2H-pyran-4-yl)-1H-pyrazole, 4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine, 2-[5-(4-Chlorophenyl)-3-(2,2,6,6-tetramethyltetrahydro-2H-pyran-4-yl)-1H-pyrazol-1-yl]-N,N-diethylaniline, 1-(2-Chlorophenyl)-5-(4-chlorophenyl)-3-(tetrahydro-2H-pyran-4-yl)-1H-pyrazole, 5-(4-Chlorophenyl)-3-(2,2-dimethyltetrahydro-2H-pyran-4-yl)-1-(4-methoxy-2-methylphenyl)-1H-pyrazole, 5-(4-Chlorophenyl)-1-(2-pyrrolidin-1-ylphenyl)-3-(2,2,6,6-tetramethyltetrahydro-2H-pyran-4-yl)-1H-pyrazole, 5-(4-Chlorophenyl)-1-(2-ethylphenyl)-3-(tetrahydro-2H-pyran-4-yl)-1H-pyrazole, 5-(4-Chlorophenyl)-1-(2,4-dichlorophenyl)-3-(tetrahydro-2H-pyran-4-yl)-1H-pyrazole, 5-(4-Chlorophenyl)-3-(tetrahydro-2H-pyran-4-yl)-1-[2-(trifluoromethoxy)phenyl]-1H-pyrazole, 5-(4-Chlorophenyl)-1-(2,6-dichlorophenyl)-3-(tetrahydro-2H-pyran-4-yl)-1H-pyrazole, 5-{4-[2-(1H-Imidazol-1-yl)ethoxy]phenyl}-1-(2-methoxyphenyl)-3-(2,2,6,6-tetramethyltetrahydro-2H-pyran-4-yl)-1H-pyrazole, 2-{4-[1-(2-Methoxyphenyl)-3-(2,2,6,6-tetramethyltetrahydro-2H-pyran-4-yl)-1H-pyrazol-5-yl]phenoxy}-N,N-dimethylethanamine, 1-(2-Methoxyphenyl)-5-[4-(methylsulfonyl)phenyl]-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-phenol, 5-[1-(2-Methoxyphenyl)-3-(2,2,6,6-tetramethyltetrahydro-2H-pyran-4-yl)-1H-pyrazol-5-yl]-pyridin-2-amine, 4-({4-[1-(2-Methoxyphenyl)-3-(2,2,6,6-tetramethyltetrahydro-2H-pyran-4-yl)-1H-pyrazol-5-yl]phenyl}carbonyl)morpholine, N-[2-(Dimethylamino)ethyl]-4-[1-(2-methoxyphenyl)-3-(2,2,6,6-tetramethyltetrahydro-2H-pyran-4-yl)-1H-pyrazol-5-yl]benzamide, 4-[1-(2-Methoxyphenyl)-3-(2,2,6,6-tetramethyltetrahydro-2H-pyran-4-yl)-1H-pyrazol-5-yl]benzamide, 1-({4-[1-(2-Methoxyphenyl)-3-(2,2,6,6-tetramethyltetrahydro-2H-pyran-4-yl)-1H-pyrazol-5-yl]phenyl}carbonyl)-4-methyl piperazine, N-(2-Hydroxyethyl)-4-[1-(2-methoxyphenyl)-3-(2,2,6,6-tetramethyltetrahydro-2H-pyran-4-yl)-1H-pyrazol-5-yl]-benzamide, 3-[1-(2-Methoxyphenyl)-3-(2,2,6,6-tetramethyltetrahydro-2H-pyran-4-yl)-1H-pyrazol-5-yl]-pyridine-1-oxide, 5-(4-Chlorophenyl)-1-[2,4-dichloro-6-(trifluoromethyl)phenyl]-3-(tetrahydro-2H-pyran-4-yl)-1H-pyrazole, 5-(4-Chlorophenyl)-1-[2,6-dichloro-4-(trifluoromethyl)phenyl]-3-(tetrahydro-2H-pyran-4-yl)-1H-pyrazole, 2-[5-(4-Chlorophenyl)-3-(tetrahydro-2H-pyran-4-yl)-1H-pyrazol-1-yl]-benzonitrile, 5-(4-Chlorophenyl)-1-(2-methoxyphenyl)-3-(2,2,6,6-tetramethyl-3,6-dihydro-2H-pyran-4-yl)-1H-pyrazole, 5-(4-Chlorophenyl)-3-[(trans)-2,6-dimethyl-3,6-di hydro-2H-pyran-4-yl]-1-(2-methoxyphenyl)-1H-pyrazole, 5-(4-Chlorophenyl)-1-(2-methoxyphenyl)-3-(2,2,5,5-tetramethyl-2,5-di hydrofuran-3-yl)-1H-pyrazole, 5-(4-Chlorophenyl)-1-(2-methoxyphenyl)-3-(2,2,5,5-tetramethyl-2,5-dihydrofuran-3-yl)-1H-pyrazole, and 5-(4-Chlorophenyl)-1-(2-methoxyphenyl)-3-(2,2,5,5-tetramethyl-tetrahydrofuran-3-yl)-1H-pyrazole.

Particularly, a pharmaceutical composition of the present invention comprises at least a compound selected from:

5-(4-Chloro-phenyl)-1-(2-methoxy-phenyl)-3-(2,2,6,6-tetramethyl-tetrahydro-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-benzonitrile, 5-(4-Chloro-2-fluorophenyl)-1-(2-methoxyphenyl)-3-(2,2,6,6-tetramethyltetrahydro-2H-pyran-4-yl)-1H-pyrazole, 5-(1,3-Benzodioxol-5-yl)-1-(2-methoxyphenyl)-3-(2,2,6,6-tetramethyltetrahydro-2H-pyran-4-yl)-1H-pyrazole, 1-(2-Methoxyphenyl)-5-(4-methoxyphenyl)-3-(2,2,6,6-tetramethyltetrahydro-2H-pyran-4-yl)-1H-pyrazole, 1-(2-Methoxyphenyl)-5-[4-(methylsulfanyl)phenyl]-3-(2,2,6,6-tetramethyltetrahydro-2H-pyran-4-yl)-1H-pyrazole, 5-(4-Chlorophenyl)-1-[2-(1-methylethoxy)phenyl]-3-(2,2,6,6-tetramethyltetrahydro-2H-pyran-4-yl)-1H-pyrazole, 5-(4,4-Dimethylcyclohex-1-en-1-yl)-1-(2-methoxyphenyl)-3-(2,2,6,6-tetramethyltetrahydro-2H-pyran-4-yl)-1H-pyrazole, 5-(4-Ethoxyphenyl)-1-(2-methoxyphenyl)-3-(2,2,6,6-tetramethyltetrahydro-2H-pyran-4-yl)-1H-pyrazole, 1-(2-Methoxyphenyl)-5-(4-methylphenyl)-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-N,N-dimethylaniline, 1-{4-[1-(2-Methoxyphenyl)-3-(2,2,6,6-tetramethyltetrahydro-2H-pyran-4-yl)-1H-pyrazol-5-yl]phenyl}ethanone, 2-Methoxy-5-[1-(2-methoxyphenyl)-3-(2,2,6,6-tetramethyltetrahydro-2H-pyran-4-yl)-1H-pyrazol-5-yl]pyridine, 5-(5-Chlorothiophen-2-yl)-1-(2-methoxyphenyl)-3-(2,2,6,6-tetramethyltetrahydro-2H-pyran-4-yl)-1H-pyrazole, 5-(4-tert-Butylphenyl)-1-(2-methoxyphenyl)-3-(2,2,6,6-tetramethyltetrahydro-2H-pyran-4-yl)-1H-pyrazole, 1-(2-Methoxyphenyl)-5-phenyl-3-(2,2,6,6-tetramethyltetrahydro-2H-pyran-4-yl)-1H-pyrazole, Ethyl 4-[1-(2-methoxyphenyl)-3-(2,2,6,6-tetramethyltetrahydro-2H-pyran-4-yl)-1H-pyrazol-5-yl]benzoate, 1-(2-Methoxyphenyl)-5-(4-methylthiophen-2-yl)-3-(2,2,6,6-tetramethyltetrahydro-2H-pyran-4-yl)-1H-pyrazole, 2-Ethoxy-5-[1-(2-methoxyphenyl)-3-(2,2,6,6-tetramethyltetrahydro-2H-pyran-4-yl)-1H-pyrazol-5-yl]-pyridine, 1-(2-Methoxyphenyl)-5-(3-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1-methyl-1H-indole, 2-[1-(2-Methoxyphenyl)-3-(2,2,6,6-tetramethyltetrahydro-2H-pyran-4-yl)-1H-pyrazol-5-yl]-aniline, 5-[1-(2-Methoxyphenyl)-3-(2,2,6,6-tetramethyltetrahydro-2H-pyran-4-yl)-1H-pyrazol-5-yl]-2-methylpyridine, 1-(2-Methoxyphenyl)-5-[4-(1-methylethoxy)phenyl]-3-(2,2,6,6-tetramethyltetrahydro-2H-pyran-4-yl)-1H-pyrazole, 2-Chloro-4-[1-(2-methoxyphenyl)-3-(2,2,6,6-tetramethyltetrahydro-2H-pyran-4-yl)-1H-pyrazol-5-yl]pyridine, 1-(2-Methoxyphenyl)-3-(2,2,6,6-tetramethyltetrahydro-2H-pyran-4-yl)-5-thiophen-2-yl-1H-pyrazole, 5-(2,3-Dihydro-1,4-benzodioxin-6-yl)-1-(2-methoxyphenyl)-3-(2,2,6,6-tetramethyltetrahydro-2H-pyran-4-yl)-1H-pyrazole, 1-(2-Methoxyphenyl)-5-(5-methylfuran-2-yl)-3-(2,2,6,6-tetramethyltetrahydro-2H-pyran-4-yl)-1H-pyrazole, 5-(3,4-Dimethoxyphenyl)-1-(2-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-N,N-dimethylpyridin-2-amine, 4-[1-(2-Methoxyphenyl)-3-(2,2,6,6-tetramethyltetrahydro-2H-pyran-4-yl)-1H-pyrazol-5-yl]pyridine, 4-[1-(2-Methoxyphenyl)-3-(2,2,6,6-tetramethyltetrahydro-2H-pyran-4-yl)-1H-pyrazol-5-yl]-2-methylpyridine, 3-Methoxy-5-[1-(2-methoxyphenyl)-3-(2,2,6,6-tetramethyltetrahydro-2H-pyran-4-yl)-1H-pyrazol-5-yl]-pyridine, N-{2-[1-(2-Methoxyphenyl)-3-(2,2,6,6-tetramethyltetrahydro-2H-pyran-4-yl)-1H-pyrazol-5-yl]-phenyl}-acetamide, 5-Cyclopent-1-en-1-yl-1-(2-methoxyphenyl)-3-(2,2,6,6-tetramethyltetrahydro-2H-pyran-4-yl)-1H-pyrazole, 2-[1-(2-Methoxyphenyl)-3-(2,2,6,6-tetramethyltetrahydro-2H-pyran-4-yl)-1H-pyrazol-5-yl]-5-methyl-1,3-thiazole, 2-Methoxy-5-[1-(2-methoxyphenyl)-3-(2,2,6,6-tetramethyltetrahydro-2H-pyran-4-yl)-1H-pyrazol-5-yl]pyrimidine, 5-(1-Benzofuran-2-yl)-1-(2-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1H-indole, 5-(3,5-Dimethoxyphenyl)-1-(2-methoxyphenyl)-3-(2,2,6,6-tetramethyltetrahydro-2H-pyran-4-yl)-1H-pyrazole, 1-{4-[1-(2-Methoxyphenyl)-3-(2,2,6,6-tetramethyltetrahydro-2H-pyran-4-yl)-1H-pyrazol-5-yl]-phenyl}ethanol, 3-[1-(2-Methoxyphenyl)-3-(2,2,6,6-tetramethyltetrahydro-2H-pyran-4-yl)-1H-pyrazol-5-yl]-pyridine, 1-(2-tert-Butoxyphenyl)-5-(4-chlorophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N,N-dimethylaniline, 2-[5-(4-Chlorophenyl)-3-(2,2,6,6-tetramethyltetrahydro-2H-pyran-4-yl)-1H-pyrazol-1-yl]-N-methylaniline, 5-(4-Chlorophenyl)-3-[(trans)-2,6-dimethyltetrahydro-2H-pyran-4-yl]-1-(2-methoxyphenyl)-1H-pyrazole, 5-(4-Chlorophenyl)-3-(2,2-dimethyltetrahydro-2H-pyran-4-yl)-1-(2-methoxyphenyl)-1H-pyrazole, 5-(4-Chlorophenyl)-3-[(2R,4r,6S)-2,6-di methyltetrahydro-2H-pyran-4-yl]-1-(2-methoxyphenyl)-1H-pyrazole, 5-(4-Chlorophenyl)-1-(2-methoxyphenyl)-3-[(2R,4S)-2-(1-methylethyl)tetrahydro-2H-pyran-4-yl]-1H-pyrazole, 5-(4-Chlorophenyl)-1-(2-nitrophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N-ethylaniline, 3-[(trans)-2,6-Dimethyltetrahydro-2H-pyran-4-yl]-1-(2-methoxyphenyl)-5-phenyl-1H-pyrazole, 2-[5-(4-Chlorophenyl)-3-(2,2,6,6-tetramethyltetrahydro-2H-pyran-4-yl)-1H-pyrazol-1-yl]-aniline, 5-(4-Chlorophenyl)-1-(2-methoxyphenyl)-3-[(trans)-2-(1-methylethyl)tetrahydro-2H-pyran-4-yl]-1H-pyrazole, 4-Bromo-5-(4-chlorophenyl)-1-(2-methoxyphenyl)-3-(2,2,6,6-tetramethyltetrahydro-2H-pyran-4-yl)-1H-pyrazole, 5-(4-Chlorophenyl)-1-(2-methoxyphenyl)-3-(tetrahydro-2H-pyran-4-yl)-1H-pyrazole, 4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine, 2-[5-(4-Chlorophenyl)-3-(2,2,6,6-tetramethyltetrahydro-2H-pyran-4-yl)-1H-pyrazol-1-yl]-N,N-diethylaniline, 1-(2-Chlorophenyl)-5-(4-chlorophenyl)-3-(tetrahydro-2H-pyran-4-yl)-1H-pyrazole, 5-(4-Chlorophenyl)-3-(2,2-dimethyltetrahydro-2H-pyran-4-yl)-1-(4-methoxy-2-methylphenyl)-1H-pyrazole, 5-(4-Chlorophenyl)-1-(2-pyrrolidin-1-ylphenyl)-3-(2,2,6,6-tetramethyltetrahydro-2H-pyran-4-yl)-1H-pyrazole, 5-(4-Chlorophenyl)-1-(2-ethylphenyl)-3-(tetrahydro-2H-pyran-4-yl)-1H-pyrazole, 2-Methoxy-3-[1-(2-methoxyphenyl)-3-(2,2,6,6-tetramethyltetrahydro-2H-pyran-4-yl)-1H-pyrazol-5-yl]pyridine, 5-(4-Chlorophenyl)-1-(2,4-dichlorophenyl)-3-(tetrahydro-2H-pyran-4-yl)-1H-pyrazole, 5-(4-Chlorophenyl)-1-(2-methoxyphenyl)-3-(2,2,6,6-tetramethyl-3,6-dihydro-2H-pyran-4-yl)-1H-pyrazole, 5-(4-Chlorophenyl)-3-[(trans)-2,6-dimethyl-3,6-dihydro-2H-pyran-4-yl]-1-(2-methoxyphenyl)-1H-pyrazole, 5-(4-Chlorophenyl)-1-(2-methoxyphenyl)-3-(2,2,5,5-tetramethyl-2,5-di hydrofuran-3-yl)-1H-pyrazole, 5-(4-Chlorophenyl)-1-(2-methoxyphenyl)-3-(2,2,5,5-tetramethyl-2,5-dihydrofuran-3-yl)-1H-pyrazole, and 5-(4-Chlorophenyl)-1-(2-methoxyphenyl)-3-(2,2,5,5-tetramethyl-tetrahydrofuran-3-yl)-1H-pyrazole.

More particularly, a pharmaceutical composition of the present invention comprises at least a compound selected from:

5-(4-Chloro-phenyl)-1-(2-methoxy-phenyl)-3-(2,2,6,6-tetramethyl-tetrahydro-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-benzonitrile, 5-(4-Chloro-2-fluorophenyl)-1-(2-methoxyphenyl)-3-(2,2,6,6-tetramethyltetrahydro-2H-pyran-4-yl)-1H-pyrazole, 5-(1,3-Benzodioxol-5-yl)-1-(2-methoxyphenyl)-3-(2,2,6,6-tetramethyltetrahydro-2H-pyran-4-yl)-1H-pyrazole, 1-(2-Methoxyphenyl)-5-(4-methoxyphenyl)-3-(2,2,6,6-tetramethyltetrahydro-2H-pyran-4-yl)-1H-pyrazole, 1-(2-Methoxyphenyl)-5-[4-(methylsulfanyl)phenyl]-3-(2,2,6,6-tetramethyltetrahydro-2H-pyran-4-yl)-1H-pyrazole, 5-(4-Chlorophenyl)-1-[2-(1-methylethoxy)phenyl]-3-(2,2,6,6-tetramethyltetrahydro-2H-pyran-4-yl)-1H-pyrazole, 5-(4,4-Dimethylcyclohex-1-en-1-yl)-1-(2-methoxyphenyl)-3-(2,2,6,6-tetramethyltetrahydro-2H-pyran-4-yl)-1H-pyrazole, 5-(4-Ethoxyphenyl)-1-(2-methoxyphenyl)-3-(2,2,6,6-tetramethyltetrahydro-2H-pyran-4-yl)-1H-pyrazole, 1-(2-Methoxyphenyl)-5-(4-methylphenyl)-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-N,N-dimethylaniline, 1-{4-[1-(2-Methoxyphenyl)-3-(2,2,6,6-tetramethyltetrahydro-2H-pyran-4-yl)-1H-pyrazol-5-yl]phenyl}ethanone, 2-Methoxy-5-[1-(2-methoxyphenyl)-3-(2,2,6,6-tetramethyltetrahydro-2H-pyran-4-yl)-1H-pyrazol-5-yl]pyridine, 5-(5-Chlorothiophen-2-yl)-1-(2-methoxyphenyl)-3-(2,2,6,6-tetramethyltetrahydro-2H-pyran-4-yl)-1H-pyrazole, 5-(4-tert-Butylphenyl)-1-(2-methoxyphenyl)-3-(2,2,6,6-tetramethyltetrahydro-2H-pyran-4-yl)-1H-pyrazole, 1-(2-Methoxyphenyl)-5-phenyl-3-(2,2,6,6-tetramethyltetrahydro-2H-pyran-4-yl)-1H-pyrazole, Ethyl 4-[1-(2-methoxyphenyl)-3-(2,2,6,6-tetramethyltetrahydro-2H-pyran-4-yl)-1H-pyrazol-5-yl]benzoate, 1-(2-Methoxyphenyl)-5-(4-methylthiophen-2-yl)-3-(2,2,6,6-tetramethyltetrahydro-2H-pyran-4-yl)-1H-pyrazole, 2-Ethoxy-5-[1-(2-methoxyphenyl)-3-(2,2,6,6-tetramethyltetrahydro-2H-pyran-4-yl)-1H-pyrazol-5-yl]-pyridine, 1-(2-Methoxyphenyl)-5-(3-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1-methyl-1H-indole, 2-[1-(2-Methoxyphenyl)-3-(2,2,6,6-tetramethyltetrahydro-2H-pyran-4-yl)-1H-pyrazol-5-yl]-aniline, 5-[1-(2-Methoxyphenyl)-3-(2,2,6,6-tetramethyltetrahydro-2H-pyran-4-yl)-1H-pyrazol-5-yl]-2-methylpyridine, 1-(2-Methoxyphenyl)-5-[4-(1-methylethoxy)phenyl]-3-(2,2,6,6-tetramethyltetrahydro-2H-pyran-4-yl)-1H-pyrazole, 2-Chloro-4-[1-(2-methoxyphenyl)-3-(2,2,6,6-tetramethyltetrahydro-2H-pyran-4-yl)-1H-pyrazol-5-yl]pyridine, 1-(2-Methoxyphenyl)-3-(2,2,6,6-tetramethyltetrahydro-2H-pyran-4-yl)-5-thiophen-2-yl-1H-pyrazole, 5-(2,3-Dihydro-1,4-benzodioxin-6-yl)-1-(2-methoxyphenyl)-3-(2,2,6,6-tetramethyltetrahydro-2H-pyran-4-yl)-1H-pyrazole, 1-(2-Methoxyphenyl)-5-(5-methylfuran-2-yl)-3-(2,2,6,6-tetramethyltetrahydro-2H-pyran-4-yl)-1H-pyrazole, 5-(3,4-Dimethoxyphenyl)-1-(2-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-N,N-dimethylpyridin-2-amine, 4-[1-(2-Methoxyphenyl)-3-(2,2,6,6-tetramethyltetrahydro-2H-pyran-4-yl)-1H-pyrazol-5-yl]-2-methylpyridine, 5-Cyclopent-1-en-1-yl-1-(2-methoxyphenyl)-3-(2,2,6,6-tetramethyltetrahydro-2H-pyran-4-yl)-1H-pyrazole, 2-Methoxy-5-[1-(2-methoxyphenyl)-3-(2,2,6,6-tetramethyltetrahydro-2H-pyran-4-yl)-1H-pyrazol-5-yl]pyrimidine, 5-(1-Benzofuran-2-yl)-1-(2-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1H-indole, 5-(3,5-Dimethoxyphenyl)-1-(2-methoxyphenyl)-3-(2,2,6,6-tetramethyltetrahydro-2H-pyran-4-yl)-1H-pyrazole, 1-{4-[1-(2-Methoxyphenyl)-3-(2,2,6,6-tetramethyltetrahydro-2H-pyran-4-yl)-1H-pyrazol-5-yl]-phenyl}ethanol, 3-[1-(2-Methoxyphenyl)-3-(2,2,6,6-tetramethyltetrahydro-2H-pyran-4-yl)-1H-pyrazol-5-yl]-pyridine, 2-[5-(4-Chlorophenyl)-3-(2,2,6,6-tetramethyltetrahydro-2H-pyran-4-yl)-1H-pyrazol-1-yl]-N,N-dimethylaniline, 2-[5-(4-Chlorophenyl)-3-(2,2,6,6-tetramethyltetrahydro-2H-pyran-4-yl)-1H-pyrazol-1-yl]-N-methylaniline, 5-(4-Chlorophenyl)-3-[(trans)-2,6-dimethyltetrahydro-2H-pyran-4-yl]-1-(2-methoxyphenyl)-1H-pyrazole, 5-(4-Chlorophenyl)-3-(2,2-dimethyltetrahydro-2H-pyran-4-yl)-1-(2-methoxyphenyl)-1H-pyrazole, 5-(4-Chlorophenyl)-3-[(2R,4r,6S)-2,6-di methyltetrahydro-2H-pyran-4-yl]-1-(2-methoxyphenyl)-1H-pyrazole, 5-(4-Chlorophenyl)-1-(2-methoxyphenyl)-3-[(2R,4S)-2-(1-methylethyl)tetrahydro-2H-pyran-4-yl]-1H-pyrazole, 5-(4-Chlorophenyl)-1-(2-nitrophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N-ethylaniline, 3-[(trans)-2,6-Dimethyltetrahydro-2H-pyran-4-yl]-1-(2-methoxyphenyl)-5-phenyl-1H-pyrazole, 2-[5-(4-Chlorophenyl)-3-(2,2,6,6-tetramethyltetrahydro-2H-pyran-4-yl)-1H-pyrazol-1-yl]-aniline, 5-(4-Chlorophenyl)-1-(2-methoxyphenyl)-3-[(trans)-2-(1-methylethyl)tetrahydro-2H-pyran-4-yl]-1H-pyrazole, 4-Bromo-5-(4-chlorophenyl)-1-(2-methoxyphenyl)-3-(2,2,6,6-tetramethyltetrahydro-2H-pyran-4-yl)-1H-pyrazole, 5-(4-Chlorophenyl)-1-(2-methoxyphenyl)-3-(tetrahydro-2H-pyran-4-yl)-1H-pyrazole, 4-(2-{4-[1-(2-Methoxyphenyl)-3-(2,2,6,6-tetramethyltetrahydro-2H-pyran-4-yl)-1H-pyrazol-5-yl]phenoxy}ethyl) morpholine, 2-[5-(4-Chlorophenyl)-3-(2,2,6,6-tetramethyltetrahydro-2H-pyran-4-yl)-1H-pyrazol-1-yl]-N,N-diethylaniline, 1-(2-Chlorophenyl)-5-(4-chlorophenyl)-3-(tetrahydro-2H-pyran-4-yl)-1H-pyrazole, 5-(4-Chlorophenyl)-3-(2,2-dimethyltetrahydro-2H-pyran-4-yl)-1-(4-methoxy-2-methylphenyl)-1H-pyrazole, 5-(4-Chlorophenyl)-1-(2-methoxyphenyl)-3-(2,2,6,6-tetramethyl-3,6-di hydro-2H-pyran-4-yl)-1H-pyrazole, 5-(4-Chlorophenyl)-3-[(trans)-2,6-dimethyl-3,6-di hydro-2H-pyran-4-yl]-1-(2-methoxyphenyl)-1H-pyrazole, 5-(4-Chlorophenyl)-1-(2-methoxyphenyl)-3-(2,2,5,5-tetramethyl-2,5-di hydrofuran-3-yl)-1H-pyrazole, 5-(4-Chlorophenyl)-1-(2-methoxyphenyl)-3-(2,2,5,5-tetramethyl-2,5-dihydrofuran-3-yl)-1H-pyrazole, and 5-(4-Chlorophenyl)-1-(2-methoxyphenyl)-3-(2,2,5,5-tetramethyl-tetrahydrofuran-3-yl)-1H-pyrazole.

Most particular, a pharmaceutical composition of the present invention comprises at least a compound selected from:

5-(4-Chloro-phenyl)-1-(2-methoxy-phenyl)-3-(2,2,6,6-tetramethyl-tetrahydro-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-benzonitrile, 1-(2-Methoxyphenyl)-5-(4-methoxyphenyl)-3-(2,2,6,6-tetramethyltetrahydro-2H-pyran-4-yl)-1H-pyrazole, 5-(4-Ethoxyphenyl)-1-(2-methoxyphenyl)-3-(2,2,6,6-tetramethyltetrahydro-2H-pyran-4-yl)-1H-pyrazole, 2-Methoxy-5-[1-(2-methoxyphenyl)-3-(2,2,6,6-tetramethyltetrahydro-2H-pyran-4-yl)-1H-pyrazol-5-yl]pyridine, 5-(5-Chlorothiophen-2-yl)-1-(2-methoxyphenyl)-3-(2,2,6,6-tetramethyltetrahydro-2H-pyran-4-yl)-1H-pyrazole, 2-Ethoxy-5-[1-(2-methoxyphenyl)-3-(2,2,6,6-tetramethyltetrahydro-2H-pyran-4-yl)-1H-pyrazol-5-yl]-pyridine, 5-(4-Chlorophenyl)-1-(2-methoxyphenyl)-3-(2,2,6,6-tetramethyl-1,1-dioxidotetrahydro-2H-thiopyran-4-yl)-1H-pyrazole, and 5-(4-Chlorophenyl)-1-(2-methoxyphenyl)-3-(2,2,5,5-tetramethyl-tetrahydrofuran-3-yl)-1H-pyrazole.

The present invention also features a method of treating a subject suffering from or diagnosed with a disease, disorder, or condition mediated by N-type calcium channel activity, comprising administering to the subject a therapeutically effective amount of at least one compound of Formula (I).

The present invention also features a method for preventing or inhibiting the progression of an N-type calcium channel mediated condition in a subject in need thereof, comprising administering to said subject a therapeutically effective amount of at least one compound of Formula (I).

Such disease, disorder, or condition can include, but is not limited to pain and the diseases that lead to such pain, and associated symptoms or complications thereof.

It is a further embodiment of the invention to provide a process for making a pharmaceutical composition comprising admixing any of the compounds according to Formula (I) and a pharmaceutically acceptable carrier.

The invention also features pharmaceutical compositions which include, without limitation, one or more of the disclosed compounds, and pharmaceutically acceptable carriers or excipients.

In a further embodiment of the invention, a method for treating or ameliorating an N-type calcium channel mediated condition in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 0.5 mg/dose to about 1000 mg/dose. More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

In a further embodiment of the invention, a method for preventing or inhibiting the progression of an N-type calcium channel mediated condition in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) Terms

Some terms are defined below and by their usage throughout this disclosure.

It should also be noted that any atom with unsatisfied valences in the text, schemes, examples, structural formulae and any tables herein is assumed to have the hydrogen atom or atoms to satisfy the valences.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-4}$alkyl" means a saturated branched or straight-chain hydrocarbon radical having from 1 up to 4 carbon atoms in a linear or branched arrangement. The term includes atom groups such as methyl, ethyl, 1-propyl, 2-propyl, 1-butyl, 2-butyl, tert-butyl and the like. An alkyl radical may be attached to a core molecule by any atom where allowed by available valences.

The term "$C_{1-4}$alkoxy" means an alkyl radical having from 1 up to 4 carbon atoms in a linear or branched arrangement, as in the formula: —O—$C_{1-4}$alkyl. The term includes atom groups such as methoxy, ethoxy, propoxy, butoxy and the like. An alkoxy radical may be attached to a core molecule by any atom where allowed by available valences.

The term "$C_{3-8}$cycloalkyl" means a saturated or partially unsaturated, monocyclic, polycyclic or benzofused hydrocarbon ring system radical. The term also includes $C_{3-8}$cycloalkyl, $C_{5-6}$cycloalkyl, $C_{5-8}$cycloalkyl and benzofused $C_{3-8}$cycloalkyl ring systems. Examples include cyclopropyl, cyclobutyl, cyclopentyl, cyclohexyl, cyclohexyl, cyclohexenyl, cycloheptyl, cyclooctyl, 1H-indenyl, indanyl, bicyclo[2.2.1]heptyl, bicyclo[2.2.1]heptanyl and the like. A $C_{3-8}$cycloalkyl radical may be attached to a core molecule by any ring atom where allowed by available valences.

The term "aryl" means an unsaturated, aromatic monocyclic or polycyclic hydrocarbon ring system radical. Examples of aryl ring systems include phenyl, naphthalenyl, azulenyl, anthracenyl and the like. An aryl radical may be attached to a core molecule by any ring atom where allowed by available valences.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member.

Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heterocyclyl" means a saturated or partially unsaturated, monocyclic or polycyclic "hetero" ring system radical. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl, 2,5-diaza-bicyclo[2.2.1]heptanyl, 2-oxa-5-aza-bicyclo[2.2.1]heptanyl and the like. A heterocyclyl radical may be attached to a core molecule by any ring atom where allowed by available valences.

The term "heterocyclyl" also includes a benzofused-heterocyclyl ring system radical. The term "benzofused-heterocyclyl" means a heterocyclyl ring system radical having a benzene ring fused on the ring system on adjacent carbons, such as indolinyl (also referred to as 2,3-dihydro-indolyl), benzo[1,3]dioxolyl, 2,3-dihydro-1,4-benzodioxinyl, 2,3-dihydro-benzofuranyl, 1,2-dihydro-phthalazinyl and the like. A benzofused-heterocyclyl radical may be attached to a core molecule by any ring atom where allowed by available valences.

The term "heteroaryl" means an unsaturated monocyclic, polycyclic aromatic "hetero" ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like. A heteroaryl radical may be attached to a core molecule by any ring atom where allowed by available valences.

The term "heteroaryl" also includes a benzofused-heteroaryl ring system radical. The term "benzofused-heteroaryl" means a heteroaryl ring system radical having a benzene ring fused on the ring system on adjacent carbons, such as indolizinyl, indolyl, azaindolyl, isoindolyl, benzofuranyl, benzothienyl, indazolyl, azaindazolyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like. A benzofused-heteroaryl radical may be attached to a core molecule by any ring atom where when allowed by available valences.

The term "fused tricyclic heteroaryl" means a heteroaryl bicyclic ring system radical having a heteroaryl ring fused on the bicyclic ring system on adjacent carbon ring atoms, such as 1H-pyrazolo[4,3-g]quinolinyl and the like.

The term "$C_{1-4}$alkoxy-$C_{1-4}$alkyl" means a radical of the formula: —$C_{1-4}$alkyl-O—$C_{1-4}$alkyl.

The term "$C_{1-4}$alkoxy-$C_{1-4}$alkylcarbonyl" means a radical of the formula: —C(O)—$C_{1-4}$alkyl-O—$C_{1-4}$alkyl.

The term "$C_{1-4}$alkoxycarbonyl" means a radical of the formula: —C(O)—O—$C_{1-4}$alkyl.

The term "($C_{1-4}$alkoxy)imino-$C_{1-4}$alkyl" means a radical of the formula: —C[=N($C_{1-4}$alkoxy)].

The term "$C_{1-4}$alkylcarbonyl" means a radical of the formula: —C(O)—$C_{1-4}$alkyl.

The term "$C_{1-4}$alkylsulfonyl" means a radical of the formula: —$SO_2$—$C_{1-4}$alkyl.

The term "$C_{1-4}$alkylsulfonylamino" means a radical of the formula: —NH—$SO_2$—$C_{1-4}$alkyl.

The terms "amino," "($C_{1-4}$alkyl)amino" and "($C_{1-4}$alkyl)$_2$ amino" mean a radical of the formula: —NH$_2$, —NH—$C_{1-4}$ alkyl and —N($C_{1-4}$alkyl)$_2$, respectively.

The terms "amino-$C_{1-4}$alkyl," "($C_{1-4}$alkyl)amino-$C_{1-4}$ alkyl," and "($C_{1-4}$alkyl)$_2$amino-$C_{1-4}$alkyl" mean a radical of the formula: —$C_{1-4}$alkyl-NH$_2$, —$C_{1-4}$alkyl-NH—$C_{1-4}$alkyl, and —$C_{1-4}$alkyl-N($C_{1-4}$alkyl)$_2$, respectively.

The term "[($C_{1-4}$alkyl)($C_{1-4}$alkoxy)]aminocarbonyl" means a radical of the formula: —C(O)—N[($C_{1-4}$alkyl)($C_{1-4}$ alkoxy)].

The terms "(amino-$C_{1-4}$alkyl)aminocarbonyl," "[($C_{1-4}$ alkyl)amino-$C_{1-4}$alkyl]-aminocarbonyl," and "[($C_{1-4}$alkyl)$_2$ amino-$C_{1-4}$alkyl]aminocarbonyl" mean a radical of the formula: —C(O)—NH—$C_{1-4}$alkyl-NH$_2$, —C(O)—NH—$C_{1-4}$ alkyl-NH—$C_{1-4}$alkyl, and —C(O)—NH—$C_{1-4}$alkyl-N($C_{1-4}$ alkyl)$_2$, respectively.

The terms "amino-$C_{1-4}$alkylcarbonyl," "($C_{1-4}$alkyl)amino-$C_{1-4}$alkylcarbonyl," and "($C_{1-4}$alkyl)$_2$amino-$C_{1-4}$alkylcarbonyl" mean a radical of the formula: —C(O)—$C_{1-4}$alkyl-NH$_2$, —C(O)—$C_{1-4}$alkyl-NH—$C_{1-4}$alkyl, and —C(O)—$C_{1-4}$ alkyl-N($C_{1-4}$alkyl)$_2$, respectively.

The terms "aminocarbonyl," "($C_{1-4}$alkyl)aminocarbonyl," and "($C_{1-4}$alkyl)$_2$-aminocarbonyl" mean a radical of the formula: —N($C_{1-4}$alkyl)-C(O)—NH$_2$, —N($C_{1-4}$alkyl)-C(O)—NH—$C_{1-4}$alkyl, and —N($C_{1-4}$alkyl)-C(O)—N($C_{1-4}$alkyl)$_2$, respectively.

The terms "aminocarbonyl-$C_{1-4}$alkyl," "($C_{1-4}$alkyl)aminocarbonyl-$C_{1-4}$alkyl," and "($C_{1-4}$alkyl)$_2$aminocarbonyl-$C_{1-4}$ alkyl" mean a radical of the formula: —$C_{1-4}$alkyl-C(O)—NH$_2$, —$C_{1-4}$alkyl-C(O)—NH—$C_{1-4}$alkyl, and —$C_{1-4}$ alkyl-C(O)—N($C_{1-4}$alkyl)$_2$, respectively.

The terms "(aminocarbonyl)amino," "[($C_{1-4}$alkyl)aminocarbonyl]amino," and "[($C_{1-4}$alkyl)$_2$aminocarbonyl] amino" mean a radical of the formula: —NH—C(O)—NH$_2$, —NH—C(O)—NH—$C_{1-4}$alkyl, and —NH—C(O)—N($C_{1-4}$ alkyl)$_2$, respectively.

The terms "(aminocarbonyl)($C_{1-4}$alkyl)amino," "[($C_{1-4}$ alkyl)aminocarbonyl]-($C_{1-4}$alkyl)amino," and "[($C_{1-4}$alkyl)$_2$ aminocarbonyl]($C_{1-4}$alkyl)amino" mean a radical of the formula: —N($C_{1-4}$alkyl)-[C(O)—NH$_2$], —N($C_{1-4}$alkyl)-[C (O)—NH—$C_{1-4}$alkyl], and —N($C_{1-4}$alkyl)-[C(O)—N($C_{1-4}$ alkyl)$_2$], respectively.

The terms "aminosulfonyl," "($C_{1-4}$alkyl)aminosulfonyl," and "($C_{1-4}$alkyl)$_2$amino-sulfonyl" mean a radical of the formula: —SO$_2$—NH$_2$, —SO$_2$—NH—$C_{1-4}$alkyl, and —SO$_2$— N($C_{1-4}$alkyl)$_2$, respectively.

The term "aryl-sulfonyl" means a radical of the formula: —SO$_2$-aryl.

The term "carboxy" means a radical of the formula: —C(O)OH.

The term "halogen" or "halo" means a radical selected from the group consisting of chloro, bromo, fluoro or iodo.

The term "oxo" means a radical of the formula: =O.

The terms "trifluoro$C_{1-4}$alkoxy" and "trifluoro$C_{1-4}$alkyl" mean a radical of the formula: —O—$C_{1-3}$alkyl-CF$_3$ and —$C_{1-3}$alkyl-CF$_3$, respectively, wherein $C_{1-3}$alkyl is substituted on the terminal carbon atom with three fluoro atoms.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "each instance" means that substitution may occur on a variable when the variable is referred to in any configuration. For example, the term "wherein each instance of heteroaryl is substituted" means that substitution may occur as indicated on the heteroaryl ring in each instance heteroaryl is referred to in a heteroaryl, (heteroaryl)aryl or (heteroaryl)heteroaryl substituent. When the term "each instance" is not used, substitution may occur only on the variable referred to.

The term "each selected from" means that, for a variable having multiple substituents, each substituent may be independently selected from the indicated group.

In general, IUPAC nomenclature rules are used herein.

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The term "composition" is intended to encompass a product comprising the specified ingredients in the specified amounts, as well as any product which results, directly or indirectly, from combinations of the specified ingredients in the specified amounts.

The term "subject" as used herein, refers to a patient, such as an animal, a mammal or a human, who has been the object of treatment, observation or experiment and is at risk of (or susceptible to) developing an N-type calcium channel mediated disorder.

The term "administering" further means that the individual ingredients to be combined may be administered at the same time or at different times during the treatment period, either as one preparation or as different preparations. Accordingly, the invention should be so interpreted that it encompasses any and every administration mode at the same time or at different times. The range of the combination of the compound of the invention and the other therapeutic agent useful for the above-mentioned disorders encompasses, in principle, all combinations of the compound of the invention and any and every pharmaceutical agent useful for the above-mentioned disorders.

The term "treating" refers, without limitation, to facilitating the eradication of, preventing, ameliorating or otherwise inhibiting the progression of or promoting stasis of an N-type calcium channel mediated disorder.

The term "N-Type calcium channel blocker" is intended to encompass a compound that interacts with the N-Type calcium channel to substantially reduce or eliminate its functional activity, thereby decreasing the flow of calcium ions through the channel and the rise of intracellular calcium concentrations.

The term "N-Type calcium channel-modulated" refers to the condition of being affected by the modulation of the N-Type calcium channel including the condition of being affected by the inhibition of the N-Type calcium channel, such as, for example, pain, the diseases that lead to such pain and treatments that lead to the reduction of such pain.

As used herein, unless otherwise noted, the term "affect" or "affected" (when referring to a disease, syndrome, condition or disorder that is affected by the inhibition of MGL) shall include a reduction in the frequency and severity of one or more symptoms or manifestations of said disease, syndrome, condition or disorder; and include the prevention of the development of one or more symptoms or manifestations of said disease, syndrome, condition or disorder or the development of the disease, condition, syndrome or disorder.

The term "prodrug" means a compound of Formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions. Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "*Design of Prodrugs*", ed. H. Bundgaard, Elsevier, 1985.

The term "metabolite" means a prodrug form of a compound of Formula (I) or a form thereof converted by in vivo metabolism or a metabolic process to a relatively less active functional derivative of said compound.

The term "medicament" or "medicine" refers to a product containing a compound of Formula (I) or a form thereof. The present invention includes use of such a medicament for treating an N-type calcium channel mediated disorder.

The term "combination form" refers to the use of a combination product comprising a compound of Formula (I) or a form, pharmaceutical composition, medicine or medicament thereof and at least one therapeutic agent for treating an N-type calcium channel mediated disorder.

Methods are known in the art for determining effective doses for therapeutic and prophylactic purposes for the disclosed pharmaceutical compositions or the disclosed drug combinations, whether or not formulated in the same composition.

For therapeutic purposes, the term "therapeutically effective amount" or "effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the progression of a disorder), the term "therapeutically effective amount" refers to that amount of each active compound or pharmaceutical agent, alone or in combination, that treats or inhibits in a subject the progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together. The effective amount of said compound is from about 0.001 mg/kg/day to about 300 mg/kg/day.

Advantageously, the effective amount of a combination product for treating an N-type calcium channel mediated disorder may be a reduced amount of either or both the compound or therapeutic agent compared to the effective amount of the compound or therapeutic agent otherwise recommended for treating the condition. Therefore, it is contemplated that the compound is administered to the subject before, during or after the time the agent is administered.

The term "pharmaceutically acceptable salt" refers to non-toxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule that, in a given configuration, cannot be superimposed on its mirror image. This is in contrast to achiral molecules that can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration according to the Cahn-lngold-Prelog priority rules. In the "E" configuration, the substituents having the highest priorities are on opposite sides in relationship to the carbon-carbon double bond. In the "Z" configuration, the substituents having the highest priorities are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

B) Compounds

Representative compounds of the present invention are listed in Table 1 below:

TABLE 1

| STRUCTURE | COMPOUND # | NAME |
|---|---|---|
| 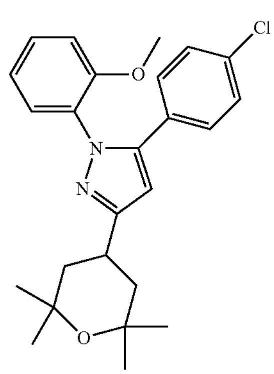 | 1 | 5-(4-Chloro-phenyl)-1-(2-methoxy-phenyl)-3-(2,2,6,6-tetramethyl-tetrahydro-pyran-4-yl)-1H-pyrazole |

TABLE 1-continued

| STRUCTURE | COMPOUND # | NAME |
|---|---|---|
| 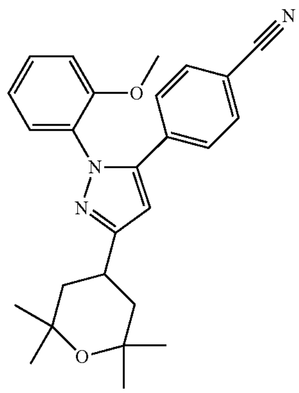 [SMILES: COc1ccccc1-n1nc(C2CC(C)(C)OC(C)(C)C2)cc1-c1ccc(C#N)cc1] | 2 | 4-[1-(2-Methoxyphenyl)-3-(2,2,6,6-tetramethyltetrahydro-2H-pyran-4-yl)-1H-pyrazol-5-yl]-benzonitrile |
| 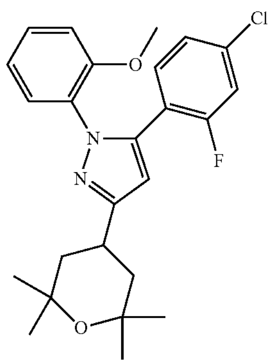 [SMILES: COc1ccccc1-n1nc(C2CC(C)(C)OC(C)(C)C2)cc1-c1ccc(Cl)cc1F] | 3 | 5-(4-Chloro-2-fluorophenyl)-1-(2-methoxyphenyl)-3-(2,2,6,6-tetramethyltetrahydro-2H-pyran-4-yl)-1H-pyrazole |
| 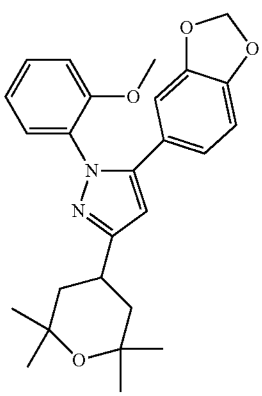 [SMILES: COc1ccccc1-n1nc(C2CC(C)(C)OC(C)(C)C2)cc1-c1ccc2c(c1)OCO2] | 4 | 5-(1,3-Benzodioxol-5-yl)-1-(2-methoxyphenyl)-3-(2,2,6,6-tetramethyltetrahydro-2H-pyran-4-yl)-1H-pyrazole |
| 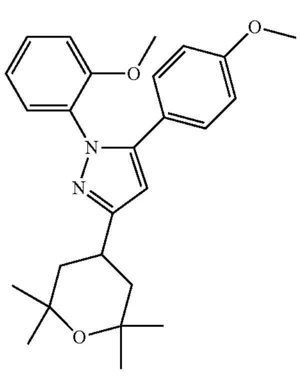 [SMILES: COc1ccc(-c2cc(C3CC(C)(C)OC(C)(C)C3)nn2-c2ccccc2OC)cc1] | 5 | 1-(2-Methoxyphenyl)-5-(4-methoxyphenyl)-3-(2,2,6,6-tetramethyltetrahydro-2H-pyran-4-yl)-1H-pyrazole |

TABLE 1-continued

| STRUCTURE | COMPOUND # | NAME |
|---|---|---|
| 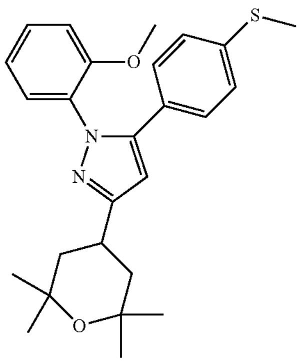 | 6 | 1-(2-Methoxyphenyl)-5-[4-(methylsulfanyl)phenyl]-3-(2,2,6,6-tetramethyltetrahydro-2H-pyran-4-yl)-1H-pyrazole |
| 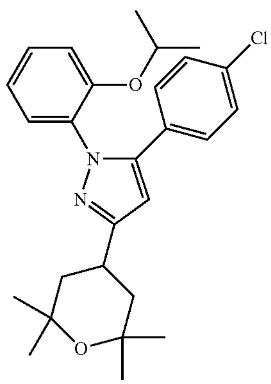 [SMILES: CC(C)Oc1ccccc1-n1nc(C2CC(C)(C)OC(C)(C)C2)cc1-c1ccc(Cl)cc1] | 7 | 5-(4-Chlorophenyl)-1-[2-(1-methylethoxy)phenyl]-3-(2,2,6,6-tetramethyltetrahydro-2H-pyran-4-yl)-1H-pyrazole |
| 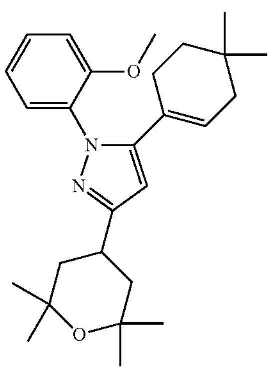 [SMILES: COc1ccccc1-n1nc(C2CC(C)(C)OC(C)(C)C2)cc1C1=CCC(C)(C)CC1] | 8 | 5-(4,4-Dimethylcyclohex-1-en-1-yl)-1-(2-methoxyphenyl)-3-(2,2,6,6-tetramethyltetrahydro-2H-pyran-4-yl)-1H-pyrazole |
| 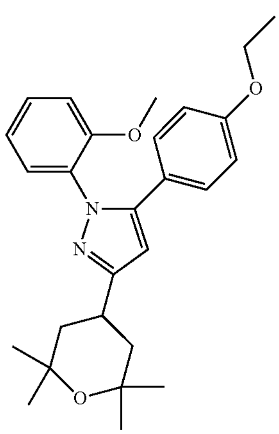 [SMILES: CCOc1ccc(-c2cc(C3CC(C)(C)OC(C)(C)C3)nn2-c2ccccc2OC)cc1] | 9 | 5-(4-Ethoxyphenyl)-1-(2-methoxyphenyl)-3-(2,2,6,6-tetramethyltetrahydro-2H-pyran-4-yl)-1H-pyrazole |

TABLE 1-continued

| STRUCTURE | COMPOUND # | NAME |
|---|---|---|
| 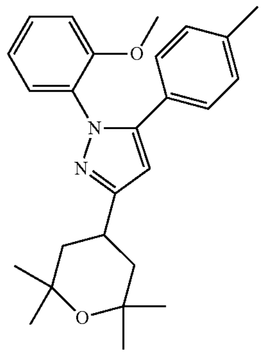 [SMILES: COc1ccccc1-n1nc(C2CC(C)(C)OC(C)(C)C2)cc1-c1ccc(C)cc1] | 10 | 1-(2-Methoxyphenyl)-5-(4-methylphenyl)-3-(2,2,6,6-tetramethyltetrahydro-2H-pyran-4-yl)-1H-pyrazole |
| 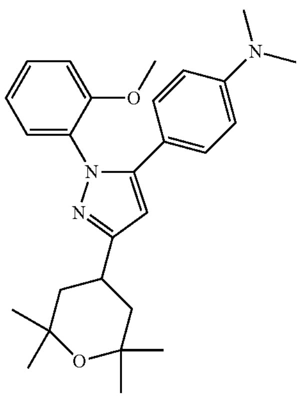 [SMILES: COc1ccccc1-n1nc(C2CC(C)(C)OC(C)(C)C2)cc1-c1ccc(N(C)C)cc1] | 11 | 4-[1-(2-Methoxyphenyl)-3-(2,2,6,6-tetramethyltetrahydro-2H-pyran-4-yl)-1H-pyrazol-5-yl]-N,N-dimethylaniline |
| 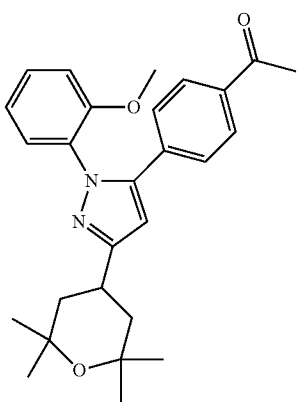 [SMILES: COc1ccccc1-n1nc(C2CC(C)(C)OC(C)(C)C2)cc1-c1ccc(C(C)=O)cc1] | 12 | 1-{4-[1-(2-Methoxyphenyl)-3-(2,2,6,6-tetramethyltetrahydro-2H-pyran-4-yl)-1H-pyrazol-5-yl]phenyl}ethanone |
| 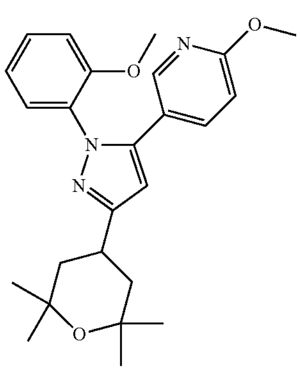 [SMILES: COc1ccc(-c2cc(C3CC(C)(C)OC(C)(C)C3)nn2-c2ccccc2OC)cn1] | 13 | 2-Methoxy-5-[1-(2-methoxyphenyl)-3-(2,2,6,6-tetramethyltetrahydro-2H-pyran-4-yl)-1H-pyrazol-5-yl]pyridine |

TABLE 1-continued

| STRUCTURE | COMPOUND # | NAME |
|---|---|---|
| 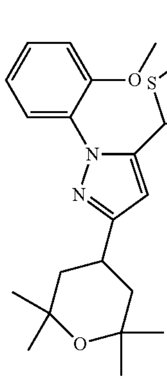 | 14 | 5-(5-Chlorothiophen-2-yl)-1-(2-methoxyphenyl)-3-(2,2,6,6-tetramethyltetrahydro-2H-pyran-4-yl)-1H-pyrazole |
| 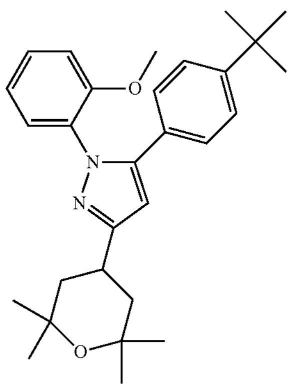 [SMILES: COc1ccccc1-n1nc(C2CC(C)(C)OC(C)(C)C2)cc1-c1ccc(C(C)(C)C)cc1] | 15 | 5-(4-tert-Butylphenyl)-1-(2-methoxyphenyl)-3-(2,2,6,6-tetramethyltetrahydro-2H-pyran-4-yl)-1H-pyrazole |
| 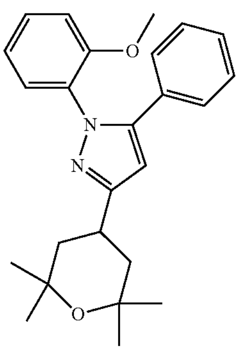 [SMILES: COc1ccccc1-n1nc(C2CC(C)(C)OC(C)(C)C2)cc1-c1ccccc1] | 16 | 1-(2-Methoxyphenyl)-5-phenyl-3-(2,2,6,6-tetramethyltetrahydro-2H-pyran-4-yl)-1H-pyrazole |
| 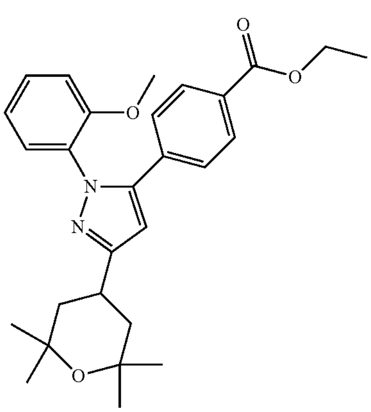 [SMILES: CCOC(=O)c1ccc(-c2cc(C3CC(C)(C)OC(C)(C)C3)nn2-c2ccccc2OC)cc1] | 17 | Ethyl 4-[1-(2-methoxyphenyl)-3-(2,2,6,6-tetramethyltetrahydro-2H-pyran-4-yl)-1H-pyrazol-5-yl]benzoate |

TABLE 1-continued

| STRUCTURE | COMPOUND # | NAME |
|---|---|---|
| 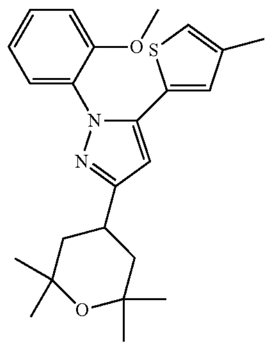 [SMILES: COc1ccccc1-n1nc(C2CC(C)(C)OC(C)(C)C2)cc1-c1cc(C)cs1] | 18 | 1-(2-Methoxyphenyl)-5-(4-methylthiophen-2-yl)-3-(2,2,6,6-tetramethyltetrahydro-2H-pyran-4-yl)-1H-pyrazole |
| 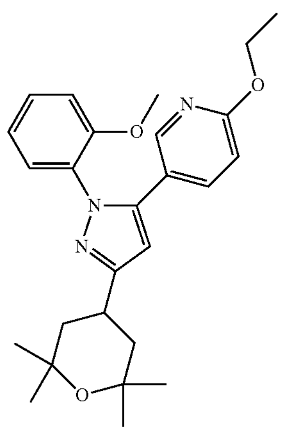 [SMILES: CCOc1ccc(-c2cc(C3CC(C)(C)OC(C)(C)C3)nn2-c2ccccc2OC)cn1] | 19 | 2-Ethoxy-5-[1-(2-methoxyphenyl)-3-(2,2,6,6-tetramethyltetrahydro-2H-pyran-4-yl)-1H-pyrazol-5-yl]-pyridine |
| 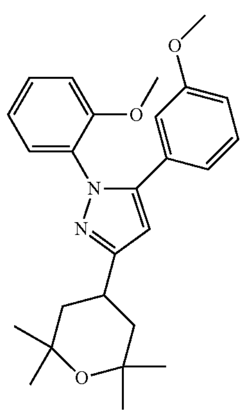 [SMILES: COc1cccc(-c2cc(C3CC(C)(C)OC(C)(C)C3)nn2-c2ccccc2OC)c1] | 20 | 1-(2-Methoxyphenyl)-5-(3-methoxyphenyl)-3-(2,2,6,6-tetramethyltetrahydro-2H-pyran-4-yl)-1H-pyrazole |
| 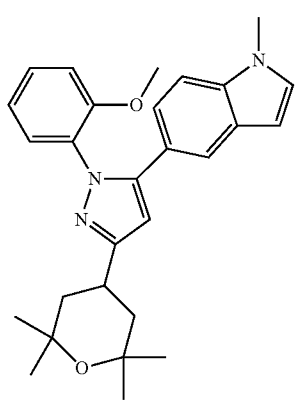 [SMILES: COc1ccccc1-n1nc(C2CC(C)(C)OC(C)(C)C2)cc1-c1ccc2c(ccn2C)c1] | 21 | 5-[1-(2-Methoxyphenyl)-3-(2,2,6,6-tetramethyltetrahydro-2H-pyran-4-yl)-1H-pyrazol-5-yl]-1-methyl-1H-indole |

TABLE 1-continued

| STRUCTURE | COMPOUND # | NAME |
|---|---|---|
| 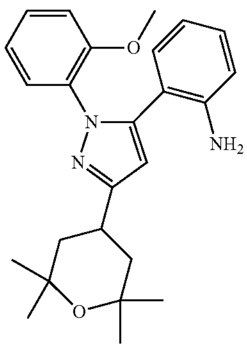 [SMILES: COc1ccccc1-n1nc(C2CC(C)(C)OC(C)(C)C2)cc1-c1ccccc1N] | 22 | 2-[1-(2-Methoxyphenyl)-3-(2,2,6,6-tetramethyltetrahydro-2H-pyran-4-yl)-1H-pyrazol-5-yl]-aniline |
| 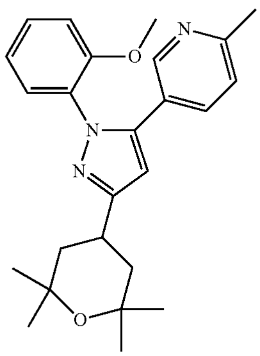 [SMILES: COc1ccccc1-n1nc(C2CC(C)(C)OC(C)(C)C2)cc1-c1ccc(C)nc1] | 23 | 5-[1-(2-Methoxyphenyl)-3-(2,2,6,6-tetramethyltetrahydro-2H-pyran-4-yl)-1H-pyrazol-5-yl]-2-methylpyridine |
| 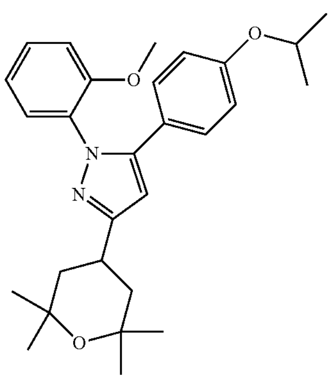 [SMILES: COc1ccccc1-n1nc(C2CC(C)(C)OC(C)(C)C2)cc1-c1ccc(OC(C)C)cc1] | 24 | 1-(2-Methoxyphenyl)-5-[4-(1-methylethoxy)phenyl]-3-(2,2,6,6-tetramethyltetrahydro-2H-pyran-4-yl)-1H-pyrazole |
| 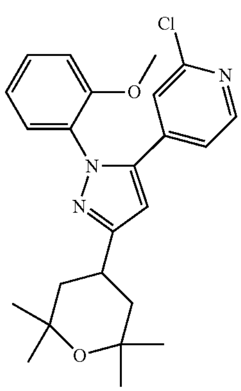 [SMILES: COc1ccccc1-n1nc(C2CC(C)(C)OC(C)(C)C2)cc1-c1ccnc(Cl)c1] | 25 | 2-Chloro-4-[1-(2-methoxyphenyl)-3-(2,2,6,6-tetramethyltetrahydro-2H-pyran-4-yl)-1H-pyrazol-5-yl]pyridine |

TABLE 1-continued

| STRUCTURE | COMPOUND # | NAME |
|---|---|---|
| 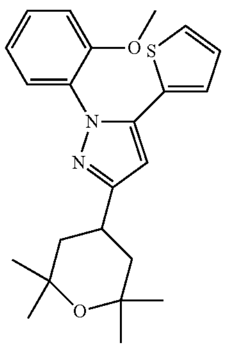 [SMILES: COc1ccccc1-n1nc(C2CC(C)(C)OC(C)(C)C2)cc1-c1cccs1] | 26 | 1-(2-Methoxyphenyl)-3-(2,2,6,6-tetramethyltetrahydro-2H-pyran-4-yl)-5-thiophen-2-yl-1H-pyrazole |
| 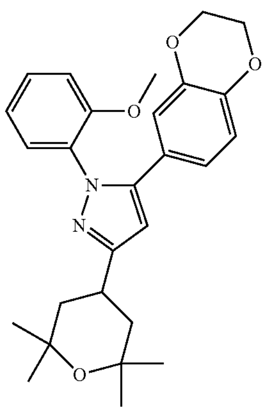 [SMILES: COc1ccccc1-n1nc(C2CC(C)(C)OC(C)(C)C2)cc1-c1ccc2c(c1)OCCO2] | 27 | 5-(2,3-Dihydro-1,4-benzodioxin-6-yl)-1-(2-methoxyphenyl)-3-(2,2,6,6-tetramethyltetrahydro-2H-pyran-4-yl)-1H-pyrazole |
| 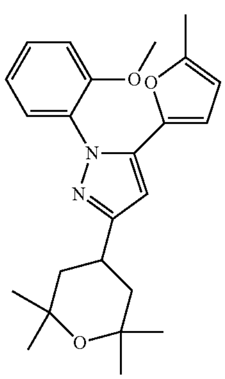 [SMILES: COc1ccccc1-n1nc(C2CC(C)(C)OC(C)(C)C2)cc1-c1ccc(C)o1] | 28 | 1-(2-Methoxyphenyl)-5-(5-methylfuran-2-yl)-3-(2,2,6,6-tetramethyltetrahydro-2H-pyran-4-yl)-1H-pyrazole |
| 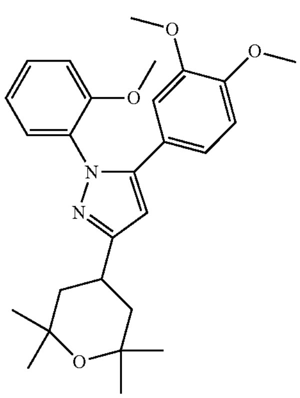 [SMILES: COc1ccc(-c2cc(C3CC(C)(C)OC(C)(C)C3)nn2-c2ccccc2OC)cc1OC] | 29 | 5-(3,4-Dimethoxyphenyl)-1-(2-methoxyphenyl)-3-(2,2,6,6-tetramethyltetrahydro-2H-pyran-4-yl)-1H-pyrazole |

TABLE 1-continued

| STRUCTURE | COMPOUND # | NAME |
|---|---|---|
| 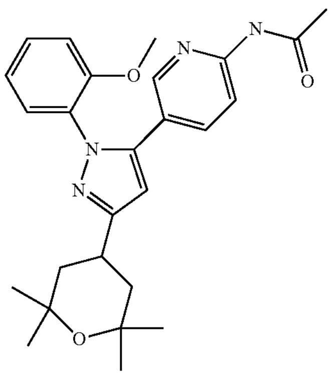 [SMILES: COc1ccccc1-n1nc(C2CC(C)(C)OC(C)(C)C2)cc1-c1ccc(NC(C)=O)nc1] | 30 | N-{5-[1-(2-Methoxyphenyl)-3-(2,2,6,6-tetramethyltetrahydro-2H-pyran-4-yl)-1H-pyrazol-5-yl]pyridin-2-yl}acetamide |
| 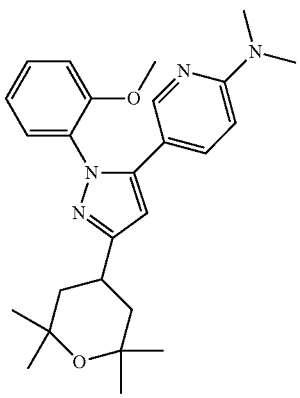 [SMILES: COc1ccccc1-n1nc(C2CC(C)(C)OC(C)(C)C2)cc1-c1ccc(N(C)C)nc1] | 31 | 5-[1-(2-Methoxyphenyl)-3-(2,2,6,6-tetramethyltetrahydro-2H-pyran-4-yl)-1H-pyrazol-5-yl]-N,N-dimethylpyridin-2-amine |
| 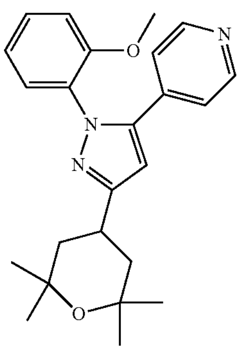 | 32 | 4-[1-(2-Methoxyphenyl)-3-(2,2,6,6-tetramethyltetrahydro-2H-pyran-4-yl)-1H-pyrazol-5-yl]pyridine |
| 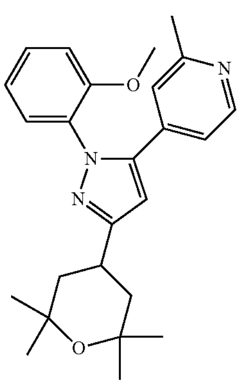 [SMILES: COc1ccccc1-n1nc(C2CC(C)(C)OC(C)(C)C2)cc1-c1ccnc(C)c1] | 33 | 4-[1-(2-Methoxyphenyl)-3-(2,2,6,6-tetramethyltetrahydro-2H-pyran-4-yl)-1H-pyrazol-5-yl]-2-methylpyridine |

TABLE 1-continued

| STRUCTURE | COMPOUND # | NAME |
|---|---|---|
| 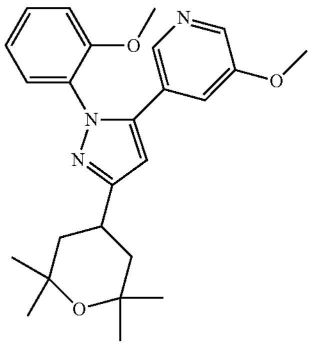 [SMILES: COc1cncc(-c2cc(C3CC(C)(C)OC(C)(C)C3)nn2-c2ccccc2OC)c1] | 34 | 3-Methoxy-5-[1-(2-methoxyphenyl)-3-(2,2,6,6-tetramethyltetrahydro-2H-pyran-4-yl)-1H-pyrazol-5-yl]-pyridine |
| 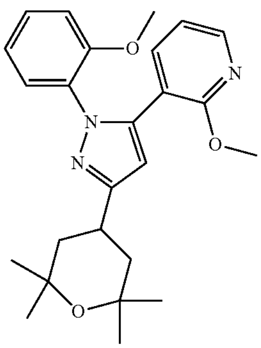 [SMILES: COc1ccccc1-n1nc(C2CC(C)(C)OC(C)(C)C2)cc1-c1cccnc1OC] | 35 | 2-Methoxy-3-[1-(2-methoxyphenyl)-3-(2,2,6,6-tetramethyltetrahydro-2H-pyran-4-yl)-1H-pyrazol-5-yl]-pyridine |
| 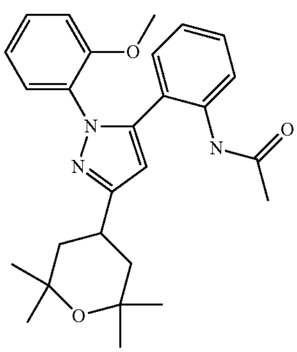 [SMILES: COc1ccccc1-n1nc(C2CC(C)(C)OC(C)(C)C2)cc1-c1ccccc1NC(C)=O] | 36 | N-{2-[1-(2-Methoxyphenyl)-3-(2,2,6,6-tetramethyltetrahydro-2H-pyran-4-yl)-1H-pyrazol-5-yl]-phenyl}-acetamide |
| 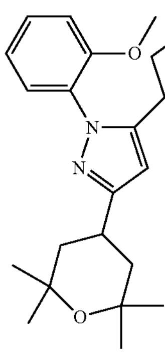 | 37 | 5-Cyclopent-1-en-1-yl-1-(2-methoxyphenyl)-3-(2,2,6,6-tetramethyltetrahydro-2H-pyran-4-yl)-1H-pyrazole |

TABLE 1-continued

| STRUCTURE | COMPOUND # | NAME |
|---|---|---|
| 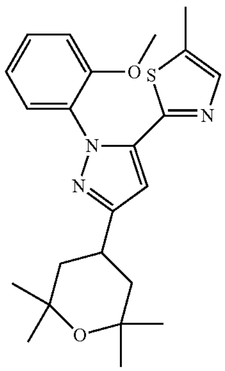 [SMILES: COc1ccccc1-n1nc(C2CC(C)(C)OC(C)(C)C2)cc1-c1ncc(C)s1] | 38 | 2-[1-(2-Methoxyphenyl)-3-(2,2,6,6-tetramethyltetrahydro-2H-pyran-4-yl)-1H-pyrazol-5-yl]-5-methyl-1,3-thiazole |
| 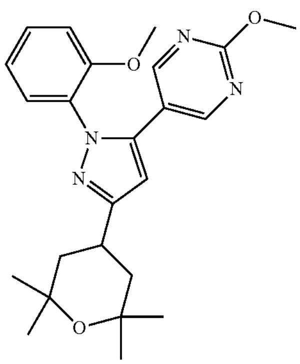 [SMILES: COc1ncc(-c2cc(C3CC(C)(C)OC(C)(C)C3)nn2-c2ccccc2OC)cn1] | 39 | 2-Methoxy-5-[1-(2-methoxyphenyl)-3-(2,2,6,6-tetramethyltetrahydro-2H-pyran-4-yl)-1H-pyrazol-5-yl]pyrimidine |
| 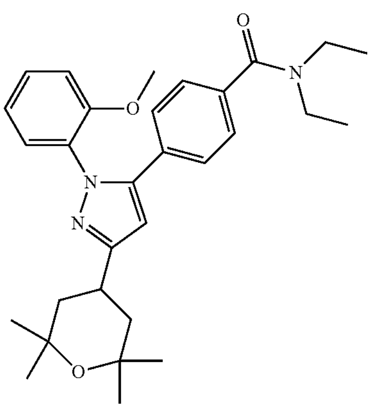 [SMILES: CCN(CC)C(=O)c1ccc(-c2cc(C3CC(C)(C)OC(C)(C)C3)nn2-c2ccccc2OC)cc1] | 40 | N,N-Diethyl-4-[1-(2-methoxyphenyl)-3-(2,2,6,6-tetramethyltetrahydro-2H-pyran-4-yl)-1H-pyrazol-5-yl]-benzamide |
| 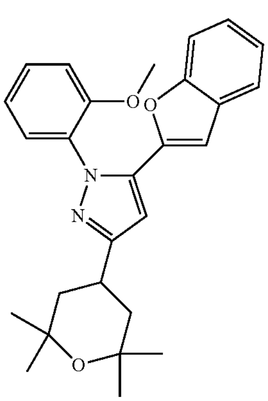 [SMILES: COc1ccccc1-n1nc(C2CC(C)(C)OC(C)(C)C2)cc1-c1cc2ccccc2o1] | 41 | 5-(1-Benzofuran-2-yl)-1-(2-methoxyphenyl)-3-(2,2,6,6-tetramethyltetrahydro-2H-pyran-4-yl)-1H-pyrazole |

TABLE 1-continued

| STRUCTURE | COMPOUND # | NAME |
|---|---|---|
| 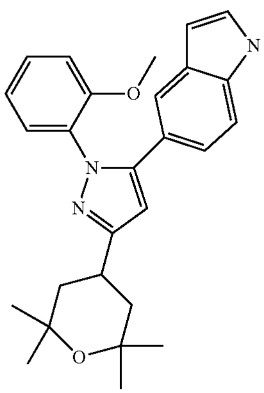 [SMILES: COc1ccccc1-n1nc(C2CC(C)(C)OC(C)(C)C2)cc1-c1ccc2[nH]ccc2c1] | 42 | 5-[1-(2-Methoxyphenyl)-3-(2,2,6,6-tetramethyltetrahydro-2H-pyran-4-yl)-1H-pyrazol-5-yl]-1H-indole |
| 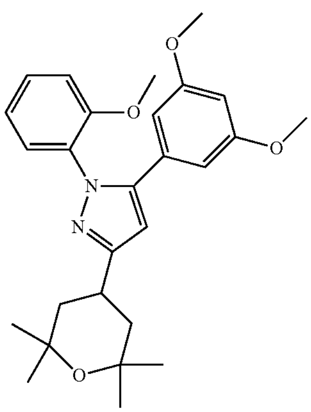 [SMILES: COc1cc(OC)cc(-c2cc(C3CC(C)(C)OC(C)(C)C3)nn2-c2ccccc2OC)c1] | 43 | 5-(3,5-Dimethoxyphenyl)-1-(2-methoxyphenyl)-3-(2,2,6,6-tetramethyltetrahydro-2H-pyran-4-yl)-1H-pyrazole |
| 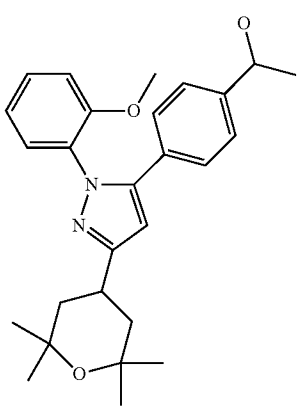 [SMILES: COc1ccccc1-n1nc(C2CC(C)(C)OC(C)(C)C2)cc1-c1ccc(C(C)O)cc1] | 44 | 1-{4-[1-(2-Methoxyphenyl)-3-(2,2,6,6-tetramethyltetrahydro-2H-pyran-4-yl)-1H-pyrazol-5-yl]-phenyl}-ethanol |
| 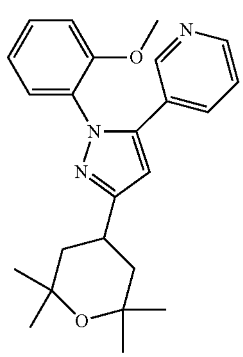 [SMILES: COc1ccccc1-n1nc(C2CC(C)(C)OC(C)(C)C2)cc1-c1cccnc1] | 45 | 3-[1-(2-Methoxyphenyl)-3-(2,2,6,6-tetramethyltetrahydro-2H-pyran-4-yl)-1H-pyrazol-5-yl]-pyridine |

TABLE 1-continued

| STRUCTURE | COMPOUND # | NAME |
|---|---|---|
| 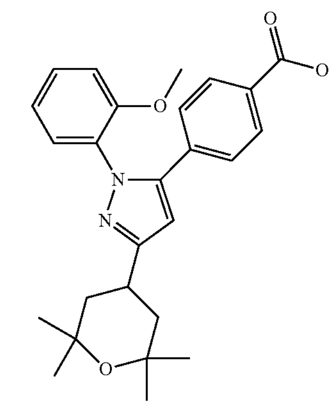 [SMILES: COc1ccccc1-n1nc(C2CC(C)(C)OC(C)(C)C2)cc1-c1ccc(C(=O)O)cc1] | 46 | 4-[1-(2-Methoxyphenyl)-3-(2,2,6,6-tetramethyltetrahydro-2H-pyran-4-yl)-1H-pyrazol-5-yl]-benzoic acid |
| 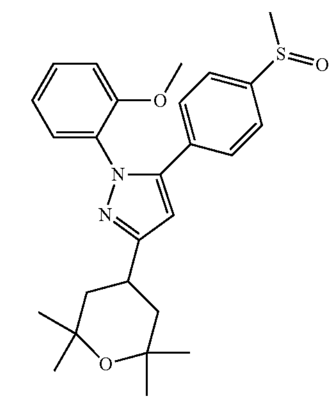 [SMILES: COc1ccccc1-n1nc(C2CC(C)(C)OC(C)(C)C2)cc1-c1ccc(S(C)=O)cc1] | 47 | 5-(4-Methanesulfinyl-phenyl)-1-(2-methoxy-phenyl)-3-(2,2,6,6-tetramethyl-tetrahydro-pyran-4-yl)-1H-pyrazole |
| 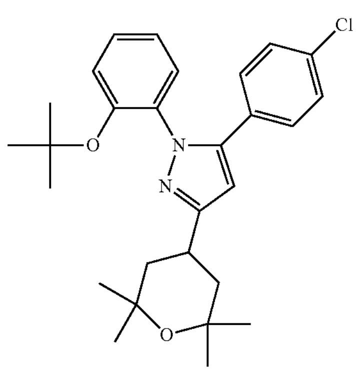 [SMILES: CC(C)(C)Oc1ccccc1-n1nc(C2CC(C)(C)OC(C)(C)C2)cc1-c1ccc(Cl)cc1] | 48 | 1-(2-tert-Butoxyphenyl)-5-(4-chlorophenyl)-3-(2,2,6,6-tetramethyltetrahydro-2H-pyran-4-yl)-1H-pyrazole |
| 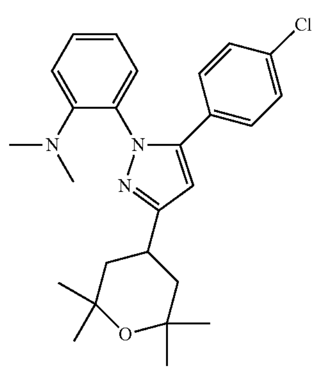 [SMILES: CN(C)c1ccccc1-n1nc(C2CC(C)(C)OC(C)(C)C2)cc1-c1ccc(Cl)cc1] | 49 | 2-[5-(4-Chlorophenyl)-3-(2,2,6,6-tetramethyltetrahydro-2H-pyran-4-yl)-1H-pyrazol-1-yl]-N,N-dimethylaniline |

TABLE 1-continued

| STRUCTURE | COMPOUND # | NAME |
|---|---|---|
| 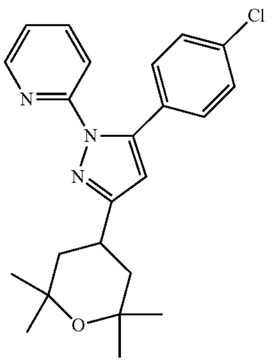 [SMILES: CC1(C)CC(c2cc(-c3ccc(Cl)cc3)n(-c3ccccn3)n2)CC(C)(C)O1] | 50 | 2-[5-(4-Chloro-phenyl)-3-(2,2,6,6-tetramethyl-tetrahydro-pyran-4-yl)-pyrazol-1-yl]-pyridine |
| 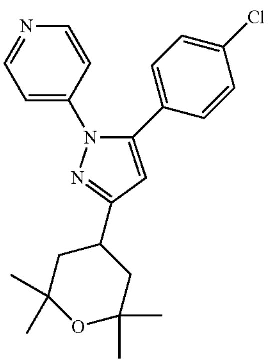 [SMILES: CC1(C)CC(c2cc(-c3ccc(Cl)cc3)n(-c3ccncc3)n2)CC(C)(C)O1] | 51 | 4-[5-(4-Chlorophenyl)-3-(2,2,6,6-tetramethyltetrahydro-2H-pyran-4-yl)-1H-pyrazol-1-yl]-pyridine |
| 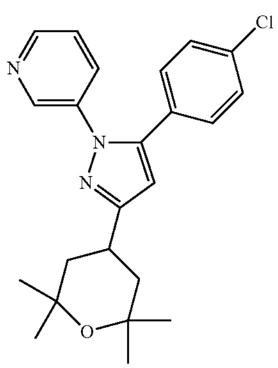 [SMILES: CC1(C)CC(c2cc(-c3ccc(Cl)cc3)n(-c3cccnc3)n2)CC(C)(C)O1] | 52 | 3-[5-(4-Chlorophenyl)-3-(2,2,6,6-tetramethyltetrahydro-2H-pyran-4-yl)-1H-pyrazol-1-yl]-pyridine |
| 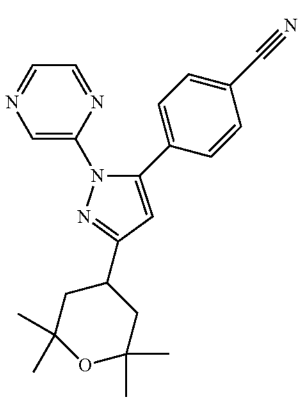 [SMILES: CC1(C)CC(c2cc(-c3ccc(C#N)cc3)n(-c3cnccn3)n2)CC(C)(C)O1] | 53 | 4-[1-Pyrazin-2-yl-3-(2,2,6,6-tetramethyltetrahydro-2H-pyran-4-yl)-1H-pyrazol-5-yl]-benzonitrile |

TABLE 1-continued
| STRUCTURE | COMPOUND # | NAME |
|---|---|---|
| 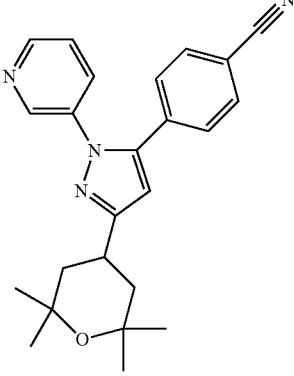 | 54 | 4-[1-Pyridin-3-yl-3-(2,2,6,6-tetramethyltetrahydro-2H-pyran-4-yl)-1H-pyrazol-5-yl]-benzonitrile |
| 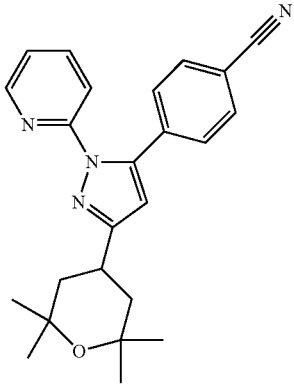 [SMILES: CC1(C)CC(c2cc(-c3ccc(C#N)cc3)n(-c3ccccn3)n2)CC(C)(C)O1] | 55 | 4-[1-Pyridin-2-yl-3-(2,2,6,6-tetramethyltetrahydro-2H-pyran-4-yl)-1H-pyrazol-5-yl]-benzonitrile |
| 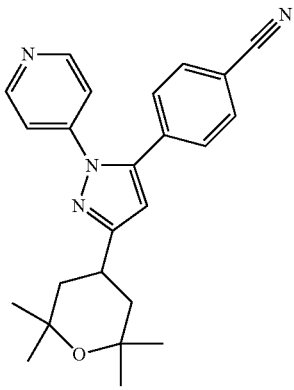 [SMILES: CC1(C)CC(c2cc(-c3ccc(C#N)cc3)n(-c3ccncc3)n2)CC(C)(C)O1] | 56 | 4-[1-Pyridin-4-yl-3-(2,2,6,6-tetramethyltetrahydro-2H-pyran-4-yl)-1H-pyrazol-5-yl]-benzonitrile |
| 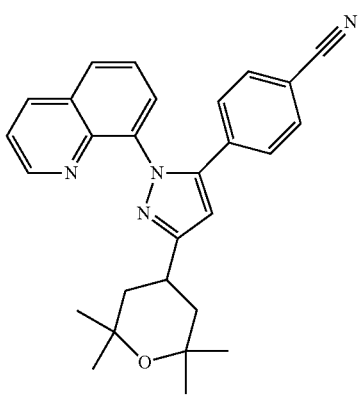 [SMILES: CC1(C)CC(c2cc(-c3ccc(C#N)cc3)n(-c3cccc4cccnc34)n2)CC(C)(C)O1] | 57 | 4-[1-Quinolin-8-yl-3-(2,2,6,6-tetramethyltetrahydro-2H-pyran-4-yl)-1H-pyrazol-5-yl]-benzonitrile |

TABLE 1-continued

| STRUCTURE | COMPOUND # | NAME |
|---|---|---|
| 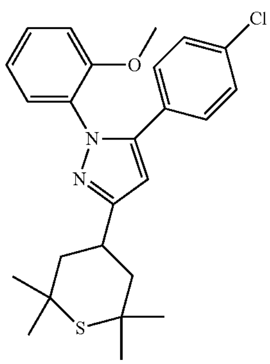 [SMILES: COc1ccccc1-n1nc(C2CC(C)(C)SC(C)(C)C2)cc1-c1ccc(Cl)cc1] | 58 | 5-(4-Chloro-phenyl)-1-(2-methoxy-phenyl)-3-(2,2,6,6-tetramethyl-tetrahydro-thiopyran-4-yl)-1H-pyrazole |
| 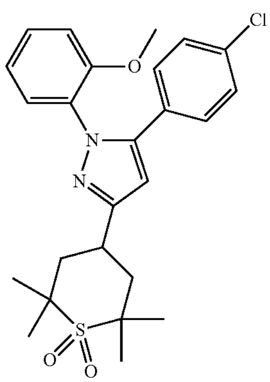 [SMILES: COc1ccccc1-n1nc(C2CC(C)(C)S(=O)(=O)C(C)(C)C2)cc1-c1ccc(Cl)cc1] | 59 | 5-(4-Chlorophenyl)-1-(2-methoxyphenyl)-3-(2,2,6,6-tetramethyl-1,1-dioxidotetrahydro-2H-thiopyran-4-yl)-1H-pyrazole |
| 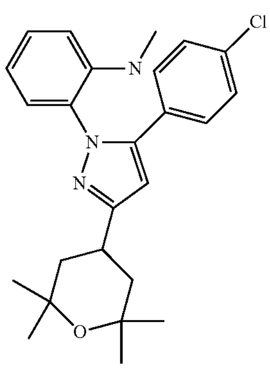 [SMILES: CNc1ccccc1-n1nc(C2CC(C)(C)OC(C)(C)C2)cc1-c1ccc(Cl)cc1] | 60 | 2-[5-(4-Chlorophenyl)-3-(2,2,6,6-tetramethyltetrahydro-2H-pyran-4-yl)-1H-pyrazol-1-yl]-N-methylaniline |
| 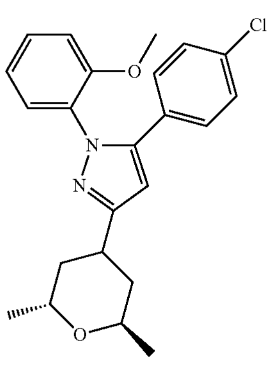 [SMILES: COc1ccccc1-n1nc(C2C[C@@H](C)O[C@H](C)C2)cc1-c1ccc(Cl)cc1] | 61 | 5-(4-Chlorophenyl)-3-[(trans)-2,6-dimethyltetrahydro-2H-pyran-4-yl]-1-(2-methoxyphenyl)-1H-pyrazole |

TABLE 1-continued

| STRUCTURE | COMPOUND # | NAME |
|---|---|---|
| 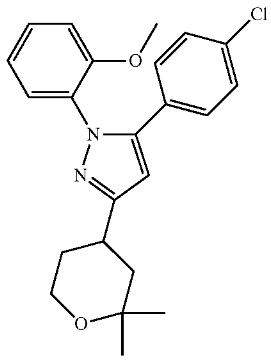 [SMILES: COc1ccccc1-n1nc(C2CCOC(C)(C)C2)cc1-c1ccc(Cl)cc1] | 62 | 5-(4-Chlorophenyl)-3-(2,2-dimethyltetrahydro-2H-pyran-4-yl)-1-(2-methoxyphenyl)-1H-pyrazole |
| 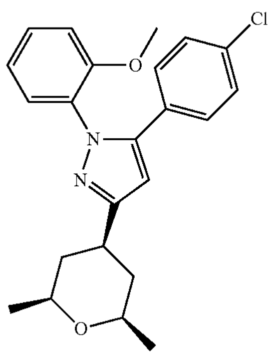 [SMILES: COc1ccccc1-n1nc([C@H]2C[C@@H](C)O[C@@H](C)C2)cc1-c1ccc(Cl)cc1] | 63 | 5-(4-Chlorophenyl-3-[(2R,4r,6S)-2,6-dimethyltetrahydro-2H-pyran-4-yl]-1-(2-methoxyphenyl)-1H-pyrazole |
| 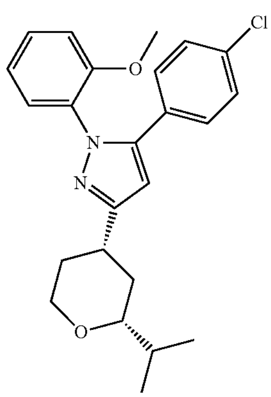 [SMILES: COc1ccccc1-n1nc([C@H]2CCO[C@@H](C(C)C)C2)cc1-c1ccc(Cl)cc1] | 64 | 5-(4-Chlorophenyl)-1-(2-methoxyphenyl)-3-[(cis)-2-(1-methylethyl)tetrahydro-2H-pyran-4-yl]-1H-pyrazole |
| 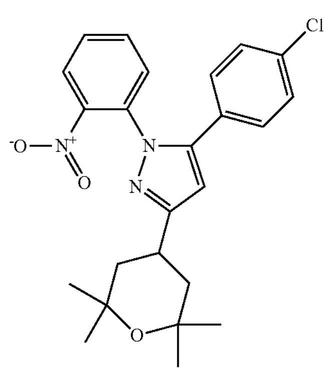 | 65 | 5-(4-Chlorophenyl)-1-(2-nitrophenyl)-3-(2,2,6,6-tetramethyltetrahydro-2H-pyran-4-yl)-1H-pyrazole |

| STRUCTURE | COMPOUND # | NAME |
|---|---|---|
| 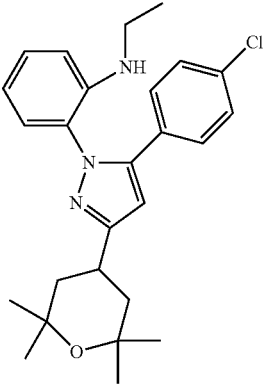 [SMILES: CCNc1ccccc1-n1nc(C2CC(C)(C)OC(C)(C)C2)cc1-c1ccc(Cl)cc1] | 66 | 2-[5-(4-Chlorophenyl)-3-(2,2,6,6-tetramethyltetrahydro-2H-pyran-4-yl)-1H-pyrazol-1-yl]-N-ethylaniline |
| 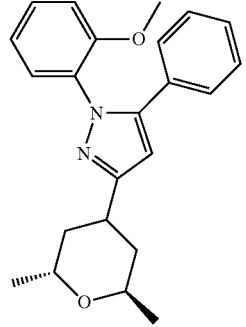 [SMILES: COc1ccccc1-n1nc(C2C[C@@H](C)O[C@H](C)C2)cc1-c1ccccc1] | 67 | 3-[(trans)-2,6-Dimethyltetrahydro-2H-pyran-4-yl]-1-(2-methoxyphenyl)-5-phenyl-1H-pyrazole |
| 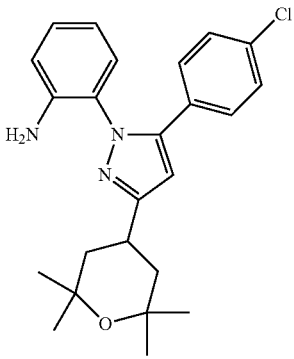 [SMILES: CC1(C)CC(c2cc(-c3ccc(Cl)cc3)n(-c3ccccc3N)n2)CC(C)(C)O1] | 68 | 2-[5-(4-Chlorophenyl)-3-(2,2,6,6-tetramethyltetrahydro-2H-pyran-4-yl)-1H-pyrazol-1-yl]aniline |
| 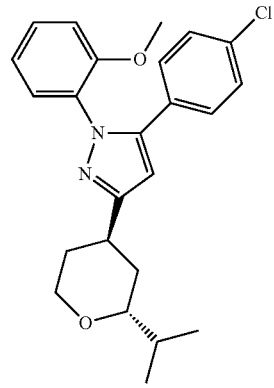 [SMILES: COc1ccccc1-n1nc([C@@H]2CCO[C@@H](C(C)C)C2)cc1-c1ccc(Cl)cc1] | 69 | 5-(4-Chlorophenyl)-1-(2-methoxyphenyl)-3-[(trans)-2-(1-methylethyl)tetrahydro-2H-pyran-4-yl]-1H-pyrazole |

TABLE 1-continued

| STRUCTURE | COMPOUND # | NAME |
|---|---|---|
| 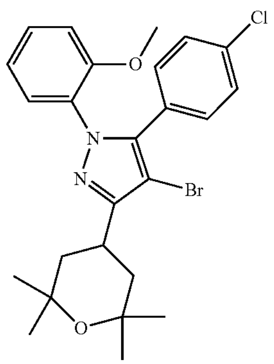 [SMILES: COc1ccccc1-n1nc(C2CC(C)(C)OC(C)(C)C2)c(Br)c1-c1ccc(Cl)cc1] | 70 | 4-Bromo-5-(4-chlorophenyl)-1-(2-methoxyphenyl)-3-(2,2,6,6-tetramethyltetrahydro-2H-pyran-4-yl)-1H-pyrazole |
| 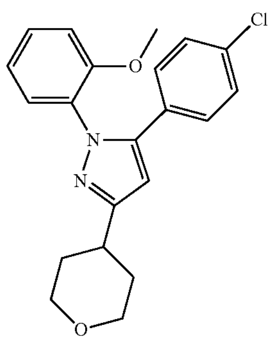 [SMILES: COc1ccccc1-n1nc(C2CCOCC2)cc1-c1ccc(Cl)cc1] | 71 | 5-(4-Chlorophenyl)-1-(2-methoxyphenyl)-3-(tetrahydro-2H-pyran-4-yl)-1H-pyrazole |
| 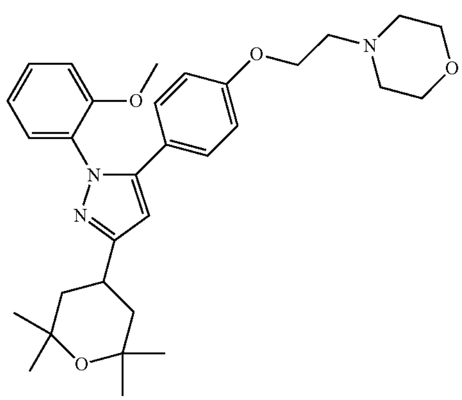 [SMILES: COc1ccccc1-n1nc(C2CC(C)(C)OC(C)(C)C2)cc1-c1ccc(OCCN2CCOCC2)cc1] | 72 | 4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine |
| 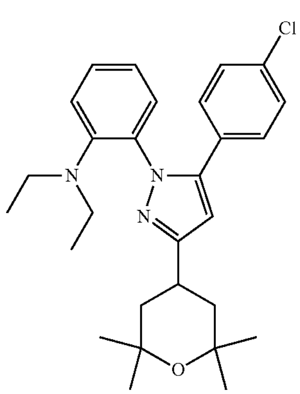 [SMILES: CCN(CC)c1ccccc1-n1nc(C2CC(C)(C)OC(C)(C)C2)cc1-c1ccc(Cl)cc1] | 73 | 2-[5-(4-Chlorophenyl)-3-(2,2,6,6-tetramethyltetrahydro-2H-pyran-4-yl)-1H-pyrazol-1-yl]-N,N-diethylaniline |

TABLE 1-continued

| STRUCTURE | COMPOUND # | NAME |
|---|---|---|
| 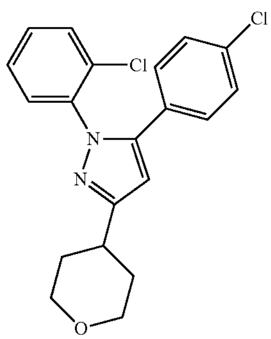 [SMILES: Clc1ccc(-c2cc(C3CCOCC3)nn2-c2ccccc2Cl)cc1] | 74 | 1-(2-Chlorophenyl)-5-(4-chlorophenyl)-3-(tetrahydro-2H-pyran-4-yl)-1H-pyrazole |
| 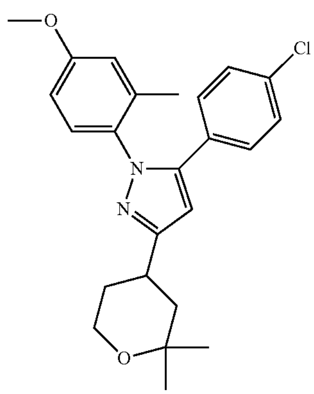 [SMILES: COc1ccc(-n2nc(C3CCOC(C)(C)C3)cc2-c2ccc(Cl)cc2)c(C)c1] | 75 | 5-(4-Chlorophenyl)-3-(2,2-dimethyltetrahydro-2H-pyran-4-yl)-1-(4-methoxy-2-methylphenyl)-1H-pyrazole |
| 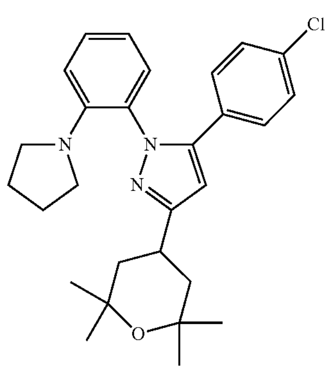 [SMILES: CC1(C)CC(c2cc(-c3ccc(Cl)cc3)n(-c3ccccc3N3CCCC3)n2)CC(C)(C)O1] | 76 | 5-(4-Chlorophenyl)-1-(2-pyrrolidin-1-ylphenyl)-3-(2,2,6,6-tetramethyltetrahydro-2H-pyran-4-yl)-1H-pyrazole |
| 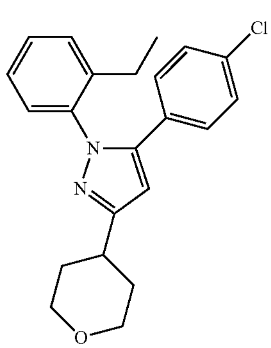 | 77 | 5-(4-Chlorophenyl)-1-(2-ethylphenyl)-3-(tetrahydro-2H-pyran-4-yl)-1H-pyrazole |

TABLE 1-continued

| STRUCTURE | COMPOUND # | NAME |
|---|---|---|
| 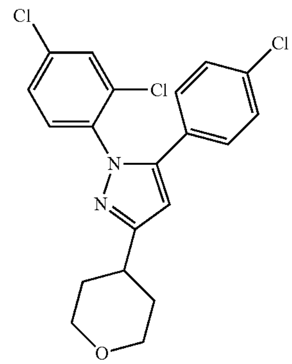 [SMILES: Clc1ccc(-c2cc(C3CCOCC3)nn2-c2ccc(Cl)cc2Cl)cc1] | 78 | 5-(4-Chlorophenyl)-1-(2,4-dichlorophenyl)-3-(tetrahydro-2H-pyran-4-yl)-1H-pyrazole |
| 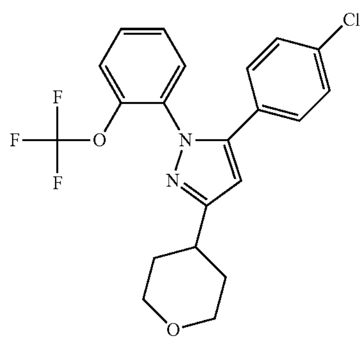 [SMILES: FC(F)(F)Oc1ccccc1-n1nc(C2CCOCC2)cc1-c1ccc(Cl)cc1] | 79 | 5-(4-Chlorophenyl)-3-(tetrahydro-2H-pyran-4-yl)-1-[2-(trifluoromethoxy)phenyl]-1H-pyrazole |
| 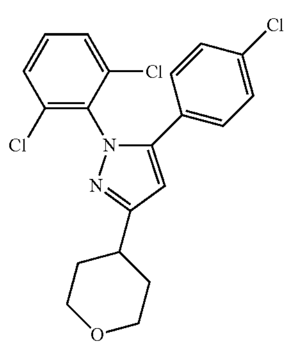 [SMILES: Clc1ccc(-c2cc(C3CCOCC3)nn2-c2c(Cl)cccc2Cl)cc1] | 80 | 5-(4-Chlorophenyl)-1-(2,6-dichlorophenyl)-3-(tetrahydro-2H-pyran-4-yl)-1H-pyrazole |
| 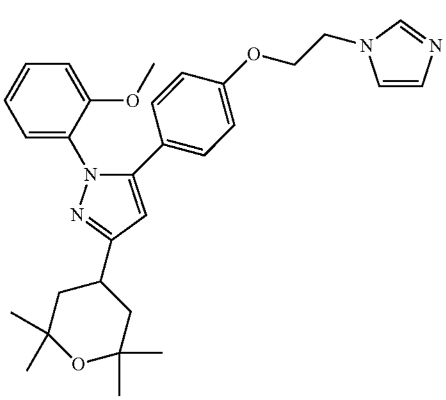 [SMILES: COc1ccccc1-n1nc(C2CC(C)(C)OC(C)(C)C2)cc1-c1ccc(OCCn2ccnc2)cc1] | 81 | 5-{4-[2-(1H-Imidazol-1-yl)ethoxy]phenyl}-1-(2-methoxyphenyl)-3-(2,2,6,6-tetramethyltetrahydro-2H-pyran-4-yl)-1H-pyrazole |

TABLE 1-continued

| STRUCTURE | COMPOUND # | NAME |
|---|---|---|
| 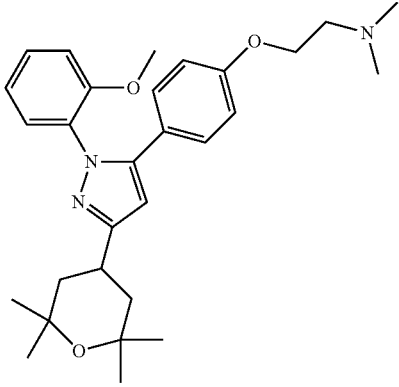 [SMILES: COc1ccccc1-n1nc(C2CC(C)(C)OC(C)(C)C2)cc1-c1ccc(OCCN(C)C)cc1] | 82 | 2-{4-[1-(2-Methoxyphenyl)-3-(2,2,6,6-tetramethyltetrahydro-2H-pyran-4-yl)-1H-pyrazol-5-yl]phenoxy}-N,N-dimethylethanamine |
| 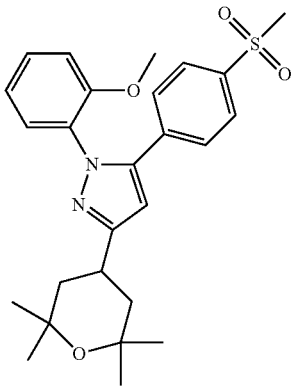 [SMILES: COc1ccccc1-n1nc(C2CC(C)(C)OC(C)(C)C2)cc1-c1ccc(S(C)(=O)=O)cc1] | 83 | 1-(2-Methoxyphenyl)-5-[4-(methylsulfonyl)phenyl]-3-(2,2,6,6-tetramethyltetrahydro-2H-pyran-4-yl)-1H-pyrazole |
| 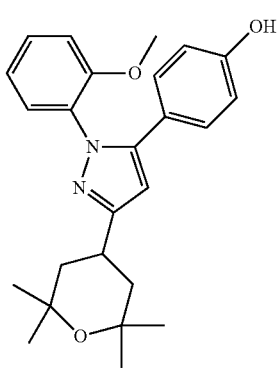 [SMILES: COc1ccccc1-n1nc(C2CC(C)(C)OC(C)(C)C2)cc1-c1ccc(O)cc1] | 84 | 4-[1-(2-Methoxyphenyl)-3-(2,2,6,6-tetramethyltetrahydro-2H-pyran-4-yl)-1H-pyrazol-5-yl]phenol |
| 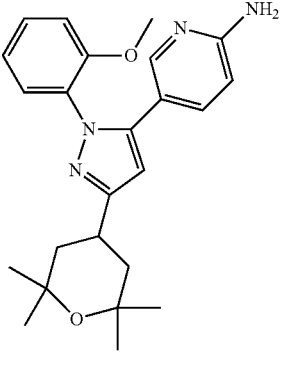 [SMILES: COc1ccccc1-n1nc(C2CC(C)(C)OC(C)(C)C2)cc1-c1ccc(N)nc1] | 85 | 5-[1-(2-Methoxyphenyl)-3-(2,2,6,6-tetramethyltetrahydro-2H-pyran-4-yl)-1H-pyrazol-5-yl]pyridin-2-amine |

TABLE 1-continued

| STRUCTURE | COMPOUND # | NAME |
|---|---|---|
| 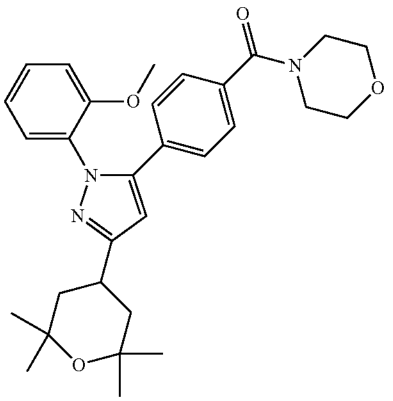 [SMILES: COc1ccccc1-n1nc(C2CC(C)(C)OC(C)(C)C2)cc1-c1ccc(C(=O)N2CCOCC2)cc1] | 86 | 4-({4-[1-(2-Methoxyphenyl)-3-(2,2,6,6-tetramethyltetrahydro-2H-pyran-4-yl)-1H-pyrazol-5-yl]phenyl}carbonyl)morpholine |
| 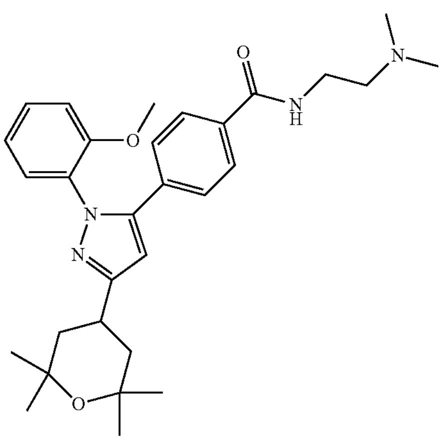 [SMILES: COc1ccccc1-n1nc(C2CC(C)(C)OC(C)(C)C2)cc1-c1ccc(C(=O)NCCN(C)C)cc1] | 87 | N-[2-(Dimethylamino)ethyl]-4-[1-(2-methoxyphenyl)-3-(2,2,6,6-tetramethyltetrahydro-2H-pyran-4-yl)-1H-pyrazol-5-yl]benzamide |
| 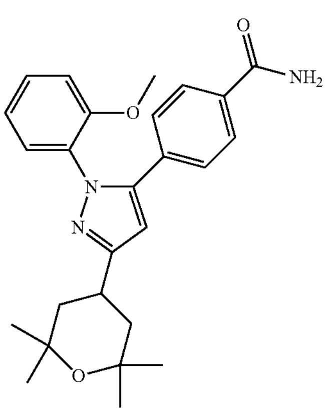 [SMILES: COc1ccccc1-n1nc(C2CC(C)(C)OC(C)(C)C2)cc1-c1ccc(C(N)=O)cc1] | 88 | 4-[1-(2-Methoxyphenyl)-3-(2,2,6,6-tetramethyltetrahydro-2H-pyran-4-yl)-1H-pyrazol-5-yl]benzamide |

TABLE 1-continued

| STRUCTURE | COMPOUND # | NAME |
|---|---|---|
| 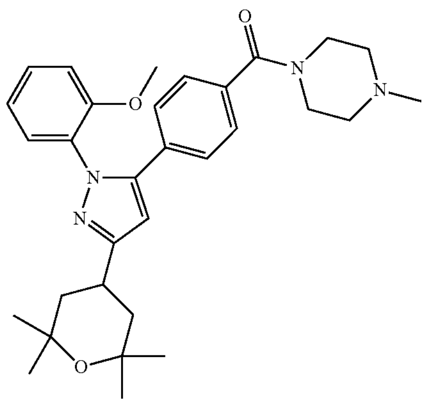 [SMILES: COc1ccccc1-n1nc(C2CC(C)(C)OC(C)(C)C2)cc1-c1ccc(C(=O)N2CCN(C)CC2)cc1] | 89 | 1-({4-[1-(2-Methoxyphenyl)-3-(2,2,6,6-tetramethyltetrahydro-2H-pyran-4-yl)-1H-pyrazol-5-yl]phenyl}carbonyl)-4-methylpiperazine |
| 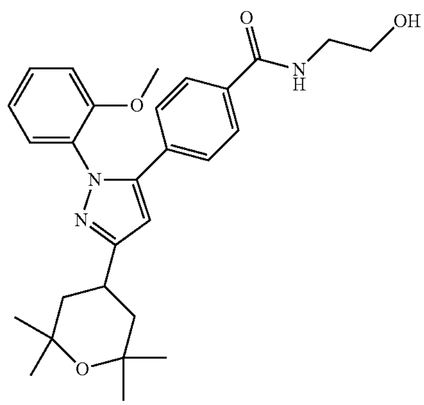 [SMILES: COc1ccccc1-n1nc(C2CC(C)(C)OC(C)(C)C2)cc1-c1ccc(C(=O)NCCO)cc1] | 90 | N-(2-Hydroxyethyl)-4-[1-(2-methoxyphenyl)-3-2,2,6,6-tetramethyltetrahydro-2H-pyran-4-yl)-1H-pyrazol-5-yl]-benzamide |
| 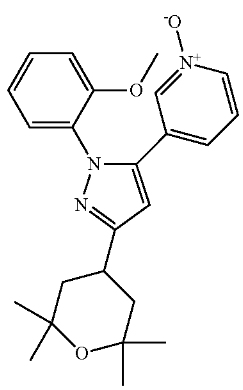 | 91 | 3-[1-(2-Methoxyphenyl)-3-(2,2,6,6-tetramethyltetrahydro-2H-pyran-4-yl)-1H-pyrazol-5-yl]-pyridine-1-oxide |
| 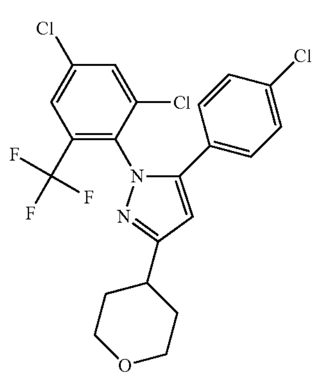 [SMILES: FC(F)(F)c1cc(Cl)cc(Cl)c1-n1nc(C2CCOCC2)cc1-c1ccc(Cl)cc1] | 92 | 5-(4-Chlorophenyl)-1-[2,4-dichloro-6-(trifluoromethyl)phenyl]-3-(tetrahydro-2H-pyran-4-yl)-1H-pyrazole |

TABLE 1-continued

| STRUCTURE | COMPOUND # | NAME |
|---|---|---|
| 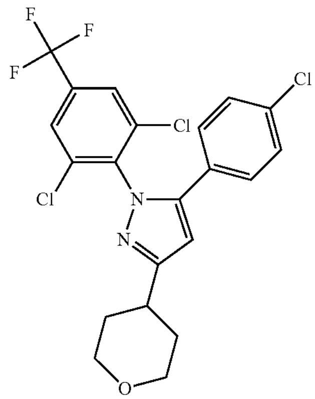 [SMILES: FC(F)(F)c1cc(Cl)c(-n2nc(C3CCOCC3)cc2-c2ccc(Cl)cc2)c(Cl)c1] | 93 | 5-(4-Chlorophenyl)-1-[2,6-dichloro-4-(trifluoromethyl)phenyl]-3-(tetrahydro-2H-pyran-4-yl)-1H-pyrazole |
| 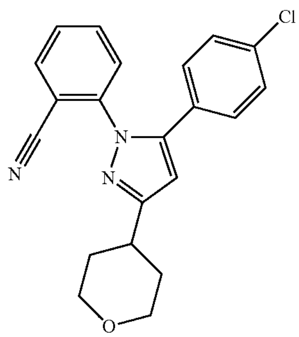 [SMILES: N#Cc1ccccc1-n1nc(C2CCOCC2)cc1-c1ccc(Cl)cc1] | 94 | 2-[5-(4-Chlorophenyl)-3-(tetrahydro-2H-pyran-4-yl)-1H-pyrazol-1-yl]benzonitrile |
| 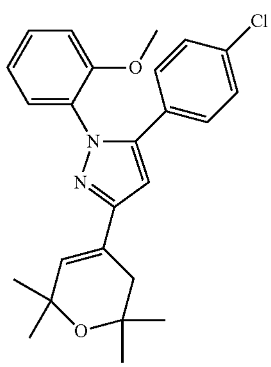 [SMILES: COc1ccccc1-n1nc(C2=CC(C)(C)OC(C)(C)C2)cc1-c1ccc(Cl)cc1] | 95 | 5-(4-Chlorophenyl)-1-(2-methoxyphenyl)-3-(2,2,6,6-tetramethyl-3,6-dihydro-2H-pyran-4-yl)-1H-pyrazole |
| 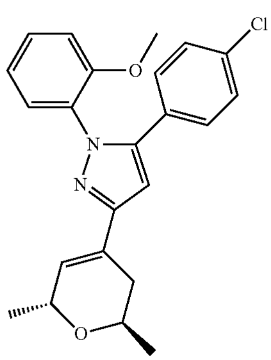 [SMILES: COc1ccccc1-n1nc(C2=C[C@@H](C)O[C@H](C)C2)cc1-c1ccc(Cl)cc1] | 96 | 5-(4-Chlorophenyl)-3-[(trans)-2,6-dimethyl-3,6-dihydro-2H-pyran-4-yl]-1-(2-methoxyphenyl)-1H-pyrazole |

TABLE 1-continued

| STRUCTURE | COMPOUND # | NAME |
|---|---|---|
| 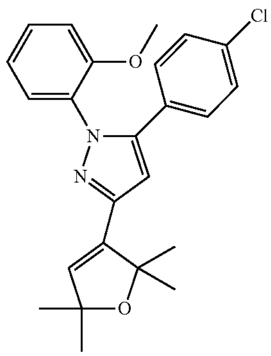 [SMILES: COc1ccccc1-n1nc(C2=CC(C)(C)OC2(C)C)cc1-c1ccc(Cl)cc1] | 97 | 5-(4-Chlorophenyl)-1-(2-methoxyphenyl)-3-(2,2,5,5-tetramethyl-2,5-dihydrofuran-3-yl)-1H-pyrazole |
| 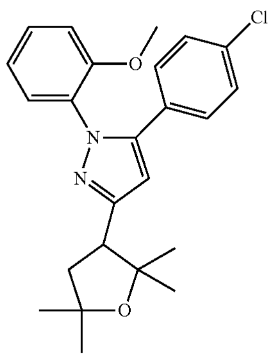 [SMILES: COc1ccccc1-n1nc(C2CC(C)(C)OC2(C)C)cc1-c1ccc(Cl)cc1] | 98 | 5-(4-Chlorophenyl)-1-(2-methoxyphenyl)-3-(2,2,5,5-tetramethyltetrahydrofuran-3-yl)-1H-pyrazole |

C) Synthesis

The invention provides methods of making the disclosed compounds according to traditional organic synthetic methods as well as matrix or combinatorial synthetic methods. Schemes A, B and C describe suggested synthetic routes. Using the scheme, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Representative compounds of the present invention can be synthesized in accordance with the general synthetic schemes described below and are illustrated more particularly in the specific synthetic examples that follow. The general schemes are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

General: 1H and 13C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ESI) were recorded in the positive mode on a Hewlett Packard 59987A spectrometer. High resolution mass spectra (HRMS) were obtained on a Micromass Autospec. E spectrometer by fast atom bombardment (FAB) technique.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Schemes A, B and C, and Examples 1 through 72. Compounds analogous to the target compounds of these examples can be made according to similar routes. The disclosed compounds are useful as pharmaceutical agents as described herein.

Abbreviations or acronyms useful herein include:

| Abbreviation | Meaning |
| --- | --- |
| BOC | tert-butyloxycarbonyl |
| BOP | benzotriazol-1-yloxy-tris(dimethylamino)phosphonium hexafluorophosphate |
| Cpd | compound |
| DCE | dichloroethane |
| DPPF | 1,1'-Bis(diphenylphosphino)ferrocene |
| DCM | dichloromethane |
| DMAP | dimethylaminopyridine |
| DMF | N,N-dimethylformamide |
| DMSO | dimethyl sulfoxide |
| DIEA | N,N-diisopropylethylamine or Hünig's base |
| EDC | 1-(3-dimethylaminopropyl)-3-ethylcarbodiimide hydrochloride |
| ESI | Electrospray Ionization |
| Et$_3$N or TEA | triethylamine |
| EtOAc | ethyl acetate |
| h/hr/hrs | hour(s) |
| HOBT | 1-hydroxybenzotriazole hydrate |
| HBTU | O-benzotriazol-1-yloxy-N,N,N',N'-tetramethyluronium hexafluorophosphate |
| LiOH | lithium hydroxide |
| MgSO$_4$ | magnesium sulfate |
| min | minute(s) |
| MS | mass spectroscopy |
| NMR | nuclear magnetic resonance spectroscopy |
| Na$_2$SO$_4$ | sodium sulfate |
| PG | protecting group |
| RT/rt | room temperature |
| RP-HPLC | reversed-phase high performance liquid chromatography |
| TFA | trifluoroacetic acid |
| THF | tetrahydrofuran |
| TLC | thin layer chromatography |
| Tos | p-toluenesulfonyl |

General Guidance

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art. The substituents for compounds of Formula (I) or a form thereof, represented in the schemes below, are as previously defined herein.

The compounds of Formula (I), wherein $X_1$, $X_2$, $X_3$, $X_4$ $R_1$, $R_2$, $R_3$, $R_4$, and Q are defined as in Formula (I), may be synthesized as outlined by the general synthetic route illustrated in Scheme A.

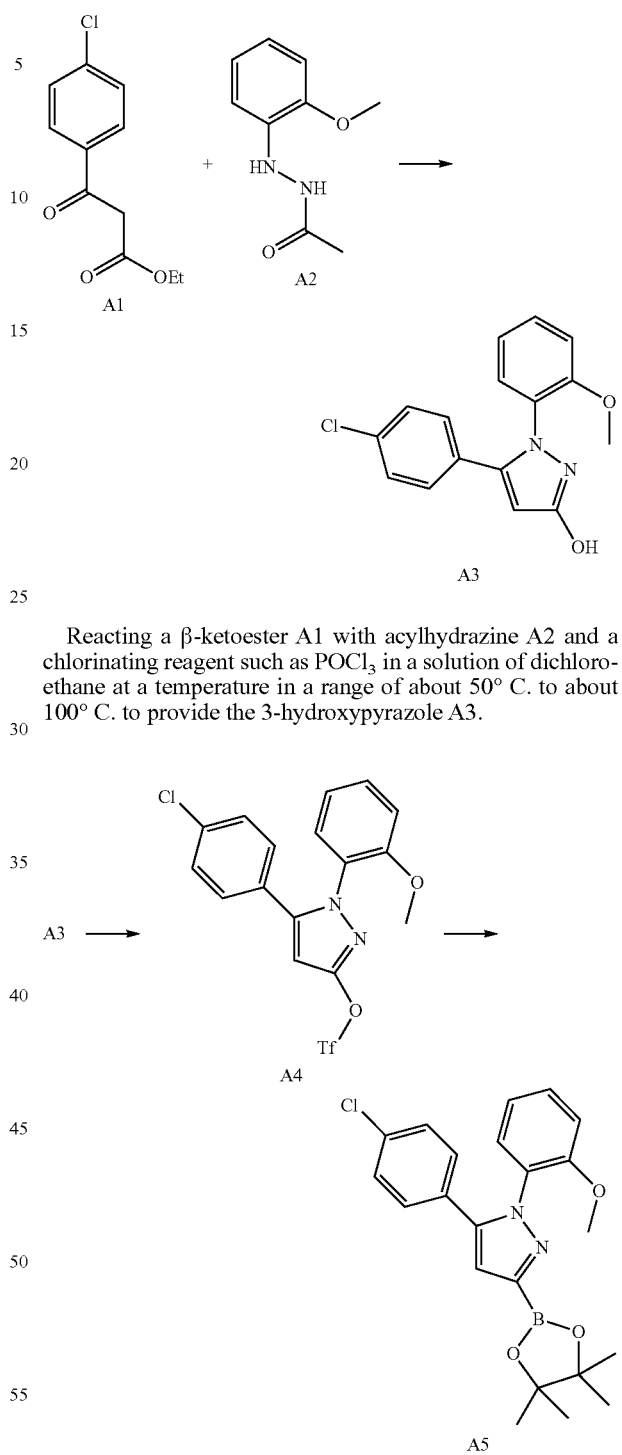

Reacting a β-ketoester A1 with acylhydrazine A2 and a chlorinating reagent such as POCl$_3$ in a solution of dichloroethane at a temperature in a range of about 50° C. to about 100° C. to provide the 3-hydroxypyrazole A3.

Converting the 3-hydroxypyrazole A3 in the presence of Hünig's base and a triflating agent such as N,N-bis(trifluoromethylsulfonyl)-aniline in a dichloroethane solvent at a temperature in a range of from about 50° C. to about 100° C. to provide the triflate A4. Converting the triflate A4 to a pyrazole-3-boronate ester A5 in the presence of bis(pinacolato)diboron using an appropriate Pd catalyst such as Pd(DPPF)Cl$_2$. A5 may also be a bis(neopentyl glycolato) ester, formed using bis(neopentyl gylcoato)diboron.

A5 ⟶ 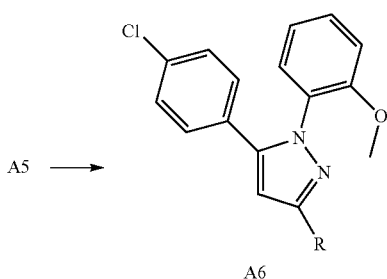

A6

Reacting the pyrazole-3-boronate ester A5 with the appropriate heteroaryl halide R—X under standard Suzuki coupling conditions using an appropriate Pd catalyst (Pd(PPh$_3$)$_4$) in a toluene/ethanol solution including Na$_2$CO$_3$ to provide a Compound A6, representative of a compound of Formula (I).

A4 ⟶ 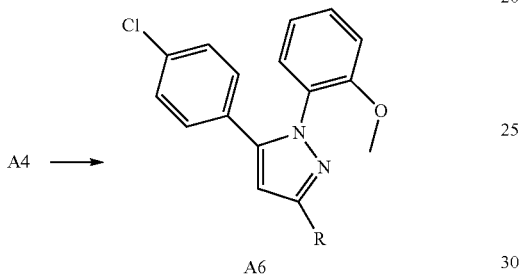

A6

Alternatively, where the appropriate heteroaryl halide was not available, reacting the triflate A4 with the appropriate boronic acid analog R—B(OH)$_2$ under standard Suzuki coupling conditions using an appropriate Pd catalyst (Pd(PPh$_3$)$_4$) in a toluene/ethanol solution including Na$_2$CO$_3$ to provide a Compound A6, representative of a compound of Formula (I).

The compounds of Formula (I), wherein $X_1$, $X_2$, $X_3$, $X_4$, $R_1$, $R_2$, $R_3$, $R_4$, and Q are defined as in Formula (I), may be synthesized as outlined by the general synthetic route illustrated in Scheme B.

Scheme B

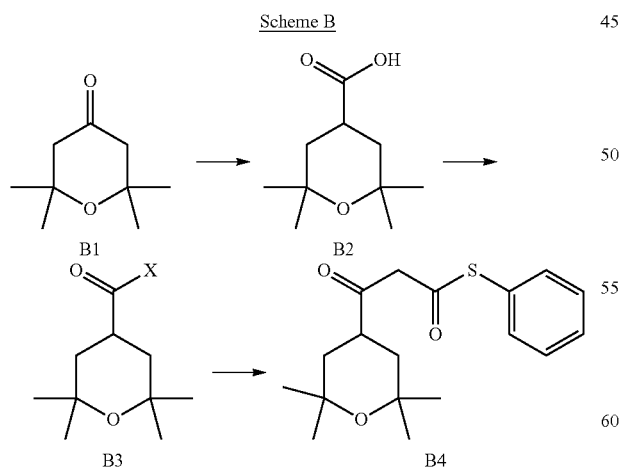

Reacting a ketone such as 2,2,6,6-tetramethyldihydro-2H-pyran-4(3H)-one B1 with toluenesulfonylmethyl isocyanide in the presence of an appropriate base such as potassium t-butoxide in a solvent such as DCE at a temperature range of 0° C. to 50° C. provides an intermediate cyano compound, which can then be hydrolyzed to the add B2 by refluxing in an aqueous KOH solution. Compound B2 is subsequently converted to the acid chloride B3 (X=Cl) by reacting B2 with an appropriate reagent such as oxalyl chloride or more preferably to a benzotriazole amide B3 (X=benzotriazole) by reacting B2 with benzotriazole and thionyl chloride in a solvent such as DCE at RT. Reacting B3 in the presence of Hünig's base with acylthiophenol in a DCM solution containing an appropriate Lewis acid such as MgBr$_2$ provides Compound B4 (Org. Lett., 2007, 9(21), pp. 4139-4142).

B4 ⟶ 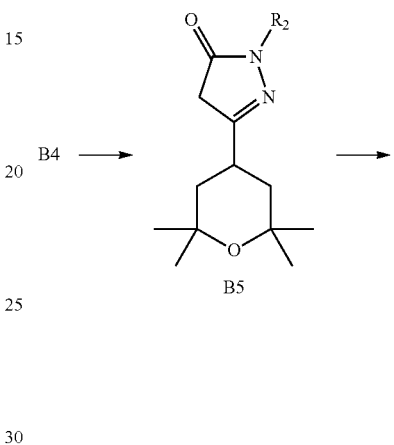 ⟶

B5

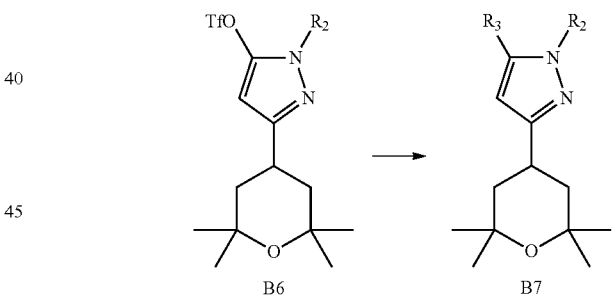

B6        B7

Reacting Compound B4 with R$_2$-hydrazine hydrochloride in a methanol solution to provide Compound B5, and then converting the Compound B5 in the presence of Hünig's base and a triflating agent such as N,N-bis-(trifluoromethyl-sulfonyl)-aniline in a dichloroethane solvent at a temperature in a range of about 50° C. to about 100° C. to provide the triflate B6.

Finally, reacting the triflate B6 with the appropriate heteroaryl halide R$_3$—X under standard Suzuki coupling conditions using an appropriate Pd catalyst (Pd(PPh$_3$)$_4$) in a toluene/ethanol solution including Na$_2$CO$_3$ to provide a Compound B7, representative of a compound of Formula (I).

The compounds of Formula (I), wherein $X_1$, $X_2$, $X_3$, $X_4$, $R_1$, $R_2$, $R_3$, $R_4$, and Q are defined as in Formula (I), may be synthesized as outlined by the general synthetic route illustrated in Scheme C.

Scheme C

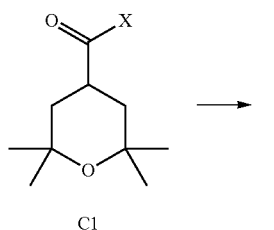

C1

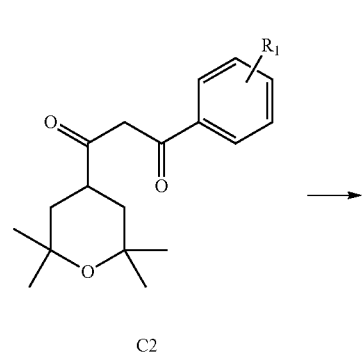

C2

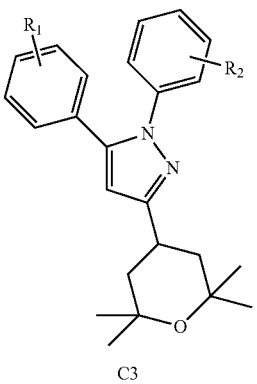

C3

Compounds C1 where X is an appropriate leaving group such as chloride or more preferably benzotriazole may be obtained as described in Scheme B. C1 is then converted to a diketone C2 (which may exist in the enone form) by reacting C1 with an appropriate $R_1$-acetophenone in the presence of a base such as DIEA and a Lewis acid such as $MgBr_2$ in a solvent such as DCE at RT (Org. Lett., 2007, 9(21), pp. 4139-4142). Pyrazoles C3 are then obtained by reaction of the diketone C2 with a $R_2$-hydrazine hydrochloride in a solvent such as methanol and a base such as TEA at a temperature between RT and 80° C. to provide Compound C3 that is representative of a compound of Formula (I).

EXAMPLES

The following examples are offered by way of illustration; the invention should not be construed as being limited by the chemical reactions and conditions expressed.

Example 1

5-(4-Chloro-phenyl)-1-(2-methoxy-phenyl)-3-(2,2,6,6-tetramethyl-tetrahydro-pyran-4-yl)-1H-pyrazole

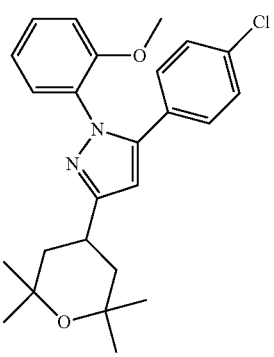 [SMILES: COc1ccccc1-n1nc(C2CC(C)(C)OC(C)(C)C2)cc1-c1ccc(Cl)cc1]

Step A)
2,2,6,6-Tetramethyl-tetrahydro-pyran-4-carboxylic acid

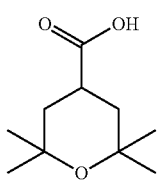

To a solution of 2,2,6,6-tetramethyl-tetrahydro-pyran-4-one (3.00 g, 19.20 mmol), p-toluenesulfonylmethyl isocyanide (4.90 g, 24.96 mmol), and t-butanol (3.06 mL, 32.64 mmol) in 75 mL dimethoxyethane at 0° C. was added potassium t-butoxide (5.38 g, 48.01 mmol) at such a rate that the temperature did not increase above 10° C. After addition was complete the mixture was allow to attain RT and then heated at 35° C. overnight. The mixture was then cooled to RT and 50 mL of diethyl ether was added and the mixture was filtered. The filtrate was concentrated and redissolved in 50 mL of diethyl ether and filtered to remove the ppt. The filtrate was again concentrated and then dissolved in 50 mL of 2.25 M KOH and refluxed overnight. The mixture was cooled and washed with 2×50 mL of DCM. The pH of the aqueous layer was then adjusted to 2 with conc HCl and the product extracted with EtOAc (2×50 mL). The organic phase was dried over $Na_2SO_4$, filtered and concentrated to give 2.85 g (80%) of the title compound as an off-white solid which was used without further purification.

¹H NMR (CHLOROFORM-d) δ: 2.78 (tt, J=12.9, 3.3 Hz, 1H), 1.77 (dd, J=12.9, 3.3 Hz, 2H), 1.39 (t, J=12.9 Hz, 2H), 1.20 (s, 6H), 1.17 (s, 6H).

Step B) Benzotriazol-1-yl-(2,2,6,6-tetramethyl-tetrahydro-pyran-4-yl)-methanone

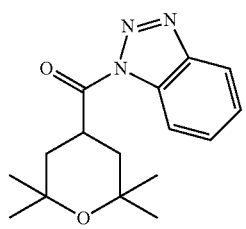 [SMILES: CC1(C)CC(C(=O)n2nnc3ccccc32)CC(C)(C)O1]

To a mixture of 2,2,6,6-tetramethyl-tetrahydro-pyran-4-carboxylic acid (1.4 g, 6.8 mmol) and benzotriazole (2.4 g, 20.3 mmol) in 34 mL of DCM was added thionyl chloride (0.55 mL, 7.4 mmol) dropwise and the mixture was allowed to stir for 8 hrs at RT. The mixture was filtered to remove the ppt and the filtrate washed with saturated NaHCO₃ (2×40 mL) and then brine (50 mL). The organic layer was dried over Na₂SO₄ and concentrated to give 1.9 g (97%) of a white ppt.

¹H NMR (CHLOROFORM-d) δ: 8.23 (d, J=8.3 Hz, 1H), 8.07 (d, J=8.3 Hz, 1H), 7.60 (ddd, J=8.3, 7.2, 1.0 Hz, 1H), 7.46 (ddd, J=8.3, 7.2, 1.0 Hz, 1H), 4.39 (tt, J=12.8, 3.3 Hz, 1H), 1.93 (dd, J=12.8, 3.3 Hz, 2H), 1.69 (t, J=12.8 Hz, 2H), 1.36 (s, 6H), 1.22 (s, 6H).

Step C) 3-Oxo-3-(2,2,6,6-tetramethyl-tetrahydro-pyran-4-yl)-thiopropionic acid S-phenyl ester

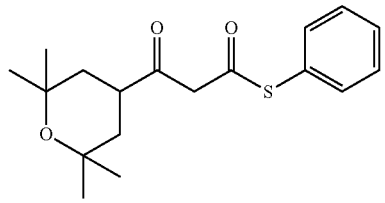 [SMILES: CC1(C)CC(C(=O)CC(=O)Sc2ccccc2)CC(C)(C)O1]

To a mixture of benzotriazol-1-yl-(2,2,6,6-tetramethyl-tetrahydro-pyran-4-yl)-methanone (1.70 g, 5.62 mmol), magnesium bromide diethyl etherate (4.14 g, 16.06 mmol), and S-phenyl thioacetate (0.76 mL, 5.35 mmol) in 21 mL of DCM at RT was added dropwise DIEA (3.95 mL, 21.41 mmol). The mixture was stirred overnight and then diluted with 50 mL of DCM and washed with 1N HCl (100 mL) and brine (100 mL). The organic layer was dried over Na₂SO₄, concentrated, and the residue purified by flash chromatography on silica gel to give 1.2 g (70%) of a colorless oil. Mass spectrum (ESI, m/z): Calculated for $C_{18}H_{24}O_3S$, 321.1 (M+H), found 321.1.

Step D) 2-(2-Methoxy-phenyl)-5-(2,2,6,6-tetramethyl-tetrahydro-pyran-4-yl)-2,4-dihydro-pyrazol-3-one

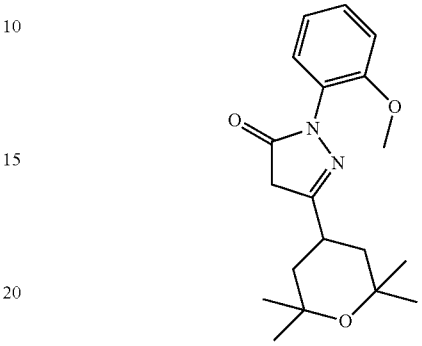

A solution of 3-oxo-3-(2,2,6,6-tetramethyl-tetrahydro-pyran-4-yl)-thiopropionic acid S-phenyl ester (1.20 g, 3.75 mmol) and 2-methoxyphenylhyradrazine hydrochloride (0.72 g, 4.12 mmol) in 10 mL of ethanol was heated to 80° C. for 4 hrs. The mixture was concentrated and the residue dissolved in EtOAc (100 mL) and washed with brine. The residue was purified by flash chromatography to give 1.0 g (81%) of title compound as a white solid.

¹H NMR (CHLOROFORM-d) δ: 7.32-7.39 (m, 2H), 7.01-7.06 (m, 2H), 3.87 (s, 3H), 3.40 (s, 2H), 3.05 (tt, J=12.9, 3.3 Hz, 1H), 1.84 (dd, J=12.9, 3.3 Hz, 2H), 1.45 (t, J=12.9 Hz, 2H), 1.33 (s, 6H), 1.27 (s, 6H).

Step E) Trifluoro-methanesulfonic acid 2-(2-methoxy-phenyl)-5-(2,2,6,6-tetramethyl-tetrahydro-pyran-4-yl)-2H-pyrazol-3-yl ester

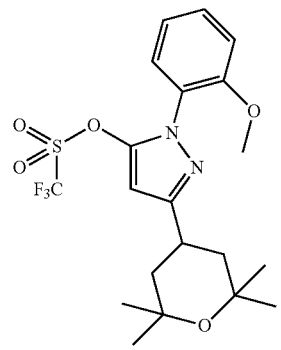 [SMILES: COc1ccccc1-n1nc(C2CC(C)(C)OC(C)(C)C2)cc1OS(=O)(=O)C(F)(F)F]

A mixture of 2-(2-methoxy-phenyl)-5-(2,2,6,6-tetramethyl-tetrahydro-pyran-4-yl)-2,4-dihydro-pyrazol-3-one (1.00 g, 3.03 mmol), triethylamine (0.63 mL, 4.54 mmol), and N-phenyl-bis-trifluoromethanesulfonimide (1.19 g, 3.33 mmol) was heated at 60° C. for 2 hrs in 10 mL of dichloroethane. The reaction was diluted with 50 mL of EtOAc and washed with NaHCO3 (50 mL) and brine (50 mL). The residue was purified by flash chromatography on silica gel to give 1.40 g (95%) of the title compound as a colorless oil.

¹H NMR (CHLOROFORM-d) δ: 7.46 (m, 1H), 7.42 (dd, J=7.8, 1.5 Hz, 1H), 7.09 (m, 1H), 7.05 (dd, J=8.3, 0.8 Hz, 1H), 6.12 (s, 1H), 3.85 (s, 3H), 3.26 (tt, J=12.8, 3.4 Hz, 1H), 1.94 (dd, J=13.1, 3.3 Hz, 2H), 1.53 (t, J=12.8 Hz, 2H), 1.35 (s, 6H), 1.28 (s, 6H).

Step F) 5-(4-Chloro-phenyl)-1-(2-methoxy-phenyl)-3-(2,2,6,6-tetramethyl-tetrahydro-pyran-4-yl)-1H-pyrazole A flask is charged with trifluoromethanesulfonic acid 2-(2-methoxy-phenyl)-5-(2,2,6,6-tetramethyl-tetrahydro-pyran-4-yl)-2H-pyrazol-3-yl ester (1.10 g, 3.70 mmol), 4-chlorophenyl boronic acid (0.630 g, 4.07 mmol), Pd(PPh$_3$)$_4$ (0.24 g, 5 mol %), 2 M Na$_2$CO$_3$ (16 mL), EtOH (16 mL) and toluene (32 mL) and heated at 80° C. for 6 h. The reaction was diluted with EtOAc (100 mL) and washed with saturated aqueous NaHCO$_3$ (2×100 mL) and brine (100 mL), and the organic layer dried over Na$_2$SO$_4$ and evaporated. The crude product was purified by flash silica gel chromatography eluting with 10% EtOAc/hexanes to give 0.68 g (66%) of the title compound as a white solid.

$^1$H NMR (CHLOROFORM-d) δ: 7.35 (dd, J=7.8, 1.6 Hz, 1H), 7.27 (td, J=7.8, 1.8 Hz, 1H), 7.11-7.15 (m, 2H), 7.03-7.08 (m, 2H), 6.96 (td, J=7.8, 1.6 Hz, 1H), 6.79 (dd, J=7.8, 1.8 Hz, 1H), 6.29 (s, 1H), 3.40 (s, 3H), 3.26 (tt, J=12.9, 3.3 Hz, 1H), 1.90 (dd, J=12.9, 3.3 Hz, 2H), 1.50 (t, 3H), 1.28 (s, 6H), 1.19 (s, 6H). Mass spectrum (ESI, m/z): Calculated for C$_{25}$H$_{29}$ClN$_2$O$_2$, 425.2 (M+H), found 425.1.

Example 2

4-[1-(2-Methoxyphenyl)-3-(2,2,6,6-tetramethyltetrahydro-2H-pyran-4-yl)-1H-pyrazol-5-yl]-benzonitrile

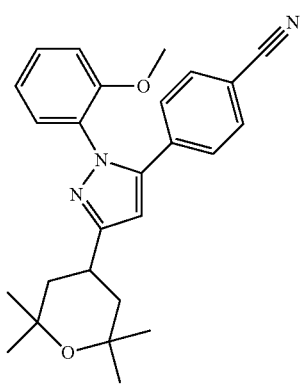 [SMILES: COc1ccccc1-n1nc(C2CC(C)(C)OC(C)(C)C2)cc1-c1ccc(C#N)cc1]

Prepared according to the procedure in Example 1.

$^1$H NMR (CHLOROFORM-d) δ: 7.50-7.58 (m, 2H), 7.47 (dd, J=7.7, 1.6 Hz, 1H), 7.34-7.42 (m, J=8.0, 8.0, 1.8 Hz, 1H), 7.29-7.33 (m, 2H), 7.07 (td, J=7.6, 1.3 Hz, 1H), 6.88 (dd, J=8.3, 1.3 Hz, 1H), 6.46 (s, 1H), 3.45 (s, 3H), 3.30-3.41 (m, 1H), 1.99 (dd, J=13.3, 3.4 Hz, 2H), 1.59 (t, J=12.8 Hz, 2H), 1.37 (s, 6H), 1.27 (s, 6H). Mass spectrum (ESI, m/z): Calculated for C$_{26}$H$_{29}$N$_3$O$_2$, 415.5 (M+H), found 415.1.

Example 3

5-(4-Chloro-2-fluorophenyl)-1-(2-methoxyphenyl)-3-(2,2,6,6-tetramethyltetrahydro-2H-pyran-4-yl)-1H-pyrazole

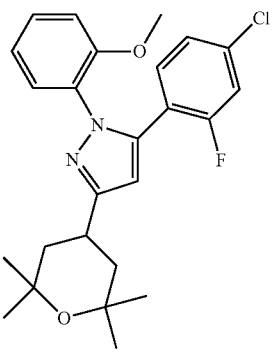 [SMILES: COc1ccccc1-n1nc(C2CC(C)(C)OC(C)(C)C2)cc1-c1ccc(Cl)cc1F]

Prepared according to the procedure in Example 1.

$^1$H NMR (CHLOROFORM-d) δ: 7.45 (dd, J=7.8, 1.8 Hz, 1H), 7.33 (s, 1H), 7.07-7.13 (m, 1H), 7.02 (d, J=1.3 Hz, 1H), 6.96-7.00 (m, 2H), 6.84 (dd, J=8.3, 1.0 Hz, 1H), 6.43 (d, 1H), 3.51 (s, 3H), 3.31-3.42 (m, 1H), 2.00 (dd, J=13.3, 3.4 Hz, 2H), 1.59 (t, J=12.9 Hz, 2H), 1.37 (s, 6H), 1.29 (s, 6H)). Mass spectrum (ESI, m/z): Calculated for C$_{25}$H$_{28}$ClN$_2$O$_2$, 443.2 (M+H), found 443.1.

Example 4

5-(1,3-Benzodioxol-5-yl)-1-(2-methoxyphenyl)-3-(2,2,6,6-tetramethyltetrahydro-2H-pyran-4-yl)-1H-pyrazole

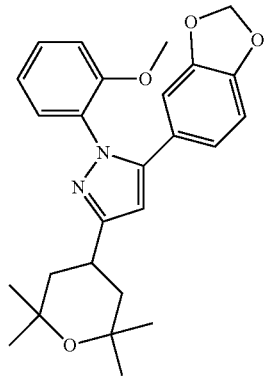 [SMILES: COc1ccccc1-n1nc(C2CC(C)(C)OC(C)(C)C2)cc1-c1ccc2c(c1)OCO2]

Prepared according to the procedure in Example 1.

$^1$H NMR (CHLOROFORM-d) δ: 7.32-7.43 (m, 2H), 7.02 (td, J=7.6, 1.3 Hz, 1H), 6.91 (dd, J=8.3, 1.0 Hz, 1H), 6.64-6.74 (m, 3H), 6.31 (s, 1H), 5.93 (s, 2H), 3.57 (s, 3H), 3.27-3.40 (m, 1H), 1.99 (dd, J=13.3, 3.4 Hz, 2H), 1.53-1.66 (m,

2H), 1.37 (s, 6H), 1.28 (s, 6H). Mass spectrum (ESI, m/z): Calculated for $C_{26}H_{30}N_2O_4$, 435.2 (M+H), found 435.2.

Example 5

1-(2-Methoxyphenyl)-5-(4-methoxyphenyl)-3-(2,2,6,6-tetramethyltetrahydro-2H-pyran-4-yl)-1H-pyrazole

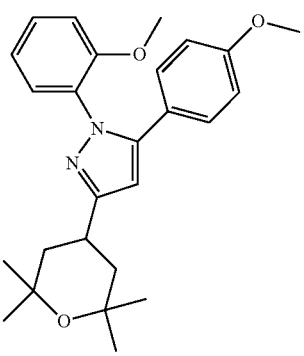

Prepared according to the procedure in Example 1.

$^1$H NMR (CHLOROFORM-d) δ: 7.40 (dd, J=7.7, 1.6 Hz, 1H), 7.32 (td, J=7.9, 1.6 Hz, 1H), 7.10-7.15 (m, 2H), 7.00 (td, J=7.6, 1.3 Hz, 1H), 6.84-6.89 (m, J=8.3, 1.0 Hz, 1H), 6.73-6.78 (m, 2H), 6.31 (s, 1H), 3.75 (s, 3H), 3.48 (s, 3H), 3.29-3.38 (m, 1H), 1.99 (dd, J=13.3, 3.4 Hz, 2H), 1.59 (t, J=12.9 Hz, 2H), 1.36 (s, 6H), 1.26 (s, 6H). Mass spectrum (ESI, m/z): Calculated for $C_{26}H_{32}N_2O_3$, 421.2 (M+H), found 421.1.

Example 6

1-(2-Methoxyphenyl)-5-[4-(methylsulfanyl)phenyl]-3-(2,2,6,6-tetramethyltetrahydro-2H-pyran-4-yl)-1H-pyrazole

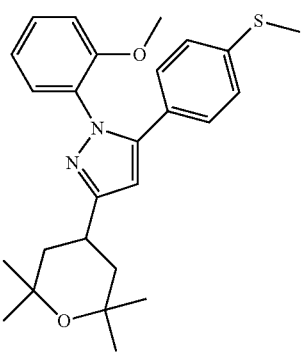

Prepared according to the procedure in Example 1.

$^1$H NMR (CHLOROFORM-d) δ: 7.42 (dd, J=7.7, 1.6 Hz, 1H), 7.31-7.37 (m, 1H), 7.07-7.15 (m, 4H), 6.99-7.05 (m, 1H), 6.88 (d, J=7.6 Hz, 1H), 6.36 (s, 1H), 3.49 (s, 3H), 3.35 (s, 1H), 2.45 (s, 3H), 1.99 (dd, J=13.1, 3.3 Hz, 2H), 1.59 (t, J=12.9 Hz, 2H), 1.36 (s, 6H), 1.28 (s, 6H). Mass spectrum (ESI, m/z): Calculated for $C_{26}H_{32}N_2O_2S$, 437.1 (M+H), found 437.1.

Example 7

5-(4-Chlorophenyl)-1-[2-(1-methylethoxy)phenyl]-3-(2,2,6,6-tetramethyltetrahydro-2H-pyran-4-yl)-1H-pyrazole

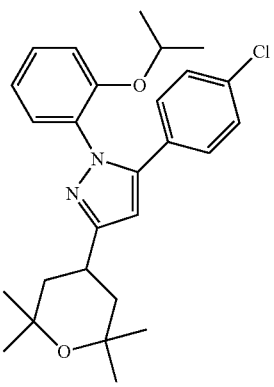 [SMILES: CC(C)Oc1ccccc1-n1nc(C2CC(C)(C)OC(C)(C)C2)cc1-c1ccc(Cl)cc1]

Prepared according to the procedure in Example 1.

$^1$H NMR (CHLOROFORM-d) δ: 7.44 (dd, J=7.8, 1.8 Hz, 1H), 7.17-7.28 (m, 1H), 7.05-7.15 (m, 4H), 6.92-7.00 (m, 1H), 6.74 (d, J=7.8 Hz, 1H), 6.26 (s, 1H), 4.13 (spt, J=6.0 Hz, 1H), 3.24 (tt, J=12.8, 3.3 Hz, 1H), 1.88 (dd, J=13.3, 3.4 Hz, 2H), 1.45-1.53 (m, 2H), 1.28 (s, 6H), 1.19 (s, 6H) Mass spectrum (ESI, m/z): Calculated for $C_{27}H_{33}ClN_2O_2$, 453.2 (M+H), found 453.2.

Example 8

5-(4,4-Dimethylcyclohex-1-en-1-yl)-1-(2-methoxyphenyl)-3-(2,2,6,6-tetramethyltetrahydro-2H-pyran-4-yl)-1H-pyrazole

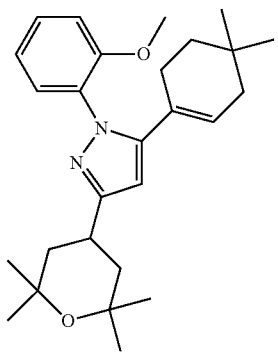

Prepared according to the procedure in Example 1.

$^1$H NMR (CHLOROFORM-d) δ: 7.32-7.41 (m, 2H), 6.99-7.06 (m, 1H), 6.89-6.98 (m, 1H), 6.14 (s, 1H), 5.44-5.53 (m, 1H), 3.74 (s, 3H), 3.20-3.35 (m, 1H), 2.13-2.22 (m, J=6.3, 4.3, 2.1, 2.1 Hz, 2H), 1.95 (dd, J=13.1, 3.3 Hz, 2H), 1.68-1.77 (m, 2H), 1.54 (t, J=12.9 Hz, 2H), 1.38 (t, J=6.4 Hz, 2H), 1.34 (s,

6H), 1.23-1.29 (m, 6H). Mass spectrum (ESI, m/z): Calculated for $C_{27}H_{38}N_2O_2$, 423.3 (M+H), found 423.3.

Example 9

5-(4-Ethoxyphenyl)-1-(2-methoxyphenyl)-3-(2,2,6,6-tetramethyltetrahydro-2H-pyran-4-yl)-1H-pyrazole

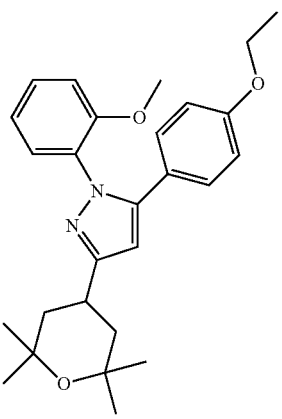 [SMILES: CCOc1ccc(-c2cc(C3CC(C)(C)OC(C)(C)C3)nn2-c2ccccc2OC)cc1]

Prepared according to the procedure in Example 1.

$^1$H NMR (CHLOROFORM-d) δ: 7.32 (dd, J=7.8, 1.8 Hz, 1H), 7.22-7.29 (m, 1H), 6.99-7.07 (m, 2H), 6.93 (td, J=7.6, 1.1 Hz, 1H), 6.79 (dd, J=8.3, 1.0 Hz, 1H), 6.61-6.72 (m, 2H), 6.23 (s, 1H), 3.91 (q, J=7.0 Hz, 2H), 3.41 (s, 3H), 3.25 (tt, J=12.8, 3.3 Hz, 1H), 1.90 (dd, J=13.3, 3.4 Hz, 2H), 1.48-1.57 (m, 2H), 1.31 (t, J=6.9 Hz, 3H), 1.28 (s, 6H), 1.19 (s, 6H). Mass spectrum (ESI, m/z): Calculated for $C_{27}H_{34}N_2O_3$, 435.2 (M+H), found 435.2.

Example 10

1-(2-Methoxyphenyl)-5-(4-methylphenyl)-3-(2,2,6,6-tetramethyltetrahydro-2H-pyran-4-yl)-1H-pyrazole

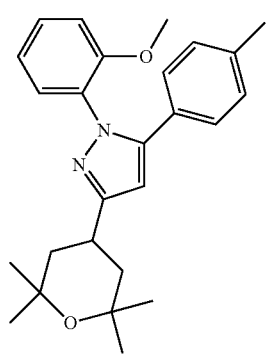

Prepared according to the procedure in Example 1.

$^1$H NMR (CHLOROFORM-d) δ: 7.32 (dd, J=7.7, 1.6 Hz, 1H), 7.22-7.28 (m, 1H), 6.98-7.03 (m, 2H), 6.88-6.98 (m, 3H), 6.79 (dd, J=8.3, 1.0 Hz, 1H), 6.26 (s, 1H), 3.40 (s, 3H), 3.20-3.31 (m, 1H), 2.22 (s, 3H), 1.91 (dd, J=13.4, 3.3 Hz, 2H), 1.45-1.55 (m, 2H), 1.28 (s, 6H), 1.19 (s, 6H). Mass spectrum (ESI, m/z): Calculated for $C_{26}H_{32}N_2O_2$, 405.2 (M+H), found 405.2.

Example 11

4-[1-(2-Methoxyphenyl)-3-(2,2,6,6-tetramethyltetrahydro-2H-pyran-4-yl)-1H-pyrazol-5-yl]-N,N-dimethylaniline

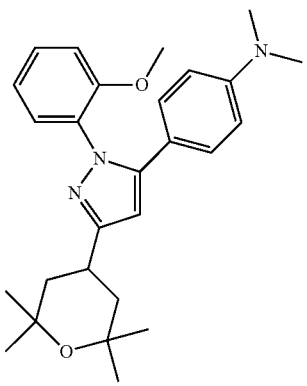

Prepared according to the procedure in Example 1.

$^1$H NMR (CHLOROFORM-d) δ: 7.38 (dd, J=7.7, 1.6 Hz, 1H), 7.32-7.36 (m, 1H), 7.05-7.11 (m, 2H), 7.00 (td, J=7.6, 1.3 Hz, 1H), 6.91 (dd, J=8.3, 1.0 Hz, 1H), 6.49-6.61 (m, 2H), 6.30 (s, 1H), 3.55 (s, 3H), 3.34 (s, 1H), 2.93 (s, 6H), 1.99 (dd, J=13.3, 3.4 Hz, 2H), 1.60 (t, J=12.9 Hz, 2H), 1.36 (s, 6H), 1.28 (s, 6H). Mass spectrum (ESI, m/z): Calculated for $C_{27}H_{35}N_3O_2$, 434.3 (M+H), found 434.3

Example 12

1-{4-[1-(2-Methoxyphenyl)-3-(2,2,6,6-tetramethyltetrahydro-2H-pyran-4-yl)-1H-pyrazol-5-yl]-phenyl}-ethanone

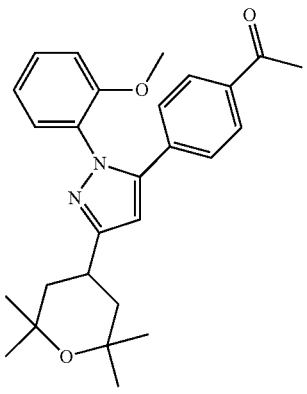 [SMILES: COc1ccccc1-n1nc(C2CC(C)(C)OC(C)(C)C2)cc1-c1ccc(C(C)=O)cc1]

Prepared according to the procedure in Example 1.

$^1$H NMR (CHLOROFORM-d) δ: 7.68-7.78 (m, 2H), 7.38 (dd, J=7.7, 1.6 Hz, 1H), 7.28 (td, J=8.0, 1.8 Hz, 1H), 7.20-7.24 (m, 2H), 6.97 (td, J=7.7, 1.3 Hz, 1H), 6.78 (dd, J=8.5, 1.1 Hz, 1H), 6.38 (s, 1H), 3.36 (s, 3H), 3.23-3.32 (m, 1H), 2.49 (s, 3H), 1.91 (dd, J=13.3, 3.4 Hz, 2H), 1.51 (t, J=12.9 Hz, 2H), 1.28 (s, 6H), 1.19 (s, 6H). Mass spectrum (ESI, m/z): Calculated for C$_{27}$H$_{32}$N$_2$O$_3$, 433.2 (M+H), found 433.2.

Example 13

2-Methoxy-5-[1-(2-methoxyphenyl)-3-(2,2,6,6-tetramethyltetrahydro-2H-pyran-4-yl)-1H-pyrazol-5-yl]-pyridine

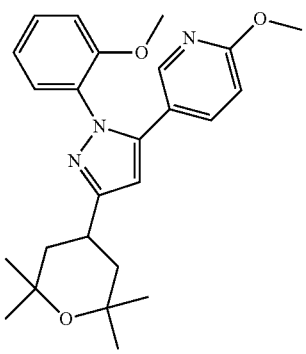

Prepared according to the procedure in Example 1.

$^1$H NMR (CHLOROFORM-d) δ: 8.07 (d, J=2.0 Hz, 1H), 7.41 (dd, J=7.7, 1.6 Hz, 1H), 7.33-7.38 (m, 2H), 6.97-7.10 (m, 1H), 6.89 (dd, J=8.3, 1.0 Hz, 1H), 6.61 (d, J=8.6 Hz, 1H), 6.35 (s, 1H), 3.91 (s, 3H), 3.55 (s, 3H), 3.29-3.41 (m, 1H), 1.99 (dd, J=13.3, 3.4 Hz, 2H), 1.59 (t, J=12.9 Hz, 2H), 1.37 (s, 6H), 1.28 (s, 6H). Mass spectrum (ESI, m/z): Calculated for C$_{25}$H$_{31}$N$_3$O$_3$, 422.2 (M+H), found 422.2.

Example 14

5-(5-Chlorothiophen-2-yl)-1-(2-methoxyphenyl)-3-(2,2,6,6-tetramethyltetrahydro-2H-pyran-4-yl)-1H-pyrazole

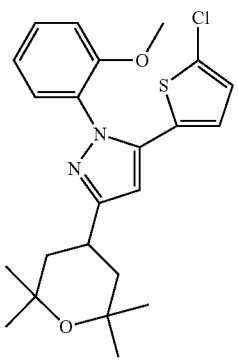 [SMILES: COc1ccccc1-n1nc(C2CC(C)(C)OC(C)(C)C2)cc1-c1ccc(Cl)s1]

Prepared according to the procedure in Example 1.

$^1$H NMR (CHLOROFORM-d) δ: 7.35-7.40 (m, 1H), 7.30 (dd, J=7.8, 1.8 Hz, 1H), 6.98 (td, J=7.6, 1.1 Hz, 1H), 6.91 (d, J=8.3 Hz, 1H), 6.63 (d, J=4.0 Hz, 1H), 6.52 (d, J=4.0 Hz, 1H), 6.31 (s, 1H), 3.60 (s, 3H), 3.19-3.27 (m, 1H), 1.88 (dd, J=13.3, 3.4 Hz, 2H), 1.41-1.52 (m, 2H), 1.27 (s, 6H), 1.19 (s, 6H). Mass spectrum (ESI, m/z): Calculated for C$_{23}$H$_{27}$ClN$_2$OS$_2$, 41.1 (M+H), found 431.1.

Example 15

5-(4-tert-Butylphenyl)-1-(2-methoxyphenyl)-3-(2,2,6,6-tetramethyltetrahydro-2H-pyran-4-yl)-1H-pyrazole

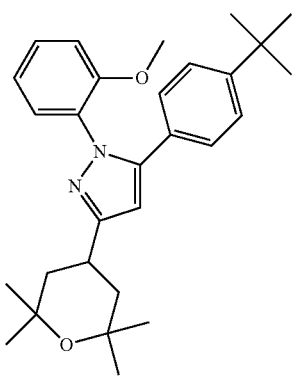 [SMILES: COc1ccccc1-n1nc(C2CC(C)(C)OC(C)(C)C2)cc1-c1ccc(C(C)(C)C)cc1]

Prepared according to the procedure in Example 1.

$^1$H NMR (CHLOROFORM-d) δ: 7.44 (dd, J=7.8, 1.8 Hz, 1H), 7.35 (td, J=7.8, 1.8 Hz, 1H), 7.23-7.28 (m, 2H), 7.09-7.20 (m, 2H), 7.03 (td, J=7.6, 1.3 Hz, 1H), 6.88 (dd, J=8.3, 1.0 Hz, 1H), 6.37 (s, 1H), 3.44 (s, 3H), 3.35 (m, 1H), 2.00 (dd, J=13.3, 3.4 Hz, 2H), 1.60 (t, J=12.9 Hz, 2H), 1.37 (s, 6H), 1.27-1.31 (m, 15H). Mass spectrum (ESI, m/z): Calculated for C$_{29}$H$_{38}$N$_2$O$_2$, 447.3 (M+H), found 447.3.

Example 16

1-(2-Methoxyphenyl)-5-phenyl-3-(2,2,6,6-tetramethyltetrahydro-2H-pyran-4-yl)-1H-pyrazole

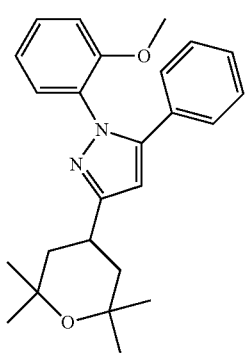 [SMILES: COc1ccccc1-n1nc(C2CC(C)(C)OC(C)(C)C2)cc1-c1ccccc1]

Prepared according to the procedure in Example 1.

$^1$H NMR (CHLOROFORM-d) δ: 7.36-7.43 (m, 2H), 7.19-7.31 (m, 5H), 7.03 (td, J=7.6, 1.1 Hz, 1H), 6.90 (dd, J=8.3, 1.0 Hz, 1H), 6.43 (s, 1H), 3.50 (s, 3H), 3.18-3.47 (m, 1H), 2.00 (dd, J=13.1, 3.3 Hz, 2H), 1.60 (t, J=12.9 Hz, 2H), 1.38 (s, 6H), 1.29 (s, 6H). Mass spectrum (ESI, m/z): Calculated for $C_{25}H_{30}N_2O_2$, 391.2 (M+H), found 391.2.

Example 17

Ethyl 4-[1-(2-methoxyphenyl)-3-(2,2,6,6-tetramethyltetrahydro-2H-pyran-4-yl)-1H-pyrazol-5-yl]-benzoate

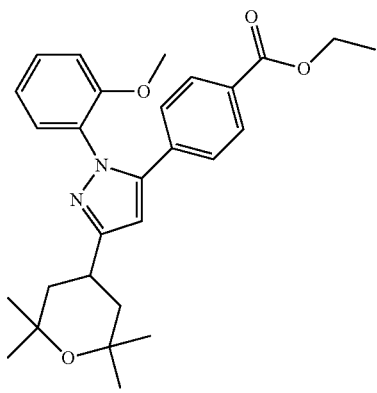 [SMILES: CCOC(=O)c1ccc(-c2cc(C3CC(C)(C)OC(C)(C)C3)nn2-c2ccccc2OC)cc1]

Prepared according to the procedure in Example 1.
$^1$H NMR (CHLOROFORM-d) δ: 7.92 (d, J=8.6 Hz, 2H), 7.46 (dd, J=7.8, 1.8 Hz, 1H), 7.31-7.38 (m, 1H), 7.23-7.30 (m, 2H), 7.04 (td, J=7.6, 1.3 Hz, 1H), 6.85 (dd, J=8.3, 1.0 Hz, 1H), 6.45 (s, 1H), 4.35 (q, J=7.2 Hz, 2H), 3.42 (s, 3H), 3.30-3.40 (m, 1H), 1.99 (dd, J=13.1, 3.3 Hz, 2H), 1.59 (t, J=12.9 Hz, 2H), 1.33-1.40 (m, 9H), 1.28 (s, 6H). Mass spectrum (ESI, m/z): Calculated for $C_{28}H_{34}N_2O_4$, 463.3 (M+H), found 463.3.

Example 18

1-(2-Methoxyphenyl)-5-(4-methylthiophen-2-yl)-3-(2,2,6,6-tetramethyltetrahydro-2H-pyran-4-yl)-1H-pyrazole

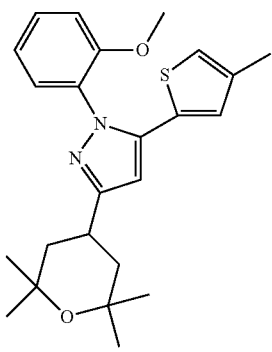

Prepared according to the procedure in Example 1.
$^1$H NMR (CHLOROFORM-d) δ: 7.33-7.39 (m, 1H), 7.31 (dd, J=7.8, 1.8 Hz, 1H), 6.97 (td, J=7.6, 1.3 Hz, 1H), 6.90 (d, J=8.3 Hz, 1H), 6.66 (s, 1H), 6.56 (d, J=1.3 Hz, 1H), 6.34 (s, 1H), 3.58 (s, 3H), 3.18-3.28 (m, 1H), 2.06 (s, 3H), 1.89 (dd, J=13.1, 3.3 Hz, 2H), 1.44-1.54 (m, 2H), 1.27 (s, 6H), 1.19 (s, 6H). Mass spectrum (ESI, m/z): Calculated for $C_{24}H_{30}N_2O_2S$, 411.2 (M+H), found 411.2.

Example 19

2-Ethoxy-5-[1-(2-methoxyphenyl)-3-(2,2,6,6-tetramethyltetrahydro-2H-pyran-4-yl)-1H-pyrazol-5-yl]-pyridine

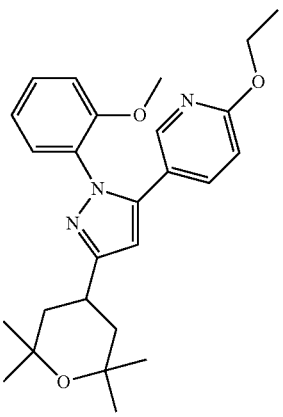 [SMILES: CCOc1ccc(-c2cc(C3CC(C)(C)OC(C)(C)C3)nn2-c2ccccc2OC)cn1]

Prepared according to the procedure in Example 1.
$^1$H NMR (CHLOROFORM-d) δ: 7.97 (s, 1H), 7.21-7.36 (m, 3H), 6.94 (t, J=7.5 Hz, 1H), 6.81 (d, J=8.3 Hz, 1H), 6.51 (d, J=8.6 Hz, 1H), 6.27 (s, 1H), 4.23 (q, J=7.1 Hz, 2H), 3.47 (s, 3H), 3.22-3.34 (m, 1H), 1.83-1.96 (m, 2H), 1.50 (t, J=12.8 Hz, 2H), 1.24-1.38 (m, 9H), 1.20 (s, 6H). Mass spectrum (ESI, m/z): Calculated for $C_{26}H_{33}N_3O_3$, 436.2 (M+H), found 436.3.

Example 20

1-(2-Methoxyphenyl)-5-(3-methoxyphenyl)-3-(2,2,6,6-tetramethyltetrahydro-2H-pyran-4-yl)-1H-pyrazole

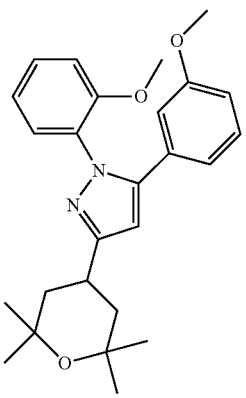 [SMILES: COc1cccc(-c2cc(C3CC(C)(C)OC(C)(C)C3)nn2-c2ccccc2OC)c1]

Prepared according to the procedure in Example 1.
$^1$H NMR (CHLOROFORM-d) δ: 7.43 (dd, J=7.7, 1.6 Hz, 1H), 7.29-7.39 (m, 1H), 7.15 (t, J=8.0 Hz, 1H), 7.03 (td, J=7.6, 1.1 Hz, 1H), 6.88 (dd, J=8.3, 1.0 Hz, 1H), 6.83 (dt, J=7.9, 1.1 Hz, 1H), 6.78 (ddd, J=8.3, 2.6, 0.8 Hz, 1H), 6.71-6.74 (m, 1H), 6.40 (s, 1H), 3.62 (s, 3H), 3.48 (s, 3H), 3.36 (tt, J=12.8, 3.4 Hz, 1H), 2.00 (dd, J=13.3, 3.4 Hz, 2H), 1.60 (t, J=12.9 Hz, 2H), 1.37 (s, 6H), 1.04-1.33 (m, 6H). Mass spectrum (ESI, m/z): Calculated for $C_{26}H_{32}N_2O_3$, 421.2 (M+H), found 421.2.

Example 21

5-[1-(2-Methoxyphenyl)-3-(2,2,6,6-tetramethyltetrahydro-2H-pyran-4-yl)-1H-pyrazol-5-yl]-1-methyl-1H-indole

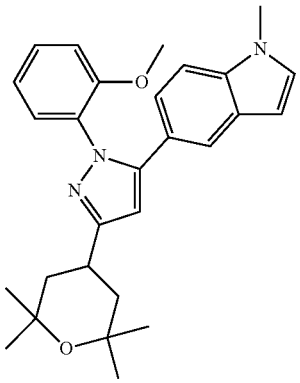 [SMILES: COc1ccccc1-n1nc(C2CC(C)(C)OC(C)(C)C2)cc1-c1ccc2c(ccn2C)c1]

Prepared according to the procedure in Example 1.
$^{1}$H NMR (CHLOROFORM-d) δ: 7.43 (d, J=1.3 Hz, 1H), 7.30 (dd, J=7.8, 1.5 Hz, 1H), 7.25 (td, J=7.9, 1.6 Hz, 1H), 7.09 (d, J=8.6 Hz, 1H), 6.94-6.99 (m, 2H), 6.90 (td, J=7.7, 1.3 Hz, 1H), 6.80 (dd, J=8.3, 1.0 Hz, 1H), 6.30-6.33 (m, 2H), 3.68 (s, 3H), 3.43 (s, 3H), 3.29-3.37 (m, 1H), 1.93 (dd, J=13.1, 3.3 Hz, 2H), 1.53 (t, J=12.8 Hz, 2H), 1.29 (s, 6H), 1.20 (s, 6H). Mass spectrum (ESI, m/z): Calculated for $C_{28}H_{33}N_3O_2$, 444.3 (M+H), found 444.2.

Example 22

2-[1-(2-Methoxyphenyl)-3-(2,2,6,6-tetramethyltetrahydro-2H-pyran-4-yl)-1H-pyrazol-5-yl]-aniline

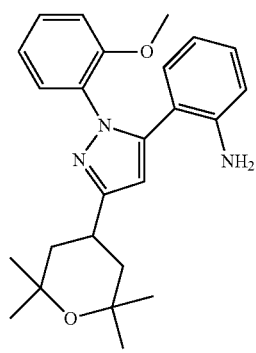 [SMILES: COc1ccccc1-n1nc(C2CC(C)(C)OC(C)(C)C2)cc1-c1ccccc1N]

Prepared according to the procedure in Example 1.
$^{1}$H NMR (CHLOROFORM-d) δ: 7.29 (dd, J=7.8, 1.8 Hz, 1H), 7.22 (ddd, J=8.3, 7.5, 1.6 Hz, 1H), 6.98 (td, J=7.7, 1.8 Hz, 1H), 6.88 (td, J=7.6, 1.1 Hz, 1H), 6.76 (dd, J=8.3, 1.0 Hz, 1H), 6.72 (dd, J=7.6, 1.5 Hz, 1H), 6.61 (dd, J=8.2, 0.9 Hz, 1H), 6.45-6.50 (m, 1H), 6.33 (s, 1H), 3.49 (s, 3H), 3.29-3.43 (m, 1H), 3.25 (br s, 2H), 1.91 (dd, J=13.3, 3.4 Hz, 2H), 1.50 (t, J=12.9 Hz, 2H), 1.29 (s, 6H), 1.20 (s, 6H). Mass spectrum (ESI, m/z): Calculated for $C_{25}H_{31}N_3O_2$, 406.2 (M+H), found 406.2.

Example 23

5-[1-(2-Methoxyphenyl)-3-(2,2,6,6-tetramethyltetrahydro-2H-pyran-4-yl)-1H-pyrazol-5-yl]-2-methylpyridine

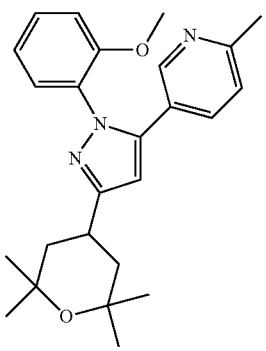

Prepared according to the procedure in Example 1.
$^{1}$H NMR (CHLOROFORM-d) δ: 8.41 (d, J=1.7 Hz, 1H), 7.42 (dd, J=7.8, 1.7 Hz, 1H), 7.33-7.38 (m, 2H), 6.96-7.07 (m, 2H), 6.88 (dd, J=8.3, 1.0 Hz, 1H), 6.41 (s, 1H), 3.51 (s, 3H), 3.36 (tt, J=12.8, 3.3 Hz, 1H), 2.52 (s, 3H), 1.99 (dd, J=13.2, 3.4 Hz, 2H), 1.60 (t, J=13.0 Hz, 2H), 1.28 (s, 6H), 1.20 (s, 6H). Mass spectrum (ESI, m/z): Calculated for $C_{25}H_{31}N_3O_2$, 406.2 (M+H), found 406.2.

Example 24

1-(2-Methoxyphenyl)-5-[4-(1-methylethoxy)phenyl]-3-(2,2,6,6-tetramethyltetrahydro-2H-pyran-4-yl)-1H-pyrazole

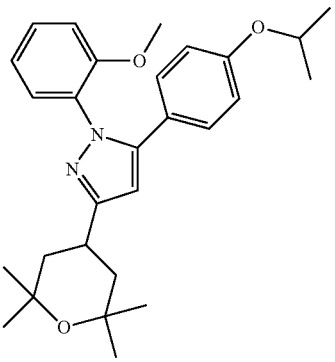 [SMILES: COc1ccccc1-n1nc(C2CC(C)(C)OC(C)(C)C2)cc1-c1ccc(OC(C)C)cc1]

Prepared according to the procedure in Example 1.
$^{1}$H NMR (CHLOROFORM-d) δ: 7.41 (dd, J=7.7, 1.6 Hz, 1H), 7.33 (td, J=8.0, 1.8 Hz, 1H), 7.06-7.16 (m, 2H), 7.02 (td, J=7.6, 1.1 Hz, 1H), 6.88 (dd, J=8.2, 1.1 Hz, 1H), 6.65-6.80 (m, 2H), 6.32 (s, 1H), 4.51 (spt, J=6.1 Hz, 1H), 3.49 (s, 3H), 3.34 (tt, J=12.8, 3.2 Hz, 1H), 1.99 (dd, J=13.3, 3.4 Hz, 2H), 1.59 (t, J=12.9 Hz, 2H), 1.37 (s, 6H), 1.31 (d, J=6.1 Hz, 6H), 1.28 (s, 6H). Mass spectrum (ESI, m/z): Calculated for $C_{28}H_{36}N_2O_3$, 449.3 (M+H), found 449.3.

Example 25

2-Chloro-4-[1-(2-methoxyphenyl)-3-(2,2,6,6-tetramethyltetrahydro-2H-pyran-4-yl)-1H-pyrazol-5-yl]-pyridine

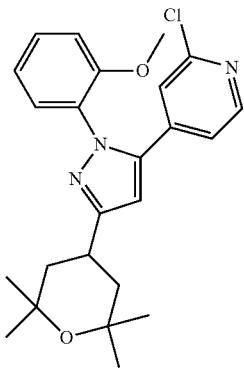 [SMILES: COc1ccccc1-n1nc(C2CC(C)(C)OC(C)(C)C2)cc1-c1ccnc(Cl)c1]

Prepared according to the procedure in Example 1.

$^1$H NMR (CHLOROFORM-d) δ: 8.15 (d, J=5.3 Hz, 1H), 7.39 (dd, J=7.7, 1.6 Hz, 1H), 7.34 (td, J=8.0, 1.8 Hz, 1H), 7.12 (s, 1H), 7.02 (td, J=7.6, 1.1 Hz, 1H), 6.87 (dd, J=5.3, 1.5 Hz, 1H), 6.84 (dd, J=8.3, 1.0 Hz, 1H), 6.46 (s, 1H), 3.43 (s, 3H), 3.22-3.32 (m, 1H), 1.89 (dd, J=13.1, 3.3 Hz, 2H), 1.49 (t, J=13.0 Hz, 2H), 1.28 (s, 6H), 1.20 (s, 6H). Mass spectrum (ESI, m/z): Calculated for $C_{24}H_{28}ClN_3O_2$, 426.2 (M+H), found 426.2.

Example 26

1-(2-Methoxyphenyl)-3-(2,2,6,6-tetramethyltetrahydro-2H-pyran-4-yl)-5-thiophen-2-yl-1H-pyrazole

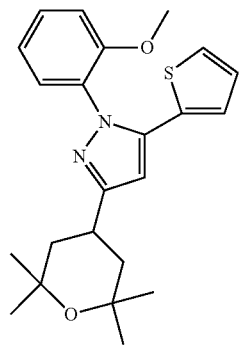 [SMILES: COc1ccccc1-n1nc(C2CC(C)(C)OC(C)(C)C2)cc1-c1cccs1]

Prepared according to the procedure in Example 1.

$^1$H NMR (CHLOROFORM-d) δ: 7.29-7.45 (m, 2H), 7.09 (dd, J=5.1, 1.0 Hz, 1H), 6.93-7.04 (m, 1H), 6.89 (d, J=8.1 Hz, 1H), 6.75-6.85 (m, 1H), 6.71 (d, J=2.8 Hz, 1H), 6.36 (s, 1H), 3.55 (s, 3H), 3.24 (tt, J=12.8, 3.3 Hz, 1H), 1.89 (dd, J=13.1, 3.3 Hz, 2H), 1.50 (t, J=13.0 Hz, 2H), 1.27 (s, 6H), 1.22 (s, 6H). Mass spectrum (ESI, m/z): Calculated for $C_{23}H_{28}N_2O_2S$, 397.2 (M+H), found 397.2.

Example 27

5-(2,3-Dihydro-1,4-benzodioxin-6-yl)-1-(2-methoxyphenyl)-3-(2,2,6,6-tetramethyltetrahydro-2H-pyran-4-yl)-1H-pyrazole

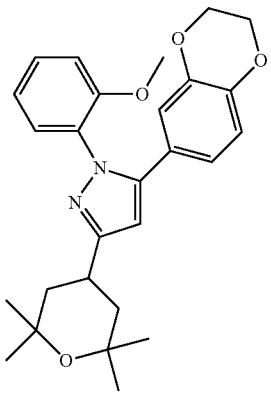 [SMILES: COc1ccccc1-n1nc(C2CC(C)(C)OC(C)(C)C2)cc1-c1ccc2c(c1)OCCO2]

Prepared according to the procedure in Example 1.

$^1$H NMR (CHLOROFORM-d) δ: 7.32-7.40 (m, 2H), 7.01 (td, J=7.6, 1.3 Hz, 1H), 6.91 (dd, J=8.3, 1.0 Hz, 1H), 6.76 (d, J=2.0 Hz, 1H), 6.70-6.73 (m, 1H), 6.65-6.68 (m, 1H), 6.31 (s, 1H), 4.01-4.31 (m, 4H), 3.57 (s, 3H), 3.34 (tt, J=12.8, 3.4 Hz, 1H), 1.98 (dd, J=13.3, 3.4 Hz, 2H), 1.58 (t, J=12.9 Hz, 2H), 1.36 (s, 6H), 1.28 (s, 6H). Mass spectrum (ESI, m/z): Calculated for $C_{27}H_{32}N_2O_4$, 449.2 (M+H), found 449.2.

Example 28

1-(2-Methoxyphenyl)-5-(5-methylfuran-2-yl)-3-(2,2,6,6-tetramethyltetrahydro-2H-pyran-4-yl)-1H-pyrazole

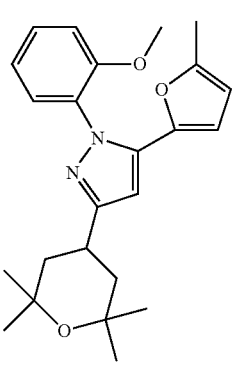 [SMILES: COc1ccccc1-n1nc(C2CC(C)(C)OC(C)(C)C2)cc1-c1ccc(C)o1]

Prepared according to the procedure in Example 1.

$^1$H NMR (CHLOROFORM-d) δ: 7.36 (m, 1H), 7.29 (m, 1H), 6.95 (m, 2H), 6.43 (s, 1H), 5.74 (m, 1H), 5.42 (m, 1H), 3.62 (s, 3H), 3.25 (tt, J=12.8, 3.4 Hz, 1H), 2.20 (s, 3H), 1.98 (dd, J=13.3, 3.4 Hz, 2H), 1.58 (t, J=12.9 Hz, 2H), 1.30 (s, 6H), 1.26 (s, 6H). Mass spectrum (ESI, m/z): Calculated for $C_{24}H_{30}N_2O_3$, 395.2 (M+H), found 395.1.

Example 29

5-(3,4-Dimethoxyphenyl)-1-(2-methoxyphenyl)-3-(2,2,6,6-tetramethyltetrahydro-2H-pyran-4-yl)-1H-pyrazole

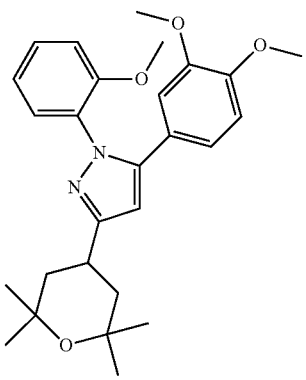

Prepared according to the procedure in Example 1.

$^1$H NMR (CHLOROFORM-d) δ: 7.41 (dd, J=7.7, 1.6 Hz, 1H), 7.33-7.39 (m, 1H), 7.03 (td, J=7.6, 1.1 Hz, 1H), 6.91 (dd, J=8.3, 1.0 Hz, 1H), 6.86 (dd, J=8.3, 2.0 Hz, 1H), 6.77 (d, J=8.3 Hz, 1H), 6.67 (d, J=2.0 Hz, 1H), 3.86 (s, 3H), 3.62 (s, 3H), 3.54 (s, 3H), 3.33-3.43 (m, 1H), 1.98-2.03 (m, 2H), 1.60 (t, J=12.9 Hz, 2H), 1.37 (s, 6H), 1.29 (s, 6H). Mass spectrum (ESI, m/z): Calculated for $C_{27}H_{34}N_2O_4$, 451.2 (M+H), found 451.2.

Example 30

N-{5-[1-(2-Methoxyphenyl)-3-(2,2,6,6-tetramethyltetrahydro-2H-pyran-4-yl)-1H-pyrazol-5-yl]-pyridin-2-yl}-acetamide

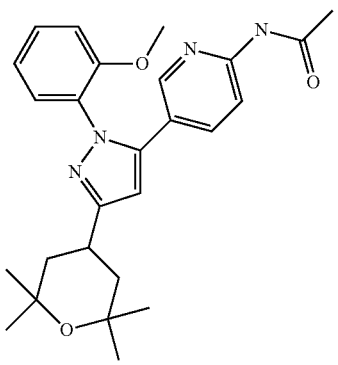 [SMILES: COc1ccccc1-n1nc(C2CC(C)(C)OC(C)(C)C2)cc1-c1ccc(NC(C)=O)nc1]

Prepared according to the procedure in Example 1.

$^1$H NMR (CHLOROFORM-d) δ: 8.16 (d, J=1.5 Hz, 2H), 8.08 (d, J=8.6 Hz, 1H), 7.49 (dd, J=8.7, 2.4 Hz, 1H), 7.43 (dd, J=7.7, 1.6 Hz, 1H), 7.34-7.40 (m, 1H), 7.04 (td, J=7.6, 1.1 Hz, 1H), 6.85-6.91 (m, 1H), 6.41 (s, 1H), 3.53 (s, 3H), 3.36 (tt, J=12.8, 3.3 Hz, 1H), 2.18 (s, 3H), 1.99 (dd, J=13.3, 3.4 Hz, 2H), 1.46-1.66 (m, 2H), 1.37 (s, 6H), 1.29 (s, 6H). Mass spectrum (ESI, m/z): Calculated for $C_{26}H_{32}N_4O_3$, 449.2 (M+H), found 449.2.

Example 31

5-[1-(2-Methoxyphenyl)-3-(2,2,6,6-tetramethyltetrahydro-2H-pyran-4-yl)-1H-pyrazol-5-yl]-N,N-dimethylpyridin-2-amine

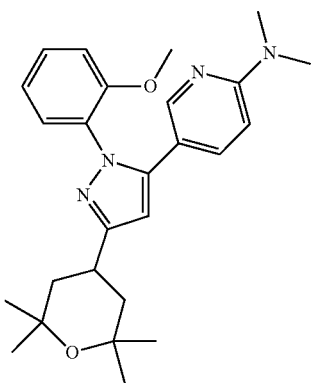

Prepared according to the procedure in Example 1.

$^1$H NMR (CHLOROFORM-d) δ: 7.99 (s, 1H), 7.49 (d, J=9.3 Hz, 1H), 7.35 (t, J=7.8 Hz, 1H), 7.28 (d, J=7.6 Hz, 1H), 6.97 (t, J=7.6 Hz, 1H), 6.89 (d, J=8.3 Hz, 1H), 6.61 (d, J=9.5 Hz, 1H), 6.35 (s, 1H), 3.59 (s, 3H), 3.10-3.32 (m, 7H), 1.83-1.92 (m, 2H), 1.49 (t, J=13.0 Hz, 2H), 1.28 (s, 6H), 1.20 (s, 6H). Mass spectrum (ESI, m/z): Calculated for $C_{26}H_{34}N_4O_2$, 435.3 (M+H), found 435.3.

Example 32

4-[1-(2-Methoxyphenyl)-3-(2,2,6,6-tetramethyltetrahydro-2H-pyran-4-yl)-1H-pyrazol-5-yl]-pyridine

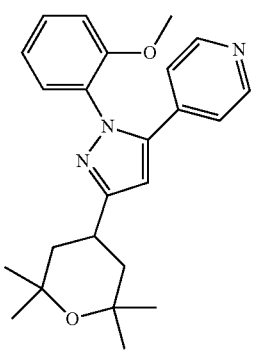 [SMILES: COc1ccccc1-n1nc(C2CC(C)(C)OC(C)(C)C2)cc1-c1ccncc1]

Prepared according to the procedure in Example 1.

$^1$H NMR (CHLOROFORM-d) δ: 8.38-8.44 (m, 2H), 7.40 (dd, J=7.7, 1.6 Hz, 1H), 7.24-7.35 (m, 1H), 6.87-7.05 (m, 3H), 6.81 (dd, J=8.3, 1.0 Hz, 1H), 6.44 (s, 1H), 3.37 (s, 3H), 3.28 (tt, J=12.8, 3.3 Hz, 1H), 1.90 (dd, J=13.2, 3.2 Hz, 2H), 1.50 (t, J=13.0 Hz, 2H), 1.29 (s, 6H), 1.21 (s, 6H). Mass spectrum (ESI, m/z): Calculated for $C_{24}H_{29}N_3O_2$, 392.2 (M+H), found 392.2.

Example 33

4-[1-(2-Methoxyphenyl)-3-(2,2,6,6-tetramethyltetrahydro-2H-pyran-4-yl)-1H-pyrazol-5-yl]-2-methylpyridine

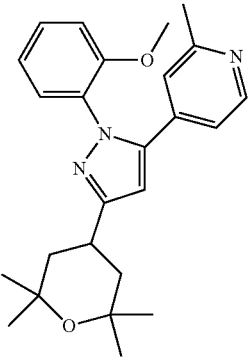 [SMILES: COc1ccccc1-n1nc(C2CC(C)(C)OC(C)(C)C2)cc1-c1ccnc(C)c1]

Prepared according to the procedure in Example 1.
$^1$H NMR (CHLOROFORM-d) δ: 8.34 (d, J=5.1 Hz, 1H), 7.46 (dd, J=7.7, 1.6 Hz, 1H), 7.36-7.42 (m, 1H), 7.07 (td, J=7.7, 1.2 Hz, 1H), 7.02 (s, 1H), 6.90 (dd, J=8.4, 1.1 Hz, 1H), 6.84 (dd, J=5.1, 1.2 Hz, 1H), 6.51 (s, 1H), 3.48 (s, 3H), 3.28-3.43 (m, 1H), 2.47 (s, 3H), 1.98 (dd, J=13.2, 3.4 Hz, 2H), 1.58 (t, J=12.8 Hz, 2H), 1.28 (s, 6H), 1.21 (s, 6H). Mass spectrum (ESI, m/z): Calculated for $C_{25}H_{31}N_3O_2$, 406.2 (M+H), found 406.2.

Example 34

3-Methoxy-5-[1-(2-methoxyphenyl)-3-(2,2,6,6-tetramethyltetrahydro-2H-pyran-4-yl)-1H-pyrazol-5-yl]-pyridine

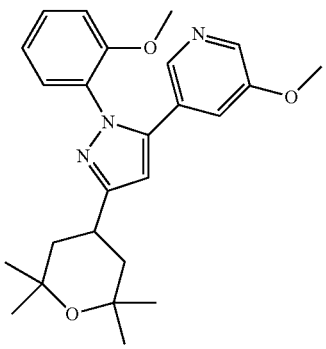

Prepared according to the procedure in Example 1.
$^1$H NMR (CHLOROFORM-d) δ: 8.18 (dd, J=4.6, 2.2 Hz, 2H), 7.45 (dd, J=7.7, 1.6 Hz, 1H), 7.37 (td, J=7.9, 1.7 Hz, 1H), 7.01-7.09 (m, 1H), 6.93 (dd, J=2.7, 2.0 Hz, 1H), 6.90 (dd, J=8.3, 1.0 Hz, 1H), 6.46 (s, 1H), 3.67 (s, 3H), 3.52 (s, 3H), 3.37 (tt, J=12.8, 3.3 Hz, 1H), 2.00 (dd, J=13.2, 3.4 Hz, 2H), 1.60 (t, J=12.8 Hz, 2H), 1.29 (s, 6H), 1.25 (s, 6H). Mass spectrum (ESI, m/z): Calculated for $C_{25}H_{31}N_3O_3$, 422.2 (M+H), found 422.2.

Example 35

2-Methoxy-3-[1-(2-methoxyphenyl)-3-(2,2,6,6-tetramethyltetrahydro-2H-pyran-4-yl)-1H-pyrazol-5-yl]-pyridine

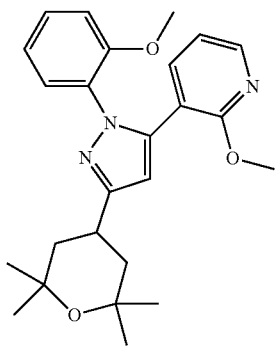

Prepared according to the procedure in Example 1.
$^1$H NMR (CHLOROFORM-d) δ: 7.99 (dd, J=4.9, 2.0 Hz, 1H), 7.33 (dd, J=7.8, 1.7 Hz, 1H), 7.26 (dd, J=7.3, 2.0 Hz, 1H), 7.16-7.22 (m, 1H), 6.84-6.96 (m, 1H), 6.73 (dd, J=8.3, 1.0 Hz, 1H), 6.68 (dd, J=7.3, 5.1 Hz, 1H), 6.35 (s, 1H), 3.70 (s, 3H), 3.39 (s, 3H), 3.23-3.34 (m, 1H), 1.93 (dd, J=13.2, 3.4 Hz, 2H), 1.52 (t, J=13.0 Hz, 2H), 1.28 (s, 6H), 1.22 (s, 6H). Mass spectrum (ESI, m/z): Calculated for $C_{25}H_{31}N_3O_3$, 422.2 (M+H), found 422.2.

Example 36

N-{2-[1-(2-Methoxyphenyl)-3-(2,2,6,6-tetramethyltetrahydro-2H-pyran-4-yl)-1H-pyrazol-5-yl]-phenyl}-acetamide

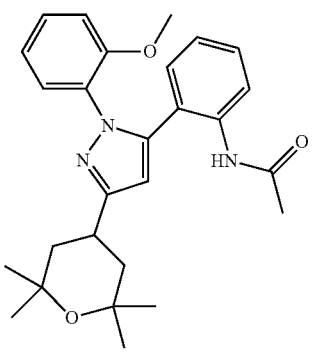 [SMILES: COc1ccccc1-n1nc(C2CC(C)(C)OC(C)(C)C2)cc1-c1ccccc1NC(C)=O]

Prepared according to the procedure in Example 1.
$^1$H NMR (CHLOROFORM-d) δ: 8.26 (d, J=8.1 Hz, 1H), 7.52 (br. s., 1H), 7.45 (dd, J=7.8, 1.5 Hz, 1H), 7.14-7.32 (m, 2H), 7.01 (td, J=7.6, 1.1 Hz, 1H), 6.85-6.96 (m, 2H), 6.78 (d, J=7.6 Hz, 1H), 6.33 (s, 1H), 3.43-3.46 (m, 3H), 3.45 (s, 3H), 3.31-3.42 (m, 1H), 2.12 (s, 3H), 2.01 (dd, J=13.1, 3.3 Hz, 2H), 1.59 (t, J=12.9 Hz, 2H), 1.29 (s, 6H), 1.25 (s, 6H). Mass spectrum (ESI, m/z): Calculated for $C_{27}H_{33}N_3O_3$, 448.2 (M+H), found 448.2.

Example 37

5-Cyclopent-1-en-1-yl-1-(2-methoxyphenyl)-3-(2,2,6,6-tetramethyltetrahydro-2H-pyran-4-yl)-1H-pyrazole

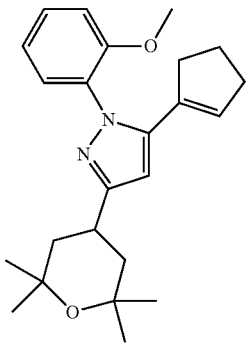 [SMILES: COc1ccccc1-n1nc(C2CC(C)(C)OC(C)(C)C2)cc1C1=CCCC1]

Prepared according to the procedure in Example 1.

$^1$H NMR (CHLOROFORM-d) δ: 7.43 (td, J=8.0, 1.8 Hz, 1H), 7.34 (dd, J=7.7, 1.6 Hz, 1H), 7.04-7.07 (m, 1H), 6.98-7.03 (m, 1H), 6.20 (s, 1H), 5.30-5.37 (m, 1H), 3.76 (s, 3H), 3.33 (tt, J=12.8, 3.3 Hz, 1H), 2.43-2.57 (m, 2H), 2.25-2.39 (m, 2H), 1.94 (dd, J=13.3, 3.4 Hz, 2H), 1.81-1.90 (m, 2H), 1.54 (t, J=12.9 Hz, 2H), 1.35 (s, 6H), 1.27 (s, 6H).). Mass spectrum (ESI, m/z): Calculated for $C_{24}H_{32}N_2O_2$, 381.2 (M+H), found 381.2.

Example 38

2-[1-(2-Methoxyphenyl)-3-(2,2,6,6-tetramethyltetrahydro-2H-pyran-4-yl)-1H-pyrazol-5-yl]-5-methyl-1,3-thiazole

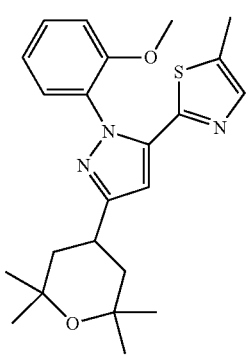 [SMILES: COc1ccccc1-n1nc(C2CC(C)(C)OC(C)(C)C2)cc1-c1ncc(C)s1]

Prepared according to the procedure in Example 1.

$^1$H NMR (CHLOROFORM-d) δ: 7.42 (td, J=7.9, 1.6 Hz, 1H), 7.33-7.38 (m, 2H), 7.02 (td, J=7.6, 1.1 Hz, 1H), 6.94 (dd, J=8.2, 0.9 Hz, 1H), 6.75 (s, 1H), 3.59 (s, 3H), 3.22-3.31 (m, 1H), 2.30 (d, J=1.0 Hz, 3H), 1.89 (dd, J=13.3, 3.4 Hz, 2H), 1.50 (t, J=13.0 Hz, 2H), 1.27 (s, 6H), 1.19 (s, 6H). Mass spectrum (ESI, m/z): Calculated for $C_{23}H_{29}N_3O_2$, 412.2 (M+H), found 412.2.

Example 39

2-Methoxy-5-[1-(2-methoxyphenyl)-3-(2,2,6,6-tetramethyltetrahydro-2H-pyran-4-yl)-1H-pyrazol-5-yl]-pyrimidine

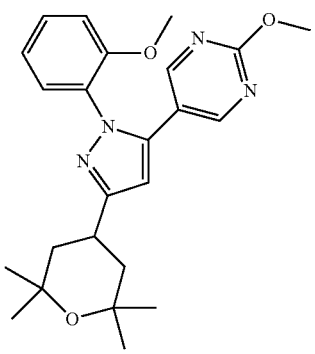

Prepared according to the procedure in Example 1.

$^1$H NMR (CHLOROFORM-d) δ: 8.28 (s, 2H), 7.27-7.33 (m, 1H), 6.97 (td, J=7.6, 1.1 Hz, 1H), 6.83 (dd, J=8.3, 1.0 Hz, 1H), 6.32 (s, 1H), 3.92 (s, 3H), 3.51 (s, 3H), 3.23-3.32 (m, 1H), 3.20-3.34 (m, 1H), 1.90 (dd, J=13.1, 3.3 Hz, 2H), 1.50 (t, J=12.9 Hz, 2H), 1.28 (s, 6H), 1.20 (s, 6H). Mass spectrum (ESI, m/z): Calculated for $C_{24}H_{30}N_4O_3$, 423.2 (M+H), found 423.2.

Example 40

N,N-Diethyl-4-[1-(2-methoxyphenyl)-3-(2,2,6,6-tetramethyltetrahydro-2H-pyran-4-yl)-1H-pyrazol-5-yl]-benzamide

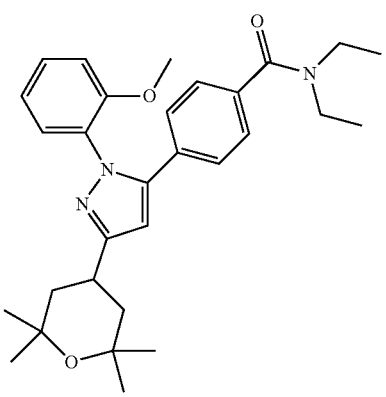 [SMILES: CCN(CC)C(=O)c1ccc(-c2cc(C3CC(C)(C)OC(C)(C)C3)nn2-c2ccccc2OC)cc1]

Prepared according to the procedure in Example 1.

$^1$H NMR (DMSO-d$_6$) δ: 7.39-7.45 (m, 2H), 7.18-7.26 (m, 4H), 7.04-7.09 (m, 2H), 6.58 (s, 1H), 3.17-3.27 (m, 1H), 3.06-3.16 (m, 4H), 1.89 (dd, J=13.0, 2.9 Hz, 2H), 1.43 (t,

J=12.9 Hz, 2H), 1.30 (s, 6H), 1.16 (s, 6H), 0.95-1.14 (m, 6H). Mass spectrum (ESI, m/z): Calculated for $C_{30}H_{39}N_3O_3$, 490.3 (M+H), found 490.3.

Example 41

5-(1-Benzofuran-2-yl)-1-(2-methoxyphenyl)-3-(2,2,6,6-tetramethyltetrahydro-2H-pyran-4-yl)-1H-pyrazole

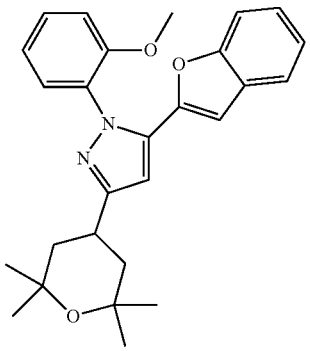 [SMILES: COc1ccccc1-n1nc(C2CC(C)(C)OC(C)(C)C2)cc1-c1cc2ccccc2o1]

Prepared according to the procedure in Example 1.
$^1$H NMR (CHLOROFORM-d) δ: 7.40-7.46 (m, 1H), 7.34-7.39 (m, 2H), 7.32 (d, J=7.6 Hz, 1H), 7.18 (td, J=7.7, 1.3 Hz, 1H), 7.07-7.12 (m, 1H), 7.04 (td, J=7.6, 1.3 Hz, 1H), 6.98 (dd, J=8.3, 1.0 Hz, 1H), 6.70 (s, 1H), 5.89 (d, J=1.0 Hz, 1H), 3.59 (s, 3H), 3.29 (tt, J=12.9, 3.3 Hz, 1H), 1.93 (dd, J=13.3, 3.4 Hz, 2H), 1.41-1.59 (m, 2H), 1.29 (s, 6H), 1.20 (s, 6H).). Mass spectrum (ESI, m/z): Calculated for $C_{27}H_{30}N_2O_3$, 431.2 (M+H), found 431.2.

Example 42

5-[1-(2-Methoxyphenyl)-3-(2,2,6,6-tetramethyltetrahydro-2H-pyran-4-yl)-1H-pyrazol-5-yl]-1H-indole

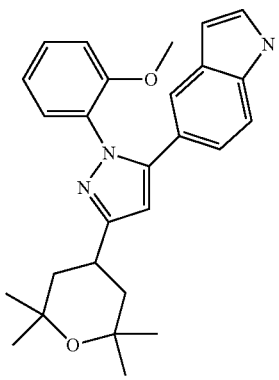 [SMILES: COc1ccccc1-n1nc(C2CC(C)(C)OC(C)(C)C2)cc1-c1ccc2[nH]ccc2c1]

Prepared according to the procedure in Example 1.
$^1$H NMR (CHLOROFORM-d) δ: 8.18 (br. s., 1H), 7.54-7.56 (m, 1H), 7.34-7.40 (m, 2H), 7.26 (s, 1H), 7.20-7.24 (m, 1H), 7.04 (dd, J=8.5, 1.6 Hz, 1H), 6.99 (td, J=7.6, 1.1 Hz, 1H), 6.88-6.92 (m, 1H), 6.50 (t, J=2.1 Hz, 1H), 6.43 (s, 1H), 3.53 (s, 3H), 3.41-3.51 (m, 1H), 2.03 (dd, J=13.1, 3.3 Hz, 2H), 1.61 (t, J=12.9 Hz, 2H), 1.38 (s, 6H), 1.30 (s, 6H). Mass spectrum (ESI, m/z): Calculated for $C_{27}H_{31}N_3O_2$, 430.2 (M+H), found 430.2.

Example 43

5-(3,5-Dimethoxyphenyl)-1-(2-methoxyphenyl)-3-(2,2,6,6-tetramethyltetrahydro-2H-pyran-4-yl)-1H-pyrazole

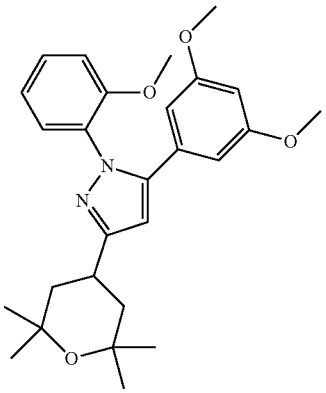

Prepared according to the procedure in Example 1.
$^1$H NMR (CHLOROFORM-d) δ: 7.34 (dd, J=7.7, 1.6 Hz, 1H), 7.25 (td, J=7.8, 1.8 Hz, 1H), 7.05 (m, 1H), 6.94 (td, J=7.6, 1.1 Hz, 1H), 6.83 (dd, J=8.3, 1.3 Hz, 1H), 6.35-6.41 (m, 2H), 6.31 (s, 1H), 3.79 (s, 3H), 3.54 (s, 3H), 3.52 (s, 3H), 3.29-3.44 (m, 1H), 1.87-2.07 (m, 2H), 1.60 (t, J=12.9 Hz, 2H), 1.37 (s, 6H), 1.28 (s, 6H). Mass spectrum (ESI, m/z): Calculated for $C_{27}H_{34}N_2O_4$, 451.2 (M+H), found 451.1.

Example 44

3-[1-(2-Methoxyphenyl)-3-(2,2,6,6-tetramethyltetrahydro-2H-pyran-4-yl)-1H-pyrazol-5-yl]-pyridine

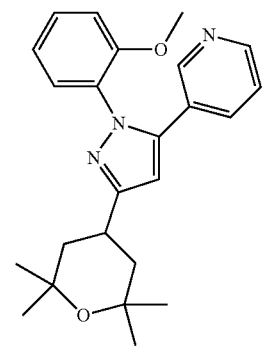 [SMILES: COc1ccccc1-n1nc(C2CC(C)(C)OC(C)(C)C2)cc1-c1cccnc1]

Prepared according to the procedure in Example 1.
$^1$H NMR (CHLOROFORM-d) δ: 8.54 (d, J=1.5 Hz, 1H), 8.47 (dd, J=4.8, 1.5 Hz, 1H), 7.40-7.50 (m, 2H), 7.31-7.39 (m, 1H), 7.11-7.20 (m, 1H), 7.04 (td, J=7.6, 1.1 Hz, 1H), 6.86 (dd, J=8.3, 1.0 Hz, 1H), 6.43 (s, 1H), 3.46 (s, 3H), 3.30-3.40 (m, 1H), 1.99 (dd, J=13.3, 3.4 Hz, 2H), 1.59 (t, J=12.9 Hz, 2H), 1.36 (s, 6H), 1.28 (s, 6H). Mass spectrum (ESI, m/z): Calculated for $C_{24}H_{29}N_3O_2$, 392.2 (M+H), found 392.2.

Example 45

1-{4-[1-(2-Methoxyphenyl)-3-(2,2,6,6-tetramethyltetrahydro-2H-pyran-4-yl)-1H-pyrazol-5-yl]-phenyl}-ethanol

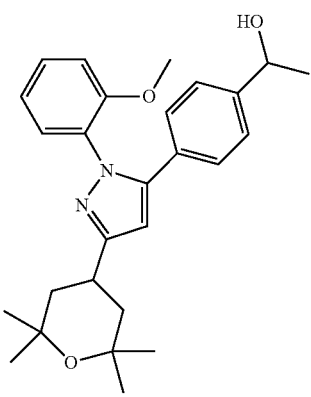 [SMILES: COc1ccccc1-n1nc(C2CC(C)(C)OC(C)(C)C2)cc1-c1ccc(C(C)O)cc1]

To a solution of 1-{4-[1-(2-methoxyphenyl)-3-(2,2,6,6-tetramethyltetrahydro-2H-pyran-4-yl)-1H-pyrazol-5-yl]-phenyl}-ethanone (Example 12) (20 mg, 0.05 mmol) in 1 mL of ethanol was added sodium borohydride (1.8 mg, 0.05 mmol) and the mixture stirred for 1 hr at RT. The solution was diluted with 5 mL of 50% $CH_3CN$ in 0.1% $TFA/H_2O$ and purified by RP-HPLC, eluting with a linear gradient of 50%-100% $CH_3CN$ in 0.1% $TFA/H_2O$ over 10 mins to give 20 mg (86%) of the title compound a white solid containing 0.5 eq of TFA.

$^1$H NMR (CHLOROFORM-d) δ: 7.33-7.44 (m, 2H), 7.25-7.30 (m, 2H), 7.18-7.23 (m, 2H), 7.03 (td, J=7.6, 1.3 Hz, 1H), 6.91 (d, J=8.1 Hz, 1H), 6.41 (s, 1H), 4.89 (q, J=6.4 Hz, 0H), 3.52 (s, 3H), 3.36-3.47 (m, 0H), 2.00 (dd, J=13.3, 3.4 Hz, 2H), 1.59 (t, J=12.8 Hz, 2H), 1.48 (d, J=6.6 Hz, 3H), 1.38 (s, 6H), 1.29 (s, 6H). Mass spectrum (ESI, m/z): Calculated for $C_{27}H_{34}N_2O_3$, 435.2 (M+H), found 435.2.

Example 46

4-[1-(2-Methoxyphenyl)-3-(2,2,6,6-tetramethyltetrahydro-2H-pyran-4-yl)-1H-pyrazol-5-yl]-benzoic acid

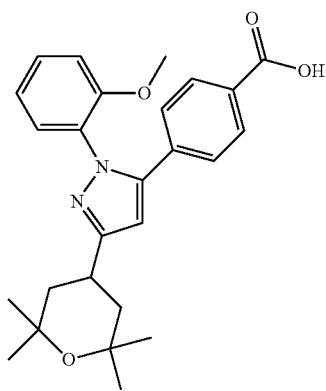 [SMILES: COc1ccccc1-n1nc(C2CC(C)(C)OC(C)(C)C2)cc1-c1ccc(C(=O)O)cc1]

To a solution of ethyl 4-[1-(2-methoxyphenyl)-3-(2,2,6,6-tetramethyltetrahydro-2H-pyran-4-yl)-1H-pyrazol-5-yl]-benzoate (Example 17) (200 mg, 0.43 mmol) in 3 mL of methanol was added 0.07 mL of 50% NaOH soln (1.30 mmol) and the mixture heated at 50° C. for 8 hrs. The mixture was diluted with 50 mL of EtOAc and washed with 50 mL of 1N HCL and 50 mL of brine. The organic layer was dried over $Na_2SO_4$ and concentrated to give 185 mg (93%) of a white solid.

$^1$H NMR (CHLOROFORM-d) δ: 11.30 (br. s., 1H), 7.87 (d, J=8.3 Hz, 2H), 7.40 (dd, J=7.8, 1.5 Hz, 1H), 7.24-7.31 (m, 1H), 7.21 (d, J=8.6 Hz, 2H), 6.96 (td, J=7.6, 1.1 Hz, 1H), 6.77 (d, J=7.6 Hz, 1H), 6.39 (s, 1H), 3.34 (s, 3H), 3.25-3.32 (m, 1H), 1.91 (dd, J=13.1, 3.3 Hz, 2H), 1.51 (t, J=12.9 Hz, 2H), 1.28 (s, 6H), 1.20 (s, 6H). Mass spectrum (ESI, m/z): Calculated for $C_{26}H_{30}N_2O_4$, 435.2 (M+H), found 435.2.

Example 47

5-(4-Methanesulfinyl-phenyl)-1-(2-methoxy-phenyl)-3-(2,2,6,6-tetramethyl-tetrahydro-pyran-4-yl)-1H-pyrazole

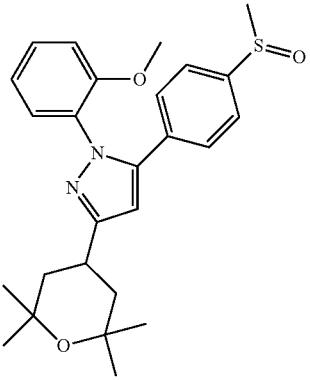 [SMILES: COc1ccccc1-n1nc(C2CC(C)(C)OC(C)(C)C2)cc1-c1ccc(S(C)=O)cc1]

Prepared according to the procedure in Example 1.

$^1$H NMR (CHLOROFORM-d) δ: 7.52 (d, J=8.3 Hz, 2H), 7.45 (d, J=7.8 Hz, 1H), 7.32-7.39 (m, 3H), 7.04 (t, J=7.7 Hz, 1H), 6.85 (d, J=8.3 Hz, 1H), 6.44 (s, 1H), 3.44 (s, 3H), 3.35 (tt, J=12.8, 3.1 Hz, 1H), 2.70 (s, 3H), 1.98 (dd, J=13.1, 3.1 Hz, 2H), 1.58 (t, J=12.8 Hz, 2H), 1.36 (s, 6H), 1.27 (s, 6H). Mass spectrum (ESI, m/z): Calculated for $C_{26}H_{32}N_2O_3S$, 453.2 (M+H), found 453.3.

Example 48

2-(5-(4-Chlorophenyl)-3-(2,2,6,6-tetramethyltetrahydro-2H-pyran-4-yl)-1H-pyrazol-1-yl)phenol

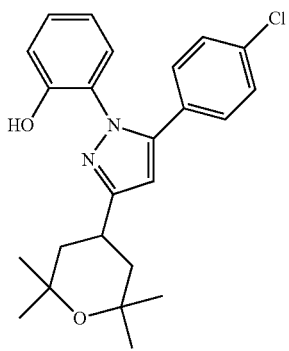 [SMILES: CC1(C)CC(c2cc(-c3ccc(Cl)cc3)n(-c3ccccc3O)n2)CC(C)(C)O1]

To a solution of 5-(4-chloro-phenyl)-1-(2-methoxy-phenyl)-3-(2,2,6,6-tetramethyl-tetrahydro-pyran-4-yl)-1H-pyrazole (Example 1) (105 mg, 0.25 mmol) in mL of DCM at −78° C. was added a 1M solution of boron tribromide (0.33 mL, 0.33 mmol) in DCM. After 1 hr at −78° C. the reaction was quenched with 3 mL of 1N HCl and then diluted with 50 mL of EtOAc. The organic layer was washed with 50 mL of NaHCO$_3$ and brine, and dried over Na$_2$SO$_4$. The crude product was purified by silica gel chromatography (Thomson Scientific 12-g cartridge, 2-40% EtOAc in heptane in column volumes) to give 60 mg (59%) of the title compound as a white solid.

$^1$H NMR (CHLOROFORM-d) d: 9.55 (s, 1H), 7.31-7.39 (m, 2H), 7.22-7.27 (m, 2H), 7.12-7.20 (m, 2H), 6.65-6.69 (m, 2H), 6.38 (s, 1H), 3.32 (tt, J=12.8, 3.3 Hz, 1H), 1.97 (dd, J=13.3, 3.4 Hz, 2H), 1.58 (t, J=12.9 Hz, 2H), 1.39 (s, 6H), 1.29 (s, 6H). Mass spectrum (ESI, m/z): Calculated for C$_{24}$H$_{27}$ClN$_2$O$_2$, 411.2 (M+H), found 411.1.

Example 49

1-(2-tert-Butoxyphenyl)-5-(4-chlorophenyl)-3-(2,2,6,6-tetramethyltetrahydro-2H-pyran-4-yl)-1H-pyrazole

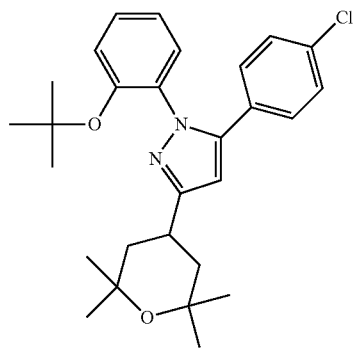 [SMILES: CC(C)(C)Oc1ccccc1-n1nc(C2CC(C)(C)OC(C)(C)C2)cc1-c1ccc(Cl)cc1]

To a solution of 2-(5-(4-chlorophenyl)-3-(2,2,6,6-tetramethyltetrahydro-2H-pyran-4-yl)-1H-pyrazol-1-yl)phenol (Example 48) (45 mg, 0.11 mmol) in 1 mL of toluene was added N,N-dimethylformamide di-tert-butyl acetal (136 mg, 0.66 mmol) and the mixture heated overnight at 80° C. The mixture was diluted with 50 mL of EtOAc and washed with 50 mL of brine, and the organic layer was dried over Na$_2$SO$_4$. The crude product was purified by silica gel chromatography (Thomson Scientific 12-g cartridge, 2-20% EtOAc/heptane in 10 column volumes) and then by RP-HPLC (50% CH$_3$CN to 100% in 0.1% TFA/H2O over 10 mins) to give 26 mg (51%) the title compound as a white solid.

$^1$H NMR (CHLOROFORM-d) δ: 7.63 (dd, J=7.7, 1.6 Hz, 1H), 7.27-7.34 (m, 1H), 7.18-7.24 (m, 3H), 7.09-7.15 (m, 2H), 6.96-7.02 (m, 1H), 6.36 (s, 1H), 3.26-3.42 (m, 1H), 1.93 (dd, J=13.0, 2.9 Hz, 2H), 1.57 (t, J=12.8 Hz, 2H), 1.38 (s, 6H), 1.28 (s, 6H), 1.00 (s, 9H). Mass spectrum (ESI, m/z): Calculated for C$_{28}$H$_{35}$ClN$_2$O$_2$, 467.2 (M+H), found 467.2.

Example 50

2-[5-(4-Chlorophenyl)-3-(2,2,6,6-tetramethyltetrahydro-2H-pyran-4-yl)-1H-pyrazol-1-yl]-N,N-dimethylaniline

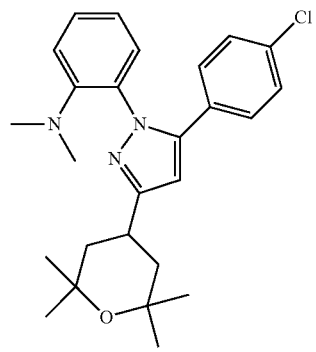 [SMILES: CN(C)c1ccccc1-n1nc(C2CC(C)(C)OC(C)(C)C2)cc1-c1ccc(Cl)cc1]

Step A) 1-(4-Chloro-phenyl)-3-(2,2,6,6-tetramethyl-tetrahydro-pyran-4-yl)-propane-1,3-dione

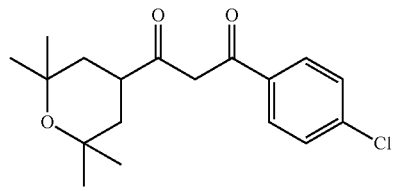 [SMILES: CC1(C)CC(C(=O)CC(=O)c2ccc(Cl)cc2)CC(C)(C)O1]

To a mixture of benzotriazol-1-yl-(2,2,6,6-tetramethyl-tetrahydro-pyran-4-yl)-methanone (1.00 g, 3.13 mmol), magnesium bromide diethyl etherate (1.62 g, 6.26 mmol), and 1-(4-chloro-phenyl)-ethanone (0.39 mL, 2.98 mmol) in 10 mL of DCM at RT was added dropwise DIEA (1.74 mL, 9.40 mmol). The mixture was stirred overnight and then diluted with 50 mL of DCM and washed with 1N HCl (100 mL) and brine (100 mL). The organic layer was dried over Na$_2$SO$_4$, concentrated, and the residue purified by flash chromatography on silica gel to give 0.70 g (69%) of a white solid.

Mass spectrum (ESI, m/z): Calculated for $C_{18}H_{23}ClO_3$, 323.1 (M+H), found 323.0.

Step B) 2-[5-(4-Chlorophenyl)-3-(2,2,6,6-tetramethyltetrahydro-2H-pyran-4-yl)-1H-pyrazol-1-yl]-N,N-dimethylaniline

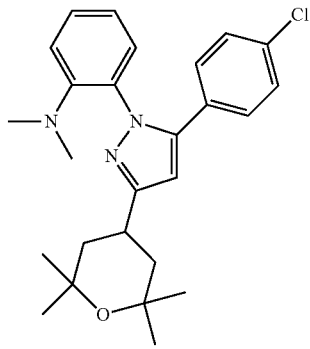 [SMILES: CN(C)c1ccccc1-n1nc(C2CC(C)(C)OC(C)(C)C2)cc1-c1ccc(Cl)cc1]

A mixture of (2-hydrazino-phenyl)-dimethyl-amine hydrochloride (105 mg, 0.56 mmol), 1-(4-chloro-phenyl)-3-(2,2,6,6-tetramethyl-tetrahydro-pyran-4-yl)-propane-1,3-dione (162 mg, 0.50 mmol), and triethylamine (0.08 mL, 0.56 mmol), in 1.4 mL of methanol was stirred at RT for 8 hrs. The mixture was diluted with 20 mL of EtOAc and washed with saturated $NaHCO_3$ (40 mL) and brine (40 mL). The organic layer was dried over $Na_2SO_4$, concentrated, and the residue purified by flash chromatography on silica gel to give 115 mg (47%) of the title compound as a white solid.

$^1$H NMR (Methanol-$d_4$) δ: 7.28-7.41 (m, 2H), 7.20-7.27 (m, 2H), 7.11-7.18 (m, 2H), 7.07 (td, J=7.6, 1.0 Hz, 1H), 6.95 (d, J=8.1 Hz, 1H), 6.54 (s, 1H), 3.32-3.38 (m, 1H), 2.24 (s, 6H), 1.93 (dd, J=13.4, 3.3 Hz, 2H), 1.58 (t, J=13.0 Hz, 2H), 1.38 (s, 6H), 1.25 (s, 6H). Mass spectrum (ESI, m/z): Calculated for $C_{26}H_{32}ClN_3O$, 438.2 (M+H), found 438.2.

Example 51

2-[5-(4-Chloro-phenyl)-3-(2,2,6,6-tetra methyl-tetrahydro-pyran-4-yl)-pyrazol-1-yl]-pyridine

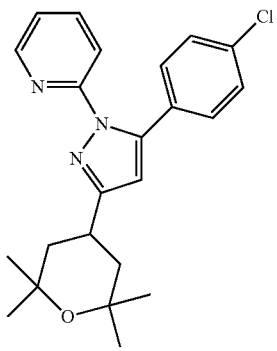 [SMILES: CC1(C)CC(c2cc(-c3ccc(Cl)cc3)n(-c3ccccn3)n2)CC(C)(C)O1]

Prepared according to the procedure in Example 50.
$^1$H NMR (CHLOROFORM-d) δ: 8.40 (d, J=3.1 Hz, 1H), 7.74 (td, J=7.8, 2.0 Hz, 1H), 7.39 (d, J=8.2 Hz, 1H), 7.26-7.31 (m, 2H), 7.16-7.24 (m, 3H), 6.38 (s, 1H), 3.36 (tt, J=12.8, 3.2 Hz, 1H), 1.95 (dd, J=13.3, 3.1 Hz, 2H), 1.57 (t, J=12.9 Hz, 2H), 1.36 (s, 6H), 1.27 (s, 6H). Mass spectrum (ESI, m/z): Calcd. for $C_{23}H_{26}ClN_3O$, 396.2 (M+H), found 396.2.

Example 52

4-[5-(4-Chlorophenyl)-3-(2,2,6,6-tetramethyltetrahydro-2H-pyran-4-yl)-1H-pyrazol-1-yl]-pyridine

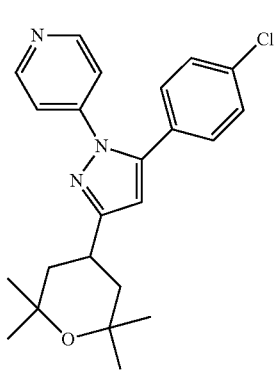 [SMILES: CC1(C)CC(c2cc(-c3ccc(Cl)cc3)n(-c3ccncc3)n2)CC(C)(C)O1]

Prepared according to the procedure in Example 50.
$^1$H NMR (METHANOL-$d_4$) δ: 8.56-8.71 (m, 2H), 7.67-7.78 (m, 2H), 7.47-7.54 (m, 2H), 7.35-7.44 (m, 2H), 6.70 (s, 1H), 3.36-3.43 (m, 1H), 1.96 (dd, J=13.3, 3.5 Hz, 2H), 1.59 (t, J=12.9 Hz, 2H), 1.39 (s, 6H), 1.25 (s, 6H). Mass spectrum (ESI, m/z): Calculated for $C_{23}H_{26}ClN_3O$, 396.2 (M+H), found 396.3.

Example 53

3-[5-(4-Chlorophenyl)-3-(2,2,6,6-tetramethyltetrahydro-2H-pyran-4-yl)-1H-pyrazol-1-yl]-pyridine

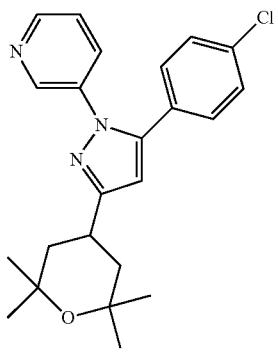 [SMILES: CC1(C)CC(c2cc(-c3ccc(Cl)cc3)n(-c3cccnc3)n2)CC(C)(C)O1]

Prepared according to the procedure in Example 50.
$^1$H NMR (METHANOL-$d_4$) δ: 8.46-8.73 (m, 2H), 7.93 (d, J=8.2 Hz, 1H), 7.64 (dd, J=8.0, 4.9 Hz, 1H), 7.35-7.46 (m, 2H), 7.21-7.32 (m, 2H), 6.61 (s, 1H), 3.37-3.41 (m, 0H), 1.95 (dd, J=13.3, 3.5 Hz, 2H), 1.59 (t, J=12.9 Hz, 2H), 1.38 (s, 6H), 1.25 (s, 6H). Mass spectrum (ESI, m/z): Calculated for C$_{23}$H$_{26}$ClN$_3$O, 396.2 (M+H), found 396.3.

Example 54

4-[1-Pyrazin-2-yl-3-(2,2,6,6-tetramethyltetrahydro-2H-pyran-4-yl)-1H-pyrazol-5-yl]-benzonitrile

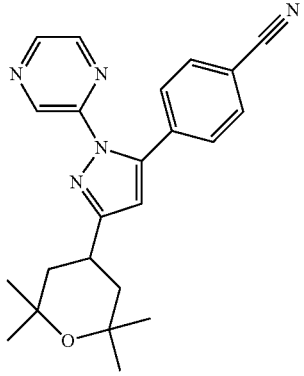 [SMILES: CC1(C)CC(c2cc(-c3ccc(C#N)cc3)n(-c3cnccn3)n2)CC(C)(C)O1]

Step A) 4-[3-Oxo-3-(2,2,6,6-tetramethyl-tetrahydro-pyran-4-yl)-propionyl]-benzonitrile

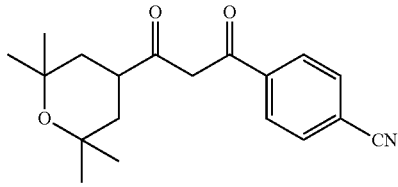 [SMILES: CC1(C)CC(C(=O)CC(=O)c2ccc(C#N)cc2)CC(C)(C)O1]

Prepared according to the procedure in Example 50, Step (A), substituting 1-(4-cyano-phenyl)-ethanone for 1-(4-chloro-phenyl)-ethanone.

Mass spectrum (ESI, m/z): Calculated for C$_{19}$H$_{23}$NO$_3$, 314.2 (M+H), found 314.3

Step B) 4-[1-Pyrazin-2-yl-3-(2,2,6,6-tetramethyltetrahydro-2H-pyran-4-yl)-1H-pyrazol-5-yl]benzonitrile Prepared according to the procedure in Example 50.

$^1$H NMR (CHLOROFORM-d) δ: 9.05 (d, J=1.2 Hz, 1H), 8.48 (d, J=2.7 Hz, 1H), 8.19-8.21 (m, 1H), 7.62-7.71 (m, 2H), 7.36-7.44 (m, 2H), 6.47 (s, 1H), 3.35 (tt, J=12.8, 3.2 Hz, 1H), 1.95 (dd, J=13.3, 3.1 Hz, 2H), 1.53-1.61 (m, 2H), 1.38 (s, 6H), 1.28 (s, 6H). Mass spectrum (ESI, m/z): Calculated for C$_{23}$H$_{25}$N$_5$O, 388.2 (M+H), found 388.2.

Example 55

4-[1-Pyridin-3-yl-3-(2,2,6,6-tetramethyltetrahydro-2H-pyran-4-yl)-1H-pyrazol-5-yl]-benzonitrile

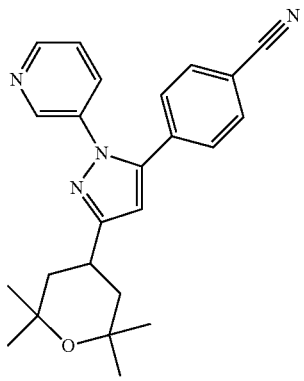 [SMILES: CC1(C)CC(c2cc(-c3ccc(C#N)cc3)n(-c3cccnc3)n2)CC(C)(C)O1]

Prepared according to the procedure in Example 54.

$^1$H NMR (CHLOROFORM-d) δ: 8.58 (d, J=4.3 Hz, 1H), 8.51 (s, 1H), 7.67 (dd, J=8.2, 1.6 Hz, 1H), 7.61-7.65 (m, 2H), 7.31-7.38 (m, 3H), 6.50 (s, 1H), 3.34 (tt, J=12.8, 3.4 Hz, 1H), 1.95 (dd, J=13.3, 3.5 Hz, 2H), 1.57 (t, J=12.9 Hz, 2H), 1.38 (s, 6H), 1.28 (s, 6H). Mass spectrum (ESI, m/z): Calculated for C$_{24}$H$_{26}$N$_4$O, 387.2 (M+H), found 387.3.

Example 56

4-[1-Pyridin-2-yl-3-(2,2,6,6-tetramethyltetrahydro-2H-pyran-4-yl)-1H-pyrazol-5-yl]-benzonitrile

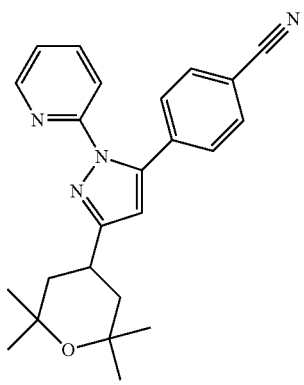 [SMILES: CC1(C)CC(c2cc(-c3ccc(C#N)cc3)n(-c3ccccn3)n2)CC(C)(C)O1]

Prepared according to the procedure in Example 54.

$^1$H NMR (CHLOROFORM-d) δ: 8.29-8.32 (m, 1H), 7.78-7.83 (m, J=7.8, 7.8, 2.0 Hz, 2H), 7.56-7.63 (m, 3H), 7.34-7.39 (m, 2H), 7.21-7.24 (m, 1H), 6.45 (s, 1H), 3.35 (tt, J=12.7, 3.3 Hz, 1H), 1.94 (dd, J=13.3, 3.1 Hz, 2H), 1.50-1.61 (m, 2H), 1.37 (s, 6H), 1.27 (s, 6H). Mass spectrum (ESI, m/z): Calculated for $C_{24}H_{26}N_4O$, 387.2 (M+H), found 387.3.

Example 57

4-[1-Pyridin-4-yl-3-(2,2,6,6-tetramethyltetrahydro-2H-pyran-4-yl)-1H-pyrazol-5-yl]-benzonitrile

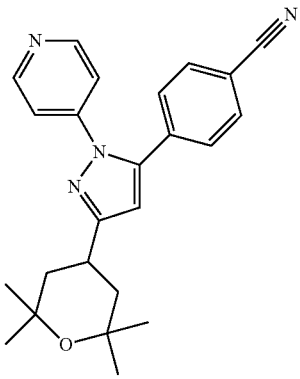 [SMILES: CC1(C)CC(c2cc(-c3ccc(C#N)cc3)n(-c3ccncc3)n2)CC(C)(C)O1]

Prepared according to the procedure in Example 54.

$^1$H NMR (METHANOL-$d_4$) δ: 8.66 (d, J=5.9 Hz, 2H), 7.80-7.88 (m, 2H), 7.72 (d, J=7.0 Hz, 2H), 7.55-7.65 (m, 2H), 6.80 (s, 1H), 3.38-3.44 (m, 1H), 1.97 (dd, J=13.3, 3.1 Hz, 2H), 1.59 (t, J=12.9 Hz, 2H), 1.39 (s, 6H), 1.26 (s, 6H). Mass spectrum (ESI, m/z): Calculated for $C_{24}H_{26}N_4O$, 387.2 (M+H), found 387.3.

Example 58

4-[1-Quinolin-8-yl-3-(2,2,6,6-tetramethyltetrahydro-2H-pyran-4-yl)-1H-pyrazol-5-yl]-benzonitrile

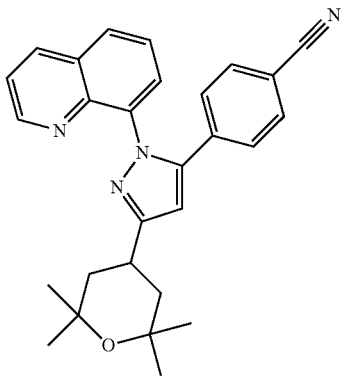 [SMILES: CC1(C)CC(c2cc(-c3ccc(C#N)cc3)n(-c3cccc4cccnc34)n2)CC(C)(C)O1]

Prepared according to the procedure in Example 54.

$^1$H NMR (CHLOROFORM-d) δ: 8.91 (dd, J=4.5, 1.8 Hz, 1H), 8.36 (dd, J=8.4, 1.8 Hz, 1H), 7.99 (dd, J=8.2, 1.2 Hz, 1H), 7.76 (dd, J=7.4, 1.6 Hz, 1H), 7.63-7.69 (m, 1H), 7.55 (dd, J=8.4, 4.5 Hz, 1H), 7.40 (d, J=8.6 Hz, 2H), 7.22-7.26 (m, 2H), 6.61 (s, 1H), 3.40 (tt, J=12.9, 3.3 Hz, 1H), 2.01 (dd, J=13.1, 3.3 Hz, 2H), 1.62 (t, J=12.9 Hz, 2H), 1.36 (s, 6H), 1.28 (s, 6H). Mass spectrum (ESI, m/z): Calculated for $C_{28}H_{28}N_4O$, 437.2 (M+H), found 437.3.

Example 59

5-(4-Chloro-phenyl)-1-(2-methoxy-phenyl)-3-(2,2,6,6-tetramethyl-tetrahydro-thiopyran-4-yl)-1H-pyrazole

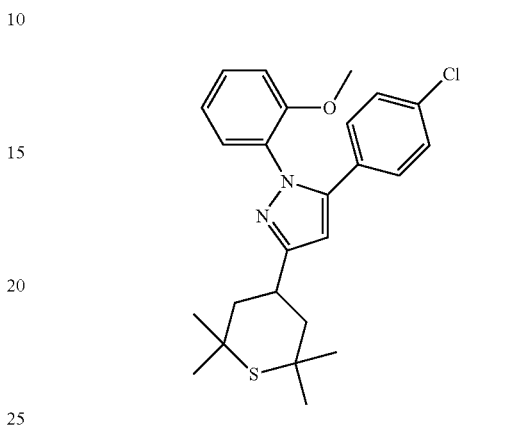

Step A) 2,2,6,6-Tetramethyl-tetrahydro-thiopyran-4-carboxylic acid

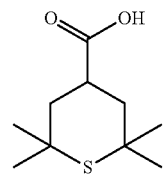

This compound was prepared from 2,2,6,6-tetramethyl-tetrahydro-thiopyran-4-one (JOC, (1970), 35(3), 592) according to the procedure in Example 1, Step (A).

$^1$H NMR (CHLOROFORM-d) δ: 2.82 (tt, J=12.7, 2.6 Hz, 1H), 2.06 (dd, J=13.4, 2.4 Hz, 2H), 1.65 (t, J=13.1 Hz, 2H), 1.47 (s, 6H), 1.28 (s, 6H).

Step B) Benzotriazol-1-yl-(2,2,6,6-tetramethyl-tetrahydro-thiopyran-4-yl)-methanone

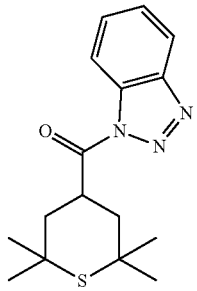 [SMILES: CC1(C)CC(C(=O)n2nnc3ccccc32)CC(C)(C)S1]

This compound was prepared from 2,2,6,6-tetramethyl-tetrahydro-thiopyran-4-carboxylic acid according to the procedure in Example 1, Step (B).

$^1$H NMR (CHLOROFORM-d) δ: 8.30 (d, J=8.3 Hz, 2H), 8.14 (d, J=8.3 Hz, 2H), 7.68 (t, J=7.7 Hz, 2H), 7.47-7.58 (m, 2H), 4.47 (tt, J=12.4, 2.3 Hz, 1H), 2.18 (dd, J=13.2, 2.4 Hz, 2H), 1.86-2.01 (m, 2H), 1.63 (s, 6H), 1.33 (s, 6H).

Step C) 3-Oxo-3-(2,2,6,6-tetramethyl-tetrahydro-thiopyran-4-yl)-thiopropionic acid S-phenyl ester

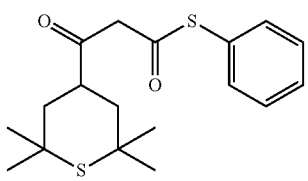 [SMILES: CC1(C)CC(C(=O)CC(=O)Sc2ccccc2)CC(C)(C)S1]

This compound was prepared from benzotriazol-1-yl-(2,2,6,6-tetramethyl-tetrahydro-thiopyran-4-yl)-methanone according to the procedure in Example 1, Step (C). The compound exists as a mixture of keto and enol forms in a ratio of 1:1.2.

$^1$H NMR (CHLOROFORM-d) (keto form) δ: 7.33-7.53 (m, 5H), 3.82 (s, 2H), 2.88-3.13 (m, 1H), 1.83-1.96 (m, 2H), 1.49-1.65 (m, 2H), 1.44 (s, 6H), 1.26 (s, 6H). $^1$H NMR (CHLOROFORM-d) (enol form) δ: 12.67 (s, 1H), 7.31-7.53 (m, 5H), 5.53 (s, 1H), 2.50-2.63 (m, 1H), 1.85-1.97 (m, 2H), 1.52-1.66 (m, 2H), 1.46 (s, 6H), 1.26 (s, 6H). Mass spectrum (ESI, m/z): Calculated for $C_{18}H_{24}O_2S_2$, 337.1 (M+H), found 337.2.

Step D) 2-(2-Methoxy-phenyl)-5-(2,2,6,6-tetramethyl-tetrahydro-thiopyran-4-yl)-2H-pyrazol-3-ol

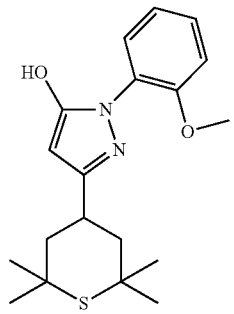

This compound was prepared from 3-oxo-3-(2,2,6,6-tetramethyl-tetrahydro-thiopyran-4-yl)-thiopropionic acid S-phenyl ester according to the procedure in Example 1, Step (D).

$^1$H NMR (DMSO-d$_6$) δ: 7.32-7.44 (m, 1H), 7.20 (s, 1H), 7.13 (d, J=8.1 Hz, 1H), 6.89-7.04 (m, 1H), 5.25 (br. s., 1H), 3.74 (s, 3H), 2.78-3.02 (m, 1H), 1.96 (dd, J=13.2, 2.4 Hz, 2H), 1.47-1.53 (m, 2H), 1.45 (s, 6H), 1.20 (s, 6H). Mass spectrum (ESI, m/z): Calculated for $C_{19}H_{26}N_2O_2S$, 347.2 (M+H), found 347.2.

Step E) Trifluoro-methanesulfonic acid 2-(2-methoxy-phenyl)-5-(2,2,6,6-tetramethyl-tetrahydro-thiopyran-4-yl)-2H-pyrazol-3-yl ester This compound was prepared from 2-(2-methoxy-phenyl)-5-(2,2,6,6-tetramethyl-tetrahydro-thiopyran-4-yl)-2H-pyrazol-3-ol according to the procedure in Example 1, Step (E).

$^1$H NMR (CHLOROFORM-d) δ: 7.30-7.39 (m, 2H), 6.98 (td, J=7.6, 1.1 Hz, 1H), 6.95 (dd, J=8.4, 0.9 Hz, 1H), 6.02 (s, 1H), 3.74 (s, 3H), 3.14 (tt, J=12.6, 2.8 Hz, 1H), 2.01 (dd, J=13.4, 2.7 Hz, 2H), 1.62 (t, J=13.0 Hz, 2H), 1.45 (s, 6H), 1.21 (s, 6H). Mass spectrum (ESI, m/z): Calculated for $C_{20}H_{25}F_3N_2O_4S$, 479.1 (M+H), found 479.1.

Step F) 5-(4-Chloro-phenyl)-1-(2-methoxy-phenyl)-3-(2,2,6,6-tetramethyl-tetrahydro-thiopyran-4-yl)-1H-pyrazole This compound was prepared from trifluoromethanesulfonic acid 2-(2-methoxy-phenyl)-5-(2,2,6,6-tetramethyl-tetrahydro-thiopyran-4-yl)-2H-pyrazol-3-yl ester according to the procedure in Example 1, Step (F).

$^1$H NMR (CHLOROFORM-d) δ: 7.41 (dd, J=7.7, 1.6 Hz, 1H), 7.36 (td, J=7.9, 1.7 Hz, 1H), 7.19-7.23 (m, 2H), 7.10-7.14 (m, 2H), 7.03 (td, J=7.6, 1.1 Hz, 1H), 6.87 (dd, J=8.3, 1.0 Hz, 1H), 6.37 (s, 1H), 3.48 (s, 3H), 3.29-3.38 (m, 1H), 2.14 (dd, J=13.4, 2.7 Hz, 2H), 1.76 (t, J=13.0 Hz, 2H), 1.55 (s, 6H), 1.30 (s, 6H). Mass spectrum (ESI, m/z): Calculated for $C_{25}H_{29}ClN_2OS$, 441.2 (M+H), found 441.1.

Example 60

5-(4-Chlorophenyl)-1-(2-methoxyphenyl)-3-(2,2,6,6-tetramethyl-1,1-dioxidotetrahydro-2H-thiopyran-4-yl)-1H-pyrazole

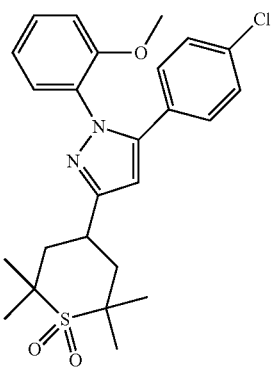 [SMILES: COc1ccccc1-n1nc(C2CC(C)(C)S(=O)(=O)C(C)(C)C2)cc1-c1ccc(Cl)cc1]

To a solution of 5-(4-chloro-phenyl)-1-(2-methoxy-phenyl)-3-(2,2,6,6-tetramethyl-tetrahydro-thiopyran-4-yl)-1H-pyrazole (Example 59) (83.0 mg, 0.188 mmol) in 1 mL of DCM was added m-chloroperoxybenzoic acid (77%) (84.3 mg, 0.376 mmol) and the mixture stirred for 1 hr at RT. The mixture was diluted with 20 mL of EtOAc and washed with sat'd $NaHCO_3$ (2×20 mL) and brine (20 mL). The organic layer was dried over $Na_2SO_4$, concentrated, and the residue purified by flash chromatography on silica gel to give 85 mg (95%) of a white solid.

$^1$H NMR (CHLOROFORM-d) δ: 7.32-7.46 (m, 2H), 7.19-7.26 (m, 2H), 7.07-7.14 (m, 2H), 6.99-7.07 (m, 1H), 6.89 (d, J=8.2 Hz, 1H), 6.39 (s, 1H), 3.51-3.59 (m, 1H), 3.50 (s, 3H), 2.37 (t, J=13.7 Hz, 2H), 2.14 (dd, J=14.5, 2.7 Hz, 2H), 1.64 (s, 6H), 1.45 (s, 6H). Mass spectrum (ESI, m/z): Calculated for $C_{25}H_{29}ClN_2O_3S$, 473.2 (M+H), found 473.2.

Example 61

5-(4-Chlorophenyl)-1-(2-nitrophenyl)-3-(2,2,6,6-tetramethyltetrahydro-2H-pyran-4-yl)-1H-pyrazole

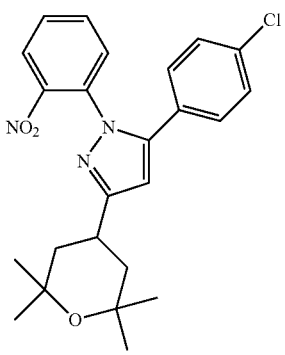 [SMILES: CC1(C)CC(c2cc(-c3ccc(Cl)cc3)n(-c3ccccc3[N+](=O)[O-])n2)CC(C)(C)O1]

Compound prepared according to the procedure in Example 50.

$^1$H NMR (CHLOROFORM-d) δ: 7.92 (dd, J=7.8, 1.5 Hz, 1H), 7.58 (td, J=7.6, 1.6 Hz, 1H), 7.51 (td, J=7.7, 1.5 Hz, 1H), 7.31 (dd, J=7.8, 1.3 Hz, 1H), 7.22-7.28 (m, 2H), 7.11-7.17 (m, 2H), 6.39 (s, 1H), 3.19-3.32 (m, 1H), 1.92 (dd, J=13.3, 3.4 Hz, 2H), 1.48-1.59 (m, 2H), 1.35 (s, 6H), 1.26 (s, 6H). Mass spectrum ESI-MS (m/z): Calcd. for $C_{24}H_{26}ClN_3O_3$: 440.2 (M+1); found: 440.2.

Example 62

2-(5-(4-Chlorophenyl)-3-(2,2,6,6-tetramethyltetrahydro-2H-pyran-4-yl)-1H-pyrazol-1-yl)aniline

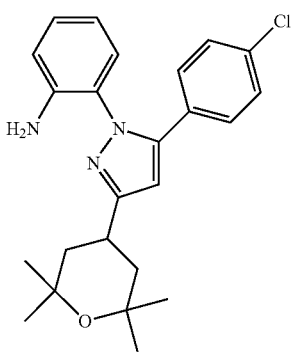 [SMILES: CC1(C)CC(c2cc(-c3ccc(Cl)cc3)n(-c3ccccc3N)n2)CC(C)(C)O1]

To a solution of 5-(4-chlorophenyl)-1-(2-nitrophenyl)-3-(2,2,6,6-tetramethyltetrahydro-2H-pyran-4-yl)-1H-pyrazole (Example 61) (1.10 g, 2.50 mmol) in 20 mL of ethanol and 20 mL of acetic acid was added iron powder (1.12 g, 20.0 mmol) and the mixture heated to 90° C. for 1 hr. The mixture was filtered through Celite and concentrated and the residue purified by silica gel chromatography (40-g cartridge, 10-25% EtOAc/heptane) to give 1.0 g (98%) the title compound as a white solid.

$^1$H NMR (CHLOROFORM-d) δ: 7.20-7.26 (m, 2H), 7.11-7.19 (m, 3H), 6.84 (dd, J=8.1, 1.3 Hz, 1H), 6.78 (dd, J=7.8, 1.3 Hz, 1H), 6.59-6.66 (m, 1H), 6.39 (s, 1H), 3.25-3.37 (m, 1H), 2.10 (s, 2H), 1.95 (dd, J=13.3, 3.4 Hz, 2H), 1.57 (t, J=13.0 Hz, 2H), 1.36 (s, 6H), 1.27 (s, 6H). Mass spectrum ESI-MS (m/z): Calcd. for $C_{24}H_{28}ClN_3O$: 410.2 (M+1); found: 410.2.

Example 63

2-[5-(4-Chlorophenyl)-3-(2,2,6,6-tetramethyltetrahydro-2H-pyran-4-yl)-1H-pyrazol-1-yl]-N-methylaniline

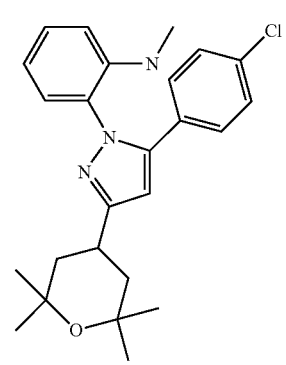

To a solution of 2-(5-(4-chlorophenyl)-3-(2,2,6,6-tetramethyltetrahydro-2H-pyran-4-yl)-1H-pyrazol-1-yl)aniline (Example 62) (25 mg, 0.06 mmol, 1 eq) in THF (2 mL) was added formaldehyde (13.64 of a 37% aqueous solution, 0.18 mmol, 3 eq). After 15 min, acetic acid (0.1 mL) and sodium cyanoborohydride (12 mg, 0.18 mmol, 3 eq) were added and the solution stirred 5 hrs. Aqueous saturated NaHCO$_3$ was added, the solution extracted with DCM, the organics combined, dried over MgSO$_4$ and concentrated. Purification by RP-HPLC, eluting with a linear gradient of 20%-100% CH$_3$CN in 0.1% TFA/H$_2$O followed by freebasing with aqueous MP-carbonate resin in DCM and concentration gave 8.6 mg (32%) the title compound.

$^1$H NMR (CHLOROFORM-d) δ: 8.41 (d, J=1.7 Hz, 1H), 7.42 (dd, J=7.8, 1.7 Hz, 1H), 7.33-7.38 (m, 2H), 6.96-7.07 (m, 2H), 6.88 (dd, J=8.3, 1.0 Hz, 1H), 6.41 (s, 1H), 3.51 (s, 3H), 3.36 (tt, J=12.8, 3.3 Hz, 1H), 2.52 (s, 3H), 1.99 (dd, J=13.2, 3.4 Hz, 2H), 1.60 (t, J=13.0 Hz, 2H), 1.28 (s, 6H), 1.25 (s, 6H). Mass spectrum (ESI, m/z): Calculated for C$_{25}$H$_{30}$ClN$_3$O, 424.2 (M+H), found 424.2.

Example 64

5-(4-Chlorophenyl)-3-[(2R,4r,6S)-2,6-dimethyltetrahydro-2H-pyran-4-yl]-1-(2-methoxyphenyl)-1H-pyrazole

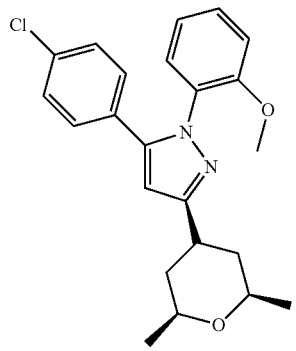

This compound prepared according to the procedures in Example 1, substituting (2R,4r,6S)-2,6-dimethyltetrahydro-2H-pyran-4-carboxylic acid (WO 2007/070201) in step B.

$^1$H NMR (CHLOROFORM-d) δ: 7.35-7.44 (m, 2H), 7.22-7.30 (m, 2H), 7.13-7.18 (m, 2H), 7.03 (td, J=7.6, 1.1 Hz, 1H), 6.92 (d, J=8.3 Hz, 1H), 6.41 (s, 1H), 3.61-3.73 (m, 2H), 3.55 (s, 3H), 3.16 (tt, 1H), 2.00-2.09 (m, 2H), 1.39-1.53 (m, 2H), 1.29 (d, J=6.3 Hz, 6H). Mass spectrum (ESI, m/z): Calcd. for C$_{23}$H$_{25}$ClN$_2$O$_2$, 397.2 (M+H), found 397.2.

Example 65

5-(4-Chlorophenyl)-3-((trans)-2,6-dimethyltetrahydro-2H-pyran-4-yl)-1-(2-methoxyphenyl)-1H-pyrazole

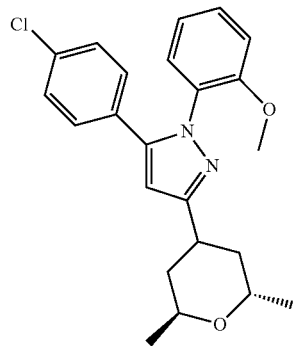 [SMILES: COc1ccccc1-n1nc(C2C[C@H](C)O[C@@H](C)C2)cc1-c1ccc(Cl)cc1]

a) N'-(2-methoxyphenyl)acetohydrazide

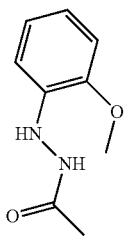

To a solution of N'-(2-methoxyphenyl)acetohydrazide (7.40 g, 53.56 mmol) in 54 mL of toluene at RT was slowly added acetic anhydride (5.57 mL, 58.91 mmol) and the mixture left to stand at RT for 1 hr. The ppt that formed was collected by filtration and washed with toluene to give 7.78 g (80%) of an off-white solid.

$^1$H NMR (CHLOROFORM-d) δ: 7.48 (br. s., 1H), 6.77-6.99 (m, 4H), 6.33 (br. s., 1H), 3.89 and 3.88 (rotational isomers, s, 3H), 2.05 and 2.15 (rotational isomers, s, 3H).

b) 5-(4-Chlorophenyl)-1-(2-methoxyphenyl)-1H-pyrazol-3(2H)-one

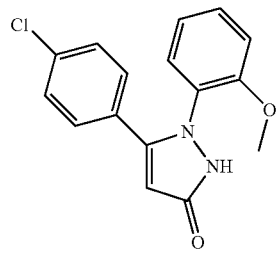 [SMILES: COc1ccccc1-n1[nH]c(=O)cc1-c1ccc(Cl)cc1]

To a mixture of N'-(2-methoxyphenyl)acetohydrazide (2.90 g, 16.09 mmol) and ethyl 3-(4-chlorophenyl)-3-oxopropanoate (3.65 g, 16.09 mmol) in 10 mL of DCE was added drop wise phosphorus trichloride (1.41 mL, 16.09 mmol). The mixture was heated to 50° C. and all solids dissolved. After 2 hrs at 50° C. the mixture was cooled to RT and the ppt was collected by filtration and washed with water and EtOAc and dried to give 2.50 g (49%) of a white solid.

$^1$H NMR (DMSO-d$_6$) δ: 7.29-7.42 (m, 4H), 7.15 (d, J=8.3 Hz, 2H), 6.95-7.09 (m, 2H), 5.93 (s, 1H), 3.44 (s, 3H). Mass spectrum (ESI, m/z): Calcd. for $C_{16}H_{13}ClN_2O_2$, 301.1 (M+H), found 301.2.

c) 5-(4-Chlorophenyl)-1-(2-methoxyphenyl)-1H-pyrazol-3-yl trifluoromethanesulfonate

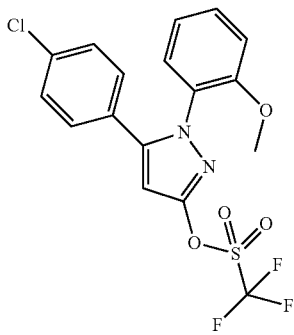 [SMILES: COc1ccccc1-n1nc(OS(=O)(=O)C(F)(F)F)cc1-c1ccc(Cl)cc1]

A mixture of 5-(4-chlorophenyl)-1-(2-methoxyphenyl)-1H-pyrazol-3(2H)-one (2.50 g, 8.31 mmol), DIEA (2.15 mL, 12.47 mmol), and N-phenyl-bis(trifluoromethanesulfonimide) (3.56 g, 9.98 mmol) in 40 mL of dichloroethane was heated at 70° C. for 1 hr. The reaction was diluted with 100 mL of EtOAc and washed with NaHCO3 (100 mL) and brine (100 mL). The residue was purified by flash chromatography on silica gel to give 3.20 g (89%) of the title compound as a colorless oil.

$^1$H NMR (CHLOROFORM-d) δ: 7.28-7.37 (m, 2H), 7.15-7.19 (m, 2H), 7.02-7.09 (m, 2H), 6.97 (td, J=7.7, 1.3 Hz, 1H), 6.81 (dd, J=8.7, 1.1 Hz, 1H), 6.31 (s, 1H), 3.43 (s, 3H). Mass spectrum (ESI, m/z): Calcd. for $C_{17}H_{12}ClF_3N_2O_4S$, 433.0 (M+H), found 433.0.

d) 5-(4-Chlorophenyl)-1-(2-methoxyphenyl)-3-(4,4,5,5-tetramethyl-1,3,2-dioxaborolan-2-yl)-1H-pyrazole

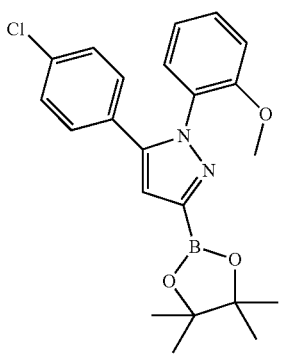 [SMILES: COc1ccccc1-n1nc(B2OC(C)(C)C(C)(C)O2)cc1-c1ccc(Cl)cc1]

A vial was charged with 5-(4-chlorophenyl)-1-(2-methoxyphenyl)-1H-pyrazol-3-yl trifluoromethanesulfonate (220 mg, 0.51 mmol), potassium acetate (150 mg, 1.53 mmol), bis(pinacolato)diboron (194 mg, 0.76 mmol), Pd(dppf)Cl$_2$ (41 mg, 0.05 mmol), and 2 mL of dioxane and heated for 10 hrs at 85° C. The reaction was diluted with EtOAc (50 mL) and washed with water (2×50 mL) and brine (50 mL), and the organic layer dried over Na$_2$SO$_4$ and evaporated. The crude product was purified by silica gel chromatography (Thomson Scientific 12-g cartridge, 10-100% EtOAc/heptane in 10 column volumes) to give 190 mg (90%) of the title compound as a white solid.

$^1$H NMR (CHLOROFORM-d) δ: 7.47 (dd, J=7.7, 1.6 Hz, 1H), 7.34 (td, J=7.9, 1.6 Hz, 1H), 7.17-7.22 (m, 2H), 7.10-7.15 (m, 2H), 7.01 (td, J=7.6, 1.1 Hz, 1H), 6.92 (s, 1H), 6.80-6.85 (m, 1H), 3.42 (s, 3H), 1.37 (s, 12H). Mass spectrum (ESI, m/z): Calcd. for $C_{23}H_{24}BClN_2O_3$, 411.2 (M+H), found 411.2.

e) trans-2,6-Dimethyl-3,6-dihydro-2H-pyran-4-yl trifluoromethanesulfonate

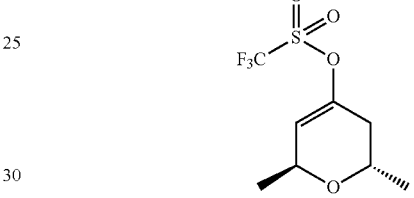

To a solution of trans-2,6-dimethyldihydro-2H-pyran-4(3H)-one (J. Org. Chem., vol 69, p 1716, 2004) (350 mg, 2.73 mmol) in 9 mL of THF at −78° C. was added a 1 M solution of LiHMDS in THF (3.0 mL, 3.00 mmol). After 10 mins at −78° C. a soln of N-phenyl-bis(trifluoromethanesulfonimide) (1073 mg, 3.00 mmol) in 5 mL of THF was added and the mixture allowed to attain RT. The mixture was diluted with 50 mL of ether and washed with 50 mL of 1N HCl, 50 mL of 1N NaOH and brine. The organic layer was dried over Na$_2$SO$_4$ and conc. The crude product was purified by silica gel chromatography (25-g cartridge, 1-10% EtOAc/heptane in 10 column volumes) to give 70 mg (10%) of the title compound as a colorless oil. $^1$H NMR (CHLOROFORM-d) δ: 5.69-5.71 (m, 1H), 4.42-4.51 (m, 1H), 3.91-4.01 (m, 1H), 2.23-2.31 (m, J=4.0 Hz, 1H), 2.12-2.22 (m, 1H), 1.24 (d, J=10.4 Hz, 3H), 1.22 (d, J=9.9 Hz, 3H).

f) 5-(4-chlorophenyl)-3-((trans)-2,6-dimethyl-3,6-dihydro-2H-pyran-4-yl)-1-(2-methoxyphenyl)-1H-pyrazole

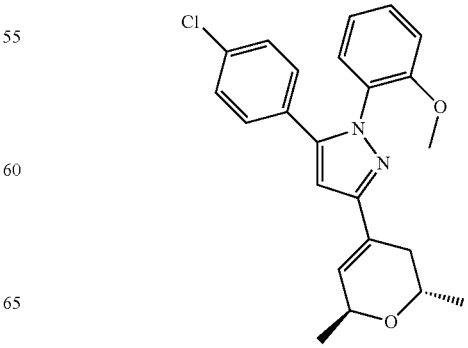

A flask is charged with 5-(4-chlorophenyl)-1-(2-methoxyphenyl)-3-(4,4,5,5-tetramethyl-1,3,2-dioxaborolan-2-yl)-1H-pyrazole (1.10 g, 3.70 mmol), trans-2,6-dimethyl-3,6-dihydro-2H-pyran-4-yltrifluoromethanesulfonate (1.06 g, 4.07 mmol), Pd(PPh$_3$)$_4$ (0.24 g, 5 mol %), 2 M Na$_2$CO$_3$ (16 mL), EtOH (16 mL) and toluene (32 mL) and heated at 80° C. for 6 h. The reaction was diluted with EtOAc (100 mL) and washed with saturated aqueous NaHCO$_3$ (2×100 mL) and brine (100 mL), and the organic layer dried over Na$_2$SO$_4$ and evaporated. The crude product was purified by silica gel chromatography (Thomson Scientific 25-g cartridge, 10-100% EtOAc/heptane in 10 column volumes) to give 0.68 g (66%) of the title compound as a white solid.

$^1$H NMR (CHLOROFORM-d) δ: 7.46 (dd, J=7.7, 1.6 Hz, 1H), 7.32-7.38 (m, 1H), 7.19-7.24 (m, 2H), 7.11-7.17 (m, 2H), 7.04 (td, J=7.6, 1.1 Hz, 1H), 6.86 (dd, J=8.3, 1.0 Hz, 1H), 6.60 (s, 1H), 6.32 (t, J=2.1 Hz, 1H), 4.53-4.65 (m, 1H), 4.02 (ddd, J=9.1, 6.1, 3.3 Hz, 1H), 3.46 (s, 3H), 2.71 (dd, J=17.1, 3.4 Hz, 1H), 2.24-2.38 (m, J=17.0, 8.9, 2.5, 2.5 Hz, 1H), 1.34 (dd, 6H). Mass spectrum (ESI, m/z): Calcd. for C$_{23}$H$_{23}$ClN$_2$O$_2$, 395.1 (M+H), found 395.2.

g) 5-(4-Chlorophenyl)-3-((trans)-2,6-dimethyltetrahydro-2H-pyran-4-yl)-1-(2-methoxyphenyl)-1H-pyrazole A mixture of 5-(4-chlorophenyl)-3-((trans)-2,6-dimethyl-3,6-dihydro-2H-pyran-4-yl)-1-(2-methoxyphenyl)-1H-pyrazole (50 mg, 0.13 mmol), and platinum oxide (3 mg) in 5 mL of methanol was stirred under a balloon of hydrogen for 6 hrs. The mixture was filtered through Celite and concentrated. The crude product was purified by silica gel chromatography (Thomson Scientific 12-g cartridge, 5-40% EtOAc/heptane in 10 column volumes) and then by RP-HPLC (50% CH3CN to 100% in 0.1% TFA/H$_2$O over 15 mins) to give 35 mg (60%) the title compound as a partial TFA salt (0.5 eq TFA).

$^1$H NMR (CHLOROFORM-d) δ: 7.26-7.34 (m, 2H), 7.12-7.18 (m, 2H), 7.02-7.09 (m, 2H), 6.94 (td, J=7.6, 1.3 Hz, 1H), 6.78-6.84 (m, 1H), 6.29 (s, 1H), 4.30 (quin, J=6.5 Hz, 1H), 3.81-3.92 (m, 1H), 3.43 (s, 3H), 3.26 (tt, J=12.5, 3.8 Hz, 1H), 1.86-1.99 (m, 2H), 1.74-1.83 (m, 1H), 1.33-1.45 (m, 1H), 1.30 (d, J=6.8 Hz, 3H), 1.13 (d, 3H). Mass spectrum (ESI, m/z): Calcd. for C$_{23}$H$_{25}$ClN$_2$O$_2$, 397.2 (M+H), found 397.2.

Example 66

5-(4-Chlorophenyl)-3-(2,2-dimethyltetrahydro-2H-pyran-4-yl)-1-(2-methoxyphenyl)-1H-pyrazole

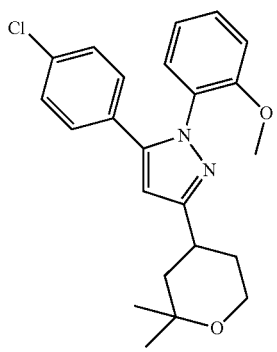 [SMILES: COc1ccccc1-n1nc(C2CCOC(C)(C)C2)cc1-c1ccc(Cl)cc1]

Step A)
2,2-Dimethyltetrahydro-2H-pyran-4-carbonyl chloride

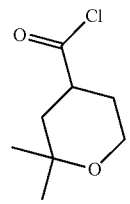

To a solution of 2,2-dimethyltetrahydro-2H-pyran-4-carboxylic acid (530 mg, 3.35 mmol) in 10 mL of DCM at 0° C. was added 1 drop of DMF followed by oxalyl chloride (0.33 mL, 3.69 mmol) and the reaction stirred at RT for 3 hrs. The reaction was then concentrated and used with out further purification.

$^1$H NMR (CHLOROFORM-d) d: 3.72-3.80 (m, 1H), 3.59 (td, J=12.3, 2.4 Hz, 1H), 3.01 (tt, J=12.3, 3.7 Hz, 1H), 1.85-1.96 (m, 2H), 1.65 (qd, J=12.5, 5.1 Hz, 1H), 1.51-1.59 (m, 1H), 1.21 (s, 3H), 1.16 (s, 3H).

Step B) (Z)-3-(4-Chlorophenyl)-1-(2,2-dimethyltetrahydro-2H-pyran-4-yl)-3-hydroxyprop-2-en-1-one

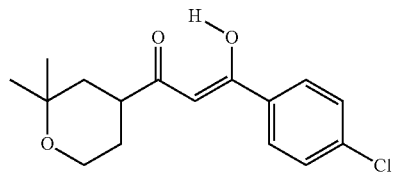 [SMILES: CC1(C)CC(C(=O)/C=C(\O)c2ccc(Cl)cc2)CCO1]

To a mixture of 2,2-dimethyltetrahydro-2H-pyran-4-carbonyl chloride (0.55 g, 3.14 mmol), magnesium bromide diethyl etherate (1.35 g, 5.23 mmol), and 4-chloroacetophenone (0.34 mL, 2.62 mmol) in 12 mL of DCM at RT was added dropwise DIEA (1.45 mL, 7.85 mmol). The mixture was stirred overnight and then diluted with 50 mL of DCM and washed with 1N HCl (100 mL) and brine (100 mL). The organic layer was dried over Na$_2$SO$_4$, concentrated, and the crude product was purified by silica gel chromatography (Thomson Scientific 25-g cartridge, 2-20% EtOAc/heptane in 10 column volumes) to give 0.45 g (58%) of the title compound as a light orange solid. The NMR of this compound shows that it exists in the enone form in CDCl$_3$.

$^1$H NMR (CHLOROFORM-d) d: 16.20 (br. s., 1H), 7.82-7.87 (m, 2H), 7.41-7.47 (m, 2H), 6.16 (s, 1H), 3.82-3.89 (m, 1H), 3.73 (td, J=12.1, 2.9 Hz, 1H), 2.74 (tt, J=12.3, 3.9 Hz, 1H), 1.56-1.84 (m, 4H), 1.29 (s, 3H), 1.28 (s, 3H). Mass spectrum (ESI, m/z): Calcd. for C$_{16}$H$_{19}$ClO$_3$, 295.1 (M+H), found 295.0.

Step C) 5-(4-Chlorophenyl)-3-(2,2-dimethyltetrahydro-2H-pyran-4-yl)-1-(2-methoxyphenyl)-1H-pyrazole The title compound was prepared from (Z)-3-(4-chlorophenyl)-1-(2,2-dimethyltetrahydro-2H-pyran-4-yl)-3-hydroxyprop-2-en-1-one and (2-methoxyphenyl)hydrazine hydrochloride according to the procedure in Example 50, step B.

¹H NMR (CHLOROFORM-d) δ: 7.42 (dd, J=7.7, 1.6 Hz, 1H), 7.32-7.38 (m, 1H), 7.18-7.24 (m, 2H), 7.10-7.16 (m, 2H), 7.03 (td, J=7.6, 1.3 Hz, 1H), 6.87 (dd, J=8.3, 1.0 Hz, 1H), 6.35 (s, 1H), 3.77-3.93 (m, 2H), 3.47 (s, 3H), 3.21 (tt, J=12.6, 3.8 Hz, 1H), 1.90-2.00 (m, 2H), 1.74-1.84 (m, 1H), 1.65-1.74 (m, 1H), 1.32 (s, 3H), 1.29 (s, 3H). Mass spectrum (ESI, m/z): Calcd. for $C_{23}H_{25}ClN_2O_2$, 397.2 (M+H), found 397.2.

Example 67

5-(4-Chlorophenyl)-1-(2-methoxyphenyl)-3-(2,2,5,5-tetramethyl-2,5-dihydrofuran-3-yl)-1H-pyrazole

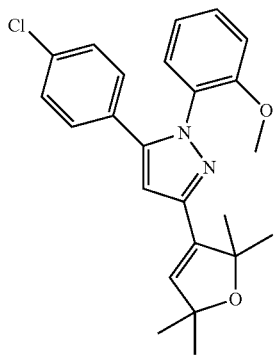 [SMILES: COc1ccccc1-n1nc(C2=CC(C)(C)OC2(C)C)cc1-c1ccc(Cl)cc1]

a) Trifluoromethanesulfonic acid 2,2,5,5-tetramethyl-2,5-dihydro-furan-3-yl ester

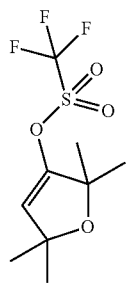

To a solution of dihydro-2,2,5,5-tetramethyl-3(2H)-furanone (2 mL, 13.0 mmol, 1 eq) in THF (45 mL) at −78° C. under Ar was added KHMDS (31.3 mL of a 0.5 M solution in toluene, 15.6 mmol, 1.2 eq). After 30 min, a solution of N-phenyl-bis(trifluoromethanesulfonimide) (5.58 g, 15.6 mmol, 1.2 eq) in THF (20 mL) was added and the solution warmed to rt over overnight. Added water, NH₄Cl, extracted with ether, dried over MgSO₄ and concentrated. Purification by column chromatography (80 g) eluting with 5 to 10% EtOAc/hexane gave the title compound (1.84 g, 51%).

¹H NMR (CHLOROFORM-d) δ: 5.69 (s, 1H), 1.38 (d, J=1.5 Hz, 12H).

b) 5,5-dimethyl-2-(2,2,5,5-tetramethyl-2,5-dihydro-furan-3-yl)-[1,3,2]dioxaborinane

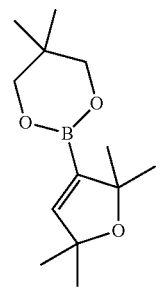 [SMILES: CC1(C)COB(C2=CC(C)(C)OC2(C)C)OC1]

To a solution of trifluoromethanesulfonic acid 2,2,5,5-tetramethyl-2,5-dihydro-furan-3-yl ester (746 mg, 2.72 mol, 1 eq) in dioxane (12 mL) was added bis(neopentyl glycolato) diboron (921 mg, 4.08 mmol, 1.5 eq), Pd(dppf)Cl₂ (222 mg, 0.27 mmol, 0.1 eq) and potassium acetate (801 mg, 8.16 mmol, 3 eq). Ar was bubbled through the solution, the vial was capped and heated to 95° C. for 2 hrs. The solution was cooled to rt, silica gel was added and concentrated. Purification by column chromatography (40 g) eluting with 3 to 15% EtOAc/hexanes gave the title compound (542 mg, 84%).

¹H NMR (CHLOROFORM-d) δ: 6.21 (s, 1H), 3.65 (s, 4H), 1.36 (s, 6H), 1.30 (s, 6H), 0.98 (s, 6H).

c) 5-(4-Chlorophenyl)-1-(2-methoxyphenyl)-3-(2,2,5,5-tetramethyl-2,5-dihydrofuran-3-yl)-1H-pyrazole To a solution of 5-(4-Chlorophenyl)-1-(2-methoxyphenyl)-1H-pyrazol-3-yl trifluoromethanesulfonate (Example 65, (c)) (337 mg, 0.78 mmol, 1 eq) in DMF (5 mL) was added 5,5-dimethyl-2-(2,2,5,5-tetramethyl-2,5-dihydro-furan-3-yl)-[1,3,2]dioxaborinane (223 mg, 0.93 mmol, 1.2 eq), sodium carbonate (198 mg, 1.87 mmol, 2.4 eq), and Pd(Ph₃P)₄ (90 mg, 0.078 mmol, 0.1 eq). Ar was bubbled through and the solution was heated to 100° C. for 5 hrs. Added water, extracted with EtOAc, dried over MgSO₄ and conc. Purification by column chromatography (24 g) eluting with 5 to 10% EA/hexanes gave the title compound (249 mg, 78%).

¹H NMR (CHLOROFORM-d) δ:7.45 (dd, J=7.7, 1.6 Hz, 1H), 7.31-7.40 (m, 1H), 7.22 (d, J=8.6 Hz, 2H), 7.09-7.17 (m, 2H), 7.01-7.09 (m, 1H), 6.85 (d, J=8.3 Hz, 1H), 6.57 (s, 1H), 6.13 (s, 1H), 3.42 (s, 3H), 1.64 (s, 6H), 1.40 (s, 6H). Mass spectrum ESI-MS (m/z): Calcd. for $C_{24}H_{25}ClN_2O_2$: 409.2 (M+1); found: 409.2.

Example 68

5-(4-Chlorophenyl)-1-(2-methoxyphenyl)-3-(2,2,5,5-tetramethyltetrahydrofuran-3-yl)-1H-pyrazole

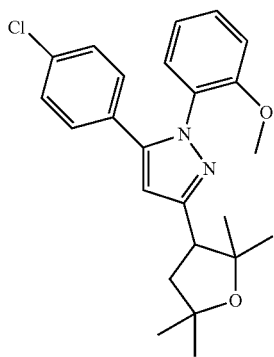 [SMILES: COc1ccccc1-n1nc(C2CC(C)(C)OC2(C)C)cc1-c1ccc(Cl)cc1]

A solution of 5-(4-chlorophenyl)-1-(2-methoxyphenyl)-3-(2,2,5,5-tetramethyl-2,5-dihydrofuran-3-yl)-1H-pyrazole (162 mg, 0.4 mmol, 1 eq) (Example 67) and $PtO_2$ (9 mg, 0.04 mmol, 0.1 eq) in ethyl acetate (10 mL) was put under a balloon of $H_2$ and stirred overnight. Additional $PtO_2$ (9 mg) was then added and the reaction stirred for 3 more days under a balloon of $H_2$. The reaction was filtered through Celite, and concentrated. Purification by HPLC eluting with 30 to 100% acetonitrile/$H_2O$ gave the title compound (70 mg, 41%).

$^1$H NMR (CHLOROFORM-d) δ: 7.42 (dd, J=7.8, 1.8 Hz, 1H), 7.34-7.40 (m, 1H), 7.20-7.25 (m, 2H), 7.11-7.17 (m, 2H), 7.05 (td, J=7.6, 1.3 Hz, 1H), 6.89 (dd, J=8.3, 1.0 Hz, 1H), 6.39 (s, 1H), 3.55 (dd, J=13.3, 6.7 Hz, 1H), 2.50 (t, J=12.8 Hz, 1H), 2.20 (dd, J=12.4, 6.8 Hz, 1H), 1.47 (s, 3H), 1.43 (s, 3H), 1.31 (s, 3H), 1.06 (s, 3H). Mass spectrum (ESI, m/z): Calcd. for $C_{24}H_{27}ClN_2O_2$, 411.2 (M+H), found 411.2.

Example 69

5-(4-chlorophenyl)-1-(2-methoxyphenyl)-3-(tetrahydro-2H-pyran-4-yl)-1H-pyrazole

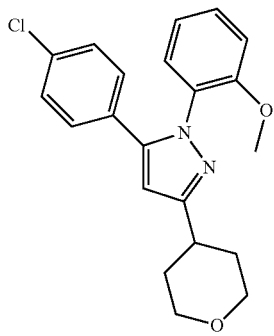 [SMILES: COc1ccccc1-n1nc(C2CCOCC2)cc1-c1ccc(Cl)cc1]

A solution of 1-(4-chlorophenyl)ethanone (2.0 g, 12.9 mmol) in anhydrous THF was cooled in a dry ice acetone bath and treated with sodium hexamethyldisilazid (14.2 mL, 1M in THF, 14.2 mmol). The resulting solution was stirred for 1 h at −78° C. and a solution of tetrahydro-pyran-4-carbonyl chloride (1.92 g, 12.9 mmol) in THF was slowly added. The resulting solution was stirred for 30 min at −78° C., allowed to warm up to room temperature and stirred for 5 h. The reaction was quenched by adding 6N HCl and extracted with EtOAc (×3). The organic fractions were combined and washed with sat. NaCl, dried over $Na_2SO_4$ and evaporated under vacuum. The resulting residue was purified by silica column chromatography to give 2 g (58%) of 1-(4-chlorophenyl)-3-(tetrahydro-2H-pyran-4-yl)propane-1,3-dione. 1-(4-chlorophenyl)-3-(tetrahydro-2H-pyran-4-yl)propane-1,3-dione 1 g (3.75 mmol) was taken in absolute ethanol (20 mL) and TEA (1.4 mL, 10 mmol) was added slowly. This solution was stirred for 20 min and added drop-wise to a solution of (2-methoxyphenyl)hydrazine hydrochloride (0.7 g, 4.0 mmol) in ethanol (20 mL). This solution was heated to 60° C. and stirred for 5 h. Ethanol was removed under vacuum and the residue was taken in EtOAc and washed with water, and sat. NaCl. The solution was dried over $Na_2SO_4$ and evaporated. The residue was purified by silica column chromatography to give 5-(4-chlorophenyl)-1-(2-methoxyphenyl)-3-(tetrahydro-2H-pyran-4-yl)-1H-pyrazole.

$^1$H NMR (400 MHz, DMSO-$d_6$) δ ppm 1.70 (dd, J=12.8, 3.9 Hz, 2H), 1.84-1.93 (m, 2H), 2.82-2.95 (m, 1H), 3.40 (s, 3H), 3.41-3.49 (m, 2H), 3.85-3.97 (m, 2H), 6.54 (s, 1H), 7.03-7.09 (m, 2H), 7.17 (d, J=8.3 Hz, 2H), 7.35 (d, J=8.6 Hz, 2H), 7.37-7.45 (m, 2H). Mass spectrum (ESI, m/z): Calcd. for $C_{21}H_{21}ClN_2O_2$, 369.1 (M+H), found 369.1.

Example 70

2-[5-(4-chlorophenyl)-3-(2,2,6,6-tetramethyltetrahydro-2H-pyran-4-yl)-1H-pyrazol-1-yl]-N-ethylaniline

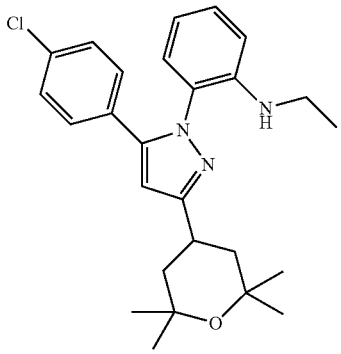 [SMILES: CCNc1ccccc1-n1nc(C2CC(C)(C)OC(C)(C)C2)cc1-c1ccc(Cl)cc1]

To a solution of 2-(5-(4-chlorophenyl)-3-(2,2,6,6-tetramethyltetrahydro-2H-pyran-4-yl)-1H-pyrazol-1-yl)aniline (Example 62) (50 mg, 0.12 mmol, 1 eq) in THF (2 mL) was added acetaldehyde (0.028 mL, 0.49 mmol, 4 eq). After 15 min, sodium cyanoborohydride (61 mg, 0.98 mmol, 8 eq) and acetic acid (0.1 mL) were added and the solution stirred 3 days. Water and $NaHCO_3$ were added, extracted with DCM, dried over $MgSO_4$ and concentrated. Purification by column chromatography (8 g) eluting with 15 to 30% EtOAc/hex gave the title compound (28.3 mg, 50%).

$^1$H NMR (CHLOROFORM-d) δ: 7.18-7.25 (m, 3H), 7.10-7.15 (m, 2H), 6.72-6.81 (m, 2H), 6.50-6.58 (m, 1H), 6.39 (s, 1H), 4.29 (br. s., 1H), 3.26-3.37 (m, 1H), 3.16 (dd, J=7.1, 5.1 Hz, 2H), 1.96 (dd, J=13.3, 3.4 Hz, 2H), 1.52-1.63 (m, 2H), 1.36 (s, 6H), 1.27 (s, 6H), 1.18 (t, J=7.1 Hz, 3H). Mass spectrum ESI (m/z): Calcd. for $C_{26}H_{32}ClN_3O$: 438.2 (M+1); found: 438.2.

Example 71

2-[5-(4-chlorophenyl)-3-(2,2,6,6-tetramethyltetrahydro-2H-pyran-4-yl)-1H-pyrazol-1-yl]-N,N-diethylaniline

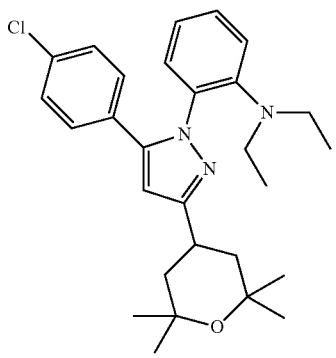 [SMILES: CCN(CC)c1ccccc1-n1nc(C2CC(C)(C)OC(C)(C)C2)cc1-c1ccc(Cl)cc1]

To a solution of 2-[5-(4-chlorophenyl)-3-(2,2,6,6-tetramethyltetrahydro-2H-pyran-4-yl)-1H-pyrazol-1-yl]-N-ethylaniline (Example 70) (25 mg, 0.06 mmol, 1 eq) in acetone (2 mL) was added potassium carbonate (84 mg, 0.6 mmol, 10 eq) and iodoethane (0.049 mL, 0.6 mmol, 10 eq), the solution heated to 60° C. overnight. The reaction was 50% complete, added iodoethane (0.049 mL) and heated to 60° C. overnight. Added water, extracted with DCM, dried over MgSO$_4$ and concentrated. Purification by silica gel column chromatography (8 g) eluting with 7 to 15% EtOAc/hex, then purification by RP-HPLC eluting with 10 to 100% acetonitrile/H$_2$O gave the title compound (12.4 mg, 46%).

$^1$H NMR (CHLOROFORM-d) δ: 7.49 (dd, J=7.7, 1.6 Hz, 1H), 7.27-7.31 (m, 1H), 7.12-7.19 (m, 2H), 7.03-7.11 (m, 3H), 6.81-6.88 (m, 1H), 6.35 (s, 1H), 3.32 (tt, J=12.8, 3.4 Hz, 1H), 2.56 (br. s., 4H), 1.92 (dd, J=13.3, 3.4 Hz, 2H), 1.50-1.60 (m, 2H), 1.36 (s, 6H), 1.27 (s, 6H), 0.51 (t, J=7.1 Hz, 6H). Mass spectrum ESI (m/z): Calcd. for C$_{28}$H$_{36}$ClN$_3$O: 466.3 (M+1); found: 466.2.

Example 72

5-(4-chlorophenyl)-1-(2-pyrrolidin-1-ylphenyl)-3-(2,2,6,6-tetramethyltetrahydro-2H-pyran-4-yl)-1H-pyrazole

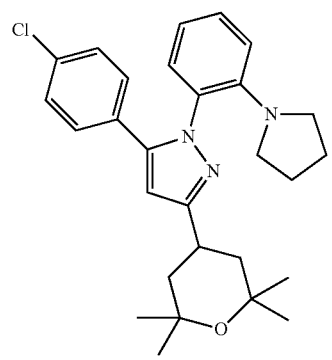 [SMILES: CC1(C)CC(c2cc(-c3ccc(Cl)cc3)n(-c3ccccc3N3CCCC3)n2)CC(C)(C)O1]

To a solution of 2-[5-(4-chlorophenyl)-3-(2,2,6,6-tetramethyltetrahydro-2H-pyran-4-yl)-1H-pyrazol-1-yl]aniline (Example 62) (25 mg, 0.06 mmol, 1 eq) in toluene (2 mL) was added diisopropylethylamine (0.52 mL, 0.3 mmol, 5 eq), and 1,4-dibromobutane (0.5 mL, 4.1 mmol, 69 eq) and the solution stirred at 130° C. in a vial for 2 days. Added water, extracted with DCM, dried over MgSO$_4$ and concentrated. Purification by column chromatography (8 g) eluting with 7 to 15% EtOAc/hex gave the title compound (10.9 mg, 38%).

$^1$H NMR (CHLOROFORM-d) δ: 7.09-7.25 (m, 6H), 6.65-6.75 (m, 2H), 6.34 (s, 1H), 3.31 (tt, J=12.8, 3.4 Hz, 1H), 2.80 (t, J=5.6 Hz, 4H), 1.85-2.00 (m, 2H), 1.46-1.83 (m, 6H), 1.36 (s, 6H), 1.22-1.31 (m, 6H). Mass spectrum ESI (m/z): Calcd. for C$_{28}$H$_{34}$ClN$_3$O: 464.2 (M+1); found: 464.2.

Example 73

5-(4-Chlorophenyl)-3-((cis)-2-isopropyltetrahydro-2H-pyran-4-yl)-1-(2-methoxyphenyl)-1H-pyrazole

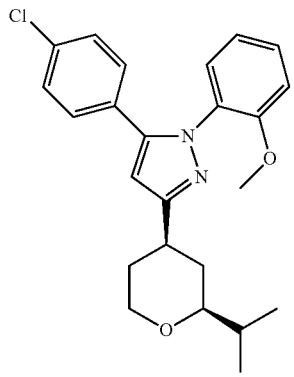 [SMILES: COc1ccccc1-n1nc([C@@H]2CCO[C@H](C(C)C)C2)cc1-c1ccc(Cl)cc1]

a) (1H-benzo[d][1,2,3]triazol-1-yl)(2-isopropyltetrahydro-2H-pyran-4-yl)methanone

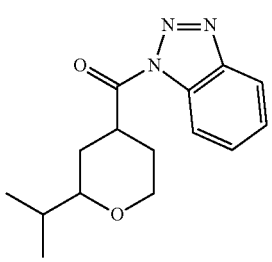 [SMILES: CC(C)C1CC(C(=O)n2nnc3ccccc32)CCO1]

Prepared from 2-isopropyltetrahydro-2H-pyran-4-carboxylic acid according to the procedure in Example 1, step (b) as a mixture of diastereomers and used without further purification.

b) 1-(4-Chlorophenyl)-3-((cis)-2-isopropyltetrahydro-2H-pyran-4-yl)propane-1,3-dione and 1-(4-Chlorophenyl)-3-((trans)-2-isopropyltetrahydro-2H-pyran-4-yl)propane-1,3-dione

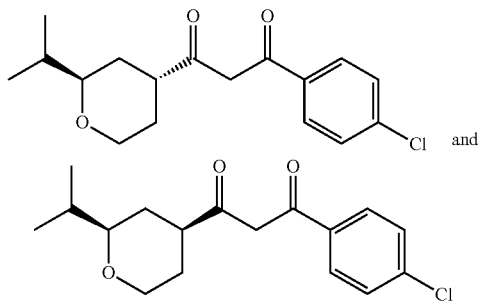

Prepared from (1H-benzo[d][1,2,3]triazol-1-yl)(2-isopropyltetrahydro-2H-pyran-4-yl)methanone and 1-(4-chlorophenyl)-ethanone according to the procedure in Example 51, step (a). The two diastereomers were separated on silica gel (Thomson Scientific 80-g cartridge, 2-20% EtOAc/heptane in 10 column volumes) and used without further purification. The first compound to elute was used in step (c), Example 73 and this formed the cis isomer. The second compound to elute was used in Example 74 and formed the trans isomer.

c) 5-(4-Chlorophenyl)-3-((cis)-2-isopropyltetrahydro-2H-pyran-4-yl)-1-(2-methoxyphenyl)-1H-pyrazole

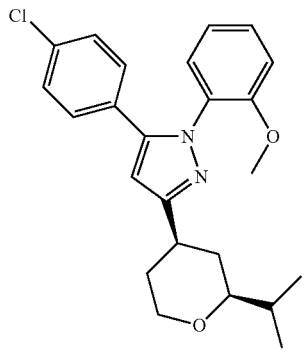 [SMILES: COc1ccccc1-n1nc([C@@H]2CCO[C@H](C(C)C)C2)cc1-c1ccc(Cl)cc1]

Prepared according to the procedure in Example 50. The compound showed 1 DNoesy enhancements consistent with the cis isomer.

$^1$H NMR (BENZENE-$d_6$) δ: 7.51 (dd, J=7.8, 1.8 Hz, 1H), 7.08-7.14 (m, 2H), 6.99-7.08 (m, 3H), 6.81 (td, J=7.7, 1.3 Hz, 1H), 6.41 (dd, J=8.3, 1.3 Hz, 1H), 6.38 (s, 1H), 4.03-4.11 (m, 1H), 3.95-4.02 (m, 1H), 3.69 (ddd, J=9.7, 6.8, 2.4 Hz, 1H), 3.44 (quin, J=4.4 Hz, 1H), 2.94 (s, 3H), 2.28-2.37 (m, 1H), 2.15-2.23 (m, 1H), 2.02-2.13 (m, 1H), 1.88-1.99 (m, 2H), 1.17 (d, J=6.8 Hz, 3H), 1.05 (d, 3H). Mass spectrum (ESI, m/z): Calculated for $C_{24}H_{27}ClN_2O_2$, 411.2 (M+H), found 411.3.

Example 74

5-(4-Chlorophenyl)-3-((trans)-2-isopropyltetrahydro-2H-pyran-4-yl)-1-(2-methoxyphenyl)-1H-pyrazole

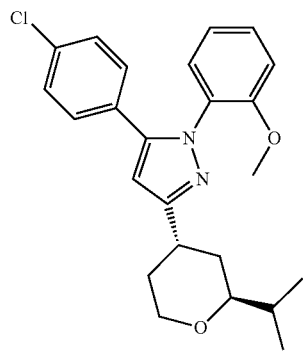 [SMILES: COc1ccccc1-n1nc([C@H]2CCO[C@H](C(C)C)C2)cc1-c1ccc(Cl)cc1]

Prepared according to the procedure in Example 73.

$^1$H NMR (CHLOROFORM-d) δ: 7.43 (dd, J=7.7, 1.6 Hz, 1H), 7.36 (td, J=7.9, 1.6 Hz, 1H), 7.19-7.25 (m, 2H), 7.12-7.18 (m, 2H), 7.04 (td, J=7.6, 1.3 Hz, 1H), 6.88 (dd, J=8.3, 1.0 Hz, 1H), 6.37 (s, 1H), 4.13-4.18 (m, 1H), 3.58 (td, J=11.9, 2.3 Hz, 1H), 3.48 (s, 3H), 3.16 (ddd, J=11.1, 6.1, 1.8 Hz, 1H), 3.04 (tt, J=12.2, 3.9 Hz, 1H), 2.08 (dt, J=13.0, 2.0 Hz, 1H), 1.92-2.00 (m, 1H), 1.80-1.89 (m, 1H), 1.70-1.80 (m, 1H), 1.46-1.56 (m, 1H), 0.99 (d, J=6.8 Hz, 3H), 0.95 (d, 3H). Mass spectrum (ESI, m/z): Calculated for $C_{24}H_{27}ClN_2O_2$, 411.2 (M+H), found 411.3.

Example 75

3-((trans)-2,6-Dimethyltetrahydro-2H-pyran-4-yl)-1-(2-methoxyphenyl)-5-phenyl-1H-pyrazole

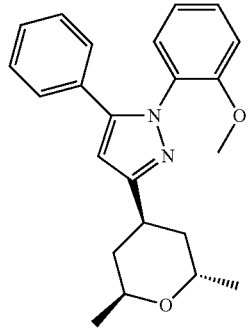

A mixture of 5-(4-chlorophenyl)-3-((trans)-2,6-dimethyl-3,6-dihydro-2H-pyran-4-yl)-1-(2-methoxyphenyl)-1H-pyrazole (50 mg, 0.13 mmol)(Example 65, step (f)), and platinum oxide (3 mg) in 5 mL of methanol was stirred under a balloon of hydrogen for 6 hrs. The mixture was filtered through Celite and concentrated. The crude product was purified by silica gel chromatography (Thomson Scientific 12-g cartridge, 5-40% EtOAc/heptane in 10 column volumes) and then by RP-HPLC (50% CH₃CN to 100% in 0.1% TFA/H₂O over 15 mins) to give 6 mg (11%) the title compound as a partial TFA salt (0.5 eq TFA).

¹H NMR (CHLOROFORM-d) δ: 7.26-7.33 (m, 2H), 7.16-7.21 (m, 3H), 7.10-7.15 (m, 2H), 6.93 (td, J=7.7, 1.3 Hz, 1H), 6.81 (dd, J=8.8, 1.3 Hz, 1H), 6.32 (s, 1H), 4.24-4.37 (m, 1H), 3.81-3.93 (m, 1H), 3.41 (s, 3H), 3.29 (tt, J=12.6, 3.9 Hz, 1H), 1.87-2.01 (m, 2H), 1.76-1.85 (m, 1H), 1.33-1.49 (m, 1H), 1.30 (d, J=6.8 Hz, 3H), 1.14 (d, J=6.1 Hz, 3H). Mass spectrum (ESI, m/z): Calcd. for $C_{23}H_{26}N_2O_2$, 363.2 (M+H), found 363.2.

Example 76

4-Bromo-5-(4-chlorophenyl)-1-(2-methoxyphenyl)-3-(2,2,6,6-tetramethyltetrahydro-2H-pyran-4-yl)-1H-pyrazole

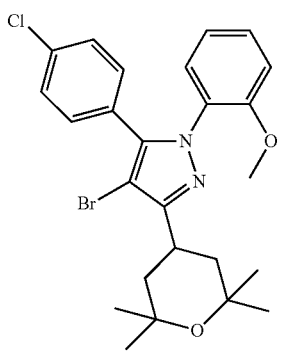 [SMILES: COc1ccccc1-n1nc(C2CC(C)(C)OC(C)(C)C2)c(Br)c1-c1ccc(Cl)cc1]

To a solution of 5-(4-chlorophenyl)-1-(2-methoxyphenyl)-3-(2,2,6,6-tetramethyltetrahydro-2H-pyran-4-yl)-1H-pyrazole (80 mg, 0.19 mmol)(Example 1) in 2 mL of DCM was added NBS (33 mg, 0.19 mmol) and the mixture stirred for 30 mins at Rt. The crude product was purified by silica gel chromatography (Thomson Scientific 12-g cartridge, 2-20% EtOAc/heptane) to give 40 mg (40%) of the title compound.

¹H NMR (CHLOROFORM-d) δ: 7.41 (dd, J=7.7, 1.6 Hz, 1H), 7.33 (td, J=8.0, 1.8 Hz, 1H), 7.25-7.30 (m, 2H), 7.17-7.23 (m, 2H), 7.02 (td, J=7.7, 1.3 Hz, 1H), 6.81 (dd, J=8.3, 1.0 Hz, 1H), 3.45 (s, 3H), 3.35-3.44 (m, 1H), 1.97 (dd, J=13.3, 3.2 Hz, 2H), 1.73-1.82 (m, 2H), 1.41 (s, 6H), 1.29 (s, 6H). Mass spectrum (ESI, m/z): Calcd. for $C_{25}H_{28}BrClN_2O_2$, 505.1/503.1 (M+H), found 505.0/503.0.

Example 77

5-(4-Chlorophenyl)-3-(2,2-dimethyltetrahydro-2H-pyran-4-yl)-1-(4-methoxy-2-methylphenyl)-1H-pyrazole

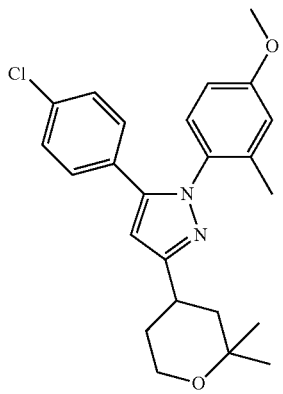 [SMILES: COc1ccc(-n2nc(C3CCOC(C)(C)C3)cc2-c2ccc(Cl)cc2)c(C)c1]

Prepared according to the procedure in Example 66.

¹H NMR (CHLOROFORM-d) δ: 7.15-7.25 (m, 3H), 7.07-7.13 (m, 2H), 6.72-6.79 (m, 2H), 6.37 (s, 1H), 3.84-3.91 (m, 2H), 3.82 (s, 3H), 3.12-3.25 (m, 1H), 1.93-1.99 (m, 1H), 1.92 (s, 3H), 1.62-1.85 (m, 3H), 1.33 (s, 3H), 1.30 (s, 3H). Mass spectrum (ESI, m/z): Calcd. for $C_{24}H_{27}ClN_2O_2$, 411.2 (M+H), found 411.3.

Example 78

1-(2-Methoxyphenyl)-5-(4-(methylsulfonyl)phenyl)-3-(2,2,6,6-tetramethyltetrahydro-2H-pyran-4-yl)-1H-pyrazole

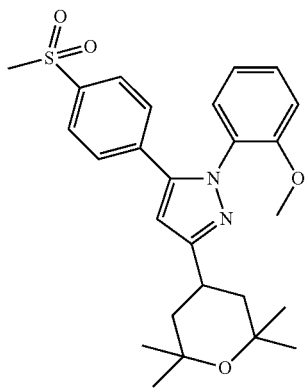 [SMILES: COc1ccccc1-n1nc(C2CC(C)(C)OC(C)(C)C2)cc1-c1ccc(S(C)(=O)=O)cc1]

Prepared according to the procedure in Example 1.

¹H NMR (CHLOROFORM-d) δ: 7.78-7.84 (m, 2H), 7.46 (dd, J=7.7, 1.6 Hz, 1H), 7.34-7.42 (m, 3H), 7.06 (td, J=7.6, 1.3 Hz, 1H), 6.83-6.91 (m, 1H), 6.48 (s, 1H), 3.45 (s, 3H), 3.36 (tt, J=12.9, 3.3 Hz, 1H), 3.04 (s, 3H), 1.99 (dd, J=13.3, 3.4 Hz,

2H), 1.58 (t, J=12.9 Hz, 2H), 1.36 (s, 6H), 1.28 (s, 6H). Mass spectrum (ESI, m/z): Calcd. for $C_{26}H_{32}N_2O_4S$, 469.2 (M+H), found 469.2.

Example 79

5-(1-(2-Methoxyphenyl)-3-(2,2,6,6-tetramethyltetrahydro-2H-pyran-4-yl)-1H-pyrazol-5-yl)pyridin-2-amine

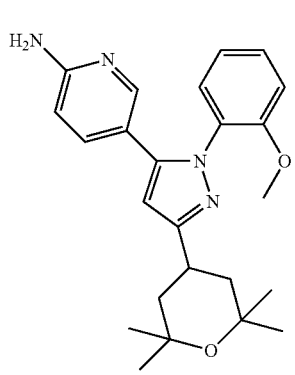 [SMILES: COc1ccccc1-n1nc(C2CC(C)(C)OC(C)(C)C2)cc1-c1ccc(N)nc1]

Prepared according to the procedure in Example 1.

$^1$H NMR (CHLOROFORM-d) δ: 7.59 (d, J=1.5 Hz, 1H), 7.43 (dd, J=9.2, 2.1 Hz, 1H), 7.31-7.37 (m, 2H), 7.00 (td, J=7.7, 1.3 Hz, 1H), 6.84-6.90 (m, 1H), 6.56 (d, J=9.1 Hz, 1H), 6.26 (s, 1H), 3.56 (s, 3H), 3.25 (tt, J=12.8, 3.4 Hz, 1H), 1.87 (dd, J=13.1, 3.3 Hz, 2H), 1.47 (t, J=12.9 Hz, 2H), 1.28 (s, 6H), 1.20 (s, 6H). Mass spectrum (ESI, m/z): Calcd. for $C_{24}H_{30}N_4O_2$, 407.2 (M+H), found 407.3.

Example 80

(4-(1-(2-Methoxyphenyl)-3-(2,2,6,6-tetramethyltetrahydro-2H-pyran-4-yl)-1H-pyrazol-5-yl)phenyl)(morpholino)methanone

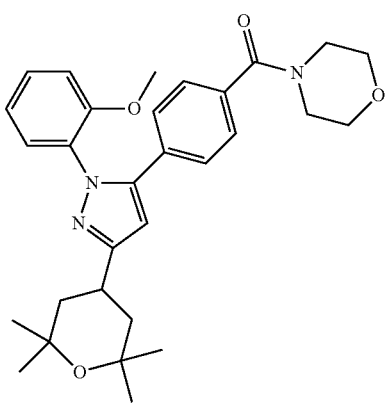 [SMILES: COc1ccccc1-n1nc(C2CC(C)(C)OC(C)(C)C2)cc1-c1ccc(C(=O)N2CCOCC2)cc1]

a) 4-(1-(2-Methoxyphenyl)-3-(2,2,6,6-tetramethyltetrahydro-2H-pyran-4-yl)-1H-pyrazol-5-yl)benzoyl chloride

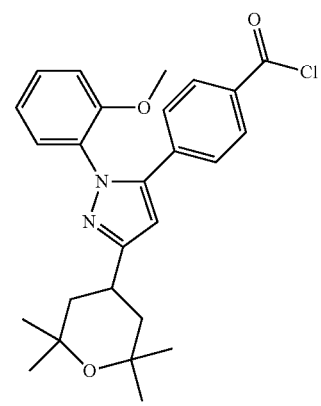 [SMILES: COc1ccccc1-n1nc(C2CC(C)(C)OC(C)(C)C2)cc1-c1ccc(C(=O)Cl)cc1]

To a solution of ethyl 4-[1-(2-methoxyphenyl)-3-(2,2,6,6-tetramethyltetrahydro-2H-pyran-4-yl)-1H-pyrazol-5-yl]-benzoic acid (Example 46) (177 mg, 0.41 mmol) in 4 mL of DCM was added oxalyl chloride (0.043 mL, 0.49 mmol) and 1 drop of DMF and the mixture stirred for 3 hrs at RT The mixture was concentrated and used without further purification in the next step.

b) (4-(1-(2-Methoxyphenyl)-3-(2,2,6,6-tetramethyltetrahydro-2H-pyran-4-yl)-1H-pyrazol-5-yl)phenyl)(morpholino)methanone To a solution of 4-(1-(2-methoxyphenyl)-3-(2,2,6,6-tetramethyltetrahydro-2H-pyran-4-yl)-1H-pyrazol-5-yl)benzoyl chloride (28 mg, 0.062 mmol) in 0.62 mL of DCM at Rt was added morpholine (0.016 mL, 0.19 mmol) and the mixture stirred for 10 mins. The solvents were evaporated and the crude product purified by RP-HPLC, eluting with a linear gradient of 30-70% CH3CN in 0.1% TFA/H$_2$O over 10 mins to give 25 mg (69%) of the title compound as white solid containing 0.6 eq of TFA.

$^1$H NMR (DMSO-d$_6$) δ: 7.37-7.46 (m, 2H), 7.28-7.34 (m, 2H), 7.22 (d, J=8.6 Hz, 2H), 7.01-7.10 (m, 2H), 6.59 (s, 1H), 3.75 (br. s., 8H), 3.39 (s, 3H), 3.18-3.27 (m, 1H), 1.89 (dd, J=13.1, 3.3 Hz, 2H), 1.43 (t, J=12.9 Hz, 2H), 1.29 (s, 6H), 1.16 (s, 6H). Mass spectrum (ESI, m/z): Calculated for C$_{30}$H$_{37}$N$_3$O$_4$, 504.3 (M+H), found 504.2.

Example 81

N-(2-(Dimethylamino)ethyl)-4-(1-(2-methoxyphenyl)-3-(2,2,6,6-tetramethyltetrahydro-2H-pyran-4-yl)-1H-pyrazol-5-yl)benzamide

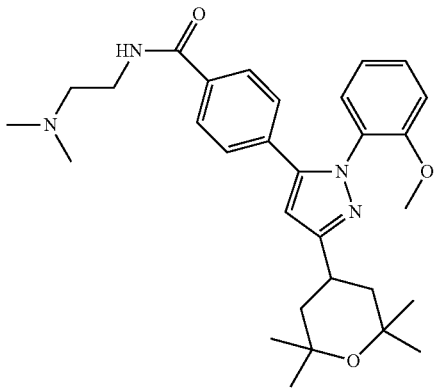 [SMILES: COc1ccccc1-n1nc(C2CC(C)(C)OC(C)(C)C2)cc1-c1ccc(C(=O)NCCN(C)C)cc1]

Prepared according to the procedure in Example 80.

$^1$H NMR (DMSO-d$_6$) δ: 9.21 (br. s., 1H), 8.63 (t, J=5.4 Hz, 1H), 7.74 (d, J=8.3 Hz, 2H), 7.35-7.47 (m, 2H), 7.28 (d, J=8.3 Hz, 2H), 7.01-7.12 (m, 2H), 6.63 (s, 1H), 3.50-3.64 (m, 4H), 2.83 (d, J=4.8 Hz, 6H), 1.89 (dd, J=12.9, 3.0 Hz, 2H), 1.43 (t, J=12.8 Hz, 2H), 1.30 (s, 6H), 1.16 (s, 6H). Mass spectrum (ESI, m/z): Calcd. for C$_{30}$H$_{40}$N$_4$O$_3$, 505.3 (M+H), found 505.2.

Example 82

4-(1-(2-Methoxyphenyl)-3-(2,2,6,6-tetramethyltetrahydro-2H-pyran-4-yl)-1H-pyrazol-5-yl)benzamide

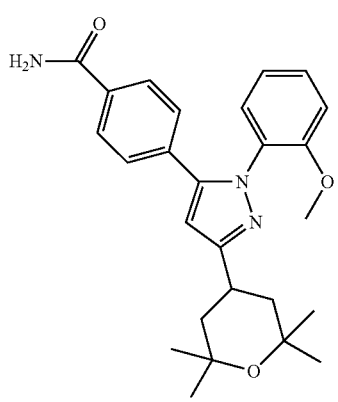 [SMILES: COc1ccccc1-n1nc(C2CC(C)(C)OC(C)(C)C2)cc1-c1ccc(C(N)=O)cc1]

Prepared according to the procedure in Example 80.

$^1$H NMR (DMSO-d$_6$) δ: 7.92 (br. s., 1H), 7.75 (d, J=8.3 Hz, 2H), 7.38-7.46 (m, 2H), 7.35 (br. s., 1H), 7.23 (d, J=8.6 Hz, 2H), 7.02-7.10 (m, 2H), 6.61 (s, 1H), 3.38 (s, 3H), 3.17-3.28 (m, 1H), 1.89 (dd, J=13.3, 3.2 Hz, 2H), 1.43 (t, J=12.9 Hz, 2H), 1.29 (s, 6H), 1.16 (s, 6H). Mass spectrum (ESI, m/z): Calcd. for C$_{26}$H$_{31}$N$_3$O$_3$, 434.2 (M+H), found 434.1.

Example 83

(4-(1-(2-Methoxyphenyl)-3-(2,2,6,6-tetramethyltetrahydro-2H-pyran-4-yl)-1H-pyrazol-5-yl)phenyl)(4-methylpiperazin-1-yl)methanone

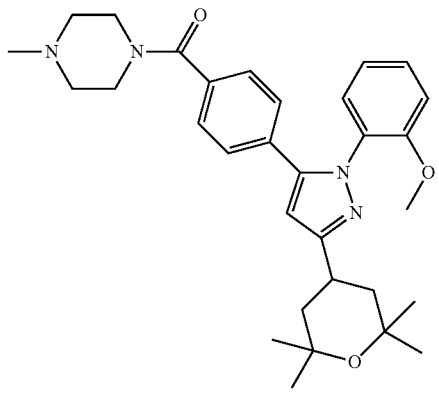 [SMILES: COc1ccccc1-n1nc(C2CC(C)(C)OC(C)(C)C2)cc1-c1ccc(C(=O)N2CCN(C)CC2)cc1]

Prepared according to the procedure in Example 80.

$^1$H NMR (DMSO-d$_6$) δ: 7.39-7.48 (m, 2H), 7.37 (d, J=8.3 Hz, 2H), 7.26 (d, J=8.3 Hz, 2H), 7.03-7.10 (m, 2H), 6.61 (s, 1H), 3.41-3.49 (br. S., 4H), 3.40 (s, 3H), 3.18-3.29 (m, 1H), 3.07 (br. s., 4H), 2.80 (s, 3H), 1.89 (dd, J=13.1, 3.3 Hz, 2H), 1.43 (t, J=12.9 Hz, 2H), 1.30 (s, 6H), 1.16 (s, 6H). Mass spectrum (ESI, m/z): Calcd. for C$_{31}$H$_{40}$N$_4$O$_3$, 517.3 (M+H), found 517.2.

Example 84

N-(2-Hydroxyethyl)-4-(1-(2-methoxyphenyl)-3-(2,2,6,6-tetramethyltetrahydro-2H-pyran-4-yl)-1H-pyrazol-5-yl)benzamide

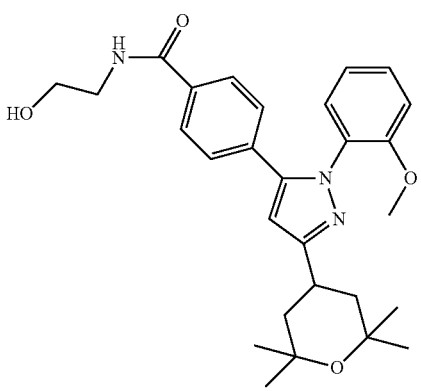 [SMILES: COc1ccccc1-n1nc(C2CC(C)(C)OC(C)(C)C2)cc1-c1ccc(C(=O)NCCO)cc1]

Prepared according to the procedure in Example 80.

$^1$H NMR (DMSO-d$_6$) δ: 8.41 (t, J=5.7 Hz, 1H), 7.73 (d, J=8.3 Hz, 2H), 7.35-7.48 (m, 2H), 7.23 (d, J=8.6 Hz, 2H), 7.01-7.11 (m, 2H), 6.62 (s, 1H), 3.43-3.52 (m, 2H), 3.39 (s, 3H), 3.28 (q, J=6.0 Hz, 2H), 3.17-3.26 (m, 1H), 1.89 (dd, J=13.1, 3.3 Hz, 2H), 1.43 (t, J=12.9 Hz, 2H), 1.29 (s, 6H), 1.16 (s, 6H). Mass spectrum (ESI, m/z): Calcd. for C$_{28}$H$_{35}$N$_3$O$_4$, 478.2 (M+H), found 478.2.

Example 85

3-(1-(2-Methoxyphenyl)-3-(2,2,6,6-tetramethyltetrahydro-2H-pyran-4-yl)-1H-pyrazol-5-yl)pyridine 1-oxide

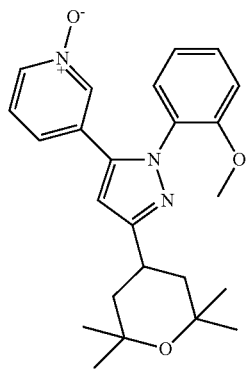

To a solution of 3-[1-(2-methoxyphenyl)-3-(2,2,6,6-tetramethyltetrahydro-2H-pyran-4-yl)-1H-pyrazol-5-yl]-pyridine (9 mg, 0.023 mmol) (Example 44) in 1 mL of DCM at Rt was added m-chloroperoxybenzoic acid (60%)(7.9 mg, 0.028 mmol) and the mixture stirred for 1 hr at Rt. The solvents were evaporated and the crude product purified by RP-HPLC, eluting with a linear gradient of 30-70% CH$_3$CN in 0.1% TFA/H$_2$O over 10 mins to give 8 mg (71%) of the title compound as white solid containing 0.5 eq of TFA.

$^1$H NMR (CHLOROFORM-d) δ: 8.18 (s, 1H), 8.14 (dd, J=5.9, 1.4 Hz, 1H), 7.39 (dd, J=7.8, 1.5 Hz, 1H), 7.30-7.37 (m, 1H), 7.10-7.18 (m, 2H), 7.01 (td, J=7.6, 1.1 Hz, 1H), 6.84 (d, J=8.3 Hz, 1H), 6.41 (s, 1H), 3.49 (s, 3H), 3.19-3.33 (m, 1H), 1.89 (dd, J=13.1, 3.3 Hz, 2H), 1.49 (t, J=12.9 Hz, 3H), 1.29 (s, 6H), 1.20 (s, 6H). Mass spectrum (ESI, m/z): Calculated for C$_{24}$H$_{29}$N$_3$O$_3$, 408.2 (M+H), found 408.2.

Example 86

5-(4-chlorophenyl)-1-(2-methoxyphenyl)-3-(2,2,6,6-tetramethyl-3,6-dihydro-2H-pyran-4-yl)-1H-pyrazole

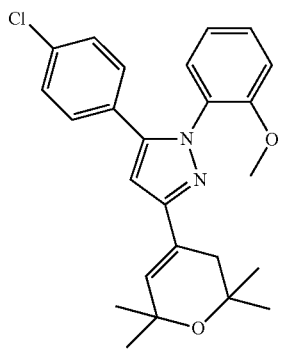 [SMILES: COc1ccccc1-n1nc(C2=CC(C)(C)OC(C)(C)C2)cc1-c1ccc(Cl)cc1]

Prepared according to the procedure in Example 65.
$^1$H NMR (CHLOROFORM-d) δ: 7.39 (dd, J=7.7, 1.6 Hz, 1H), 7.27 (td, J=7.9, 1.6 Hz, 1H), 7.10-7.16 (m, 2H), 7.02-7.09 (m, 2H), 6.97 (td, J=7.6, 1.1 Hz, 1H), 6.74-6.80 (m, 1H), 6.55 (s, 1H), 6.23 (s, 1H), 3.38 (s, 3H), 2.44 (d, J=1.3 Hz, 2H), 1.28 (s, 6H), 1.25 (s, 6H). Mass spectrum (ESI, m/z): Calculated for C$_{25}$H$_{27}$ClN$_2$O$_2$, 423.2 (M+H), found 423.2.

Example 87

5-(4-Chlorophenyl)-1-(2-ethylphenyl)-3-(tetrahydro-2H-pyran-4-yl)-1H-pyrazole

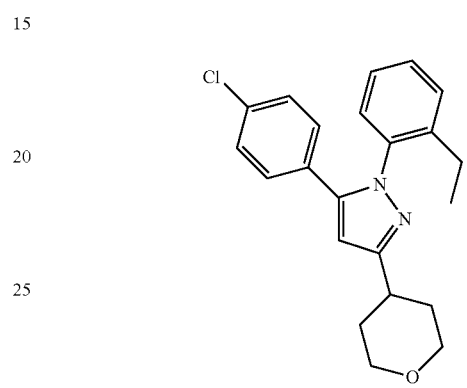

Prepared according to the procedure in Example 69.
$^1$H NMR (400 MHz, CHLOROFORM-d) δ ppm 0.99 (t, J=7.6 Hz, 3H), 1.83-2.03 (m, 4H), 2.31 (q, J=7.6 Hz, 2H), 2.95-3.05 (m, 1H), 3.56 (td, J=11.6, 2.4 Hz, 2H), 4.03-4.11 (m, 2H), 6.38 (s, 1H), 7.05-7.11 (m, 2H), 7.16-7.25 (m, 4H), 7.28-7.32 (m, 1H), 7.32-7.38 (m, 1H).

Example 88

5-(4-Chlorophenyl)-1-(2,4-dichlorophenyl)-3-(tetrahydro-2H-pyran-4-yl)-1H-pyrazole

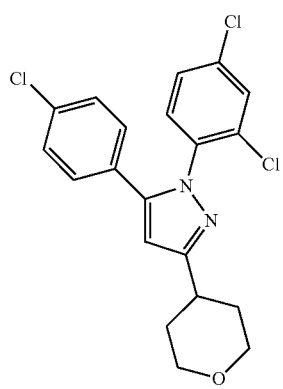 [SMILES: Clc1ccc(-c2cc(C3CCOCC3)nn2-c2ccc(Cl)cc2Cl)cc1]

Prepared according to the procedure in Example 69.
$^1$H NMR (400 MHz, CHLOROFORM-d) δ ppm 1.82-2.04 (m, 4H), 2.95-3.06 (m, 1H), 3.60 (td, J=11.6, 2.3 Hz, 2H), 4.08 (dt, J=9.5, 2.1 Hz, 2H), 6.44 (s, 1H), 7.13 (m, 2H), 7.28 (m, 2H), 7.36-7.43 (m, 2H), 7.49 (d, J=2.3 Hz, 1H).

Example 89

1-(2-Chlorophenyl)-5-(4-chlorophenyl)-3-(tetrahydro-2H-pyran-4-yl)-1H-pyrazole

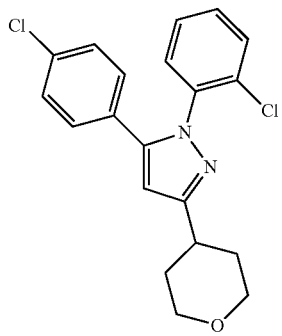 [SMILES: Clc1ccc(-c2cc(C3CCOCC3)nn2-c2ccccc2Cl)cc1]

Prepared according to the procedure in Example 69.

¹H NMR (400 MHz, CHLOROFORM-d) δ ppm 1.82-2.03 (m, 4H), 2.97-3.07 (m, 1H), 3.56 (td, J=11.6, 2.4 Hz, 2H), 4.04-4.11 (m, 2H), 6.38 (s, 1H), 7.11 (m, 2H), 7.22 (m, 2H), 7.31-7.38 (m, 2H), 7.40-7.45 (m, 2H).

General Procedure for Examples 90-93

A solution of 1-(4-chlorophenyl)ethanone (2.0 g, 12.9 mmol) in anhydrous THF was cooled in a dry ice acetone bath and treated with sodium hexamethyldisilazid (14.2 mL, 1M in THF, 14.2 mmol). The resulting solution was stirred for 1 h at −78° C. and a solution of tetrahydro-pyran-4-carbonyl chloride (1.92 g, 12.9 mmol) in THF was slowly added. The resulting solution was stirred for 30 min at −78° C., allowed to warm up to room temperature and stirred for 5 h. The reaction was quenched by adding 6N HCl and extracted with EtOAc (×3). The organic fractions were combined and washed with sat. NaCl, dried over Na₂SO₄ and evaporated under vacuum. The resulting residue was purified by silica-gel column chromatography to give 2 g (58%) of 1-(4-chlorophenyl)-3-(tetrahydro-2H-pyran-4-yl)propane-1,3-dione. 1-(4-chlorophenyl)-3-(tetrahydro-2H-pyran-4-yl)propane-1,3-dione 100 mg (0.375 mmol) and the free base of the corresponding hydrazine (1.1 equivalent) were dissolved in acetic acid and heated at 100° C. for 18 h. Acetic acid was removed under vacuum and the residue was purified by reverse phase HPLC.

Example 90

2-[5-(4-Chlorophenyl)-3-(tetrahydro-2H-pyran-4-yl)-1H-pyrazol-1-yl]benzonitrile

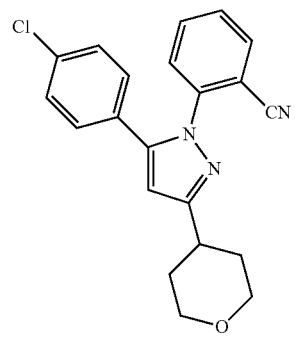 [SMILES: N#Cc1ccccc1-n1nc(C2CCOCC2)cc1-c1ccc(Cl)cc1]

¹H NMR (400 MHz, CHLOROFORM-d) δ ppm 1.93-2.20 (m, 4H), 3.14-3.31 (m, 1H), 3.63 (td, J=11.6, 2.7 Hz, 2H), 4.12-4.24 (m, 2H), 7.18 (s, 1H), 7.26-7.32 (m, 1H), 7.57-7.66 (m, 3H), 7.82 (d, J=8.8 Hz, 1H), 8.11-8.20 (m, 2H), 8.33 (d, J=8.3 Hz, 1H).

Example 91

5-(4-Chlorophenyl)-1-(2,6-dichlorophenyl)-3-(tetrahydro-2H-pyran-4-yl)-1H-pyrazole

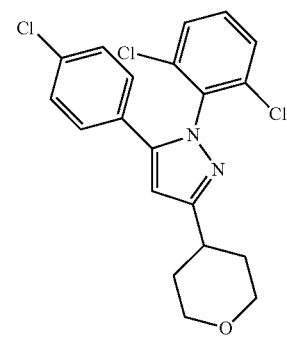 [SMILES: Clc1ccc(-c2cc(C3CCOCC3)nn2-c2c(Cl)cccc2Cl)cc1]

¹H NMR (400 MHz, CHLOROFORM-d) δ ppm 1.84-2.04 (m, 4H), 2.99-3.09 (m, 1H), 3.56 (td, J=11.5, 2.3 Hz, 2H), 4.07 (ddd, J=11.5, 3.9, 2.3 Hz, 2H), 6.39 (s, 1H), 7.15-7.19 (m, 2H), 7.21-7.26 (m, 2H), 7.27-7.32 (m, 1H), 7.37 (s, 1H), 7.39 (d, J=1.5 Hz, 1H).

Example 92

5-(4-Chlorophenyl)-1-[2,6-dichloro-4-(trifluoromethyl)phenyl]-3-(tetrahydro-2H-pyran-4-yl)-1H-pyrazole

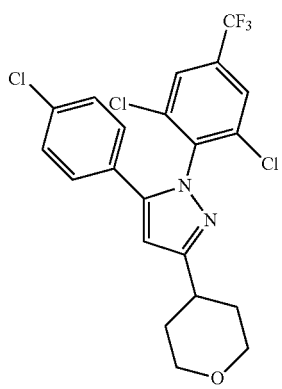 [SMILES: FC(F)(F)c1cc(Cl)c(-n2nc(C3CCOCC3)cc2-c2ccc(Cl)cc2)c(Cl)c1]

$^1$H NMR (400 MHz, CHLOROFORM-d) δ ppm 1.83-2.04 (m, 4H), 2.98-3.11 (m, 1H), 3.51-3.66 (m, 2H), 4.02-4.14 (m, 2H), 6.41 (s, 1H), 7.11-7.21 (m, 2H), 7.24-7.34 (m, 2H), 7.65 (s, 1H).

Example 93

5-(4-Chlorophenyl)-1-[2,4-dichloro-6-(trifluoromethyl)phenyl]-3-(tetrahydro-2H-pyran-4-yl)-1H-pyrazole

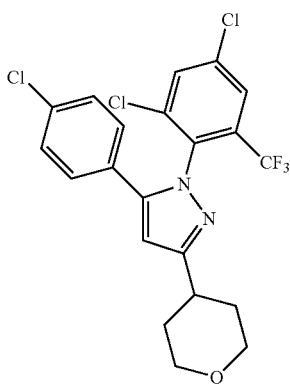 [SMILES: FC(F)(F)c1cc(Cl)cc(Cl)c1-n1nc(C2CCOCC2)cc1-c1ccc(Cl)cc1]

$^1$H NMR (400 MHz, CHLOROFORM-d) δ ppm 1.78-2.03 (m, 4H), 2.94-3.07 (m, 1H), 3.56 (td, J=11.5, 2.5 Hz, 2H), 4.00-4.10 (m, 2H), 6.40 (s, 1H), 7.06-7.18 (m, 2H), 7.21-7.33 (m, 2H), 7.68 (s, 2H).

Example 94

4-[1-(2-Methoxyphenyl-3-(2,2,6,6-tetramethyltetrahydro-2H-pyran-4-yl)-1H-pyrazol-5-yl]phenol

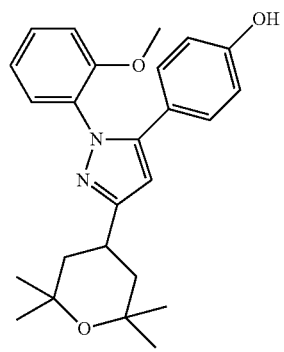 [SMILES: COc1ccccc1-n1nc(C2CC(C)(C)OC(C)(C)C2)cc1-c1ccc(O)cc1]

a) 5-(4-(Benzyloxy)phenyl)-1-(2-methoxyphenyl)-3-(2,2,6,6-tetramethyltetrahydro-2H-pyran-4-yl)-1H-pyrazole A flask was charged with trifluoro-methanesulfonic acid 2-(2-methoxy-phenyl)-5-(2,2,6,6-tetramethyl-tetrahydro-pyran-4-yl)-2H-pyrazol-3-yl ester (354 mg, 0.69 mmol) (Example 1, step E),4-(benzyloxy)phenylboronic acid (238.3 mg, 1.0 mmol), tetrakis(triphenylphosphine)palladium(0) (40 mg, 0.035 mmol), 2M Na$_2$CO$_3$ (2.8 mL) and 2:1 toluene/ethanol (10 mL) and the mixture was heated at 80° C. for 6 hrs. The resulting mixture was diluted with EtOAc and washed with sat. NaCl. EtOAc was removed under vacuum and the residue was purified by silica column chromatography to give 257.8 mg (74.5%) of the title compound.
$^1$H NMR (400 MHz, MeOH-d) δ ppm 1.24 (s, 6H), 1.36 (s, 6H), 1.56 (t, J=13.0 Hz, 2H), 1.91 (dd, J=13.4, 3.3 Hz, 2H), 3.21-3.29 (m, 1H), 3.48 (s, 3H), 5.01 (s, 2H), 6.37 (s, 1H), 6.84 (m, 2H), 6.97-7.07 (m, 2H), 7.10 (m, 2H), 7.23-7.46 (m, 7H).

b) 4-[1-(2-Methoxyphenyl)-3-(2,2,6,6-tetramethyltetrahydro-2H-pyran-4-yl)-1H-pyrazol-5-yl]phenol Palladium on carbon catalyst (5%, 400 mg) and 5-(4-(benzyloxy)phenyl)-1-(2-methoxyphenyl)-3-(2,2,6,6-tetramethyltetrahydro-2H-pyran-4-yl)-1H-pyrazole (257.8 mg, 0.52 mmol) were taken in MeOH (10 mL) and stirred under a H$_2$ atmosphere (balloon) for 18 h. The catalyst was removed by filtration and the solvent was removed under vacuum to give 211 mg (100%) of the title compound.
$^1$H NMR (400 MHz, CHLOROFORM-d) δ ppm 1.27 (s, 6H), 1.30 (s, 6H), 1.50-1.67 (m, 2H), 1.96 (dd, J=13.0, 3.2 Hz, 2H), 3.26-3.42 (m, 1H), 3.48 (s, 3H), 6.29 (s, 1H), 6.65 (d, J=8.8 Hz, 2H), 6.85 (d, J=8.3 Hz, 1H), 6.93-7.09 (m, 3H), 7.22-7.44 (m, 2H).

General Procedure for Examples 95-97

4-[1-(2-Methoxyphenyl)-3-(2,2,6,6-tetramethyltetrahydro-2H-pyran-4-yl)-1H-pyrazol-5-yl]phenol (25 mg, 0.06 mmol), from Example 94, step b, $K_2CO_3$ (200 mg, 1.45 mmol) and the corresponding alkyl halide (1 equivalent) were taken in $CH_3CN$ and heated at 70° C. for 18 h. Solvent was removed under vacuum and the residue was taken in EtOAc, washed with water, sat. NaCl and dried over $Na_2SO_4$. EtOAc was removed under vacuum and the residue was purified by silica preparative TLC.

Example 95

2-{4-[1-(2-Methoxyphenyl)-3-(2,2,6,6-tetramethyltetrahydro-2H-pyran-4-yl)-1H-pyrazol-5-yl]phenoxy}-N,N-dimethylethanamine

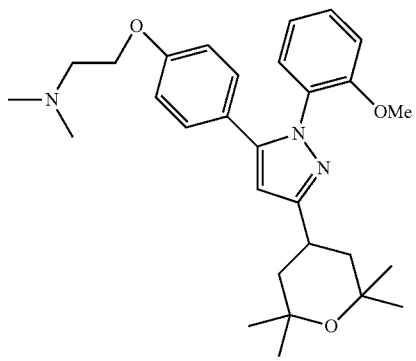

$^1$H NMR (400 MHz, MeOH-d) δ ppm 1.27 (s, 6H), 1.37 (s, 6H), 1.48-1.65 (m, 2H), 1.93 (dd, J=13.1, 3.3 Hz, 2H), 2.95 (s, 6H), 3.29-3.32 (m, 1H), 3.50-3.64 (m, 5H), 4.24-4.37 (m, 2H), 6.42 (s, 1H), 6.86-6.99 (m, 2H), 6.99-7.10 (m, 2H), 7.16-7.25 (m, 2H), 7.32 (dd, J=7.8, 1.5 Hz, 1H), 7.39-7.50 (m, 1H).

Example 96

4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine

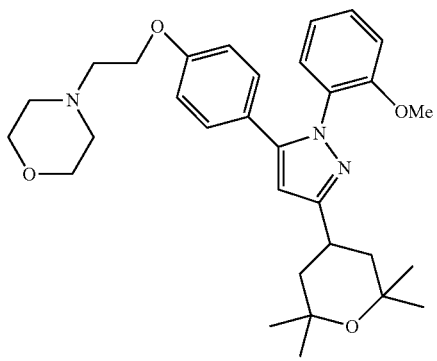 [SMILES: COc1ccccc1-n1nc(C2CC(C)(C)OC(C)(C)C2)cc1-c1ccc(OCCN2CCOCC2)cc1]

$^1$H NMR (400 MHz, MeOH-d) δ ppm 1.25 (s, 6H), 1.35 (s, 6H), 1.57 (t, J=12.9 Hz, 2H), 1.92 (dd, J=13.1, 3.3 Hz, 2H), 3.17-3.39 (m, 3H), 3.49-3.65 (m, 7H), 3.79 (br. s., 2H), 4.04 (br. s., 2H), 4.31-4.38 (m, 2H), 6.42 (s, 1H), 6.91 (m, 2H), 7.00-7.08 (m, 2H), 7.19 (m, 2H), 7.31 (dd, J=7.7, 1.6 Hz, 1H), 7.39-7.46 (m, 1H).

Example 97

5-{4-[2-(1H-Imidazol-1-yl)ethoxy]phenyl}-1-(2-methoxyphenyl)-3-(2,2,6,6-tetramethyltetrahydro-2H-pyran-4-yl)-1H-pyrazole

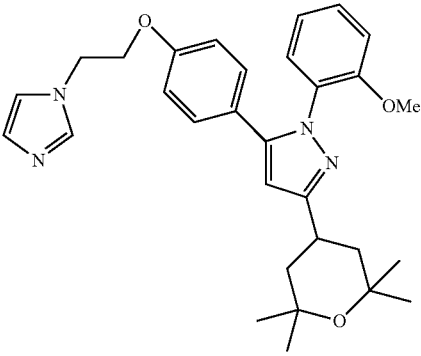 [SMILES: COc1ccccc1-n1nc(C2CC(C)(C)OC(C)(C)C2)cc1-c1ccc(OCCn2ccnc2)cc1]

$^1$H NMR (400 MHz, MeOH-d) δ ppm 1.24 (s, 6H), 1.37 (s, 6H), 1.56 (t, J=12.9 Hz, 2H), 1.92 (dd, J=13.1, 3.3 Hz, 2H), 3.54 (s, 3H), 4.26-4.39 (m, 2H), 4.60-4.71 (m, 2H), 6.39 (s, 1H), 6.83 (m, 2H), 6.99-7.08 (m, 2H), 7.14 (m, 2H), 7.30 (dd, J=8.2, 1.6 Hz, 1H), 7.41 (td, J=8.0, 1.8 Hz, 1H), 7.56 (t, J=1.8 Hz, 1H), 7.71 (t, J=1.8 Hz, 1H), 9.02 (s, 1H).

D) General Administration, Formulation, and Dosages

The present invention provides substituted pyrazole compounds, which are useful in methods for treating, ameliorating and/or preventing a disease, a syndrome, a condition or a disorder that is affected by the inhibition of N-Type calcium channel. Such methods comprise, consist of and/or consist essentially of administering to a subject, including an animal, a mammal, and a human in need of such treatment, amelioration and prevention, a therapeutically effective amount of a compound of Formula (I), or an enantiomer, diastereomer, solvate or pharmaceutically acceptable salt form thereof. In particular, the compounds of Formula (I) are useful for treating, ameliorating and preventing pain as well as diseases, syndromes, conditions or disorders causing such pain. More particularly, the compounds of Formula (I) are useful for treating, ameliorating and preventing acute pain, inflammatory pain and/or neuropathic pain, comprising administering to a subject in need thereof a therapeutically effective amount of a compound of Formula (I), as herein defined.

Acute pain, as used herein, refers to pain that comes on quickly, can be of varying severity, but is self-limiting and of relatively short duration. Examples of acute pain include, but are not limited to, post-operative pain, post-surgical pain, toothache, burn, sunburn, insect/animal bites and stings, headache and/or any pain associated with acute trauma or injury.

Inflammatory pain refers to pain arising from an inflammatory disease, condition, syndrome or disorder, including but not limited to inflammatory bowel disease, irritable bowel syndrome, visceral pain, migraine, post-operative pain, osteoarthritis, rheumatoid arthritis, back pain, low back pain, joint pain, abdominal pain, chest pain, labor pain, musculoskeletal diseases, skin diseases, toothache, pyresis, burn, sunburn, snake bite, venomous snake bite, spider bite, insect sting, neurogenic or overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache or arachnoiditis.

A further embodiment of the present invention is directed to a method for treating, ameliorating and/or preventing neuropathic pain. Neuropathic pain refers to a disease, syndrome, condition and/or disorder, involving damage to the peripheral or central nervous system, including cancer pain, neurological disorders, spine and peripheral nerve surgery, brain tumor, traumatic brain injury (TBI), chemotherapy-induced pain, pain chronification, radicular pain, HIV pain, spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

The compounds of Formula (I) have an N-type calcium channel inhibiting effect and are useful as therapeutic agents for neuropathic pain including neuropathic cold allodynia, which can be characterized by the presence of a neuropathy-associated allodynic state in which a hypersensitivity to cooling stimuli exists. Further examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising, consisting of, and/or consisting essentially of the step of administering to a subject in need of such treatment a therapeutically effective amount of a compound of Formula (I) or an enantiomer, diastereomer, solvate or pharmaceutically acceptable salt thereof.

The invention features a method for treating a subject in need thereof with an N-type calcium channel-mediated disease, said method comprising administering to the subject a therapeutically effective amount of a compound of the invention. In particular, the invention also provides a method for treating or inhibiting the progression of an N-type calcium channel-mediated disease, and associated symptoms or complications thereof in a subject, wherein the method comprises administering to the subject a therapeutically effective amount of a compound of the invention.

Embodiments of the present invention include a use of the compound of Formula (I) in the manufacture of a medicament for treating N-type calcium channel-mediated conditions.

Embodiments of the present invention include a use of the compound of Formula (I) as a medicine.

The compounds of Formula (I) may be administered orally or parenterally, and after formulation into preparations suitable for the intended administration route, they can be used as therapeutic agents for treating N-type calcium channel-mediated conditions.

One aspect of the present invention provides a method for the treatment or prevention of disorders, diseases or conditions responsive to the modulation of N-type calcium channels in a subject in need thereof which comprises administering to the subject a therapeutically or prophylactically effective amount of a compound of Formula (I) or a form thereof.

Another aspect of the present invention provides a method for the treatment or prevention of pain and the diseases that lead to such pain in a subject in need thereof which comprises administering to said subject a therapeutically or prophylactically effective amount of a compound of Formula (I) or a form thereof.

The present invention also relates to methods for treating or preventing obesity by administering a compound of Formula (I) or a form thereof, in combination with a therapeutically or prophylactically effective amount of another agent known to be useful to treat or prevent the condition.

Another aspect of the present invention provides a pharmaceutical composition comprising at least one compound of Formula (I) or a form thereof, and a pharmaceutically acceptable carrier.

The invention also features a method for treating a subject in need thereof with an N-type calcium channel-mediated disease, said method comprising administering to the subject a therapeutically effective amount of a pharmaceutical composition comprising at least one compound of the invention.

Yet another aspect of the present invention relates to the use of a compound of Formula (I), for the manufacture of a medicament useful for the treatment of an N-type calcium channel-mediated disorder in a subject in need thereof.

Yet another aspect of the present invention relates to the use of a compound of Formula (I) or a form thereof, for the manufacture of a medicament useful for the treatment or prevention of pain and the diseases that lead to such pain in a subject in need thereof.

In a clinical use of the compounds of the invention, pharmaceutically-acceptable additives may be added thereto to formulate various preparations in accordance with the intended administration route thereof, and the preparations may be administered.

Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals, including humans and other mammals. Any ordinary physician, veterinarian or clinician may readily determine the necessity, if any, of treatment with an instant compound.

Those of skill in the treatment of disorders, diseases, or conditions mediated by N-type calcium channels can determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the N-type calcium channel disorders described in the present invention using any of the compounds as defined herein, the dosage form will contain a pharmaceutically acceptable carrier containing between from about 1 mg to about 1000 mg; particularly from about 0.5 mg to about 500 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

When the compound of the invention is, for example, put into clinical use, its dose and its administration frequency may vary depending on the sex, the age, the body weight and the condition of the patient and on the type and the range of the necessary treatment with the compound. For oral administration, in general, the dose of the compound may be in a range of from about 0.01 mg/kg/day to about 100 mg/kg of body weight/day or in a range of from about 0.03 mg/kg/day to about 1 mg/kg/day. The oral administration frequency is preferably from one to a few times per day. For parenteral administration, the dose may be in a range of from about 0.001 mg/kg/day to about 10 mg/kg/day, in a range of from about 0.001 mg/kg/day to about 0.1 mg/kg/day or, in a range of from about 0.01 mg/kg/day to about 0.1 mg/kg/day. The parenteral administration frequency is preferably from one to a few times per day. For oral administration, the compositions are preferably provided in the form of tablets containing from about 1.0 mg to about 1000 mg of the active ingredient, particularly 1 mg, 5 mg, 10 mg, 15 mg, 20 mg, 25 mg, 50 mg, 75 mg, 100 mg, 150 mg, 200 mg, 250 mg, 300 mg, 400 mg, 500 mg, 600 mg, 750 mg, 800 mg, 900 mg, and 1000 mg of the active ingredient for the symptomatic adjustment of the dosage to the patient to be treated. The compounds may be administered on a regimen of 1 to 4 times per day, preferably once or twice per day.

When treating an N-type calcium channel-mediated disorder, a therapeutic effect is expected upon administering the compounds of the present invention at a daily dosage of from about 0.1 mg to about 100 mg/kg of body weight. The dosing regimen may range from a single daily dose or a divided dose two to six times a day, or in sustained release form. For a large mammal, the total daily dosage may be in a range of from about 1 mg to about 1000 mg, or a range of from about 1 mg to about 50 mg. In the case of a 70 kg adult human, the total daily dose will generally be from about 7 mg to about 350 mg. This dosage regimen may be adjusted to provide the optimal therapeutic response.

Ordinary physicians, veterinarians and clinicians may readily determine the effective dose of the pharmaceutical compound necessary to treat, prevent, inhibit, retard or stop the intended disease, and may readily treat the diseased patient with the compound.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for 1 to 4 times per day, preferably once or twice per day administration; for example, an insoluble salt of the active compound, such as the decanoate salt, may be adapted to provide a depot preparation for intramuscular injection.

The preparation may contain the compound of the invention in an amount in a range of from about 1.0 to about 100% by weight or, in a range of from about 1.0 to about 60% by weight of the preparation. The preparation may contain any other therapeutically-effective compound.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed within the scope of the present invention.

E) Use

1. Dosages

For preparing pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agents include pharmaceutical grade lecithins. Suitable flocculating agents include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms; however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as N-type calcium channel inhibitors is required for a subject in need thereof.

In their use, the compounds of the invention may be combined with any other therapeutic agents that are useful for the treatment of an N-type calcium channel-mediated disorder.

The combination includes not only the composition of compounds of the invention and one other active substance but also the composition of compounds of the invention and two or more other active substances. The scope of possible combinations of a compound of the invention and one, two or more active substances are within the knowledge of one skilled in the art for the treatment of an N-type calcium channel-mediated disorder.

The compounds of the present invention may also be combined with a non-drug therapy such as kinesitherapy, dietetic treatment or radiation therapy. The compound and the combined compositions of the invention are effective for treating and preventing pain.

2. Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

F) Biological Examples

The ability of the compounds of the present invention to treat an N-type calcium channel mediated condition was determined using the following procedures.

Example 1

Expression and Purification of Cav2.2 Stable Cell Line

The Cav2.2 ($\alpha_{1B}$) subunit (GenBank accession no. AAO53230; supplied by Lipscombe's laboratory at Brown University) was subcloned into pcDNA3.1, whereas the $\alpha_2\delta$ (M86621) and $\beta_3$ (M88751) subunits were subcloned into pBudCE4.1 vectors. Stable cell lines expressing all three subunits were generated according to the following procedure: 1) HEK293 cells were transfected with $\alpha_2\delta_{-1}/\beta_3$ expression constructs resulting in a stable cell line expressing $\alpha_2\delta_{-1}$ and $\beta_3$ subunits that were selected under 200 μg/mL of Zeocin; 2) a stable cell line expressing $\alpha_2\delta_{-1}/\beta_3$ subunits in high quantity as evidenced in its Western blots was isolated from the colony and purified; 3) this cell line was further transfected with Cav2.2 expression constructs, from which cells were subsequently selected under 400 μg/mL G418 and 200 μg/mL Zeocin; 4) these cells were clonally isolated, expanded and screened by Western blot analysis for expressing all three subunits Western blot analysis included washing the cells with phosphate-buffered saline, collecting and resuspending in lysis buffer, applying gel electrophoresis with a 4%-20% sodium dodecyl sulfate-polyacrylamide medium at 30 mA for 90 min. After transferring proteins in the gel to a nitrocellulose membrane, the blot was incubated with primary antibodies in reconstituted 2% fat dry milk, 0.5% Tween 20, 100 mM NaCl, and 10 mM Tris-HCl (pH=7.4) at 4° C. overnight. Primary antibodies were obtained from Sigma and included anti-$\alpha_{1B}$ (1:200), anti-$\alpha_2\delta_{-1}$ (1:500), and anti-$\beta_3$ (1:1,000). Furthermore, blots were incubated for 1 hour at room temperature with secondary goat anti-rabbit (1:20,000) or goat anti-mouse (1:2,000) serum that was obtained from Pierce/Thermo Fisher Scientific. Finally, X-ray film of the ECL Plus Kit from Amersham/GE Healthcare Life Sciences was used to visualize the blots.

Cultures of cells stably expressing Cav2.2 were maintained at 37° C. in low glucose-containing Dulbecco's Modified Eagle medium (low glucose) under a 5% $CO_2$ atmosphere. The medium was supplemented with 10% fetal bovine serum, 2 mM L-glutamine, 100 IU/mL penicillin, 100 mg/mL streptomycin, 400 μg/mL G418 and 200 μg/mL Zeocin.

Example 2

Automated Electrophysiology Assay

High-throughput automated patch clamp system experiments were carried out using instruments (QPatch-HT) available from Sophion Biosciences, Inc. North Brunswick, N.J. Cells were grown in T175 flasks to 50%-90% confluence were enzymatically treated with Deatchin (Genlantis, San Diego, Calif., U.S.A.), centrifuged, rinsed and resuspended in 293 SFM II media (Life Technologies, Grand Island, N.Y., U.S.A.) supplemented with 25 mM HEPES (Sigma-Aldrich, St. Louis, Mo., U.S.A.) to a concentration of $2-3\times10^6$ cells/mL. Cells were added to automated cell preparation station on the QPatch-HT (Sophion Biosciences, North Brunswick, N.J., U.S.A.) and following a 10- to 30-min recovery period with gentle stirring, the assay protocol was initiated. During the automated cell preparation, cells were collected, centrifuged and resuspended in an extracellular (EC) solution containing 132 mM NaCl, 1.8 mM $CaCl_2$, 5.4 mM KCl, 0.8 mM $MgCl_2$, 10 mM glucose, and 10 mM HEPES (pH=7.4), adjusted with sucrose to 315 mOsm. The QPlate was primed with an intracellular solution containing 135 CsCl, 10 mM EGTA, 4 MgATP, 0.3 NaGTP, and 20 mM HEPES (pH=7.2), adjusted to approximately 290 mOsm with deionized water and the EC solution. Cells were added to the prepared QPlate wells by robotic pipettes of the QPatch-HT.

For cells determined to be in stable whole-cell patch clamp, the EC solution was replaced with a barium (Ba)/triethylammonium (TEA) solution containing 140 mM TEA-Cl, 10 mM $BaCl_2$, 0.8 mM $MgCl_2$, 10 mM glucose, and 10 mM HEPES (pH=7.4). High (40 mM) $BaCl_2$ concentrations were made with adjustments of TEA-Cl (90 mM) to maintain the osmolarity. From a resting potential of −80 mV, a train of depolarizing pulses (15 pulses at 5 Hz, +20 mV) was delivered to the cell once every 30 sec for eight trains (4 min total), and the resulting currents were measured during a control period (no compound). This protocol was repeated for each subsequent addition of control buffer with or without compound (three periods total, each with four trains). The current generated in the $1^{st}$ and $15^{th}$ pulses of the last train of each period in the presence of each drug concentration was normalized to the current generated during the control period at the respective pulses (representing low- and high frequency stimulation, respectively). Data from both the second and third drug application period were analyzed for each cell. A final addition of Ba/TEA solution containing 60-100 uM $CdCl_2$ was made to block all N-type current and "zero" the currents for each cell. A buffer/compound additions were made using a "spitting" feature of the QPatch-HT, which added three repretitions of 5 μL solution at the beginning of each recording period.

To examine closed-state inactivation, cells were subjected to a channel-activating 50-msec depolarizing step pulse from −80 to +10 mV, followed by a 5-sec nonactivating step to voltages ranging from −130 to −60 mV in 10 mV increments and then a 50-ms step from −80 to +10 mV to assess the remaining current. Currents from the activating voltage pulse were normalized to the peak value of the test pulse following the −130 mV step and fit to a Boltzman equation to obtain the V1/2. Roscovitine (Sigma-Aldrich) was prepared as a 100 mM stock in dimethyl sulfoxide and diluted to the indicated working concentrations. Tetrandrine (Sigma-Aldrich) was prepared as a 4 mM stock in acidic water (pH=2.0) and then diluted to working concentrations in the external solution. ω-Conotoxin MVIIA (Sigma-Aldrich) was prepared as a 0.3 mg/mL stock solution in water, with 0.1% bovine serum albumin V (Life Technologies). Compounds of Formula (I) were diluted first into dimethyl sulfoxide and then into 10% pluronic F-127 in water (Life Technologies), sonicated for 1 min and diluted into EC buffer. Vehicle controls were run in parallel in all experiments.

Unless otherwise indicated, statistics for comparing among electrophysiological results utilized a one-way analysis of variance with Fisher's least squares determination test for pair-wise comparison. Resultant data are shown in Table 2.

TABLE 2

| QPatch % Inhibition at High and Low Frequency at 0.1 μM | | |
|---|---|---|
| Cpd | High Freq | Low Freq |
| 1 | 63 | 58 |
| 2 | 53.5 | 56.5 |
| 3 | 42 | 34 |
| 4 | 39 | 35 |
| 5 | 67 | 59 |
| 6 | 48 | 48 |
| 8 | 40 | 37 |
| 9 | 47.5 | 34 |
| 10 | 38 | 46 |
| 12 | 41 | 30 |
| 13 | 47.5 | 32 |
| 14 | 74.5 | 63 |
| 15 | 37 | 20 |
| 16 | 51 | 37 |
| 17 | 82 | 84 |
| 18 | 16 | −23 |
| 19 | 21 | 10 |
| 20 | 45 | 38 |
| 22 | 0 | 0 |
| 23 | −8 | −19 |
| 25 | 29 | 14 |
| 26 | 42 | 24 |

TABLE 2-continued

QPatch % Inhibition at High and Low Frequency at 0.1 μM

| Cpd | High Freq | Low Freq |
|---|---|---|
| 28 | −5 | −18 |
| 31 | 1 | 4 |
| 44 | 6 | 20 |
| 47 | 28 | 25 |
| 49 | 47 | 33 |
| 50 | 1 | −37 |
| 51 | 22 | −17 |
| 58 | 26 | 19 |
| 59 | 54 | 54 |
| 60 | 48 | 31 |
| 61 | 62 | 30 |
| 62 | 67 | 45 |
| 63 | 74.5 | 60 |
| 64 | 55 | 18 |
| 65 | 50 | 44 |
| 66 | 25 | 7 |
| 67 | 65 | 55 |
| 68 | 14 | −9 |
| 70 | 25 | 24 |
| 72 | 11 | 4 |
| 73 | 1 | −18 |
| 75 | 67 | 45 |
| 95 | 26 | 14 |
| 96 | 29 | −20 |
| 98 | 61 | 44.5 |

Example 3

Calcium-Dye Indicator Assay

A stable cell line (HEK parent) co-expressing the $\alpha_{1B}$ (Cav2.2), $\beta_3$ and $\alpha_2\delta$ subunits of the N-type calcium channel subunits was used. These cells were routinely grown as monolayers in low glucose-containing Dulbecco's Modified Eagle Medium supplemented with 10% FBS, 2 mM L-glutamine, 100 I.U./mL penicillin, 100 μg/mL streptomycin, 400 μg/mL G418 and 200 μg/mL Zeocin (split ratio=1:5). Cells were maintained in 5% $CO_2$ at 37° C. Compounds of Formula (I) were prepared as 10 mM stocks in DMSO from neat compound, if available. Otherwise, the 5 or 10 mM DMSO stock solutions provided in-house were used.

Calcium mobilization responses to KCl depolarization were evaluated by measuring the intensity of calcium-mediated fluorescent signal in the presence of BD Calcium Assay Dye (BD Biosciences, Franklin Lakes, N.J., U.S.A.), utilizing a Functional Drug Screening System (FDSS) by Hamamatsu Corporation (Bridgewater, N.J., U.S.A.).

Twenty-four hours prior to assay, cells were seeded in clear-base poly-D-lysine coated 384-well plates (BD Biosciences) at a density of 5,000 cells per well in culture medium and grown overnight in 5% $CO_2$ at 37° C. On the day of assay growth media were removed and cells were loaded with BD calcium assay dye (BD Biosciences) for 35 min at 37° C. under 5% $CO_2$ and then for 25 min at room temperature. Utilizing the FDSS, cells were exposed to representative compounds of Formula (I) at varying concentrations and intracellular calcium was measured for 5 min prior to the addition of 50 mM KCl for an additional 3 min of measurement.

Calculations and Formulas $IC_{50}$ values for representative compounds of Formula (I) were determined from six-point concentration-response experiments and represent the concentration of said compound required to inhibit 50% of the maximal response. Maximal fluorescence intensity (FI) achieved upon addition of 50 mM KCl was exported from the FDSS software and further analyzed using GraphPad Prism 4 (Graph Pad Software Inc., CA, U.S.A.). Data were normalized to the maximum average counts from quadruplicate wells for each condition in the presence of 50 mM KCl and to the minimum average counts in the presence of buffer. Theoretical curves were generated using nonlinear regression curve-fitting analysis of either sigmoidal concentration-response or sigmoidal concentration-response (variable slope), and the $IC_{50}$ values with the best-fit dose curve determined by GraphPad Prism were reported. Resultant data are shown in Table 3.

TABLE 3

| Cpd | FDSS $IC_{50}$ (μM) |
|---|---|
| 1 | 0.0017 |
| 2 | 0.0011 |
| 3 | 0.0010 |
| 4 | 0.0010 |
| 5 | 0.0013 |
| 6 | 0.0011 |
| 7 | 0.0012 |
| 8 | 0.0016 |
| 9 | 0.0023 |
| 10 | 0.0020 |
| 11 | 0.0024 |
| 12 | 0.0026 |
| 13 | 0.0049 |
| 14 | 0.0062 |
| 15 | 0.0049 |
| 16 | 0.0051 |
| 17 | 0.0051 |
| 18 | 0.0053 |
| 19 | 0.0054 |
| 20 | 0.0055 |
| 21 | 0.0057 |
| 22 | 0.0060 |
| 23 | 0.0062 |
| 24 | 0.0110 |
| 25 | 0.0110 |
| 26 | 0.0120 |
| 27 | 0.0015 |
| 28 | 0.0170 |
| 29 | 0.0580 |
| 31 | 0.0035 |
| 32 | 0.1400 |
| 33 | 0.0820 |
| 34 | 0.1200 |
| 36 | 0.1430 |
| 37 | 0.0340 |
| 38 | 0.1100 |
| 39 | 0.0720 |
| 40 | 0.2700 |
| 41 | 0.0650 |
| 42 | 0.0550 |
| 43 | 0.0580 |
| 44 | 0.0190 |
| 45 | 0.0710 |
| 48 | 0.1100 |
| 49 | 0.0055 |
| 60 | 0.0070 |
| 61 | 0.0015 |
| 62 | 0.0020 |
| 63 | 0.0025 |
| 64 | 0.0072 |
| 65 | 0.0078 |
| 66 | 0.0094 |
| 67 | 0.0120 |
| 68 | 0.0200 |
| 69 | 0.0200 |
| 70 | 0.0240 |
| 71 | 0.0310 |
| 72 | 0.0380 |
| 73 | 0.0500 |
| 74 | 0.0530 |
| 75 | 0.0800 |
| 76 | 0.1000 |
| 77 | 0.1500 |

TABLE 3-continued

| Cpd | FDSS IC$_{50}$ (μM) |
|---|---|
| 79 | 0.1800 |
| 80 | 0.2000 |
| 81 | 0.4000 |
| 82 | 0.7700 |
| 95 | 0.0034 |
| 96 | 0.0082 |
| 97 | 0.0130 |
| 98 | 0.0051 |

Example 4

Complete Freund's Adjuvant (CFA)-Induced Hyperalgesia

The intraplantar injection of complete Freund's adjuvant (CFA) in rodents results in a long-lasting inflammatory reaction, characterized by a pronounced hypersensitivity to both thermal and mechanical stimuli, which peaks between 24-72 hr following injection and can last for several weeks. This test predicts the analgesic, anti-allodynic and/or anti-hyperalgesic effect of numerous efficacious clinical agents, including acetaminophen, NSAIDS, such as aspirin and ibuprofen, opioids, such as morphine, and especially the N-type calcium channel blocker ziconotide, which is marketed as Prialt® for the management of severe chronic pain, including several types of neuropathic pain.

To assess whether test compounds of Formula (I) reverse established hypersensitivity, a 100 μL of CFA (suspended in a 1:1 emulsion of saline and heat-killed *Mycobacterium tuberculosis* in mineral oil) was injected into a single hind paw of Sprague-Dawley rats (typically males ranging from 150-350 g). Each rat was placed in a test chamber on a warm glass surface and allowed to acclimate for approximately 10 min. A radiant thermal stimulus (beam of light) was then focused through the glass onto the plantar surface of each hind paw in turn. The thermal stimulus was automatically shut off by a photoelectric relay when the paw was moved or when the cut-off time was reached (20 sec for radiant heat at ~5 Amps). An initial (baseline) response latency to the thermal stimulus was recorded for each animal prior to the injection of CFA. Twenty-four hr following intraplantar CFA injection, the response latency of the animal to the thermal stimulus was then re-evaluated and compared to the animal's baseline response time. Only rats that exhibited at least a 25% reduction in response latency (i.e., hyperalgesia) were included in further analysis. Immediately following the post-CFA latency assessment, test compound or vehicle (usually Solutol, hydroxypropyl methylcellulose, hydroxypropyl beta-cyclodextrin or PEG-400) was administered i.p. or p.o. to rats. Post-compound treatment withdrawal latencies were assessed at fixed time intervals, typically 30, 60 and 120 min. Resultant data for vehicle and compounds 1 and 14 of Formula (I) are shown in FIG. 1.

Throughout this application, various publications are cited. The disclosure of these publications is hereby incorporated by reference into this application to describe more fully the state of the art to which this invention pertains.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:
1. A compound of Formula (I)

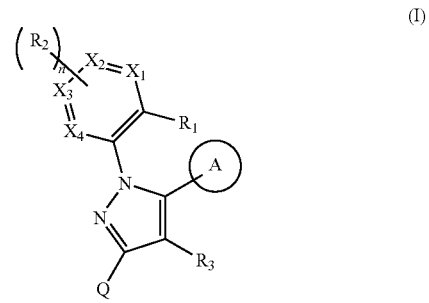

wherein
$X_1$, $X_2$, $X_3$ and $X_4$ are independently CH or N;
n is 0, 1 or 2;
$R_1$ is selected from the group consisting of $C_{1-4}$alkyl, $C_{1-4}$alkoxy, di($C_{1-4}$alkyl)amino, $C_{1-4}$alkyl-amino, amino, pyrrolidin-1-yl, nitro, halo, trifluoromethoxy, trifluoromethyl, and cyano;
$R_2$ is $C_{1-4}$alkoxy, halo, or trifluoromethyl;
wherein $R_1$ and $R_2$ alternatively can form a 6-membered heteroaryl ring with n being 1 and $R_2$ bound to $X_1$; $R_3$ is hydrogen or bromo;
ring A is selected from the group consisting of pyridine-N-oxide, benzo[1,3]dioxol-5-yl, 4,4-dimethylcyclohex-1-en-1-yl, indolyl, 1-methyl-indolyl, 2,3-dihydrobenzo[b][1,4]-dioxin-6-yl, cyclopent-1-en-1-yl, benzofuranyl, phenyl, and heteroaryl, wherein said heteroaryl is a 5 to 6 membered ring optionally containing 1 additional heteroatom selected from the group consisting of N, O and S;
wherein said phenyl and said heteroaryl is optionally substituted with $R_4$;
$R_4$ is selected from the group consisting of hydroxyl, halo, cyano, amino, carboxy, $C_{1-4}$alkyl, $C_{1-4}$alkoxy, $C_{1-4}$alkylthio, di($C_{1-4}$alkyl)amino, $C_{1-4}$alkylcarbonyl, $C_{1-4}$alkoxycarbonyl, $C_{1-4}$alkylcarbonylamino, di($C_{1-4}$alkyl)amino-carbonyl, hydroxyl-$C_{1-4}$alkyl, morpholin-4-yl-$C_{1-4}$alkoxy, imidazol-1-yl-$C_{1-4}$alkoxy, di($C_{1-4}$alkyl)amino-$C_{1-4}$alkoxy, $C_{1-4}$alkylsulfonyl, morpholin-4-yl-carbonyl, di($C_{1-4}$alkyl)amino-$C_{1-4}$ alkyl-aminocarbonyl, aminocarbonyl, 1-methyl-piperidin-4-yl-carbonyl, hydroxyl-$C_{1-4}$alkyl-aminocarbonyl and $C_{1-4}$alkylsulfinyl; and
Q is selected from the group consisting of

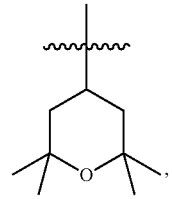

Q1

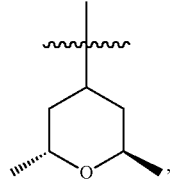

Q2

Q3 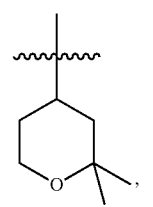
Q4 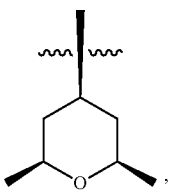
Q5 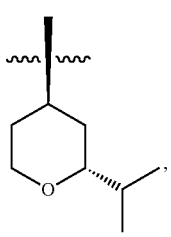
Q6 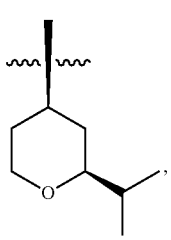
Q7 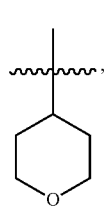
Q8 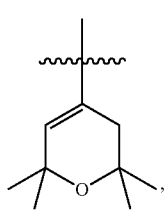
Q9 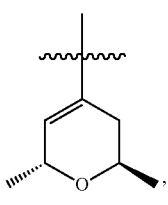
Q10 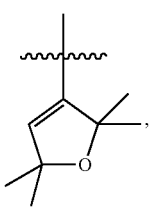
Q11 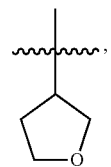
Q12 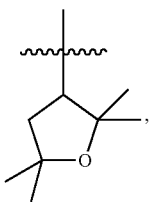
Q13 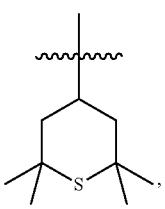
Q14 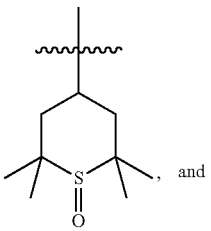, and
Q15 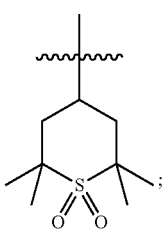;
or an enantiomer, diastereomer, solvate or pharmaceutically acceptable salt thereof.

2. The compound of claim 1, wherein Q is

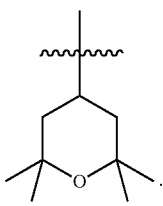
Q1

3. The compound of claim 2, wherein $R_1$ is $C_{1-4}$alkoxy.
4. The compound of claim 3, wherein ring A is phenyl, thiophen-2-yl or pyridine.
5. The compound of claim 4, wherein $R_4$ is halo, cyano or $C_{1-4}$alkoxy.
6. The compound of claim 1, wherein Q is

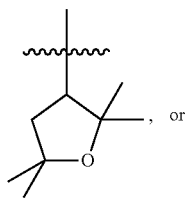
Q12, or

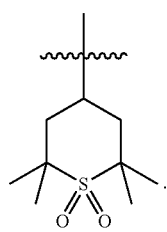
Q15

7. The compound of claim 6, wherein ring A is phenyl.
8. The compound of claim 7, wherein $R_1$ is $C_{1-4}$alkoxy and $R_4$ is halo.
9. The compound of claim 1, wherein said compound is selected from:
5-(4-Chloro-phenyl)-1-(2-methoxy-phenyl)-3-(2,2,6,6-tetramethyl-tetrahydro-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-benzonitrile,
5-(4-Chloro-2-fluorophenyl)-1-(2-methoxyphenyl)-3-(2,2,6,6-tetramethyltetrahydro-2H-pyran-4-yl)-1H-pyrazole,
5-(1,3-Benzodioxol-5-yl)-1-(2-methoxyphenyl)-3-(2,2,6,6-tetramethyltetrahydro-2H-pyran-4-yl)-1H-pyrazole,
1-(2-Methoxyphenyl)-5-(4-methoxyphenyl)-3-(2,2,6,6-tetramethyltetrahydro-2H-pyran-4-yl)-1H-pyrazole,
1-(2-Methoxyphenyl)-5-[4-(methylsulfanyl)phenyl]-3-(2,2,6,6-tetramethyltetrahydro-2H-pyran-4-yl)-1H-pyrazole,
5-(4-Chlorophenyl)-1-[2-(1-methylethoxy)phenyl]-3-(2,2,6,6-tetramethyltetrahydro-2H-pyran-4-yl)-1H-pyrazole,
5-(4,4-Dimethylcyclohex-1-en-1-yl)-1-(2-methoxyphenyl)-3-(2,2,6,6-tetramethyltetrahydro-2H-pyran-4-yl)-1H-pyrazole,
5-(4-Ethoxyphenyl)-1-(2-methoxyphenyl)-3-(2,2,6,6-tetramethyltetrahydro-2H-pyran-4-yl)-1H-pyrazole,
1-(2-Methoxyphenyl)-5-(4-methylphenyl)-3-(2,2,6,6-tetramethyltetrahydro-2H-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-N,N-dimethylaniline,
1-{4-[1-(2-Methoxyphenyl)-3-(2,2,6,6-tetramethyltetrahydro-2H-pyran-4-yl)-1H-pyrazol-5-yl]phenyl}ethanone,
2-Methoxy-5-[1-(2-methoxyphenyl)-3-(2,2,6,6-tetramethyltetrahydro-2H-pyran-4-yl)-1H-pyrazol-5-yl]pyridine,
5-(5-Chlorothiophen-2-yl)-1-(2-methoxyphenyl)-3-(2,2,6,6-tetramethyltetrahydro-2H-pyran-4-yl)-1H-pyrazole,
5-(4-tert-Butylphenyl)-1-(2-methoxyphenyl)-3-(2,2,6,6-tetramethyltetrahydro-2H-pyran-4-yl)-1H-pyrazole,
1-(2-Methoxyphenyl)-5-phenyl-3-(2,2,6,6-tetramethyltetrahydro-2H-pyran-4-yl)-1H-pyrazole,
Ethyl 4-[1-(2-methoxyphenyl)-3-(2,2,6,6-tetramethyltetrahydro-2H-pyran-4-yl)-1H-pyrazol-5-yl]benzoate,
1-(2-Methoxyphenyl)-5-(4-methylthiophen-2-yl)-3-(2,2,6,6-tetramethyltetrahydro-2H-pyran-4-yl)-1H-pyrazole,
2-Ethoxy-5-[1-(2-methoxyphenyl)-3-(2,2,6,6-tetramethyltetrahydro-2H-pyran-4-yl)-1H-pyrazol-5-yl]-pyridine,
1-(2-Methoxyphenyl)-5-(3-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1-methyl-1H-indole,
2-[1-(2-Methoxyphenyl)-3-(2,2,6,6-tetramethyltetrahydro-2H-pyran-4-yl)-1H-pyrazol-5-yl]-aniline,
5-[1-(2-Methoxyphenyl)-3-(2,2,6,6-tetramethyltetrahydro-2H-pyran-4-yl)-1H-pyrazol-5-yl]-2-methylpyridine,
1-(2-Methoxyphenyl)-5-[4-(1-methylethoxy)phenyl]-3-(2,2,6,6-tetramethyltetrahydro-2H-pyran-4-yl)-1H-pyrazole,
2-Chloro-4-[1-(2-methoxyphenyl)-3-(2,2,6,6-tetramethyltetrahydro-2H-pyran-4-yl)-1H-pyrazol-5-yl]pyridine,
1-(2-Methoxyphenyl)-3-(2,2,6,6-tetramethyltetrahydro-2H-pyran-4-yl)-5-thiophen-2-yl-1H-pyrazole,
5-(2,3-Dihydro-1,4-benzodioxin-6-yl)-1-(2-methoxyphenyl)-3-(2,2,6,6-tetramethyltetrahydro-2H-pyran-4-yl)-1H-pyrazole,
1-(2-Methoxyphenyl)-5-(5-methylfuran-2-yl)-3-(2,2,6,6-tetramethyltetrahydro-2H-pyran-4-yl)-1H-pyrazole,
5-(3,4-Dimethoxyphenyl)-1-(2-methoxyphenyl)-3-(2,2,6,6-tetramethyltetrahydro-2H-pyran-4-yl)-1H-pyrazole,
N-{5-[1-(2-Methoxyphenyl)-3-(2,2,6,6-tetramethyltetrahydro-2H-pyran-4-yl)-1H-pyrazol-5-yl]pyridin-2-yl}acetamide,
5-[1-(2-Methoxyphenyl)-3-(2,2,6,6-tetramethyltetrahydro-2H-pyran-4-yl)-1H-pyrazol-5-yl]-N,N-dimethylpyridin-2-amine,
4-[1-(2-Methoxyphenyl)-3-(2,2,6,6-tetramethyltetrahydro-2H-pyran-4-yl)-1H-pyrazol-5-yl]pyridine,
4-[1-(2-Methoxyphenyl)-3-(2,2,6,6-tetramethyltetrahydro-2H-pyran-4-yl)-1H-pyrazol-5-yl]-2-methylpyridine,
3-Methoxy-5-[1-(2-methoxyphenyl)-3-(2,2,6,6-tetramethyltetrahydro-2H-pyran-4-yl)-1H-pyrazol-5-yl]-pyridine, 2-Methoxy-3-[1-(2-methoxyphenyl)-3-(2,2,6,6-tetramethyltetrahydro-2H-pyran-4-yl)-1H-pyrazol-5-yl]-pyridine,
N-{2-[1-(2-Methoxyphenyl)-3-(2,2,6,6-tetramethyltetrahydro-2H-pyran-4-yl)-1H-pyrazol-5-yl]-phenyl}-acetamide,
5-Cyclopent-1-en-1-yl-1-(2-methoxyphenyl)-3-(2,2,6,6-tetramethyltetrahydro-2H-pyran-4-yl)-1H-pyrazole,
2-[1-(2-Methoxyphenyl)-3-(2,2,6,6-tetramethyltetrahydro-2H-pyran-4-yl)-1H-pyrazol-5-yl]-5-methyl-1,3-thiazole,
2-Methoxy-5-[1-(2-methoxyphenyl)-3-(2,2,6,6-tetramethyltetrahydro-2H-pyran-4-yl)-1H-pyrazol-5-yl]pyrimidine,
N,N-Diethyl-4-[1-(2-methoxyphenyl)-3-(2,2,6,6-tetramethyltetrahydro-2H-pyran-4-yl)-1H-pyrazol-5-yl]-benzamide,
5-(1-Benzofuran-2-yl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1H-indole,
5-(3,5-Dimethoxyphenyl)-1-(2-methoxyphenyl)-3-(2,2,6,6-tetramethyltetrahydro-2H-pyran-4-yl)-1H-pyrazole,
1-{4-[1-(2-Methoxyphenyl)-3-(2,2,6,6-tetramethyltetrahydro-2H-pyran-4-yl)-1H-pyrazol-5-yl]-phenyl}ethanol,
3-[1-(2-Methoxyphenyl)-3-(2,2,6,6-tetramethyltetrahydro-2H-pyran-4-yl)-1H-pyrazol-5-yl]-pyridine,
4-[1-(2-Methoxyphenyl)-3-(2,2,6,6-tetramethyltetrahydro-2H-pyran-4-yl)-1H-pyrazol-5-yl]-benzoic acid,
5-(4-Methanesulfinyl-phenyl)-1-(2-methoxy-phenyl)-3-(2,2,6,6-tetramethyl-tetrahydro-pyran-4-yl)-1H-pyrazole,
1-(2-tert-Butoxyphenyl)-5-(4-chlorophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N,N-dimethylaniline,
2-[5-(4-Chloro-phenyl)-3-(2,2,6,6-tetramethyl-tetrahydro-pyran-4-yl)-pyrazol-1-yl]-pyridine,
4-[5-(4-Chlorophenyl)-3-(2,2,6,6-tetramethyltetrahydro-2H-pyran-4-yl)-1H-pyrazol-1-yl]-pyridine,
3-[5-(4-Chlorophenyl)-3-(2,2,6,6-tetramethyltetrahydro-2H-pyran-4-yl)-1H-pyrazol-1-yl]-pyridine,
4-[1-Pyrazin-2-yl-3-(2,2,6,6-tetramethyltetrahydro-2H-pyran-4-yl)-1H-pyrazol-5-yl]-benzonitrile,
4-[1-Pyridin-3-yl-3-(2,2,6,6-tetramethyltetrahydro-2H-pyran-4-yl)-1H-pyrazol-5-yl]-benzonitrile,
4-[1-Pyridin-2-yl-3-(2,2,6,6-tetramethyltetrahydro-2H-pyran-4-yl)-1H-pyrazol-5-yl]-benzonitrile,
4-[1-Pyridin-4-yl-3-(2,2,6,6-tetramethyltetrahydro-2H-pyran-4-yl)-1H-pyrazol-5-yl]-benzonitrile,
4-[1-Quinolin-8-yl-3-(2,2,6,6-tetramethyltetrahydro-2H-pyran-4-yl)-1H-pyrazol-5-yl]-benzonitrile,
5-(4-Chlorophenyl)-1-(2-methoxy-phenyl)-3-(2,2,6,6-tetramethyl-tetrahydro-thiopyran-4-yl)-1H-pyrazole,
5-(4-Chlorophenyl)-1-(2-methoxyphenyl)-3-(2,2,6,6-tetramethyl-1,1-dioxidotetrahydro-2H-thiopyran-4-yl)-1H-pyrazole,
2-[5-(4-Chlorophenyl)-3-(2,2,6,6-tetramethyltetrahydro-2H-pyran-4-yl)-1H-pyrazol-1-yl]-N-methylaniline,
5-(4-Chlorophenyl)-3-[(trans)-2,6-dimethyltetrahydro-2H-pyran-4-yl]-1-(2-methoxyphenyl)-1H-pyrazole,
5-(4-Chlorophenyl)-3-(2,2-dimethyltetrahydro-2H-pyran-4-yl)-1-(2-methoxyphenyl)-1H-pyrazole,
5-(4-Chlorophenyl)-3-[(2R,4r,6S)-2,6-dimethyltetrahydro-2H-pyran-4-yl]-1-(2-methoxyphenyl)-1H-pyrazole,
5-(4-Chlorophenyl)-1-(2-methoxyphenyl)-3-[(2R,4S)-2-(1-methylethyl)tetrahydro-2H-pyran-4-yl]-1H-pyrazole,
5-(4-Chlorophenyl)-1-(2-nitrophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N-ethylaniline,
3-[(trans)-2,6-Dimethyltetrahydro-2H-pyran-4-yl]-1-(2-methoxyphenyl)-5-phenyl-1H-pyrazole,
2-[5-(4-Chlorophenyl)-3-(2,2,6,6-tetramethyltetrahydro-2H-pyran-4-yl)-1H-pyrazol-1-yl]-aniline,
5-(4-Chlorophenyl)-1-(2-methoxyphenyl)-3-[(trans)-2-(1-methylethyl)tetrahydro-2H-pyran-4-yl]-1H-pyrazole,
4-Bromo-5-(4-chlorophenyl)-1-(2-methoxyphenyl)-3-(2,2,6,6-tetramethyltetrahydro-2H-pyran-4-yl)-1H-pyrazole,
5-(4-Chlorophenyl)-1-(2-methoxyphenyl)-3-(tetrahydro-2H-pyran-4-yl)-1H-pyrazole,
4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine,
2-[5-(4-Chlorophenyl)-3-(2,2,6,6-tetramethyltetrahydro-2H-pyran-4-yl)-1H-pyrazol-1-yl]-N,N-diethylaniline,
1-(2-Chlorophenyl)-5-(4-chlorophenyl)-3-(tetrahydro-2H-pyran-4-yl)-1H-pyrazole,
5-(4-Chlorophenyl)-3-(2,2-dimethyltetrahydro-2H-pyran-4-yl)-1-(4-methoxy-2-methylphenyl)-1H-pyrazole,
5-(4-Chlorophenyl)-1-(2-pyrrolidin-1-ylphenyl)-3-(2,2,6,6-tetramethyltetrahydro-2H-pyran-4-yl)-1H-pyrazole,
5-(4-Chlorophenyl)-1-(2-ethylphenyl)-3-(tetrahydro-2H-pyran-4-yl)-1H-pyrazole,
5-(4-Chlorophenyl)-1-(2,4-dichlorophenyl)-3-(tetrahydro-2H-pyran-4-yl)-1H-pyrazole,
5-(4-Chlorophenyl)-3-(tetrahydro-2H-pyran-4-yl)-1-[2-(trifluoromethoxy)phenyl]-1H-pyrazole,
5-(4-Chlorophenyl)-1-(2,6-dichlorophenyl)-3-(tetrahydro-2H-pyran-4-yl)-1H-pyrazole,
5-{4-[2-(1H-Imidazol-1-yl)ethoxy]phenyl}-1-(2-methoxyphenyl)-3-(2,2,6,6-tetramethyltetrahydro-2H-pyran-4-yl)-1H-pyrazole,
2-{4-[1-(2-Methoxyphenyl)-3-(2,2,6,6-tetramethyltetrahydro-2H-pyran-4-yl)-1H-pyrazol-5-yl]phenoxy}-N,N-dimethylethanamine,
1-(2-Methoxyphenyl)-5-[4-(methylsulfonyl)phenyl]-3-(2,2,6,6-tetramethyltetrahydro-2H-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-phenol,
5-[1-(2-Methoxyphenyl)-3-(2,2,6,6-tetramethyltetrahydro-2H-pyran-4-yl)-1H-pyrazol-5-yl]-pyridin-2-amine,
4-({4-[1-(2-Methoxyphenyl)-3-(2,2,6,6-tetramethyltetrahydro-2H-pyran-4-yl)-1H-pyrazol-5-yl]phenyl}carbonyl)morpholine,
N-[2-(Dimethylamino)ethyl]-4-[1-(2-methoxyphenyl)-3-(2,2,6,6-tetramethyltetrahydro-2H-pyran-4-yl)-1H-pyrazol-5-yl]benzamide,
4-[1-(2-Methoxyphenyl)-3-(2,2,6,6-tetramethyltetrahydro-2H-pyran-4-yl)-1H-pyrazol-5-yl]benzamide,
1-({4-[1-(2-Methoxyphenyl)-3-(2,2,6,6-tetramethyltetrahydro-2H-pyran-4-yl)-1H-pyrazol-5-yl]phenyl}carbonyl)-4-methylpiperazine, N-(2-Hydroxyethyl)-4-[1-(2-methoxyphenyl)-3-(2,2,6,6-tetramethyltetrahydro-2H-pyran-4-yl)-1H-pyrazol-5-yl]-benzamide,
3-[1-(2-Methoxyphenyl)-3-(2,2,6,6-tetramethyltetrahydro-2H-pyran-4-yl)-1H-pyrazol-5-yl]-pyridine-1-oxide,
5-(4-Chlorophenyl)-1-[2,4-dichloro-6-(trifluoromethyl)phenyl]-3-(tetrahydro-2H-pyran-4-yl)-1H-pyrazole,
5-(4-Chlorophenyl)-1-[2,6-dichloro-4-(trifluoromethyl)phenyl]-3-(tetrahydro-2H-pyran-4-yl)-1H-pyrazole,
2-[5-(4-Chlorophenyl)-3-(tetrahydro-2H-pyran-4-yl)-1H-pyrazol-1-yl]-benzonitrile,
5-(4-Chlorophenyl)-1-(2-methoxyphenyl)-3-(2,2,6,6-tetramethyl-3,6-dihydro-2H-pyran-4-yl)-1H-pyrazole,
5-(4-Chlorophenyl)-3-[(trans)-2,6-dimethyl-3,6-dihydro-2H-pyran-4-yl]-1-(2-methoxyphenyl)-1H-pyrazole,
5-(4-Chlorophenyl)-1-(2-methoxyphenyl)-3-(2,2,5,5-tetramethyl-2,5-dihydrofuran-3-yl)-1H-pyrazole,
5-(4-Chlorophenyl)-1-(2-methoxyphenyl)-3-(2,2,5,5-tetramethyl-2,5-dihydrofuran-3-yl)-1H-pyrazole, or
5-(4-Chlorophenyl)-1-(2-methoxyphenyl)-3-(2,2,5,5-tetramethyl-tetrahydrofuran-3-yl)-1H-pyrazole.

10. The compound of claim 1, wherein said compound is selected from:
5-(4-Chloro-phenyl)-1-(2-methoxy-phenyl)-3-(2,2,6,6-tetramethyl-tetrahydro-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-benzonitrile,
5-(4-Chloro-2-fluorophenyl)-1-(2-methoxyphenyl)-3-(2,2,6,6-tetramethyltetrahydro-2H-pyran-4-yl)-1H-pyrazole,
5-(1,3-Benzodioxol-5-yl)-1-(2-methoxyphenyl)-3-(2,2,6,6-tetramethyltetrahydro-2H-pyran-4-yl)-1H-pyrazole,
1-(2-Methoxyphenyl)-5-(4-methoxyphenyl)-3-(2,2,6,6-tetramethyltetrahydro-2H-pyran-4-yl)-1H-pyrazole,
1-(2-Methoxyphenyl)-5-[4-(methylsulfanyl)phenyl]-3-(2,2,6,6-tetramethyltetrahydro-2H-pyran-4-yl)-1H-pyrazole,
5-(4-Chlorophenyl)-1-[2-(1-methylethoxy)phenyl]-3-(2,2,6,6-tetramethyltetrahydro-2H-pyran-4-yl)-1H-pyrazole,
5-(4,4-Dimethylcyclohex-1-en-1-yl)-1-(2-methoxyphenyl)-3-(2,2,6,6-tetramethyltetrahydro-2H-pyran-4-yl)-1H-pyrazole,
5-(4-Ethoxyphenyl)-1-(2-methoxyphenyl)-3-(2,2,6,6-tetramethyltetrahydro-2H-pyran-4-yl)-1H-pyrazole,
1-(2-Methoxyphenyl)-5-(4-methylphenyl)-3-(2,2,6,6-tetramethyltetrahydro-2H-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-N,N-dimethylaniline,
1-{4-[1-(2-Methoxyphenyl)-3-(2,2,6,6-tetramethyltetrahydro-2H-pyran-4-yl)-1H-pyrazol-5-yl]phenyl}ethanone,
2-Methoxy-5-[1-(2-methoxyphenyl)-3-(2,2,6,6-tetramethyltetrahydro-2H-pyran-4-yl)-1H-pyrazol-5-yl]pyridine,
5-(5-Chlorothiophen-2-yl)-1-(2-methoxyphenyl)-3-(2,2,6,6-tetramethyltetrahydro-2H-pyran-4-yl)-1H-pyrazole,
5-(4-tert-Butylphenyl)-1-(2-methoxyphenyl)-3-(2,2,6,6-tetramethyltetrahydro-2H-pyran-4-yl)-1H-pyrazole,
1-(2-Methoxyphenyl)-5-phenyl-3-(2,2,6,6-tetramethyltetrahydro-2H-pyran-4-yl)-1H-pyrazole,
Ethyl 4-[1-(2-methoxyphenyl)-3-(2,2,6,6-tetramethyltetrahydro-2H-pyran-4-yl)-1H-pyrazol-5-yl]benzoate,
1-(2-Methoxyphenyl)-5-(4-methylthiophen-2-yl)-3-(2,2,6,6-tetramethyltetrahydro-2H-pyran-4-yl)-1H-pyrazole,
2-Ethoxy-5-[1-(2-methoxyphenyl)-3-(2,2,6,6-tetramethyltetrahydro-2H-pyran-4-yl)-1H-pyrazol-5-yl]-pyridine,
1-(2-Methoxyphenyl)-5-(3-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1-methyl-1H-indole,
2-[1-(2-Methoxyphenyl)-3-(2,2,6,6-tetramethyltetrahydro-2H-pyran-4-yl)-1H-pyrazol-5-yl]-aniline,
5-[1-(2-Methoxyphenyl)-3-(2,2,6,6-tetramethyltetrahydro-2H-pyran-4-yl)-1H-pyrazol-5-yl]-2-methylpyridine,
1-(2-Methoxyphenyl)-5-[4-(1-methylethoxy)phenyl]-3-(2,2,6,6-tetramethyltetrahydro-2H-pyran-4-yl)-1H-pyrazole,
2-Chloro-4-[1-(2-methoxyphenyl)-3-(2,2,6,6-tetramethyltetrahydro-2H-pyran-4-yl)-1H-pyrazol-5-yl]pyridine,
1-(2-Methoxyphenyl)-3-(2,2,6,6-tetramethyltetrahydro-2H-pyran-4-yl)-5thiophen-2-yl-1H-pyrazole,
5-(2,3-Dihydro-1,4-benzodioxin-6-yl)-1-(2-methoxyphenyl)-3-(2,2,6,6-tetramethyltetrahydro-2H-pyran-4-yl)-1H-pyrazole,
1-(2-Methoxyphenyl)-5-(5-methylfuran-2-yl)-3-(2,2,6,6-tetramethyltetrahydro-2H-pyran-4-yl)-1H-pyrazole,
5-(3,4-Dimethoxyphenyl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-N,N-dimethylpyridin-2-amine,
4-[1-(2-Methoxyphenyl)-3-(2,2,6,6-tetramethyltetrahydro-2H-pyran-4-yl)-1H-pyrazol-5-yl]pyridine,
4-[1-(2-Methoxyphenyl)-3-(2,2,6,6-tetramethyltetrahydro-2H-pyran-4-yl)-1H-pyrazol-5-yl]-2-methylpyridine,
3-Methoxy-5-[1-(2-methoxyphenyl)-3-(2,2,6,6-tetramethyltetrahydro-2H-pyran-4-yl)-1H-pyrazol-5-yl]-pyridine,
N-{2-[1-(2-Methoxyphenyl)-3-(2,2,6,6-tetramethyltetrahydro-2H-pyran-4-yl)-1H-pyrazol-5-yl]-phenyl}-acetamide,
5-Cyclopent-1-en-1-yl-1-(2-methoxyphenyl)-3-(2,2,6,6-tetramethyltetrahydro-2H-pyran-4-yl)-1H-pyrazole,
2-[1-(2-Methoxyphenyl)-3-(2,2,6,6-tetramethyltetrahydro-2H-pyran-4-yl)-1H-pyrazol-5-yl]-5-methyl-1,3-thiazole,
2-Methoxy-5-[1-(2-methoxyphenyl)-3-(2,2,6,6-tetramethyltetrahydro-2H-pyran-4-yl)-1H-pyrazol-5-yl]pyrimidine,
5-(1-Benzofuran-2-yl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1H-indole,
5-(3,5-Dimethoxyphenyl)-1-(2-methoxyphenyl)-3-(2,2,6,6-tetramethyltetrahydro-2H-pyran-4-yl)-1H-pyrazole,
1-{4-[1-(2-Methoxyphenyl)-3-(2,2,6,6-tetramethyltetrahydro-2H-pyran-4-yl)-1H-pyrazol-5-yl]-phenyl}ethanol,
3-[1-(2-Methoxyphenyl)-3-(2,2,6,6-tetramethyltetrahydro-2H-pyran-4-yl)-1H-pyrazol-5-yl]-pyridine,
1-(2-tert-Butoxyphenyl)-5-(4-chlorophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N,N-dimethylaniline, 2-[5-(4-Chlorophenyl)-3-(2,2,6,6-tetramethyltetrahydro-2H-pyran-4-yl)-1H-pyrazol-1-yl]-N-methylaniline, 5-(4-Chlorophenyl)-3-[(trans)-2,6-dimethyltetrahydro-2H-pyran-4-yl]-1-(2-methoxyphenyl)-1H-pyrazole, 5-(4-Chlorophenyl)-3-(2,2-dimethyltetrahydro-2H-pyran-4-yl)-1-(2-methoxyphenyl)-1H-pyrazole, 5-(4-Chlorophenyl)-3-[(2R,4r,6S)-2,6-dimethyltetrahydro-2H-pyran-4-yl]-1-(2-methoxyphenyl)-1H-pyrazole, 5-(4-Chlorophenyl)-1-(2-methoxyphenyl)-3-[(2R,4S)-2-(1-methylethyl)tetrahydro-2H-pyran-4-yl]-1H-pyrazole, 5-(4-Chlorophenyl)-1-(2-nitrophenyl)-3-(2,2,6,6-tetramethyltetrahydro-2H-pyran-4-yl)-1H-pyrazole, 2-[5-(4-Chlorophenyl)-3-(2,2,6,6-tetramethyltetrahydro-2H-pyran-4-yl)-1H-pyrazol-1-yl]-N-ethylaniline, 3-[(trans)-2,6-Dimethyltetrahydro-2H-pyran-4-yl]-1-(2-methoxyphenyl)-5-phenyl-1H-pyrazole, 2-[5-(4-Chlorophenyl)-3-(2,2,6,6-tetramethyltetrahydro-2H-pyran-4-yl)-1H-pyrazol-1-yl]-aniline, 5-(4-Chlorophenyl)-1-(2-methoxyphenyl)-3-[(trans)-2-(1-methylethyl)tetrahydro-2H-pyran-4-yl]-1H-pyrazole, 4-Bromo-5-(4-chlorophenyl)-1-(2-methoxyphenyl)-3-(2,2,6,6-tetramethyltetrahydro-2H-pyran-4-yl)-1H-pyrazole, 5-(4-Chlorophenyl)-1-(2-methoxyphenyl)-3-(tetrahydro-2H-pyran-4-yl)-1H-pyrazole, 4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine, 2-[5-(4-Chlorophenyl)-3-(2,2,6,6-tetramethyltetrahydro-2H-pyran-4-yl)-1H-pyrazol-1-yl]-N,N-diethylaniline, 1-(2-Chlorophenyl)-5-(4-chlorophenyl)-3-(tetrahydro-2H-pyran-4-yl)-1H-pyrazole, 5-(4-Chlorophenyl)-3-(2,2-dimethyltetrahydro-2H-pyran-4-yl)-1-(4-methoxy-2-methylphenyl)-1H-pyrazole, 5-(4-Chlorophenyl)-1-(2-pyrrolidin-1-ylphenyl)-3-(2,2,6,6-tetramethyltetrahydro-2H-pyran-4-yl)-1H-pyrazole, 5-(4-Chlorophenyl)-1-(2-ethylphenyl)-3-(tetrahydro-2H-pyran-4-yl)-1H-pyrazole, 2-Methoxy-3-[1-(2-methoxyphenyl)-3-(2,2,6,6-tetramethyltetrahydro-2H-pyran-4-yl)-1H-pyrazol-5-yl]pyridine, 5-(4-Chlorophenyl)-1-(2,4-dichlorophenyl)-3-(tetrahydro-2H-pyran-4-yl)-1H-pyrazole, 5-(4-Chlorophenyl)-1-(2-methoxyphenyl)-3-(2,2,6,6-tetramethyl-3,6-dihydro-2H-pyran-4-yl)-1H-pyrazole, 5-(4-Chlorophenyl)-3-[(trans)-2,6-dimethyl-3,6-dihydro-2H-pyran-4-yl]-1-(2-methoxyphenyl)-1H-pyrazole, 5-(4-Chlorophenyl)-1-(2-methoxyphenyl)-3-(2,2,5,5-tetramethyl-2,5-dihydrofuran-3-yl)-1H-pyrazole, 5-(4-Chlorophenyl)-1-(2-methoxyphenyl)-3-(2,2,5,5-tetramethyl-2,5-dihydrofuran-3-yl)-1H-pyrazole, or 5-(4-Chlorophenyl)-1-(2-methoxyphenyl)-3-(2,2,5,5-tetramethyl-tetrahydrofuran-3-yl)-1H-pyrazole.

11. The compound of claim 1, wherein said compound is selected from:

5-(4-Chloro-phenyl)-1-(2-methoxy-phenyl)-3-(2,2,6,6-tetramethyl-tetrahydro-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-benzonitrile, 5-(4-Chloro-2-fluorophenyl)-1-(2-methoxyphenyl)-3-(2,2,6,6-tetramethyltetrahydro-2H-pyran-4-yl)-1H-pyrazole, 5-(1,3-Benzodioxol-5-yl)-1-(2-methoxyphenyl)-3-(2,2,6,6-tetramethyltetrahydro-2H-pyran-4-yl)-1H-pyrazole, 1-(2-Methoxyphenyl)-5-(4-methoxyphenyl)-3-(2,2,6,6-tetramethyltetrahydro-2H-pyran-4-yl)-1H-pyrazole, 1-(2-Methoxyphenyl)-5-[4-(methylsulfanyl)phenyl]-3-(2,2,6,6-tetramethyltetrahydro-2H-pyran-4-yl)-1H-pyrazole, 5-(4-Chlorophenyl)-1-[2-(1-methylethoxy)phenyl]-3-(2,2,6,6-tetramethyltetrahydro-2H-pyran-4-yl)-1H-pyrazole, 5-(4,4-Dimethylcyclohex-1-en-1-yl)-1-(2-methoxyphenyl)-3-(2,2,6,6-tetramethyltetrahydro-2H-pyran-4-yl)-1H-pyrazole, 5-(4-Ethoxyphenyl)-1-(2-methoxyphenyl)-3-(2,2,6,6-tetramethyltetrahydro-2H-pyran-4-yl)-1H-pyrazole, 1-(2-Methoxyphenyl)-5-(4-methylphenyl)-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-N,N-dimethylaniline, 1-{4-[1-(2-Methoxyphenyl)-3-(2,2,6,6-tetramethyltetrahydro-2H-pyran-4-yl)-1H-pyrazol-5-yl]phenyl}ethanone, 2-Methoxy-5-[1-(2-methoxyphenyl)-3-(2,2,6,6-tetramethyltetrahydro-2H-pyran-4-yl)-1H-pyrazol-5-yl]pyridine, 5-(5-Chlorothiophen-2-yl)-1-(2-methoxyphenyl)-3-(2,2,6,6-tetramethyltetrahydro-2H-pyran-4-yl)-1H-pyrazole, 5-(4-tert-Butylphenyl)-1-(2-methoxyphenyl)-3-(2,2,6,6-tetramethyltetrahydro-2H-pyran-4-yl)-1H-pyrazole, 1-(2-Methoxyphenyl)-5-phenyl-3-(2,2,6,6-tetramethyltetrahydro-2H-pyran-4-yl)-1H-pyrazole, Ethyl 4-[1-(2-methoxyphenyl)-3-(2,2,6,6-tetramethyltetrahydro-2H-pyran-4-yl)-1H-pyrazol-5-yl]benzoate, 1-(2-Methoxyphenyl)-5-(4-methylthiophen-2-yl)-3-(2,2,6,6-tetramethyltetrahydro-2H-pyran-4-yl)-1H-pyrazole, 2-Ethoxy-5-[1-(2-methoxyphenyl)-3-(2,2,6,6-tetramethyltetrahydro-2H-pyran-4-yl)-1H-pyrazol-5-yl]-pyridine, 1-(2-Methoxyphenyl)-5-(3-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1-methyl-1H-indole, 2-[1-(2-Methoxyphenyl)-3-(2,2,6,6-tetramethyltetrahydro-2H-pyran-4-yl)-1H-pyrazol-5-yl]-aniline, 5-[1-(2-Methoxyphenyl)-3-(2,2,6,6-tetramethyltetrahydro-2H-pyran-4-yl)-1H-pyrazol-5-yl]-2-methylpyridine, 1-(2-Methoxyphenyl)-5-[4-(1-methylethoxy)phenyl]-3-(2,2,6,6-tetramethyltetrahydro-2H-pyran-4-yl)-1H-pyrazole, 2-Chloro-4-[1-(2-methoxyphenyl)-3-(2,2,6,6-tetramethyltetrahydro-2H-pyran-4-yl)-1H-pyrazol-5-yl]pyridine, 1-(2-Methoxyphenyl)-3-(2,2,6,6-tetramethyltetrahydro-2H-pyran-4-yl)-5-thiophen-2-yl-1H-pyrazole, 5-(2,3-Dihydro-1,4-benzodioxin-6-yl)-1-(2-methoxyphenyl)-3-(2,2,6,6-tetramethyltetrahydro-2H-pyran-4-yl)-1H-pyrazole, 1-(2-Methoxyphenyl)-5-(5-methylfuran-2-yl)-3-(2,2,6,6-tetramethyltetrahydro-2H-pyran-4-yl)-1H-pyrazole, 5-(3,4-Dimethoxyphenyl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-N,N-dimethylpyridin-2-amine,
4-[1-(2-Methoxyphenyl)-3-(2,2,6,6-tetramethyltetrahydro-2H-pyran-4-yl)-1H-pyrazol-5-yl]-2-methylpyridine,
5-Cyclopent-1-en-1-yl-1-(2-methoxyphenyl)-3-(2,2,6,6-tetramethyltetrahydro-2H-pyran-4-yl)-1H-pyrazole,
2-Methoxy-5-[1-(2-methoxyphenyl)-3-(2,2,6,6-tetramethyltetrahydro-2H-pyran-4-yl)-1H-pyrazol-5-yl]pyrimidine,
5-(1-Benzofuran-2-yl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1H-indole,
5-(3,5-Dimethoxyphenyl)-1-(2-methoxyphenyl)-3-(2,2,6,6-tetramethyltetrahydro-2H-pyran-4-yl)-1H-pyrazole,
1-{4-[1-(2-Methoxyphenyl)-3-(2,2,6,6-tetramethyltetrahydro-2H-pyran-4-yl)-1H-pyrazol-5-yl]-phenyl}ethanol,
3-[1-(2-Methoxyphenyl)-3-(2,2,6,6-tetramethyltetrahydro-2H-pyran-4-yl)-1H-pyrazol-5-yl]-pyridine,
2-[5-(4-Chlorophenyl)-3-(2,2,6,6-tetramethyltetrahydro-2H-pyran-4-yl)-1H-pyrazol-1-yl]-N,N-dimethylaniline,
2-[5-(4-Chlorophenyl)-3-(2,2,6,6-tetramethyltetrahydro-2H-pyran-4-yl)-1H-pyrazol-1-yl]-N-methylaniline,
5-(4-Chlorophenyl)-3-[(trans)-2,6-dimethyltetrahydro-2H-pyran-4-yl]-1-(2-methoxyphenyl)-1H-pyrazole,
5-(4-Chlorophenyl)-3-(2,2-dimethyltetrahydro-2H-pyran-4-yl)-1-(2-methoxyphenyl)-1H-pyrazole,
5-(4-Chlorophenyl)-3-[(2R,4r,6S)-2,6-dimethyltetrahydro-2H-pyran-4-yl]-1-(2-methoxyphenyl)-1H-pyrazole,
5-(4-Chlorophenyl)-1-(2-methoxyphenyl)-3-[(2R,4S)-2-(1-methylethyl)tetrahydro-2H-pyran-4-yl]-1H-pyrazole,
5-(4-Chlorophenyl)-1-(2-nitrophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N-ethylaniline,
3-[(trans)-2,6-Dimethyltetrahydro-2H-pyran-4-yl]-1-(2-methoxyphenyl)-5-phenyl-1H-pyrazole,
2-[5-(4-Chlorophenyl)-3-(2,2,6,6-tetramethyltetrahydro-2H-pyran-4-yl)-1H-pyrazol-1-yl]-aniline,
5-(4-Chlorophenyl)-1-(2-methoxyphenyl)-3-[(trans)-2-(1-methylethyl)tetrahydro-2H-pyran-4-yl]-1H-pyrazole,
4-Bromo-5-(4-chlorophenyl)-1-(2-methoxyphenyl)-3-(2,2,6,6-tetramethyltetrahydro-2H-pyran-4-yl)-1H-pyrazole,
5-(4-Chlorophenyl)-1-(2-methoxyphenyl)-3-(tetrahydro-2H-pyran-4-yl)-1H-pyrazole,
4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine,
2-[5-(4-Chlorophenyl)-3-(2,2,6,6-tetramethyltetrahydro-2H-pyran-4-yl)-1H-pyrazol-1-yl]-N,N-diethylaniline,
1-(2-Chlorophenyl)-5-(4-chlorophenyl)-3-(tetrahydro-2H-pyran-4-yl)-1H-pyrazole,
5-(4-Chlorophenyl)-3-(2,2-dimethyltetrahydro-2H-pyran-4-yl)-1-(4-methoxy-2-methylphenyl)-1H-pyrazole,
5-(4-Chlorophenyl)-1-(2-methoxyphenyl)-3-(2,2,6,6-tetramethyl-3,6-dihydro-2H-pyran-4-yl)-1H-pyrazole,
5-(4-Chlorophenyl)-3-[(trans)-2,6-dimethyl-3,6-dihydro-2H-pyran-4-yl]-1-(2-methoxyphenyl)-1H-pyrazole,
5-(4-Chlorophenyl)-1-(2-methoxyphenyl)-3-(2,2,5,5-tetramethyl-2,5-dihydrofuran-3-yl)-1H-pyrazole,
5-(4-Chlorophenyl)-1-(2-methoxyphenyl)-3-(2,2,5,5-tetramethyl-2,5-dihydrofuran-3-yl)-1H-pyrazole, or
5-(4-Chlorophenyl)-1-(2-methoxyphenyl)-3-(2,2,5,5-tetramethyl-tetrahydrofuran-3-yl)-1H-pyrazole.

12. A compound selected from a group consisting of:
5-(4-Chloro-phenyl)-1-(2-methoxy-phenyl)-3-(2,2,6,6-tetramethyl-tetrahydro-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-benzonitrile,
1-(2-Methoxyphenyl)-5-(4-methoxyphenyl)-3-(2,2,6,6-tetramethyltetrahydro-2H-pyran-4-yl)-1H-pyrazole,
5-(4-Ethoxyphenyl)-1-(2-methoxyphenyl)-3-(2,2,6,6-tetramethyltetrahydro-2H-pyran-4-yl)-1H-pyrazole,
2-Methoxy-5-[1-(2-methoxyphenyl)-3-(2,2,6,6-tetramethyltetrahydro-2H-pyran-4-yl)-1H-pyrazol-5-yl]pyridine,
5-(5-Chlorothiophen-2-yl)-1-(2-methoxyphenyl)-3-(2,2,6,6-tetramethyltetrahydro-2H-pyran-4-yl)-1H-pyrazole,
2-Ethoxy-5-[1-(2-methoxyphenyl)-3-(2,2,6,6-tetramethyltetrahydro-2H-pyran-4-yl)-1H-pyrazol-5-yl]-pyridine,
5-(4-Chlorophenyl)-1-(2-methoxyphenyl)-3-(2,2,6,6-tetramethyl-1,1-dioxidotetrahydro-2H-thiopyran-4-yl)-1H-pyrazole, and
5-(4-Chlorophenyl)-1-(2-methoxyphenyl)-3-(2,2,5,5-tetramethyl-tetrahydrofuran-3-yl)-1H-pyrazole.

13. A pharmaceutical composition comprising at least one compound of claim 1 and at least one pharmaceutically acceptable carrier.

14. A pharmaceutical composition of claim 13, wherein said compound of claim 1 is selected from:
5-(4-Chloro-phenyl)-1-(2-methoxy-phenyl)-3-(2,2,6,6-tetramethyl-tetrahydro-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-benzonitrile,
5-(4-Chloro-2-fluorophenyl)-1-(2-methoxyphenyl)-3-(2,2,6,6-tetramethyltetrahydro-2H-pyran-4-yl)-1H-pyrazole,
5-(1,3-Benzodioxol-5-yl)-1-(2-methoxyphenyl)-3-(2,2,6,6-tetramethyltetrahydro-2H-pyran-4-yl)-1H-pyrazole,
1-(2-Methoxyphenyl)-5-(4-methoxyphenyl)-3-(2,2,6,6-tetramethyltetrahydro-2H-pyran-4-yl)-1H-pyrazole,
1-(2-Methoxyphenyl)-5-[4-(methylsulfanyl)phenyl]-3-(2,2,6,6-tetramethyltetrahydro-2H-pyran-4-yl)-1H-pyrazole,
5-(4-Chlorophenyl)-1-[2-(1-methylethoxy)phenyl]-3-(2,2,6,6-tetramethyltetrahydro-2H-pyran-4-yl)-1H-pyrazole,
5-(4,4-Dimethylcyclohex-1-en-1-yl)-1-(2-methoxyphenyl)-3-(2,2,6,6-tetramethyltetrahydro-2H-pyran-4-yl)-1H-pyrazole,
5-(4-Ethoxyphenyl)-1-(2-methoxyphenyl)-3-(2,2,6,6-tetramethyltetrahydro-2H-pyran-4-yl)-1H-pyrazole,
1-(2-Methoxyphenyl)-5-(4-methylphenyl)-3-(2,2,6,6-tetramethyltetrahydro-2H-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-N,N-dimethylaniline,
1-{4-[1-(2-Methoxyphenyl)-3-(2,2,6,6-tetramethyltetrahydro-2H-pyran-4-yl)-1H-pyrazol-5-yl]phenyl}ethanone, 2-Methoxy-5-[1-(2-methoxyphenyl)-3-(2,2,6,6-tetramethyltetrahydro-2H-pyran-4-yl)-1H-pyrazol-5-yl]pyridine,
5-(5-Chlorothiophen-2-yl)-1-(2-methoxyphenyl)-3-(2,2,6,6-tetramethyltetrahydro-2H-pyran-4-yl)-1H-pyrazole,
5-(4-tert-Butylphenyl)-1-(2-methoxyphenyl)-3-(2,2,6,6-tetramethyltetrahydro-2H-pyran-4-yl)-1H-pyrazole,
1-(2-Methoxyphenyl)-5-phenyl-3-(2,2,6,6-tetramethyltetrahydro-2H-pyran-4-yl)-1H-pyrazole,
Ethyl 4-[1-(2-methoxyphenyl)-3-(2,2,6,6-tetramethyltetrahydro-2H-pyran-4-yl)-1H-pyrazol-5-yl]benzoate,
1-(2-Methoxyphenyl)-5-(4-methylthiophen-2-yl)-3-(2,2,6,6-tetramethyltetrahydro-2H-pyran-4-yl)-1H-pyrazole,
2-Ethoxy-5-[1-(2-methoxyphenyl)-3-(2,2,6,6-tetramethyltetrahydro-2H-pyran-4-yl)-1H-pyrazol-5-yl]-pyridine,
1-(2-Methoxyphenyl)-5-(3-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1-methyl-1H-indole,
2-[1-(2-Methoxyphenyl)-3-(2,2,6,6-tetramethyltetrahydro-2H-pyran-4-yl)-1H-pyrazol-5-yl]-aniline,
5-[1-(2-Methoxyphenyl)-3-(2,2,6,6-tetramethyltetrahydro-2H-pyran-4-yl)-1H-pyrazol-5-yl]-2-methylpyridine,
1-(2-Methoxyphenyl)-5-[4-(1-methylethoxy)phenyl]-3-(2,2,6,6-tetramethyltetrahydro-2H-pyran-4-yl)-1H-pyrazole,
2-Chloro-4-[1-(2-methoxyphenyl)-3-(2,2,6,6-tetramethyltetrahydro-2H-pyran-4-yl)-1H-pyrazol-5-yl]pyridine,
1-(2-Methoxyphenyl)-3-(2,2,6,6-tetramethyltetrahydro-2H-pyran-4-yl)-5-thiophen-2-yl-1H-pyrazole,
5-(2,3-Dihydro-1,4-benzodioxin-6-yl)-1-(2-methoxyphenyl)-3-(2,2,6,6-tetramethyltetrahydro-2H-pyran-4-yl)-1H-pyrazole,
1-(2-Methoxyphenyl)-5-(5-methylfuran-2-yl)-3-(2,2,6,6-tetramethyltetrahydro-2H-pyran-4-yl)-1H-pyrazole,
5-(3,4-Dimethoxyphenyl)-1-(2-methoxyphenyl)-3-(2,2,6,6-tetramethyltetrahydro-2H-pyran-4-yl)-1H-pyrazole,
N-{5-[1-(2-Methoxyphenyl)-3-(2,2,6,6-tetramethyltetrahydro-2H-pyran-4-yl)-1H-pyrazol-5-yl]pyridin-2-yl}acetamide,
5-[1-(2-Methoxyphenyl)-3-(2,2,6,6-tetramethyltetrahydro-2H-pyran-4-yl)-1H-pyrazol-5-yl]-N,N-dimethylpyridin-2-amine,
4-[1-(2-Methoxyphenyl)-3-(2,2,6,6-tetramethyltetrahydro-2H-pyran-4-yl)-1H-pyrazol-5-yl]pyridine,
4-[1-(2-Methoxyphenyl)-3-(2,2,6,6-tetramethyltetrahydro-2H-pyran-4-yl)-1H-pyrazol-5-yl]-2-methylpyridine,
3-Methoxy-5-[1-(2-methoxyphenyl)-3-(2,2,6,6-tetramethyltetrahydro-2H-pyran-4-yl)-1H-pyrazol-5-yl]-pyridine,
2-Methoxy-3-[1-(2-methoxyphenyl)-3-(2,2,6,6-tetramethyltetrahydro-2H-pyran-4-yl)-1H-pyrazol-5-yl]-pyridine,
N-{2-[1-(2-Methoxyphenyl)-3-(2,2,6,6-tetramethyltetrahydro-2H-pyran-4-yl)-1H-pyrazol-5-yl]-phenyl}-acetamide,
5-Cyclopent-1-en-1-yl-1-(2-methoxyphenyl)-3-(2,2,6,6-tetramethyltetrahydro-2H-pyran-4-yl)-1H-pyrazole,
2-[1-(2-Methoxyphenyl)-3-(2,2,6,6-tetramethyltetrahydro-2H-pyran-4-yl)-1H-pyrazol-5-yl]-5-methyl-1,3-thiazole,
2-Methoxy-5-[1-(2-methoxyphenyl)-3-(2,2,6,6-tetramethyltetrahydro-2H-pyran-4-yl)-1H-pyrazol-5-yl]pyrimidine,
N,N-Diethyl-4-[1-(2-methoxyphenyl)-3-(2,2,6,6-tetramethyltetrahydro-2H-pyran-4-yl)-1H-pyrazol-5-yl]-benzamide,
5-(1-Benzofuran-2-yl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1H-indole,
5-(3,5-Dimethoxyphenyl)-1-(2-methoxyphenyl)-3-(2,2,6,6-tetramethyltetrahydro-2H-pyran-4-yl)-1H-pyrazole,
1-{4-[1-(2-Methoxyphenyl)-3-(2,2,6,6-tetramethyltetrahydro-2H-pyran-4-yl)-1H-pyrazol-5-yl]-phenyl}ethanol,
3-[1-(2-Methoxyphenyl)-3-(2,2,6,6-tetramethyltetrahydro-2H-pyran-4-yl)-1H-pyrazol-5-yl]-pyridine,
4-[1-(2-Methoxyphenyl)-3-(2,2,6,6-tetramethyltetrahydro-2H-pyran-4-yl)-1H-pyrazol-5-yl]-benzoic acid,
5-(4-Methanesulfinyl-phenyl)-1-(2-methoxy-phenyl)-3-(2,2,6,6-tetramethyl-tetrahydro-pyran-4-yl)-1H-pyrazole,
1-(2-tert-Butoxyphenyl)-5-(4-chlorophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N,N-dimethylaniline,
2-[5-(4-Chloro-phenyl)-3-(2,2,6,6-tetramethyl-tetrahydro-pyran-4-yl)-pyrazol-1-yl]-pyridine,
4-[5-(4-Chlorophenyl)-3-(2,2,6,6-tetramethyltetrahydro-2H-pyran-4-yl)-1H-pyrazol-1-yl]-pyridine,
3-[5-(4-Chlorophenyl)-3-(2,2,6,6-tetramethyltetrahydro-2H-pyran-4-yl)-1H-pyrazol-1-yl]-pyridine,
4-[1-Pyrazin-2-yl-3-(2,2,6,6-tetramethyltetrahydro-2H-pyran-4-yl)-1H-pyrazol-5-yl]-benzonitrile,
4-[1-Pyridin-3-yl-3-(2,2,6,6-tetramethyltetrahydro-2H-pyran-4-yl)-1H-pyrazol-5-yl]-benzonitrile,
4-[1-Pyridin-2-yl-3-(2,2,6,6-tetramethyltetrahydro-2H-pyran-4-yl)-1H-pyrazol-5-yl]-benzonitrile,
4-[1-Pyridin-4-yl-3-(2,2,6,6-tetramethyltetrahydro-2H-pyran-4-yl)-1H-pyrazol-5-yl]-benzonitrile,
4-[1-Quinolin-8-yl-3-(2,2,6,6-tetramethyltetrahydro-2H-pyran-4-yl)-1H-pyrazol-5-yl]-benzonitrile,
5-(4-Chloro-phenyl)-1-(2-methoxy-phenyl)-3-(2,2,6,6-tetramethyl-tetrahydro-thiopyran-4-yl)-1H-pyrazole,
5-(4-Chlorophenyl)-1-(2-methoxyphenyl)-3-(2,2,6,6-tetramethyl-1,1-dioxidotetrahydro-2H-thiopyran-4-yl)-1H-pyrazole,
2-[5-(4-Chlorophenyl)-3-(2,2,6,6-tetramethyltetrahydro-2H-pyran-4-yl)-1H-pyrazol-1-yl]-N-methylaniline,
5-(4-Chlorophenyl)-3-[(trans)-2,6-dimethyltetrahydro-2H-pyran-4-yl]-1-(2-methoxyphenyl)-1H-pyrazole,
5-(4-Chlorophenyl)-3-(2,2-dimethyltetrahydro-2H-pyran-4-yl)-1-(2-methoxyphenyl)-1H-pyrazole,
5-(4-Chlorophenyl)-3-[(2R,4r,6S)-2,6-dimethyltetrahydro-2H-pyran-4-yl]-1-(2-methoxyphenyl)-1H-pyrazole,
5-(4-Chlorophenyl)-1-(2-methoxyphenyl)-3-[(2R,4S)-2-(1-methylethyl)tetrahydro-2H-pyran-4-yl]-1H-pyrazole,
5-(4-Chlorophenyl)-1-(2-nitrophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N-ethylaniline, 3-[(trans)-2,6-Dimethyltetrahydro-2H-pyran-4-yl]-1-(2-methoxyphenyl)-5-phenyl-1H-pyrazole, 2-[5-(4-Chlorophenyl)-3-(2,2,6,6-tetramethyltetrahydro-2H-pyran-4-yl)-1H-pyrazol-1-yl]aniline, 5-(4-Chlorophenyl)-1-(2-methoxyphenyl)-3-[(trans)-2-(1-methylethyl)tetrahydro-2H-pyran-4-yl]-1H-pyrazole, 4-Bromo-5-(4-chlorophenyl)-1-(2-methoxyphenyl)-3-(2,2,6,6-tetramethyltetrahydro-2H-pyran-4-yl)-1H-pyrazole, 5-(4-Chlorophenyl)-1-(2-methoxyphenyl)-3-(tetrahydro-2H-pyran-4-yl)-1H-pyrazole, 4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine, 2-[5-(4-Chlorophenyl)-3-(2,2,6,6-tetramethyltetrahydro-2H-pyran-4-yl)-1H-pyrazol-1-yl]-N,N-diethylaniline, 1-(2-Chlorophenyl)-5-(4-chlorophenyl)-3-(tetrahydro-2H-pyran-4-yl)-1H-pyrazole, 5-(4-Chlorophenyl)-3-(2,2-dimethyltetrahydro-2H-pyran-4-yl)-1-(4-methoxy-2-methylphenyl)-1H-pyrazole, 5-(4-Chlorophenyl)-1-(2-pyrrolidin-1-ylphenyl)-3-(2,2,6,6-tetramethyltetrahydro-2H-pyran-4-yl)-1H-pyrazole, 5-(4-Chlorophenyl)-1-(2-ethylphenyl)-3-(tetrahydro-2H-pyran-4-yl)-1H-pyrazole, 5-(4-Chlorophenyl)-1-(2,4-dichlorophenyl)-3-(tetrahydro-2H-pyran-4-yl)-1H-pyrazole, 5-(4-Chlorophenyl)-3-(tetrahydro-2H-pyran-4-yl)-1-[2-(trifluoromethoxy)phenyl]-1H-pyrazole, 5-(4-Chlorophenyl)-1-(2,6-dichlorophenyl)-3-(tetrahydro-2H-pyran-4-yl)-1H-pyrazole, 5-{4-[2-(1H-Imidazol-1-yl)ethoxy]phenyl}-1-(2-methoxyphenyl)-3-(2,2,6,6-tetramethyltetrahydro-2H-pyran-4-yl)-1H-pyrazole, 2-{4-[1-(2-Methoxyphenyl)-3-(2,2,6,6-tetramethyltetrahydro-2H-pyran-4-yl)-1H-pyrazol-5-yl]phenoxy}-N,N-dimethylethanamine, 1-(2-Methoxyphenyl)-5-[4-(methylsulfonyl)phenyl]-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-phenol, 5-[1-(2-Methoxyphenyl)-3-(2,2,6,6-tetramethyltetrahydro-2H-pyran-4-yl)-1H-pyrazol-5-yl]-pyridin-2-amine, 4-({4-[1-(2-Methoxyphenyl)-3-(2,2,6,6-tetramethyltetrahydro-2H-pyran-4-yl)-1H-pyrazol-5-yl]phenyl}carbonyl)morpholine, N-[2-(Dimethylamino)ethyl]-4-[1-(2-methoxyphenyl)-3-(2,2,6,6-tetramethyltetrahydro-2H-pyran-4-yl)-1H-pyrazol-5-yl]benzamide, 4-[1-(2-Methoxyphenyl)-3-(2,2,6,6-tetramethyltetrahydro-2H-pyran-4-yl)-1H-pyrazol-5-yl]benzamide, 1-({4-[1-(2-Methoxyphenyl)-3-(2,2,6,6-tetramethyltetrahydro-2H-pyran-4-yl)-1H-pyrazol-5-yl]phenyl}carbonyl)-4-methylpiperazine, N-(2-Hydroxyethyl)-4-[1-(2-methoxyphenyl)-3-(2,2,6,6-tetramethyltetrahydro-2H-pyran-4-yl)-1H-pyrazol-5-yl]-benzamide, 3-[1-(2-Methoxyphenyl)-3-(2,2,6,6-tetramethyltetrahydro-2H-pyran-4-yl)-1H-pyrazol-5-yl]-pyridine-1-oxide, 5-(4-Chlorophenyl)-1-[2,4-dichloro-6-(trifluoromethyl)phenyl]-3-(tetrahydro-2H-pyran-4-yl)-1H-pyrazole, 5-(4-Chlorophenyl)-1-[2,6-dichloro-4-(trifluoromethyl)phenyl]-3-(tetrahydro-2H-pyran-4-yl)-1H-pyrazole, 2-[5-(4-Chlorophenyl)-3-(tetrahydro-2H-pyran-4-yl)-1H-pyrazol-1-yl]-benzonitrile, 5-(4-Chlorophenyl)-1-(2-methoxyphenyl)-3-(2,2,6,6-tetramethyl-3,6-dihydro-2H-pyran-4-yl)-1H-pyrazole, 5-(4-Chlorophenyl)-3-[(trans)-2,6-dimethyl-3,6-dihydro-2H-pyran-4-yl]-1-(2-methoxyphenyl)-1H-pyrazole, 5-(4-Chlorophenyl)-1-(2-methoxyphenyl)-3-(2,2,5,5-tetramethyl-2,5-dihydrofuran-3-yl)-1H-pyrazole, 5-(4-Chlorophenyl)-1-(2-methoxyphenyl)-3-(2,2,5,5-tetramethyl-2,5-dihydrofuran-3-yl)-1H-pyrazole, or 5-(4-Chlorophenyl)-1-(2-methoxyphenyl)-3-(2,2,5,5-tetramethyl-tetrahydrofuran-3-yl)-1H-pyrazole.

15. A pharmaceutical composition of claim 13, wherein said compound of claim 1 is selected from:

5-(4-Chloro-phenyl)-1-(2-methoxy-phenyl)-3-(2,2,6,6-tetramethyl-tetrahydro-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-benzonitrile, 5-(4-Chloro-2-fluorophenyl)-1-(2-methoxyphenyl)-3-(2,2,6,6-tetramethyltetrahydro-2H-pyran-4-yl)-1H-pyrazole, 5-(1,3-Benzodioxol-5-yl)-1-(2-methoxyphenyl)-3-(2,2,6,6-tetramethyltetrahydro-2H-pyran-4-yl)-1H-pyrazole, 1-(2-Methoxyphenyl)-5-(4-methoxyphenyl)-3-(2,2,6,6-tetramethyltetrahydro-2H-pyran-4-yl)-1H-pyrazole, 1-(2-Methoxyphenyl)-5-[4-(methylsulfanyl)phenyl]-3-(2,2,6,6-tetramethyltetrahydro-2H-pyran-4-yl)-1H-pyrazole, 5-(4-Chlorophenyl)-1-[2-(1-methylethoxy)phenyl]-3-(2,2,6,6-tetramethyltetrahydro-2H-pyran-4-yl)-1H-pyrazole, 5-(4,4-Dimethylcyclohex-1-en-1-yl)-1-(2-methoxyphenyl)-3-(2,2,6,6-tetramethyltetrahydro-2H-pyran-4-yl)-1H-pyrazole, 5-(4-Ethoxyphenyl)-1-(2-methoxyphenyl)-3-(2,2,6,6-tetramethyltetrahydro-2H-pyran-4-yl)-1H-pyrazole, 1-(2-Methoxyphenyl)-5-(4-methylphenyl)-3-(2,2,6,6-tetramethyltetrahydro-2H-pyran-4-yl)-1H-pyrazole, 4-[1-(2-Methoxyphenyl)-3-(2,2,6,6-tetramethyltetrahydro-2H-pyran-4-yl)-1H-pyrazol-5-yl]-N,N-dimethylaniline, 1-{4-[1-(2-Methoxyphenyl)-3-(2,2,6,6-tetramethyltetrahydro-2H-pyran-4-yl)-1H-pyrazol-5-yl]phenyl}ethanone, 2-Methoxy-5-[1-(2-methoxyphenyl)-3-(2,2,6,6-tetramethyltetrahydro-2H-pyran-4-yl)-1H-pyrazol-5-yl]pyridine, 5-(5-Chlorothiophen-2-yl)-1-(2-methoxyphenyl)-3-(2,2,6,6-tetramethyltetrahydro-2H-pyran-4-yl)-1H-pyrazole, 5-(4-tert-Butylphenyl)-1-(2-methoxyphenyl)-3-(2,2,6,6-tetramethyltetrahydro-2H-pyran-4-yl)-1H-pyrazole, 1-(2-Methoxyphenyl)-5-phenyl-3-(2,2,6,6-tetramethyltetrahydro-2H-pyran-4-yl)-1H-pyrazole, Ethyl 4-[1-(2-methoxyphenyl)-3-(2,2,6,6-tetramethyltetrahydro-2H-pyran-4-yl)-1H-pyrazol-5-yl]benzoate, 1-(2-Methoxyphenyl)-5-(4-methylthiophen-2-yl)-3-(2,2,6,6-tetramethyltetrahydro-2H-pyran-4-yl)-1H-pyrazole, 2-Ethoxy-5-[1-(2-methoxyphenyl)-3-(2,2,6,6-tetramethyltetrahydro-2H-pyran-4-yl)-1H-pyrazol-5-yl]-pyridine, 1-(2-Methoxyphenyl)-5-(3-methoxyphenyl)-3-(2,2,6,6-tetramethyltetrahydro-2H-pyran-4-yl)-1H-pyrazole, 5-[1-(2-Methoxyphenyl)-3-(2,2,6,6-tetramethyltetrahydro-2H-pyran-4-yl)-1H-pyrazol-5-yl]-1-methyl-1H-indole, 2-[1-(2-Methoxyphenyl)-3-(2,2,6,6-tetramethyltetrahydro-2H-pyran-4-yl)-1H-pyrazol-5-yl]-aniline, 5-[1-(2-Methoxyphenyl)-3-(2,2,6,6-tetramethyltetrahydro-2H-pyran-4-yl)-1H-pyrazol-5-yl]-2-methylpyridine,
1-(2-Methoxyphenyl)-5-[4-(1-methylethoxy)phenyl]-3-(2,2,6,6-tetramethyltetrahydro-2H-pyran-4-yl)-1H-pyrazole,
2-Chloro-4-[1-(2-methoxyphenyl)-3-(2,2,6,6-tetramethyltetrahydro-2H-pyran-4-yl)-1H-pyrazol-5-yl]pyridine,
1-(2-Methoxyphenyl)-3-(2,2,6,6-tetramethyltetrahydro-2H-pyran-4-yl)-5-thiophen-2-yl-1H-pyrazole,
5-(2,3-Dihydro-1,4-benzodioxin-6-yl)-1-(2-methoxyphenyl)-3-(2,2,6,6-tetramethyltetrahydro-2H-pyran-4-yl)-1H-pyrazole,
1-(2-Methoxyphenyl)-5-(5-methylfuran-2-yl)-3-(2,2,6,6-tetramethyltetrahydro-2H-pyran-4-yl)-1H-pyrazole,
5-(3,4-Dimethoxyphenyl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-N,N-dimethylpyridin-2-amine,
4-[1-(2-Methoxyphenyl)-3-(2,2,6,6-tetramethyltetrahydro-2H-pyran-4-yl)-1H-pyrazol-5-yl]pyridine,
4-[1-(2-Methoxyphenyl)-3-(2,2,6,6-tetramethyltetrahydro-2H-pyran-4-yl)-1H-pyrazol-5-yl]-2-methylpyridine,
3-Methoxy-5-[1-(2-methoxyphenyl)-3-(2,2,6,6-tetramethyltetrahydro-2H-pyran-4-yl)-1H-pyrazol-5-yl]-pyridine,
N-{2-[1-(2-Methoxyphenyl)-3-(2,2,6,6-tetramethyltetrahydro-2H-pyran-4-yl)-1H-pyrazol-5-yl]-phenyl}-acetamide,
5-Cyclopent-1-en-1-yl-1-(2-methoxyphenyl)-3-(2,2,6,6-tetramethyltetrahydro-2H-pyran-4-yl)-1H-pyrazole,
2-[1-(2-Methoxyphenyl)-3-(2,2,6,6-tetramethyltetrahydro-2H-pyran-4-yl)-1H-pyrazol-5-yl]-5-methyl-1,3-thiazole,
2-Methoxy-5-[1-(2-methoxyphenyl)-3-(2,2,6,6-tetramethyltetrahydro-2H-pyran-4-yl)-1H-pyrazol-5-yl]pyrimidine,
5-(1-Benzofuran-2-yl)-1-(2-methoxyphenyl)-3-(2,2,6,6-tetramethyltetrahydro-2H-pyran-4-yl)-1H-pyrazole,
5-[1-(2-Methoxyphenyl)-3-(2,2,6,6-tetramethyltetrahydro-2H-pyran-4-yl)-1H-pyrazol-5-yl]-1H-indole,
5-(3,5-Dimethoxyphenyl)-1-(2-methoxyphenyl)-3-(2,2,6,6-tetramethyltetrahydro-2H-pyran-4-yl)-1H-pyrazole,
1-{4-[1-(2-Methoxyphenyl)-3-(2,2,6,6-tetramethyltetrahydro-2H-pyran-4-yl)-1H-pyrazol-5-yl]-phenyl}-ethanol,
3-[1-(2-Methoxyphenyl)-3-(2,2,6,6-tetramethyltetrahydro-2H-pyran-4-yl)-1H-pyrazol-5-yl]-pyridine,
1-(2-tert-Butoxyphenyl)-5-(4-chlorophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N,N-dimethylaniline,
2-[5-(4-Chlorophenyl)-3-(2,2,6,6-tetramethyltetrahydro-2H-pyran-4-yl)-1H-pyrazol-1-yl]-N-methylaniline,
5-(4-Chlorophenyl)-3-[(trans)-2,6-dimethyltetrahydro-2H-pyran-4-yl]-1-(2-methoxyphenyl)-1H-pyrazole,
5-(4-Chlorophenyl)-3-(2,2-dimethyltetrahydro-2H-pyran-4-yl)-1-(2-methoxyphenyl)-1H-pyrazole,
5-(4-Chlorophenyl)-3-[(2R,4r,6S)-2,6-dimethyltetrahydro-2H-pyran-4-yl]-1-(2-methoxyphenyl)-1H-pyrazole,
5-(4-Chlorophenyl)-1-(2-methoxyphenyl)-3-[(2R,4S)-2-(1-methylethyl)tetrahydro-2H-pyran-4-yl]-1H-pyrazole,
5-(4-Chlorophenyl)-1-(2-nitrophenyl)-3-(2,2,6,6-tetramethyltetrahydro-2H-pyran-4-yl)-1H-pyrazole,
2-[5-(4-Chlorophenyl)-3-(2,2,6,6-tetramethyltetrahydro-2H-pyran-4-yl)-1H-pyrazol-1-yl]-N-ethylaniline,
3-[(trans)-2,6-Dimethyltetrahydro-2H-pyran-4-yl]-1-(2-methoxyphenyl)-5-phenyl-1H-pyrazole,
2-[5-(4-Chlorophenyl)-3-(2,2,6,6-tetramethyltetrahydro-2H-pyran-4-yl)-1H-pyrazol-1-yl]-aniline,
5-(4-Chlorophenyl)-1-(2-methoxyphenyl)-3-[(trans)-2-(1-methylethyl)tetrahydro-2H-pyran-4-yl]-1H-pyrazole,
4-Bromo-5-(4-chlorophenyl)-1-(2-methoxyphenyl)-3-(2,2,6,6-tetramethyltetrahydro-2H-pyran-4-yl)-1H-pyrazole,
5-(4-Chlorophenyl)-1-(2-methoxyphenyl)-3-(tetrahydro-2H-pyran-4-yl)-1H-pyrazole,
4-(2-{4-[1-(2-Methoxyphenyl)-3-(2,2,6,6-tetramethyltetrahydro-2H-pyran-4-yl)-1H-pyrazol-5-yl]phenoxy}ethyl)morpholine,
2-[5-(4-Chlorophenyl)-3-(2,2,6,6-tetramethyltetrahydro-2H-pyran-4-yl)-1H-pyrazol-1-yl]-N,N-diethylaniline,
1-(2-Chlorophenyl)-5-(4-chlorophenyl)-3-(tetrahydro-2H-pyran-4-yl)-1H-pyrazole,
5-(4-Chlorophenyl)-3-(2,2-dimethyltetrahydro-2H-pyran-4-yl)-1-(4-methoxy-2-methylphenyl)-1H-pyrazole,
5-(4-Chlorophenyl)-1-(2-pyrrolidin-1-ylphenyl)-3-(2,2,6,6-tetramethyltetrahydro-2H-pyran-4-yl)-1H-pyrazole,
5-(4-Chlorophenyl)-1-(2-ethylphenyl)-3-(tetrahydro-2H-pyran-4-yl)-1H-pyrazole,
2-Methoxy-3-[1-(2-methoxyphenyl)-3-(2,2,6,6-tetramethyltetrahydro-2H-pyran-4-yl)-1H-pyrazol-5-yl]pyridine,
5-(4-Chlorophenyl)-1-(2,4-dichlorophenyl)-3-(tetrahydro-2H-pyran-4-yl)-1H-pyrazole,
5-(4-Chlorophenyl)-1-(2-methoxyphenyl)-3-(2,2,6,6-tetramethyl-3,6-dihydro-2H-pyran-4-yl)-1H-pyrazole,
5-(4-Chlorophenyl)-3-[(trans)-2,6-dimethyl-3,6-dihydro-2H-pyran-4-yl]-1-(2-methoxyphenyl)-1H-pyrazole,
5-(4-Chlorophenyl)-1-(2-methoxyphenyl)-3-(2,2,5,5-tetramethyl-2,5-dihydrofuran-3-yl)-1H-pyrazole,
5-(4-Chlorophenyl)-1-(2-methoxyphenyl)-3-(2,2,5,5-tetramethyl-2,5-dihydrofuran-3-yl)-1H-pyrazole, or
5-(4-Chlorophenyl)-1-(2-methoxyphenyl)-3-(2,2,5,5-tetramethyl-tetrahydrofuran-3-yl)-1H-pyrazole.

16. A pharmaceutical composition of claim 13, wherein said compound of claim 1 is selected from:
5-(4-Chloro-phenyl)-1-(2-methoxy-phenyl)-3-(2,2,6,6-tetramethyl-tetrahydro-pyran-4-yl)-1H-pyrazole,
4-[1-(2-Methoxyphenyl)-3-(2,2,6,6-tetramethyltetrahydro-2H-pyran-4-yl)-1H-pyrazol-5-yl]-benzonitrile,
1-(2-Methoxyphenyl)-5-(4-methoxyphenyl)-3-(2,2,6,6-tetramethyltetrahydro-2H-pyran-4-yl)-1H-pyrazole,
5-(4-Ethoxyphenyl)-1-(2-methoxyphenyl)-3-(2,2,6,6-tetramethyltetrahydro-2H-pyran-4-yl)-1H-pyrazole,
2-Methoxy-5-[1-(2-methoxyphenyl)-3-(2,2,6,6-tetramethyltetrahydro-2H-pyran-4-yl)-1H-pyrazol-5-yl]pyridine,
5-(5-Chlorothiophen-2-yl)-1-(2-methoxyphenyl)-3-(2,2,6,6-tetramethyltetrahydro-2H-pyran-4-yl)-1H-pyrazole,
2-Ethoxy-5-[1-(2-methoxyphenyl)-3-(2,2,6,6-tetramethyltetrahydro-2H-pyran-4-yl)-1H-pyrazol-5-yl]-pyridine, 5-(4-Chlorophenyl)-1-(2-methoxyphenyl)-3-(2,2,6,6-tetramethyl-1,1-dioxidotetrahydro-2H-thiopyran-4-yl)-1H-pyrazole, or 5-(4-Chlorophenyl)-1-(2-methoxyphenyl)-3-(2,2,5,5-tetramethyl-tetrahydrofuran-3-yl)-1H-pyrazole.

17. A method of treating inflammatory pain in a subject in need thereof, comprising administering to the subject a therapeutically effective amount of a compound of claim 1 or 9.

18. A method of claim 17 wherein the inflammatory pain is due to inflammatory bowel disease, irritable bowel syndrome, visceral pain, migraine, post-operative pain, osteoarthritis, rheumatoid arthritis, back pain, lower back pain, joint pain, abdominal pain, chest pain, labor pain, musculoskeletal diseases, skin diseases, toothache, pyresis, burn, sunburn, snake bite, venomous snake bite, spider bite, insect sting, neurogenic/overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache or arachnoiditis.

19. A method for treating neuropathic pain in a subject in need thereof, comprising administering to the subject a therapeutically effective amount of a compound of claim 1 or 9.

20. The method of claim 19 wherein the neuropathic pain is cancer pain, neurological disorders, spine and peripheral nerve surgery, brain tumor, traumatic brain injury (TBI), chemotherapy-induced pain, pain chronification, radicular pain, HIV pain, spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

21. A process for making a pharmaceutical composition comprising admixing any of the compounds according to claim 1 and a pharmaceutically acceptable carrier.

* * * * *